United States Patent [19]

Schacht et al.

[11] Patent Number: 5,726,159
[45] Date of Patent: Mar. 10, 1998

[54] ANTITHROMBOTIC AGENTS

[75] Inventors: Aaron L. Schacht, Indianapolis; Robert T. Shuman, Greenwood; Gerald F. Smith; Michael R. Wiley, both of Indianapolis, all of Ind.

[73] Assignee: Eli Lilly and Company, Indianapolis, Ind.

[21] Appl. No.: 522,769

[22] Filed: Sep. 1, 1995

Related U.S. Application Data

[63] Continuation-in-part of Ser. No. 206,553, Mar. 4, 1994, abandoned, and Ser. No. 398,187, Mar. 2, 1995, abandoned.

[30] Foreign Application Priority Data

Feb. 27, 1995 [ZA] South Africa ............... 95/1617

[51] Int. Cl.$^6$ .............. A61K 38/00; C07D 223/16; C07D 205/08; C07D 239/02; C07D 211/26; C07D 211/34; C07F 9/06; C07F 9/28
[52] U.S. Cl. .............. 514/19; 540/593; 540/594; 540/595; 540/362; 544/323; 546/199; 546/246; 546/22; 548/128; 548/131; 548/190; 548/112; 548/214; 548/233; 548/535; 548/566; 548/518; 548/558; 548/326.5; 548/453; 560/34; 560/35; 560/168; 560/169; 562/126; 562/439; 562/560; 562/15; 564/15; 564/123; 558/170
[58] Field of Search .............. 514/19; 540/593–595, 540/362; 544/323; 546/199, 246, 22; 548/128, 131, 190, 214, 233, 535, 566, 518, 558, 326.5, 453, 112; 560/34, 35, 168, 169; 562/126, 439, 560, 15; 564/123, 15; 558/170

[56] References Cited

U.S. PATENT DOCUMENTS

| | | | |
|---|---|---|---|
| 4,316,889 | 2/1982 | Bajusz et al. | 514/19 |
| 4,346,078 | 8/1982 | Bajusz et al. | 514/19 |
| 4,399,065 | 8/1983 | Bajusz et al. | 530/331 |
| 4,478,745 | 10/1984 | Bajusz et al. | 530/331 |
| 4,703,036 | 10/1987 | Bajusz et al. | 514/18 |
| 5,053,392 | 10/1991 | Klein et al. | 514/18 |
| 5,153,176 | 10/1992 | Abe et al. | 514/18 |
| 5,202,416 | 4/1993 | Steuber et al. | 530/322 |
| 5,204,323 | 4/1993 | Findlay et al. | 514/2 |
| 5,250,660 | 10/1993 | Shuman et al. | 530/344 |
| 5,252,566 | 10/1993 | Shuman | 514/210 |
| 5,380,713 | 1/1995 | Balasubramanian et al. | 514/18 |
| 5,416,093 | 5/1995 | Shuman | 514/307 |
| 5,430,023 | 7/1995 | Gesellchen et al. | 514/18 |
| 5,436,229 | 7/1995 | Ruterbories et al. | 514/18 |
| 5,439,888 | 8/1995 | Shuman et al. | 514/18 |
| 5,484,772 | 1/1996 | Sall et al. | 514/18 |
| 5,488,037 | 1/1996 | Sall et al. | 514/19 |
| 5,510,369 | 4/1996 | Lumma et al. | 514/422 |
| 5,561,146 | 10/1996 | Kim et al. | 514/326 |
| 5,583,146 | 12/1996 | Kimball et al. | 514/326 |

FOREIGN PATENT DOCUMENTS

| | | |
|---|---|---|
| 16380/95 | 10/1995 | Australia . |
| 21801/95 | 1/1996 | Australia . |
| 293881 | 12/1988 | European Pat. Off. . |
| 410 411 | 1/1991 | European Pat. Off. . |
| 479 489 | 4/1992 | European Pat. Off. . |
| 526 877 | 8/1992 | European Pat. Off. . |
| 503 203 | 9/1992 | European Pat. Off. . |
| 504 064 | 9/1992 | European Pat. Off. . |
| 529 568 | 3/1993 | European Pat. Off. . |
| 530 167 | 3/1993 | European Pat. Off. . |
| 542 525 | 5/1993 | European Pat. Off. . |
| 601 459 | 6/1994 | European Pat. Off. . |
| 648 780 | 8/1994 | European Pat. Off. . |
| 623 595 | 11/1994 | European Pat. Off. . |
| 623 596 | 11/1994 | European Pat. Off. . |
| 686 642 | 12/1995 | European Pat. Off. . |
| WO 93/08211 | 4/1993 | WIPO . |
| WO 93/11152 | 6/1993 | WIPO . |
| WO 93/15756 | 8/1993 | WIPO . |
| WO 94/29335 | 12/1994 | WIPO . |
| WO 94/29336 | 12/1994 | WIPO . |
| WO 95/09634 | 4/1995 | WIPO . |
| WO 95/09858 | 4/1995 | WIPO . |
| WO 95/09859 | 4/1995 | WIPO . |
| WO 95/35309 | 12/1995 | WIPO . |
| WO 96/03374 | 2/1996 | WIPO . |
| WO 96/17860 | 6/1996 | WIPO . |
| WO 96/24609 | 8/1996 | WIPO . |
| WO 96/25426 | 8/1996 | WIPO . |

OTHER PUBLICATIONS

Misra, Raj N., et al., *Bioorg. & Med. Chem. Letters*, 4, 2165–2170, (1994).

Bajusz S., et al., *J. Med. Chem.*, 1990, 33, 1729–1735.

Fareed, J., et al., *Annals N.Y. Academy of Sciences*, 1981, 765–784.

Shuman R. T., et al., In *Peptides* (Proceedings of the Twelfth American Peptide Symposium, Jun. 16–21, 1991); ESCOM; Leiden; 1992; pp. 799–800 and 801–802.

Wilson, et al., American Heart Association, Nov. 11–14, 1991, Anaheim Convention Center, Anaheim, CA, Abstract.

Bajusz, et al., *Int. J. Peptide Res.*, 12, 1978, 217–221.

Gesellchen, et al., Tenth American Peptide Symposium, May 23–28, 1987, St. Louis, MO, Abstract and posters.

Claeson, et al., Proceedings of the Twelfth American Peptide symposium, Jun. 16–21, 1991, Cambridge, MA, pp. 824–825.

Smith, G. F., Shuman, R. T. Gesellchen, P.D., Craft, T.J., Gifford, P., Kurz, K.D., Jackson, C.V., Sandusky, G.E., and P.D., Williams, A New Family of Thrombin Inhibitors with Improved Specificity and Therapeutic Index. (Submitted to the American Heart Association, Oct., 1991, Circulation Oct., 1991, vol. 84, II-579, 1991), Abstract.

(List continued on next page.)

Primary Examiner—Sheela Huff
Attorney, Agent, or Firm—Thomas E. Jackson; David E. Boone; Robert A. Conrad

[57] ABSTRACT

This invention relates to thrombin inhibiting compounds having the Formula I

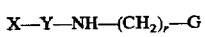

$$X\text{—}Y\text{—}NH\text{—}(CH_2)_r\text{—}G \qquad I$$

where X, Y, r and G have the values defined in the description, as well as pharmaceutical formulations containing those compounds and methods of their use as thrombin inhibitors, coagulation inhibitors, and thromboembolic disorder agents.

42 Claims, No Drawings

OTHER PUBLICATIONS

Jackson, V., Wilson, H., Frank, J., Crowe, V., Craft, T., and G. Smith. The Thrombin Inhibitor, Methyl–D–Phe–Pro–Arginal—An Effective Adjunct to Coronary Artery Thrombolysis in the Anesthetized Dog. FASEB J. 5(4)A520 (1991), Abstract 865 [copy of abstract and posters attached to CL].

Crowe, V., Frank, J., Wilson, H., Coffman, B., Smith, G., and V. Jackson. Anticoagulant and Antithrombotic Efficacy of the Novel Thrombin Inhibitor Methyl–D–Phg–Pro–Arginal in a Canine Model of Coronary Thrombosis. FASEB J. 5(4)A520 (1991), Abstract 864 [copy of abstract and posters attached to CK].

Wilson, H., Frank J., Crowe, V., Coffman, B., Smith, G., Shuman, R., and V. Jackson. Anticoagulant and Antithrombotic Efficacy of the Novel Thrombin Inhibitor, Methyl–D–Phg–Pro–Arginal, in a Canine Model of Coronary Thrombosis (Arteriosclerosis and Thrombosis, 11(5), Oct., 1991) p. 1586a. Abstract.

Jackson, V., Wilson, H., Frank, J., Crowe, V., Coffman, B., Shuman, R., and G. Smith. The Novel Thrombin Inhibitor Methyl–D–Phg–Pro–Arginal: An Effective Conjunctive Agent to Coronary Artery Thrombolysis in the Anesthetized Dog. (Arteriosclerosis and Thrombosis, 11(5), Oct., 1991) p. 1586a. Abstract.

Shuman, R.T., Rothenberger, R.B., Campbell, C.S. Smith, G.F., Jackson, C.V., Kurz, K.D., and P.D. Gesellchen. A Series of Highly Active Serine Proteinase Inhibitors. American Peptide Symposium, Jun. 1991, Abstract.

Jackson, C.V., Frank, J.D., Crowe, V.G., Craft, T.J., and G.F. Smith. Assessment of the Anticoagulant and Antithrombotic Efficacy of the Thrombin Inhibitor, BOC–Phe–Pro–Arginal, in a Canine Model of Coronary Thrombosis. *Arteriosclerosis*, 10 922A (1990).

Jackson, C.V., Frank, J.D., Crowe, V.G., Craft, T.J., and G.F. Smith. The Thrombin Inhibitor, BOC–D–Phe–Pro–Arginal. An Effective Adjunct to Coronary Artery Thrombolysis in the Anesthetized Dog. *Arteriosclerosis*, 10 923a (1990).

Shackelford, K.A., Tanzer, R.L., Shuman, R., Gesellchen, P.D., Grindey, G.B., Sundboom, J.L., Smith, G.F., and R.L. Merriman. Inhibition of Spontaneous Metastasis by Boc–D–Phe–Pro–Arginal. American Association for Cancer Research, San Francisco, 1989. *Proc. Am. Assn. Cancer Res.*, 30 86, 1989.

Neubauer, B.L., Clemens, J.A., Gesellchen, P.D., Hirsch, K.S., Hoover, D.M., Merriman, R.L., and G.F. Smith. Endocrine Characterization and Sensitivity of the PAIII Prostatic Adenocarcinoma in Male Lobund–Wistar (LW) Rats to Anti–Fibrin Agents. American Association for Cancer Research. New Orleans, May 1988, *Proc. Am. Assn. Cancer Res.*, 29 240 (1988).

Neubauer, B.L., Best, K.L., Gesellchen, P.D., Goode, R.L., Merriman, R.L., Tanzer, L.R., Shaar, C.J., Shuman, R., Sundboom, Pro–Arginal on the Metastasis of the PAIII Prostatic Adenocarcinoma in Male Lobund Wistar (LW) Rats. American Urological Association. Boston, May 1988. *J. Urol.*, 139 175A (1988).

Gesellchen, P.D., Smith, G.F., et al., Anticoagulant, Antithrombotic, and Antimetastatic Effects of a Serine Proteinase Inhibitor. 10th American Peptide Symposium, Washington University, St. Louis, MO (1987), Abstract.

Smith, G.F., Sundboom, J.L., Best, K., Gesellchen, P.D., Merriman, R.L., Shuman, R., and Neubauer, B.L. Heparin, Boc–D–Phe–Pro–Arginal, and Warfarin (Fibrin Antagonists) Inhibit Metastasis in an In Vivo Model. American Chemical Society National Meeting. Abstract BIOL 70 Biochemistry (1987).

K.D. Kurz, T. Smith, R.A. Moore, and B.W. Main. Comparison of Thrombin Inhibitors in Rat Models of Thrombosis and Thrombolysis. FASEB Journal, vol. 5 (No. 4), 1991, Abstract #886.

Tomori, et al., *Chromatographia*, vol. 19, 437–442 (1984).

Dayhoff, *Atlas of Protein Sequence and Structure*, 5, pp. 85–89 (1972).

Shuman, et al., *J. Med. Chem.*, 36(3), 314–319 (1993).

Jackson, et al., *J. Cardiovasc, Pharmacol.*, 21(4), 587–594 (1993).

Cheng, et al., *Tetrahedron Lett.*, 32 (49), 7333–7336 (1991).

Bagdy, et al., *Thrombosis and Haemostasis*, 68(2), 125–129 (1992).

*Thrombosis and Haemostasis*, 65, 1289, Nos. 2150–2151 and 2152 (1991).

Bagdy, et al., *Thrombosis and Haemostasis*, 67(3), 325–330 (1992).

Bagdy, et al., *Thrombosis and Haemostasis*, 67(3), 357–365 (1992).

Balasubramanian, et al., *J. Med. Chem.*, 36, 300–303 (1993).

Shuman, et al., Oral Activity of Tripeptide Aldehyde Thrombin Inhibitors, Thirteenth American Peptide Symposium, Jun. 20–25, 1993, Abstract.

Kurz et al., Antithrombotic Efficacy in the Rat After Intravenous and Oral Administration of a Direct Inhibitor of Thrombin FASEB, Mar. 28–Apr. 1, 1993.

Iwanowicz, et al., *Bioorg. Med. Chem. Lett.*, 2(12), 1607–1612 (1992).

Barabas, et al., *Blood Coagul. Fibrin.*, 4, 243–248 (1993).

Jackson, et al., Conjunctive Therapy with the Thrombin Inhibitor, LY 294468, and Aspirin Produced Enhanced Antireocclusive Activity When Used in a Canine Model of Streptokinase–Induced Coronary Thrombolysis. *The Pharmacologist*, 35(3), 207 (1993), Abstract #407.

Pozagay, et al., Study of the Specificity of Thrombin with Tripeptidyl–p–Nitroanilide Substrates, *Eur. J. Biochem.*, 115, 491–495 (1981).

Smith, et al., Synthesis and Pharmacological Activity of Angiotensin Converting Enzyme Inhibitors: N–(Mercaptoacyl)–4–substituted–(S)–prolines, *J. Med. Chem.*, 31, 875–885 (1988).

Jackson, et al., *The Journal of Pharmacology and Experimental Therapy*, 261(2), 546–552 (1992).

Stueber, et al., Proc. of the 13th American Peptide Symposium, Jun. 20–25, 1993.

Stürzebecher, et al., XIVth Congress of the International Society on Thrombosis and Hemostasis, Jul. 4–9, 1993.

Simoons et al., *Circulation*, 90, I–231, Abstr. 1241 (1994).

Iwanowicz, Edwin J., et al., *J. Med. Chem.*, 37, 2122–2124, (1994).

Bajusz, Symposia Biologica Hungarica vol. 25, pp. 227–298, 1984.

ANTITHROMBOTIC AGENTS

This is a continuation-in-part of application Ser. No. 08/206,553, filed Mar. 4, 1994 and now abandoned; and is a continuation-in-part of application Ser. No. 08/398,187, filed Mar. 2, 1995, and now abandoned.

This invention relates to thrombin inhibitors which are useful anticoagulants in mammals. In particular it relates to peptide derivatives having high antithrombotic activity, anticoagulant activity, and oral bioavailability.

The process of blood coagulation, thrombosis, is triggered by a complex proteolytic cascade leading to the formation of thrombin. Thrombin proteolytically removes activation peptides from the Aα-chains and Bβ-chains of fibrinogen, which is soluble in blood plasma, initiating insoluble fibrin formation.

Anticoagulation is currently achieved by the administration of heparins and coumarins.

Parenteral pharmacological control of coagulation and thrombosis is based on inhibition of thrombin through the use of heparins. Heparins act indirectly on thrombin by accelerating the inhibitory effects of endogenous antithrombin III (the main physiological inhibitor of thrombin). Because antithrombin III levels vary in plasma and because surface-bound thrombin seems resistant to this indirect mechanism, heparins can be an ineffective treatment. Because coagulation assays are believed to be associated with efficacy and with safety, heparin levels must be monitored with coagulation assays (particularly the activated partial thromboplastin time (APTT) assay). Coumarins impede the generation of thrombin by blocking the post-translational gamma-carboxylation in the synthesis of prothrombin and other proteins of this type. Because of their mechanism of action, the effect of coumarins can only develop slowly, 6–24 hours after administration. Further, they are not selective anticoagulants. Coumarins also require monitoring with coagulation assays (particularly with the prothrombin time (PT) assay).

Recently, interest in small synthetic peptides that are recognized by proteolytic enzymes in a manner similar to that of natural substrates has grown. Tripeptide aldehydes such as D-Phe-Pro-Arg-H, Boc-D-Phe-Pro-Arg-H, and D-MePhe-Pro-Arg-H, Bajusz et al., *J. Med. Chem.*, 33, 1729–1735 (1990) demonstrate potent direct inhibition of thrombin. Early clinical studies which demonstrate that D-MePhe-Pro-Arg-H sulfate is an anticoagulant in man have been reported, see Simoons et al., *Circulation*, 90, I-231, Abstr. 1241 (1994). Many investigators have synthesized analogs in an effort to develop pharmaceutical agents, for example Shuman et al., *J. Med. Chem.*, 36, 314–319 (1993). U.S. Pat. No. 4,346,078 teaches a series of anti-coagulant peptides containing an agmatine (1-amino-4-guanidinobutane) group. Agmatine derivatives and related compounds also are disclosed in the PCT application with International Publication Number WO 93/11152, as well as in European Patent Application, Publication number 601459, published 15 Jun. 1994. Such compounds differ from the former series in that the agmatine compounds lack a carbonyl moiety found in similar compounds containing an Arg group.

Although the heparins and coumarins are effective anticoagulants, and no drug has yet emerged from the known tripeptide aldehydes, and despite the continuing promise for this class of compounds, there exists a need for anticoagulants that act selectively on thrombin, and independent of antithrombin III, exert inhibitory action shortly after administration, preferably by an oral route, and do not interfere with lysis of blood clots, as required to maintain hemostasis.

The present invention is directed to the discovery that the compounds of the present invention, as defined below, are potent thrombin inhibitors that may have high bioavailability following oral administration. In addition, certain compounds of the present invention also may exhibit inhibition of factor Xa, which is involved in the coagulation cascade.

Accordingly, it is a primary object of the present invention to provide novel peptide derivatives that are potent thrombin inhibitors useful as anticoagulants.

Other objects, features, and advantages will be apparent to those skilled in the art from the following description and claims.

The present invention provides a thrombin inhibiting compound having the Formula I $$X-Y-NH-(CH_2)_r-G \qquad I$$

wherein

X is prolinyl, homoprolinyl, $R'''-(CH_2)_g-NH-CH_2-C(O)-$,

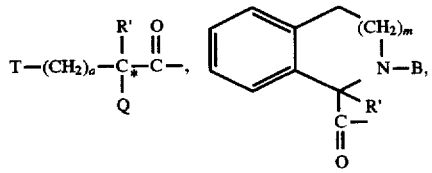

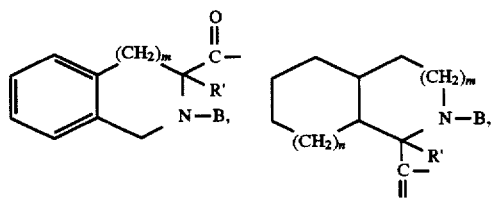

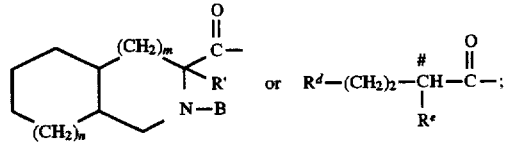

in which $R^d$ is carboxy or methylsulfonyl;

$R^e$ is $NHR^c$, $NHCOR^c$ or $NHCOOR^c$; in which $R^c$ is $C_1-C_{10}$ alkyl, $C_3-C_8$ cycloalkyl or a ($C_3-C_8$) cycloalkyl ($C_1-C_6$) alkyl radical of 4–10 carbons;

T is $C_3-C_8$ cycloalkyl, $C_1-C_8$ alkyl,

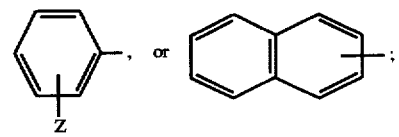

a is 0, 1 or 2; and

Q is $-OH$, $C_1-C_4$ alkoxy, or $-NH-A$;

A is hydrogen, $C_1-C_4$ alkyl, $R''SO_2-$, $R''OC(O)-$, $R''C(O)-$, $R''C(O)-$ or $-(CH_2)_g-R'''$;

g is 1, 2, or 3;

B is hydrogen or $C_1-C_4$ alkyl;

R' is hydrogen or $C_1-C_4$ alkyl;

R'' is $C_1-C_4$ alkyl, $C_1-C_4$ perfluoroalkyl, $-(CH_2)_d-R'''$, or unsubstituted or substituted aryl, where aryl is phenyl, naphthyl, a 5- or 6-membered unsubstituted or substituted aromatic heterocyclic ring, having one or two heteroatoms which are the same or different and which are selected from sulfur, oxygen and nitrogen, or a 9- or 10-membered unsubstituted or substituted fused bicyclic aromatic heterocyclic group having one or two heteroatoms which are the same or different and which are selected from sulfur, oxygen and nitrogen;

$R^m$ is —COOR$^b$, —SO$_2$(C$_1$-C$_4$ alkyl), —SO$_3$H, —P(O)(OR$^b$)$_2$ or tetrazol-5-yl;

$R^n$ is —COOR$^b$ or tetrazol-5-yl;

each $R^b$ is independently hydrogen or C$_1$-C$_4$ alkyl;

d is 1, 2, or 3;

m is 0, 1, or 2;

n is 0, 1, or 2; and

Z is hydrogen, C$_1$-C$_4$ alkyl, C$_1$-C$_4$ alkoxy, hydroxy, halo or R$_a$SO$_2$NH—, where R$_a$ is C$_1$-C$_4$ alkyl;

Y is

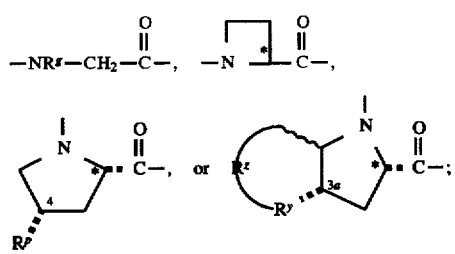

in which $R^g$ is C$_1$-C$_6$ alkyl, C$_3$-C$_8$ cycloalkyl, or —(CH$_2$)$_p$—L—(CH$_2$)$_q$—T';

$R^p$ is hydrogen, C$_1$-C$_6$ alkyl, C$_3$-C$_8$ cycloalkyl, or —(CH$_2$)$_p$—L—(CH$_2$)$_q$—T';

where p is 0, 1, 2, 3, or 4; L is a bond, —O—, —S—, or —NH—; q is 0, 1, 2 or 3; and T' is hydrogen, C$_1$-C$_4$ alkyl, C$_3$-C$_8$ cycloalkyl, —COOH, —CONH$_2$, or Ar, where Ar is unsubstituted or substituted aryl, where aryl is phenyl, naphthyl, a 5- or 6-membered unsubstituted or substituted aromatic heterocyclic ring, having one or two heteroatoms which are the same or different and which are selected from sulfur, oxygen and nitrogen, or a 9- or 10-membered unsubstituted or substituted fused bicyclic aromatic heterocyclic group having one or two heteroatoms which are the same or different and which are selected from sulfur, oxygen and nitrogen;

$R^y$ is —CH$_2$—, —O—, —S—, or —NH—; and $R^z$ is a bond or, when taken with $R^y$ and the three adjoining carbon atoms, forms a saturated carbocyclic ring of 5–8 atoms, one atom of which may be —O—, —S—, or —NH—;

r is 1, 2 or 3; and

G is —(CH$_2$)$_s$—R, where s is 0–5, —CH=CH—(CH$_2$)$_t$—R, where t is 0–3; and R is

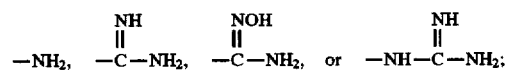

or a pharmaceutically acceptable salt thereof; or a pharmaceutically acceptable solvate of said compound or salt thereof;

provided that A is not hydrogen or t-butyloxycarbonyl when G is —(CH$_2$)$_s$—NH—C(NH)NH$_2$, Y is unsubstituted prolinyl ($R^p$ is hydrogen), and T is

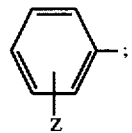

and provided further that R is not amino or guanidino when r=1 and s=0;

and provided further that A is not hydrogen, C$_1$-C$_4$ alkyl, methylsulfonyl or —(CH$_2$)$_g$—R$^m$ when G is —(CH$_2$)$_s$—R in which R is

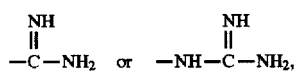

Y is

unsubstituted prolinyl ($R^p$ is hydrogen) or 4-hydroxyprolinyl ($R^p$ is OH), R' is hydrogen, T is cyclohexyl and Q is —NH—A;

and provided further that R"SO$_2$ is not arylsulfonyl when G is —(CH$_2$)$_s$—R in which R is

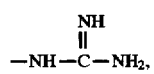

Y is unsubstituted prolinyl ($R^p$ is hydrogen) or 4-methylthioprolinyl ($R^p$ is —SCH$_3$), and Q is —NH—A.

A particular group of the above compounds of Formula I consists of those compounds of Formula I wherein X is prolinyl, homoprolinyl,

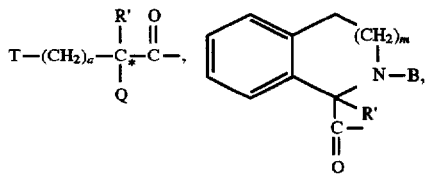

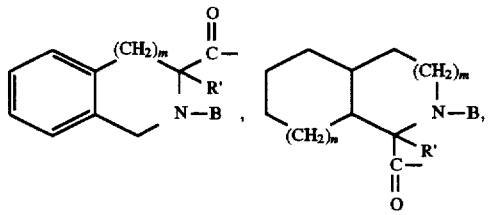

or

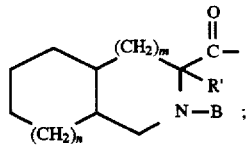

T is $C_3-C_8$ cycloalkyl, $C_1-C_8$ alkyl,

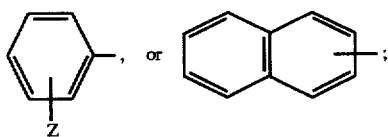 or a is 0 or 1;
Q is —OH, $C_1-C_4$ alkoxy, or —NH—A;
A is hydrogen, $C_1-C_4$ alkyl, R"SO$_2$—, R"OC(O)—, R"C(O)—, or —(CH$_2$)$_g$—COOH;
g is 1, 2, or 3;
B is hydrogen or $C_1-C_4$ alkyl;
R' is hydrogen or $C_1-C_4$ alkyl;
R" is $C_1-C_4$ alkyl, $C_1-C_4$ perfluoroalkyl, —(CH$_2$)$_d$—COOH, or unsubstituted or substituted aryl, where aryl is phenyl, naphthyl, a 5- or 6-membered unsubstituted or substituted aromatic heterocyclic ring, having one or two heteroatoms which are the same or different and which are selected from sulfur, oxygen and nitrogen, or a 9- or 10-membered unsubstituted or substituted fused bicyclic aromatic heterocyclic group having one or two heteroatoms which are the same or different and which are selected from sulfur, oxygen and nitrogen;
d is 1, 2, or 3;
m is 0, 1, or 2;
n is 0, 1, or 2; and
Z is hydrogen, $C_1-C_4$ alkyl, $C_1-C_4$ alkoxy, hydroxy, halo, or R$_a$SO$_2$NH—, where R$_a$ is $C_1-C_4$ alkyl;
Y is

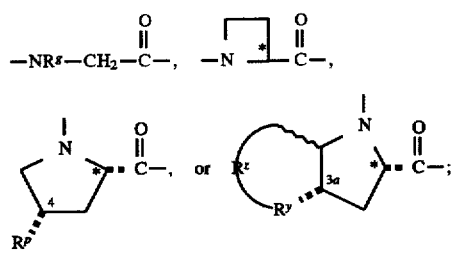

in which
R$^g$ is $C_1-C_6$ alkyl, $C_3-C_8$ cycloalkyl, or —(CH$_2$)$_p$—L—(CH$_2$)$_g$—T';
R$^p$ is hydrogen, $C_1-C_6$ alkyl, $C_3-C_8$ cycloalkyl, or —(CH$_2$)$_p$—L—(CH$_2$)$_q$—T';
where p is 0, 1, 2, 3, or 4; L is a bond, —O—, —S—, or —NH—; q is 0, 1, 2 or 3, and T' is hydrogen, $C_1-C_4$ alkyl, $C_3-C_8$ cycloalkyl, —COOH, —CONH$_2$, or Ar, where Ar is unsubstituted or substituted aryl, where aryl is phenyl, naphthyl, a 5- or 6-membered unsubstituted or substituted aromatic heterocyclic ring, having one or two heteroatoms which are the same or different and which are selected from sulfur, oxygen and nitrogen, or a 9- or 10-membered unsubstituted or substituted fused bicyclic aromatic heterocyclic group having one or two heteroatoms which are the same or different and which are selected from sulfur, oxygen and nitrogen;
R$^y$ is —CH$_2$—, —O—, —S—, or —NH—; and
R$^z$ is a bond or, when taken with R$^y$ and the three adjoining carbon atoms, forms a saturated carbocyclic ring of 5–8 atoms, one atom of which may be —O—, —S—, or —NH—;
r is 1 or 2; and
G is —(CH$_2$)$_s$—R, where s is 0–5, —CH=CH—(CH$_2$)$_t$—R, where t is 0–3; and
R is

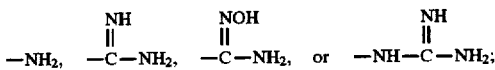

or a pharmaceutically acceptable salt thereof; or a pharmaceutically acceptable solvate of said compound or salt thereof;
provided that A is not hydrogen or t-butyloxycarbonyl when G is —(CH$_2$)$_s$—NH—C(NH)NH$_2$, Y is unsubstituted prolinyl (R$^p$ is hydrogen), and T is

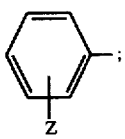

and provided further that R is not amino or guanidino when r=1 and s=0;
and provided further that A is not hydrogen, $C_1-C_4$ alkyl, methylsulfonyl or —(CH$_2$)$_g$—COOH when G is —(CH$_2$)$_s$—R in which R is

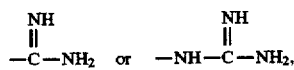

Y is

unsubstituted prolinyl (R$^p$ is hydrogen) or 4-hydroxyprolinyl (R$^p$ is OH), R' is hydrogen, T is cyclohexyl and Q is —NH—A;
and provided further that R"SO$_2$ is not arylsulfonyl when G is —(CH$_2$)$_s$—R in which R is

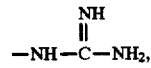

Y is unsubstituted prolinyl (R$^p$ is hydrogen) or 4-methylthioprolinyl (R$^p$ is —SCH$_3$), and Q is —NH—A.

In addition to the compounds of Formula I, the present invention provides pharmaceutical formulations comprising a compound of Formula I in association with a pharmaceutically acceptable carrier, diluent or excipient.

The present invention also provides a method of inhibiting thrombosis in mammals comprising administering to a mammal in need of treatment, an antithrombotic dose of a compound of Formula I.

The present invention further provides a method of inhibiting thrombin comprising administering to a mammal in need of treatment, a thrombin inhibiting dose of a compound of Formula I.

This invention relates to new inhibitors of thrombin, pharmaceutical compositions containing the compounds as active ingredients, and the use of the compounds as anticoagulants for prophylaxis and treatment of thromboembolic diseases such as venous thrombosis, pulmonary embolism, arterial thrombosis, in particular myocardial ischemia, myocardial infarction and cerebral thrombosis, general hypercoagulable states and local hypercoagulable states, such as following angioplasty and coronary bypass operations, and generalized tissue injury as it relates to the inflammatory process.

The term "alkyl" by itself or as part of another substituent means a straight or branched chain alkyl radical having the stated number of carbon atoms such as methyl, ethyl, n-propyl, isopropyl, n-butyl, t-butyl, isobutyl and sec-butyl. The term "perfluoroalkyl" by itself or as part of another substituent means a straight or branched chain alkyl radical having the stated number of carbon atoms in which each hydrogen atom is replaced with a fluorine atom such as trifluoromethyl, perfluoroethyl, perfluoro-n-propyl, perfluoroisopropyl, perfluoro-n-butyl, perfluoro-t-butyl, perfluoroisobutyl and perfluoro-sec-butyl.

The term "$C_3$–$C_8$ cycloalkyl" refers to the saturated alicyclic rings of three to eight carbon atoms such as cyclopropyl, methylcyclopropyl, cyclobutyl, cyclopentyl, cyclohexyl, 4-methylcyclohexyl, cyclooctyl, and the like.

The term "alkoxy" means a straight or branched chain alkyl radical having the stated number of carbon atoms bonded to the parent moiety by an oxygen atom. The term "halo" means chloro, fluoro, bromo or iodo. The term "acetyl" means $CH_3$—C(O)—. The term "t-butyloxycarbonyl" means $(CH_3)_3$C—O—C(O)— and is abbreviated "Boc". The term "benzyloxycarbonyl" means $C_6H_5CH_2$—O—C(O)— and is abbreviated "Cbz".

The term "5- or 6-membered heterocyclic ring" means any 5- or 6-membered ring that will afford a stable structure containing one or two nitrogen atoms; one sulfur atom; one oxygen atom; one nitrogen and one sulfur atom; or one nitrogen and one oxygen atom. The 5-membered ring has one or two double bonds and the 6-membered ring has two or three double bonds. Such heterocyclic systems include furyl, thienyl, pyrrolyl, pyrazolyl, oxazolyl, isoxazolyl, thiazolyl, isothiazolyl, pyranyl, pyridinyl, pyrimidinyl, pyrazinyl, oxazinyl and thiazinyl.

The term "9- or 10-membered heterocyclic ring" means any bicyclic group in which any of the above 5- or 6-membered rings is fused to a benzene ring or another 6-membered heterocyclic ring as defined above that will afford a stable structure. These heterocyclic systems include indolyl, benzothienyl, benzofuryl, benzoxazolyl, benzoisoxazolyl, benzopyrazolyl, quinolinyl, isoquinolinyl, benzimidazolyl and benzothiazolyl.

It will be appreciated that many of the above heterocycles may exist in tautomeric forms. All such forms are included within the scope of this invention.

All of the aromatic or heteroaromatic groups listed for the definition of Ar or R" are independently unsubstituted or substituted with one or two substituents that will afford a stable structure independently selected from halo, hydroxyl, $C_1$–$C_4$ alkyl, $C_1$–$C_4$ alkoxy, amino (—$NH_2$), mono($C_1$–$C_4$ alkyl)amino, —$(CH_2)_j$COOH, mercapto, —S(O)$_h$($C_1$–$C_4$ alkyl), —NHS(O)$_h$($C_1$–$C_4$ alkyl), —NHC(O)($C_1$–$C_4$ alkyl), —S(O)$_h$$NH_2$, —S(O)$_h$NH($C_1$–$C_4$ alkyl), or —S(O)$_h$N($C_1$–$C_4$ alkyl)$_2$, h is 0, 1 or 2, and j is 0, 1, 2, 3, or 4. One particularly preferred such value for the substituent R"(C)O— is 1-methylindol-2-oyl.

In the representation of Formula I, the carbonyl functionality of group X is attached to the amine functionality of the Y group. The carbonyl functionality of Y is then attached to the amino group drawn in Formula I.

The group

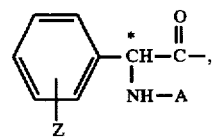

where Z and A are both hydrogen, is referred to at times herein as phenylglycyl and abbreviated Phg. Compounds wherein A is, e.g., methyl, are referred to as the $N^\alpha$-methylphenylglycyl group and abbreviated MePhg. Substituted compounds wherein Z is other than hydrogen are referred to by the type and position of the substituent group, e.g., 3'-chlorophenylglycyl or Phg(3-Cl).

The group

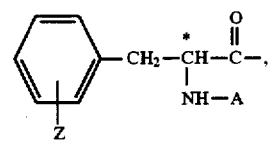

where Z and A are both hydrogen, is referred to at times herein as phenylalanyl and abbreviated Phe. Compounds wherein A is, e.g., methyl, are referred to as the $N^\alpha$-methylphenylalanyl group and abbreviated MePhe. Substituted compounds wherein Z is other than hydrogen are referred to by the type and position of the substituent group, e.g., 3'-chlorophenylalanyl or Phe(3-Cl).

The groups

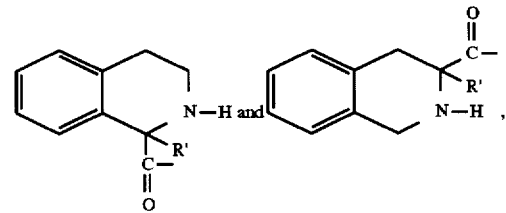

when R' is hydrogen, are referred to at times herein as 1- and 3-tetrahydro-isoquinolinecarbonyl, respectively, and are respectively abbreviated 1-Tiq and 3-Tiq.

The groups

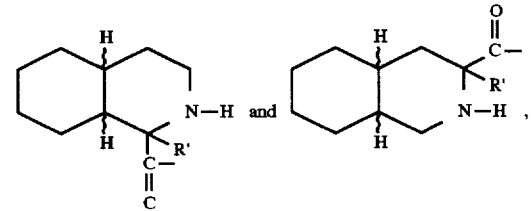

when R' is hydrogen, are referred to at times herein as 1- and 3-perhydro-isoquinolinecarbonyl, respectively, and are respectively abbreviated 1-Piq and 3-Piq. As indicated by the crooked lines, various ring fusion isomers of these substituents exist—this invention contemplates any individual isomer and combinations thereof.

The groups

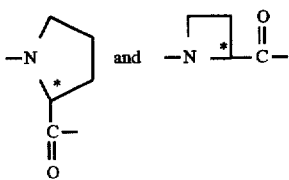

are referred to as prolinyl and azetidine-2-carbonyl, respectively, and are respectively abbreviated Pro and Azt.

The group

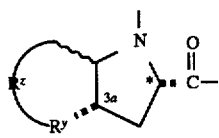

represents a saturated bicyclic system of the 4,5; 5,5; 6,5; 7,5; or 8,5 type. The stereochemistry at 3a is cis to the carbonyl; the other bridgehead bond may be either cis or trans except for the 4,5 and 5,5 systems must be cis at the bridgehead. The definitions of $R^y$ and $R^z$ provide that the variable ring, which includes the three carbon atoms shown, is a saturated carbocyclic system of 4–8 atoms. All of the ring atoms may be carbon, or one of the ring atoms may be a hetero atom selected from —O—, —S—, and —NH—. This definition includes the preferred moiety derived from octahydroindole-2-carboxylic acid, abbreviated "Ohi", as represented by

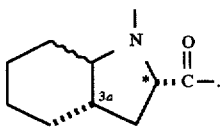

The various cis and trans forms of this moiety are contemplated by this invention.

The asterisks in radical Y denote a chiral center that is (L). The asterisk in radical X denotes a chiral center that is (D) or (DL); the # in radical X denotes a chiral center that is (L).

In addition, diastereomers may exist depending upon branching of alkyl substituents. The compounds of the present invention include mixtures of two or more diastereomers as well as each individual isomer.

Preferred compounds of the present invention include those compounds of Formula I where X is

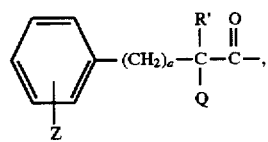

homoprolinyl, 1- or 3-Tiq, or 1- or 3-Piq, and Y is prolinyl, and pharmaceutically acceptable salts and solvates thereof. In particular, compounds wherein Q is NHA and A is hydrogen or a sulfonamide (e.g., A=R"SO$_2$—), R' is hydrogen, Z is hydrogen, and B is hydrogen are all preferred. Also, those compounds wherein R is a guanidino are preferred.

Another group of preferred compounds of the present invention includes those compounds of formula I as defined above where X is

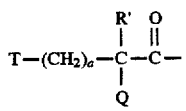

in which T is cyclohexyl, a is 1, R' is hydrogen and Q is —NH—A. One particular subgroup is one in which A is hydrogen. A second particular subgroup is one in which A is R"SO$_2$—, especially when R" is ethyl. A third particular subgroup is one in which A is —(CH$_2$)$_g$—COOH; preferably g is 1.

Particular values of Y for a compound of Formula I in which X, r and G are defined as above include (L)-prolinyl (Pro), (S)-cis-octahydro-1H-indole-2-carbonyl (Ohi) and N-(2-phenylethyl)glycyl [N(PhCH$_2$CH$_2$)Gly].

Specific compounds of Formula I of the invention are described in the Examples. A preferred species, which may be employed as a pharmaceutically acceptable salt or solvate, based upon its unexpectedly superior properties is Example 61.

As mentioned above, the invention includes pharmaceutically acceptable salts of the compounds defined by the above Formula I. A particular compound of this invention can possess one or more sufficiently basic functional groups, and accordingly react with any of a number of inorganic and organic acids, to form a pharmaceutically acceptable salt. Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, napthalene-1-sulfonate, naphthalene-2-sulfonate, mandelate, and the like. Preferred pharmaceutically acceptable acid addition salts are those formed with mineral acids such as hydrochloric acid, hydrobromic acid and sulfuric acid.

The compounds of the present invention are known to form hydrates and solvates with appropriate solvents. Preferred solvents for the preparation of solvate forms include water, alcohols, tetrahydrofuran, DMF, and DMSO. Preferred alcohols are methanol and ethanol. Other appropriate solvents may be selected based on the size of the solvent molecule. Small solvent molecules are preferred to facilitate the corresponding solvate formation. The solvate or hydrate is typically formed in the course of recrystallization or in the course of salt formation. One useful reference concerning solvates is Sykes, Peter, A Guidebook to Mechanism in Organic Chemistry, 6th Ed (1986, John Wiley & Sons, New York). As used herein, the term "solvate" includes hydrate forms, such as monohydrates and dihydrates.

The compounds of Formula I are prepared by known methods of peptide coupling. According to one such method the acid P—X'—COOH, where —X'—C(O)— is —X—, has the same meaning as defined for Formula I, and P is an amino protecting group, if necessary, is coupled with a carboxy protected Y compound to form the dipeptide (a). The carboxy protecting ester group of the Y moiety is then removed (deblocked or de-esterified) and the free acid form of the dipeptide (b) is coupled with the protected reagent (d). The above reaction sequence is illustrated by the following Scheme 1:

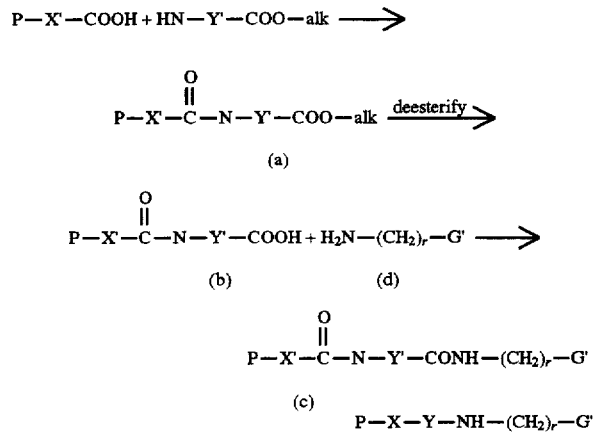

wherein G' is the same as G except R is

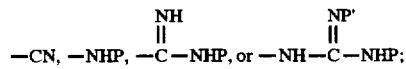

each P represents an amino protecting group, if necessary, P' is H or P, alk is lower alkyl or some similar carboxylic acid protecting group, and —Y'— is the same as Y with the amino and carboxy functionalities visible, i.e., —Y— is the same as —N—Y'—C(O)—.

If present, the cyano group in G' is elaborated to a value of R; and the protecting groups in (c) are then removed by procedures known to those skilled in the art such as hydrogenation over a metal catalyst to provide the compounds of Formula I.

The coupling of a P—X'—COOH compound with HN—Y'—COO-alk is carried out by first protecting the amino group of the amino acid, if any. Conventional amino protecting groups commonly used for temporary protection or blocking of the amino group are employed.

The amino-protecting group refers to substituents of the amino group commonly employed to block or protect the amino functionality while reacting other functional groups on the compound. Examples of such amino-protecting groups include the formyl group, the trityl group, the phthalimido group, the trichloroacetyl group, the chloroacetyl, bromoacetyl and iodoacetyl groups, urethane-type blocking groups such as benzyloxycarbonyl, t-butoxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl) isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl) ethoxycarbonyl, 2-(methylsulfonyl)ethoxycarbonyl, 2-(triphenylphosphino)ethoxycarbonyl, 9-fluoroenylmethoxycarbonyl ("FMOC"), 2-(trimethylsilyl) ethoxycarbonyl, allyloxycarbonyl, 1-(trimethylsilylmethyl) prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy) benzyloxycarbonyl, isobornyloxycarbonyl, 1-piperidyloxycarbonyl and the like; the benzoylmethylsulfonyl group, the 2-(nitro)phenylsulfenyl group, the diphenylphosphine oxide group, and the like amino-protecting groups. The species of amino-protecting group employed is not critical so long as the derivatized amino group is stable to the condition of subsequent reaction(s) on other positions of the molecule and can be removed at the appropriate point without disrupting the remainder of the molecule. Preferred amino-protecting groups are the benzyloxycarbonyl, allyloxycarbonyl, t-butoxycarbonyl, and trityl groups. Similar amino-protecting groups used in the cephalosporin, penicillin and peptide art are also embraced by the above terms. Further examples of groups referred to by the above terms are described by J. W. Barton, "Protective Groups in Organic Chemistry", J. G. W. McOmie, Ed., Plenum Press, New York, N.Y., 1973, Chapter 2, and T. W. Greene, "Protective Groups in Organic Synthesis", John Wiley and Sons, New York, N.Y., 1981, Chapter 7. The related term "protected amino" defines an amino group substituted with an amino-protecting group discussed above.

In carrying out the coupling reaction, an ester protecting group for HN—Y'—COOH is employed which is removable by conditions under which the amino protecting group remains intact. The amino protecting group of the acylating acid P—X'—COOH thus remains in place for protection of the amino group during the subsequent coupling with amine (d) to form (c).

The carboxy protecting ester group as used in the specification refers to one of the ester derivatives of the carboxylic acid group commonly employed to block or protect the carboxylic acid group while reactions are carried out on other functional groups on the compound. Examples of such carboxylic acid protecting groups include $C_1$-$C_4$ alkyl, benzyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, t-butyl, t-amyl, trityl, 4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, β-(trimethylsilyl)ethyl, β-(di(n-butyl)methylsilyl)ethyl, p-toluenesulfonylethyl, 4-nitrobenzylsulfonylethyl, allyl, cinnamyl, 1-(trimethylsilylmethyl)-prop-1-en-3-yl, and like moieties. The species of carboxy-protecting group employed is not critical so long as the derivatized carboxylic acid is stable to the conditions of subsequent reaction(s) on other positions of the molecule and can be removed at the appropriate point without disrupting the remainder of the molecule. In particular, it is important not to subject the carboxy-protected molecule to strong nucleophilic bases or reductive conditions employing highly activated metal catalysts such as Raney nickel. (Such harsh removal conditions are also to be avoided when removing amino-protecting groups discussed below.) Further examples of these groups are found in E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5.

The compounds of Formula I can also be prepared by first synthesizing the HN—Y'—CONH(CH$_2$)$_r$—G' amide precursor and then reacting with a protected X-moiety. According to one such method, (d) is prepared and coupled with PN—Y'—COOH (g) as shown below to afford the amide (h).

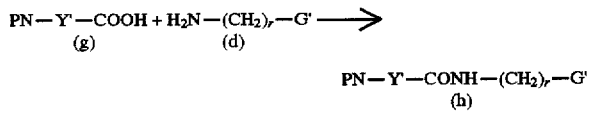

where P represents an amino protecting group such as the benzyloxycarbonyl (Cbz) group, t-butoxycarbonyl (Boc), p-toluenesulfonyl, and the like. Preferably the amino protecting group used is removable by hydrogenation or treatment with mild acid (e.g. trifluoroacetic acid) or a strong acid (e.g. HCl). Examples of other suitable amino protecting groups are provided in "Protective Groups in Organic Synthesis", Second Edition, by T. W. Greene and Peter G. M. Wuts, Chapter 7, page 309–405 (1991), John Wiley & Sons, Inc., publishers. The Boc, or other suitable protecting group, is removed from the amino nitrogen of the Y-residue which is then acylated with the desired amino acid acyl group to afford the dipeptide shown below.

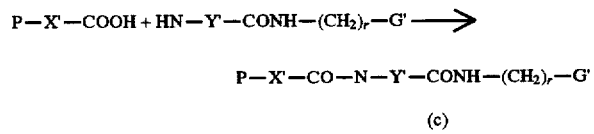

The cyano group, if present in G', is elaborated and protecting groups on (c) are removed as described earlier.

The coupling of a P—X'—COOH compound is carried out by first protecting the amino group of the amino acid, if any. Conventional amino protecting groups commonly used for temporary protection or blocking of the amino group are employed. Examples of such protecting groups are described above.

The coupling reactions described above are carried out in the cold preferably at a temperature between about −20° C. and about 15° C. The coupling reactions are carried out in an inert organic solvent such as dimethylformamide, dimethylacetamide, tetrahydrofuran, methylene chloride, chloroform, and like common solvents or a mixture of such solvents. Generally, anhydrous conditions are used when, in the coupling reaction, an active ester of the acylating acid is used.

The intermediates (d) and (g) are prepared via standard techniques of organic chemistry as summarized in the following schemes:

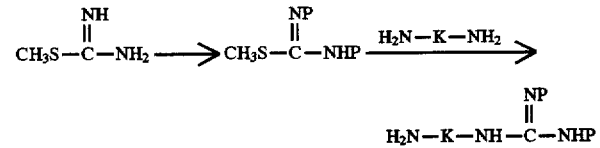

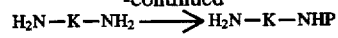

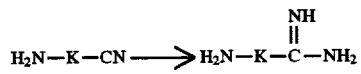

where —K—R is —(CH$_2$)$_r$—G.

According to the above sequences, protected guanidines can be prepared by doubly protecting S-methylisothiourea. A preferred blocking group is the t-butyloxycarbonyl (Boc) group which can be introduced by allowing S-methylisothiourea to react in the presence of di-t-butyl dicarbonate. Often an acid salt form of S-methylisothiourea is employed which can be sprung to the free base form in situ by dissolving the salt in water and treating with aqueous base. The di-t-butyl dicarbonate is then introduced to the reaction in a water miscible solvent, such as t-butanol, to give the doubly protected S-methylisothiourea. The desired doubly protected guanidine is then formed upon treatment with the appropriate diamine H$_2$N—K—NH$_2$ in a non reactive solvent or combination of solvents. Typically water miscible solvents such as dimethylformamide, or water, or mixtures thereof, are effectively employed. Such reaction is generally complete in about 3–72 hours. The resulting protected guanidine can then be coupled as previously described to provide the protected intermediates to the compounds of Formula I wherein R is

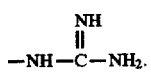

For compounds of Formula I wherein R=—NH$_2$, the intermediate is a singly protected diamine. In most cases this intermediate can be prepared by simply allowing an unprotected diamine to react with one molar equivalent of the protecting reagent. Other methods of introducing the final amine (R=—NH$_2$) will be apparent to organic chemists. For example, the amine may be obtained from some other precursor functionality, e.g., a nitro group or a cyano group.

The amidines of this invention

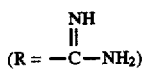

can also be prepared from a nitrile precursor. A number of procedures for accomplishing this transformation are known in the art. In particular, the use of hydrogen sulfide in a mixture of pyridine and triethylamine, followed by treatment with acetone and methyl iodide, and finally ammonium acetate in methanol, is a preferred and efficient means for making this conversion. Alternatively, heating the nitrile with hydroxylamine hydrochloride and a basic such as N,N-diisopropylethylamine in a hydroxylic solvent such as ethanol followed by catalytic hydrogenation (e.g., hydrogenolysis over palladium on carbon) can also be used to effect this transformation. This process provides the hydroxy amidine

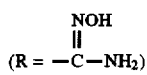

(R = —C(=NOH)—NH₂)

as an intermediate which can be isolated if desired.

The other compounds employed as initial starting materials in the synthesis of the compounds of this invention are well known and, to the extent not commercially available, are readily synthesized by standard procedures commonly employed by those of ordinary skill in the art.

The 4-substituted prolines ($R^P$ is $C_1$-$C_6$ alkyl, $C_3$-$C_8$ cycloalkyl, or —$(CH_2)_p$—L—$(CH_2)_q$—T') used for making the compounds this invention are all of the cis configuration the 4-substituent relative to the carbonyl moiety. Intermediates for introducing this functionality into the compounds of Formula I are made by standard techniques.

For example, 4-substituted proline derivatives in which the $R^P$ group contains a methylene group at the point of attachment to the proline ring can be prepared in the following manner:

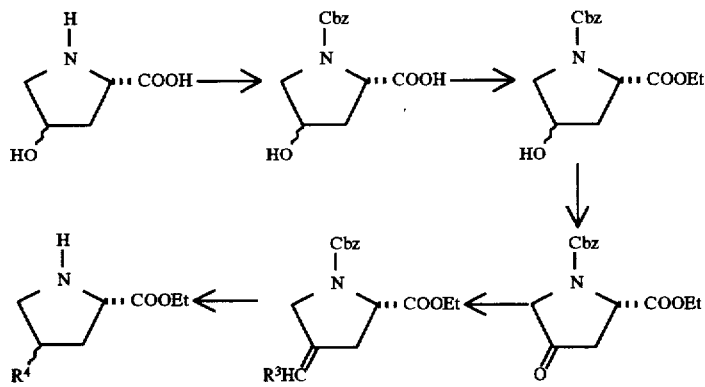

where $R^4$=$R^3CH_2$=an $R^P$ group containing a methylene group at the point of attachment to the proline ring.

A 4-hydroxyproline (both the cis and trans forms are commercially available) is first protected with an amino-protecting group—the Cbz group is particularly useful in this sequence. The resulting intermediate is then esterified (the methyl or especially ethyl esters are especially convenient) and then oxidized to give the corresponding ketone. This oxidation us accomplished under any of a number of oxidation conditions such as Jones oxidation or pyridinium chlorochromate; especially useful for this transformation is the use of pyridinium chlorochromate in a dry, non-reactive solvent such as dichloromethane. When allowed to react for 8–16 hours, this reaction is generally complete when performed at ambient temperature. This versatile ketone intermediate is then allowed to react with an appropriate Wittig reagent to give the desired olefin. Typically the appropriate $R^P$-substituted triphenylphosphonium halide is added to a dry inert solvent (e.g., tetrahydrofuran) which contains a strong base (e.g., potassium t-butoxide). The ketone is introduced and after approximately three hours at ambient temperature the desired olefin intermediate can be isolated. In order to obtain good yields of the olefin, it is preferred that a 0.4–0.6 molar excess of the Wittig reagent be employed relative to the ketone. The olefin is then reduced to the desired $R^P$-substituted proline by standard reduction techniques. Catalytic hydrogenation is the most facile method for accomplishing this transformation in the laboratory. Hydrogenation of the olefin in the presence of a catalyst (e.g., 5% palladium on carbon) in an inert solvent such as ethanol will be effective at atmospheric pressure. In the case of those intermediates in which the amino-protecting group is Cbz, hydrogenation also removes the protecting group which provides a compound which can be used for coupling to P—X'—COOH. As will be appreciated by those skilled in this art, this process will not be effective for preparing compounds where the $R^P$ group is attached to the proline ring through a hetero atom or are an aromatic ring. Thus, in the above scheme, $R^3$ will be alkyl, aralkyl (e.g., benzyl), (cycloalkyl)alkyl, etc.

A related method for preparing these intermediates is summarized by the following scheme:

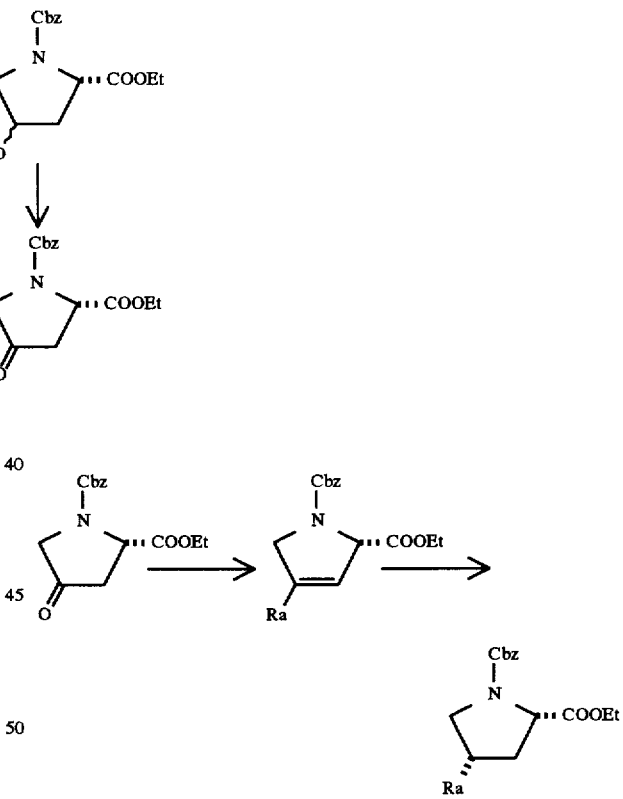

The above reaction scheme is an alternative to the Wittig reaction described earlier and is useful for preparing compounds for which Wittig reagents cannot be prepared. Thus, for preparing intermediates wherein Ra is alkyl, phenyl, and the like, the pyrrolidinone intermediate is allowed to react with an appropriate Grignard reagent. Typically a slight molar excess of the Grignard reagent is employed, usually at low temperatures (e.g., −80° to −60° C.) in a low freezing inert solvent such as tetrahydrofuran. After addition of the reagents, the reaction mixture can be permitted to warm to room temperature, after which time the reaction is usually complete within several hours. The resulting intermediate is dehydrated, for example, by treatment with trifluoroacetic acid. The 3,4-dehydro intermediate is then reduced to the desired cis intermediate using the same reductive conditions as described above for reduction of the olefin intermediate.

Intermediates wherein the hetero "L"-group is oxygen and is attached directly to the proline ring (i.e., p=0) can be prepared employing the Mitsunobu reaction (Mitsunobu, *Synthesis*, 1 (1981)):

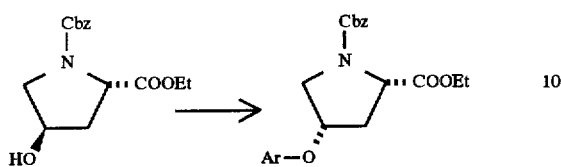

In this reaction, the trans hydroxypyrrolidinecarboxylic ester is treated with triphenylphosphine in a solvent such as tetrahydrofuran in the presence of Ar—O—H. The mixture is cooled to approximately 0° C. and diethyl azodicarboxylate is added. After warming to room temperature, the reaction is worked up to provide the desired cis intermediate.

While the scheme above depicts the reaction for compounds where L=—O—, p=q=0, and T=Ar, this sequence is useful for preparing other compounds where p=0 and L is —O—.

Intermediates wherein L is sulfur and is attached directly to the ring can be prepared by first converting the hydroxy group to a tosylate or other similar leaving group and then displacing with a thiolate anion (see, e.g., Krapcho, et al., *J. Med. Chem.*, 31, 1148–1160 (1988); Smith, et al., *J. Med. Chem.*, 31, 875–855 (1988)).

Intermediates wherein L is nitrogen and is attached directly to the ring can be prepared by first converting the hydroxy group to a tosylate or other similar leaving group and then displacing with azide. The azide can be reduced using known methods and then alkylated to provide the desired functionality (see, e.g., Smith, et al., *J. Med. Chem.*, 31, 875–855 (1988)).

The compounds of this invention containing a cis-Ohi functionality are prepared by preparing (S)-indoline carboxylic acid ethyl ester from the corresponding acid (see, Vincent, et al., *Drug Design and Discovery*, Vol. 9, pp 11–28 (1992)), and reducing this intermediate by hydrogenation over 5% Pd/C in ethanol to give the octahydroindole-2-carboxylic acid ester, generally referred to Ohi-ester as summarized below.

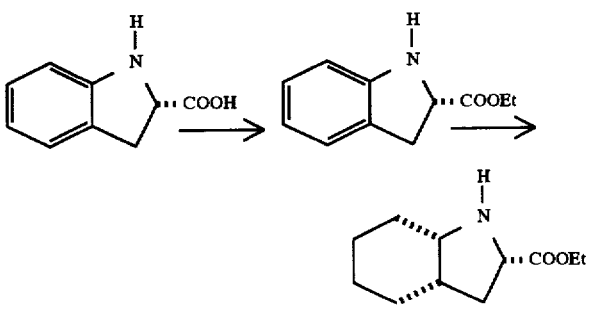

The compounds of this invention containing a trans-Ohi functionality are prepared by the method of Vincent, et al., *Drug Design and Discovery*, Vol. 9, pp 11–28 (1992)). This is summarized in the scheme shown below:

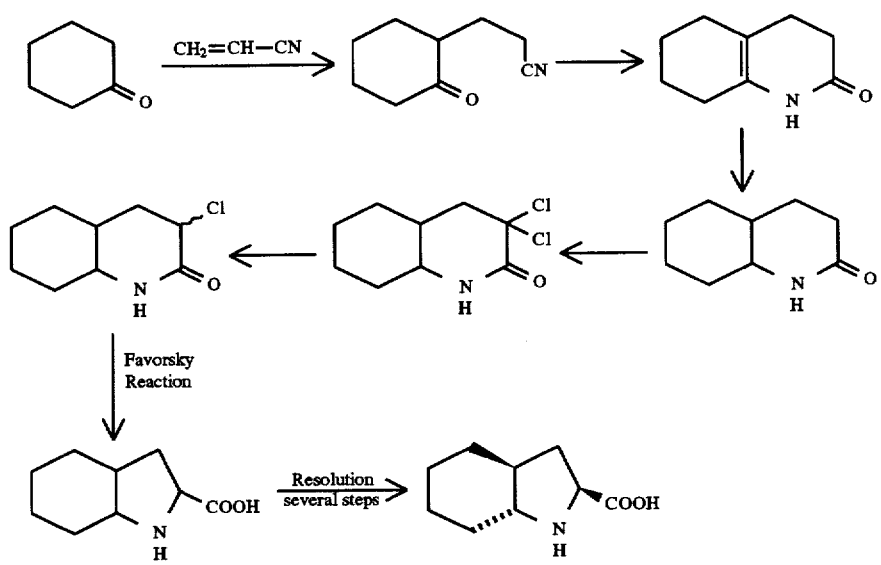

The compound of this invention containing a bicyclic system (with or without heteroatom) can be prepared by the method of Teetz, et al., *Tetrahedron Letters*, 25, 4479 (1984). Generally:

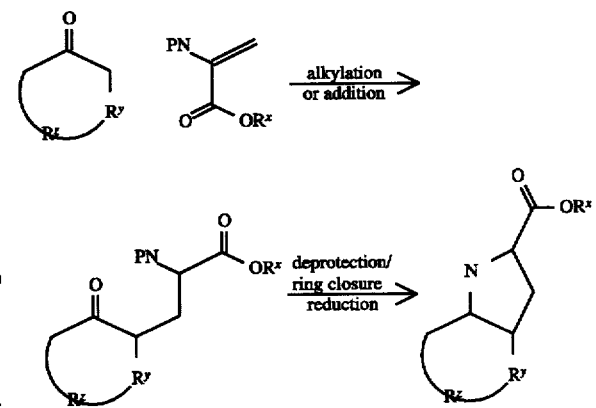

where P is a protecting group and $R^x$ is alkyl.

The intermediates for introducing the N-substituted glycine functionality (Y) used for making the compounds this invention are made by standard techniques.

For example, a haloacetate ester, such as t-butyl bromoacetate, can be converted into the desired substituted upon treatment with the appropriate primary amine:

BrCH₂COO-t-butyl+R^sNH₂→HNR^sCH₂COO-t-butyl

The t-butyl bromoacetate is allowed to react with the appropriate amine either neat or preferably in a non-reactive solvent, such as an alcohol. It is preferred that a molar excess of the amine is used to force the reaction to completion. Preferably the reaction mixture also contains a non-reactive acid scavenger, such as at least a molar equivalent of triethylamine. While the reactants are usually combined cooled (e.g., 0° C.), the reaction is usually allowed to warm to room temperature after which the reaction is usually complete within 24 hours. Although the bromoacetate is preferred, other haloacetates, such as iodoacetates and chloroacetates, can be employed for this transformation. Other ester groups can similarly be employed. The t-butyl ester is preferred because it can later be easily removed later upon treatment with anisole and trifluoroacetic acid.

A second method for preparing these intermediates is summarized by the following scheme:

R°—CHO+H₂NCH₂COOEt→R°—CH=NCH₂COOEt→R°—CH₂—NHCH₂COOEt where R°—CH₂— is an R^s-group having an unsubstituted methylene group adjacent to the point of attachment to the glycine moiety.

In the above reaction scheme, the appropriate aldehyde is mixed with glycine ester in a non-reactive solvent, such as methanol or ethanol. If a salt form of the glycine ester is used, a molar equivalent of a base, such as potassium hydroxide, can be added to allow generation of the free base of the aminoester. The reaction of the aldehyde and glycine ester formed the intermediate Schiff base which can then be reduced in situ upon treatment with a reducing agent such as sodium cyanoborohydride. Formation of the Schiff base occurs in usually less than an hour; reduction is generally complete after 10-15 hours. The methyl or ethyl esters are particularly useful as these groups can be removed (deblocked) upon treatment with lithium hydroxide in aqueous dioxane. Employing an appropriate ketone instead of aldehyde R°—CHO results in the preparation of intermediates wherein the methylene group attached to the glycine amine is substituted.

Alternatively, and especially for those compounds wherein R^s is Ar (i.e., without an intervening alkyl group), it is preferred to prepare the intermediate P—X'—CONHAr by standard techniques (e.g., reacting an activated form of P—X'—COOH with ArNH₂) and then reacting this intermediate with an alkyl haloacetate as described above to give P—X'—CONHAr—CH₂—COO-alk which can then be further transformed in the usual way.

Many of the final compounds of this invention or intermediates thereto can be interconverted by standard techniques. For example, aryl compounds which are substituted with nitro can be reduced (e.g., in the presence of sodium hydrosulfite in a non-reactive solvent, such as ethanol, water, or a mixture thereof). When the nitro compound is heated at reflux in a water/ethanol mixture in the presence of sodium hydrosulfite, reduction is usually complete within several hours. The resulting amine may be present in the final product; if the amine is present in an intermediate, it may be desirable to convert it to its final desired form (e.g., acylation to provide the acylated amine) or protected to avoid side reactions during the subsequent chemistry. If the free amine is the desired compound, the Cbz protecting group is particularly useful in this regard. Other transformations and intraconversions of this type will be apparent to skilled organic chemists.

As will be appreciated by those skilled in this art, the above transformations can be performed on the starting materials noted above, or in most cases can also be accomplished on di- or tri-peptide intermediates containing the same respective functional group. In the latter cases, the need, or lack thereof, to protect the various groups may be negated; accordingly, the order and type of chemistry involved will dictate the need and type of protecting groups as well as the sequence for accomplishing the synthesis. As will also be appreciated by skilled artisans, one may choose other protecting groups so long as they serve the purpose of protecting the functional group during subsequent chemistry but can also be removed under appropriate conditions and in an appropriate order to allow for subsequent transformations. For example, in Scheme 1 above G' includes substituents wherein R is —CN; this nitrile group can be transformed into an amidine or reduced to the amine which can optionally be further elaborated to the guanidines of this invention.

The compounds of the invention are isolated best in the form of acid addition salts. Salts of the compounds of Formula I formed with acids such as those mentioned above are useful as pharmaceutically acceptable salts for administration of the antithrombotic agents and for preparation of formulations of these agents. Other acid addition salts may be prepared and used in the isolation and purification of the peptides. For example, the salts formed with the sulfonic acids such as methanesulfonic acid, n-butanesulfonic acid, p-toluenesulfonic acid and naphthalenesulfonic acid may be so used.

A compound of Formula I is prepared by:
a) removing simultaneously or sequentially the protecting group(s) P of a corresponding compound of Formula II (P)X—Y—NH—(CH₂)ᵣ—G P)  II wherein (P)X represents a radical X which may bear one or more protecting groups P independently selected from an amino protecting group P for a compound of Formula I in which X includes a basic NH moiety and a carboxy protecting group P for a compound of Formula I in which X includes a carboxy residue and G(P) represents a radical G which may bear one or more independently selected amino protecting groups P; or b) for a compound of Formula I in which R is $$\begin{matrix} \text{NH} \\ \parallel \\ -\text{C}-\text{NH}_2, \end{matrix}$$

by hydrogenolysis of a corresponding compound of Formula I in which R is $$\begin{matrix} \text{NOH} \\ \parallel \\ -\text{C}-\text{NH}_2; \end{matrix}$$

and whereafter, when a salt of the compound of Formula I is required, forming the salt with a pharmaceutically acceptable acid.

It may be preferred to conduct process b) simultaneously with process a). For a compound of Formula I in which an acid protecting group is the t-butyl ester and/or an amino protecting groups is t-butyloxycarbonyl, the protecting group(s) may be removed by treatment with a strong acid, such as trifluoroacetic acid or anhydrous hydrogen chloride in an inert solvent, such as dioxane or dichloromethane, in the presence of anisole. For a compound of Formula I in which an acid protecting group is the benzyl ester and/or an amino protecting group is benzyloxycarbonyl, the protecting group(s) may be removed by hydrogenolysis, conveniently carried out in ethanolic hydrogen chloride over a palladium on carbon catalyst.

The preferred method for purifying the compounds of Formula I, while at the same time preparing a desired stable salt form, is that described in U.S. Pat. No. 5,250,660. According to the method, stable sulfates or hydrochlorides are provided by preparative purification over $C_{18}$ reversed-phase chromatography in which the aqueous component comprises sulfuric acid or hydrochloric acid at pH 2.5 and acetonitrile is the organic component. The pH of the acidic eluant is adjusted to between about pH 4 and about 6 with an anion exchange resin in the hydroxyl form, e.g. Bio-Rad AG-1X8. After adjustment of the pH, the solution of tripeptide sulfate or hydrochloride salt is lyophilized to provide the pure salt in dry powder form. In an example of the process, crude D-Phe-Pro-p-NHCH$_2$C$_6$H$_4$C(NH)NH$_2$ sulfate can be dissolved in water and the solution is loaded on Vydac $C_{18}$ RP HPLC 5 cm×50 cm column. A gradient of 2–10% B (A=0.01% H$_2$SO$_4$; B=acetonitrile) over 10 hours is used. Multiple fractions are collected and those containing product as determined by analytical R$^P$ HPLC are pooled. The pH of the pooled fractions is adjusted to pH 4.0–4.5 with AG-1X8 resin in hydroxide form (Bio-Rad, 3300 Ragatta Blvd., Richmond, Calif. 94804). The solution is filtered and the filtrate is lyophilized to provide the pure D-,L- diamide in the form of the sulfate salt.

The optically active isomers of the diastereomers at the radical X are also considered part of this invention. Such optically active isomers may be prepared from their respective optically active precursors by the procedures described above, or by resolving the racemic mixtures. This resolution can be carried out by derivatization with a chiral reagent followed by chromatography or by repeated crystallization. Removal of the chiral auxiliary by standard methods affords substantially optically pure isomers of the compounds of the present invention or their precursors. Further details regarding resolutions can be obtained in Jacques, et al., *Enantiomers, Racemates, and Resolutions*, John Wiley & Sons, 1981.

The compounds employed as initial starting materials in the synthesis of the compounds of this invention are well known and, to the extent not commercially available, are readily synthesized by standard procedures commonly employed by those of ordinary skill in the art.

The following Examples are provided to further describe and support the invention and to provide examples for comparison and are not to be construed as limitations thereof.

The abbreviations used in this specification have the following meanings.

Amino acid residues: Arg=arginyl, Glu=glutamyl, Gly= glycyl, Pro=prolyl, hPro=homoprolyl, Azt=azetidine-2-carbonyl, Phg=phenylglycyl, Phe=phenylalanyl, hPhe= homophenylalanyl, 1-Tiq=1,2,3,4-tetrahydroisoquinoline-1-carbonyl, 3-Tiq=1,2,3,4-tetrahydroisoquinoline-3-carbonyl, Cha=β-cyclohexylalanyl, hCha=α-amino-γ-cyclohexylbutyryl, NMI=N-methylindol-2-oyl, Ohi=cis-octahydroindol-2-oyl, 1-Piq=perhydro-isoquinoline-1-carbonyl, 3-Piq=perhydro-isoquinoline-3-carbonyl, Met= methionyl, Met(O$_2$)=S,S-dioxomethionyl.

Agm=agmatine
Boc=t-butyloxycarbonyl
Bn=benzyl
Cbz=benzyloxycarbonyl
DCC=dicyclohexylcarbodiimide
DMF=dimethylformamide
Et=ethyl
DMSO=dimethylsulfoxide
EtOAc=ethyl acetate
Et$_2$O=diethyl ether
EtOH=ethanol
Fmoc=9-fluorenylmethoxycarbonyl
FAB-MS=fast atom bombardment mass spectrum
FD-MS=field desorption mass spectrum
IS-MS=ion spray mass spectrum
HRMS=high resolution mass spectrum
HOBT=1-hydroxybenzotriazole hydrate
IR=infrared spectrum
RPHPLC=Reversed Phase High Performance Liquid Chromatography
Ph=phenyl
TFA=trifluoroacetic acid
THF=tetrahydrofuran
TLC=thin layer chromatography The following parameters for RPHPLC were employed: Solvent A: 0.05% aqueous hydrochloric acid (1.5 mL concentrated hydrochloric acid in 3 L water); Solvent B: acetonitrile; Gradient: as defined in each Example; Method 1: Column: Vydac $C_{18}$-2.5 cm×25 cm; Flow rate: 5 mL/minute; Method 2: Column: Vydac $C_{18}$-5 cm×25 cm; Flow rate: 10 mL/minute; Method 3: Column: Vydac $C_{18}$-2.5 cm×50 cm; Flow rate: 10 mL/minute.

Unless otherwise stated, pH adjustments and work up are with aqueous acid or base solutions.

In the examples, where $^1$H-NMR is shown, the product afforded by the reaction was characterized by proton NMR to confirm the indicated compound was obtained; IR without the data similarly indicates a satisfactory infrared spectrum was obtained. HRMS was used to confirm the exact mass of compounds for which a satisfactory elemental analysis was not obtained for the product of the described procedure; the elemental composition of the observed ion (e.g., MH$^+$) is indicated.

EXAMPLE 1

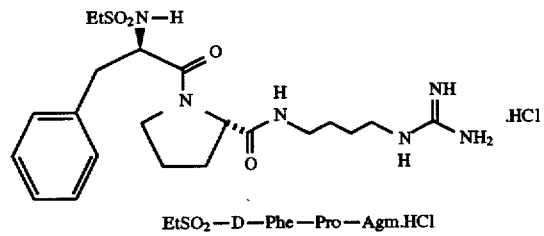

EtSO$_2$—D—Phe—Pro—Agm.HCl

A) Preparation of Boc-D-Phe-Pro-OBn

To a solution of Boc-D-Phe-OH (89.1 g, 336 mmol), Pro-OBn hydrochloride (81.2 g, 336 mmol), HOBT (50 g, 370 mmol) and N,N-diisopropylethylamine (176 mL, 1,008 mmol) at 0° C. in dichloromethane (600 mL) was added

23

1-(3-dimethylaminopropyl)-3-ethylcarbodiimide hydrochloride (71 g, 370 mmol). After stirring for 18 hours, the mixture was diluted with diethyl ether (1 L) and washed sequentially three times with 1N citric acid (250 mL), once with water (250 mL), three times with saturated aqueous sodium bicarbonate (250 mL) and once with saturated aqueous sodium chloride (250 mL). The organic phase was dried ($Na_2SO_4$), filtered, and concentrated in vacuo to yield 140 g (92.5%) of a pale yellow foam.

FD-MS, m/e 452 ($M^+$)

$^1$H NMR

B) Preparation of D-Phe-Pro-OBn.TFA

To a stirring solution of Boc-D-Phe-Pro-OBn (68 g, 150 mmol) in dichloromethane (50 mL) at 0° C., was added anisole (20 mL) followed by trifluoroacetic acid (400 mL). After stirring for 3 hours, the solvents were evaporated in vacuo and the thick oily residue was dissolved in diethyl ether (1.5 L) and refrigerated (72 hours). The white precipitate was filtered, washed with diethyl ether (300 mL) and dried to yield 59.4 g (85%) of white powder.

$^1$H NMR

C) Preparation of $EtSO_2$-D-Phe-Pro-OBn

To a stirring solution of D-Phe-Pro-OBn.TFA (12 g, 25.7 mmol) and triethylamine (7 mL, 50.2 mmol) in dichloromethane (200 mL) at −78° C. was added ethanesulfonyl chloride (2.65 mL, 28.3 mmol) dropwise via an addition funnel. The reaction vessel was warmed to 0° C. and after stirring 4 hours, water (10 mL) was added. The organic phase was washed three times with 1N hydrochloric acid (100 mL), once with a saturated sodium chloride solution (100 mL) and then the solvent was removed in vacuo. The product was purified by flash chromatography over silica gel, eluting with ethyl acetate/hexanes (6:4). The product containing fractions (judged by TLC) were combined and concentrated to give 6.62 g (58%) of a yellow oil which solidified.

$^1$H NMR

FD-MS, m/e 445 ($M^+$)

Analysis for $C_{23}H_{28}N_2O_5S$: Calc: C, 62.14; H, 6.35; N,6.30; Found: C, 61.87; H, 6.37; N 6.18.

D) Preparation of $EtSO_2$-D-Phe-Pro-OH

To a stirring solution of $EtSO_2$-D-Phe-Pro-OBn (4.5 g, 10.1 mmol) in p-dioxane (150 mL) was added a solution of lithium hydroxide monohydrate (2.1 g, 50.5 mmol) in water (75 mL). After stirring for 16 hours, the volume of the solution was reduced by half in vacuo, and the solution was diluted with water (300 mL) and 0.1N NaOH (100 mL). The aqueous phase was then washed twice with diethyl ether (250 mL), acidified with solid citric acid, and then extracted three times with ethyl acetate (150 mL). The combined ethyl acetate extracts were washed with saturated aqueous sodium chloride (200 mL), dried ($MgSO_4$), filtered and concentrated to give 3.6 g (90%) of white solid.

FD-MS, m/e 355 ($M^+$)

Analysis for $C_{16}H_{22}N_2O_5S$: Calc: C, 54.22; H, 6.26; N, 7.90; Found: C, 54.40; H, 6.42; N, 7.85.

E) Preparation of N,N'-di-Boc-S-methylisothiourea

To a stirring solution of di-t-butyl dicarbonate (100 g, 458 mmol) in t-butanol (300 mL) was added a solution of bis-S-methylisothiourea sulfate (32.7 g, 117 mmol) in water (150 mL), followed by a solution of sodium hydroxide (19.2 g, 480 mmol) in water (150 mL). After stirring for 48 hours, the mixture was concentrated to approximately one-third of the original volume in vacuo and diluted with diethyl ether (500 mL). The organic phase was washed once with water (250 mL), three times with 1N citric acid (250 mL) and once again with water (250 mL). The organic phase was then dried ($MgSO_4$), filtered and concentrated in vacuo to give 42 g (62%) of a white solid.

$^1$H NMR

F) Preparation of $N^g,N^{g'}$-di-Boc-agmatine

To a stirring solution of 1,4-butanediamine (23 g, 258 mmol) in 2:1 dimethylformamide:water (300 mL) was added a solution of N,N'-di-Boc-S-methylisothiourea (15 g, 52 mmol) in dimethylformamide (100 mL) via an addition funnel. After stirring for 2 hours, the solvents were removed in vacuo and the residue was dissolved in 1N citric acid (250 mL), diluted with water (250 mL) and washed with ethyl acetate (250 mL). The ethyl acetate phase was back extracted with 1N citric acid (100 mL) and the combined aqueous phases were basified with sodium carbonate, saturated with solid sodium chloride, and extracted twice with ethyl acetate (250 mL). The combined ethyl acetate extracts were washed with saturated aqueous sodium chloride (200 mL), dried ($MgSO_4$), filtered and concentrated to give 12.5 g (73%) of a thick syrup.

$^1$H NMR

G) Preparation of $EtSO_2$-D-Phe-Pro-Agm($Boc$)$_2$

To a stirring solution of $N^g,N^{g'}$-di-Boc-agmatine (2 g, 6 mmol) in dichloromethane (30 mL) was added $EtSO_2$-D-Phe-Pro-OH (2.1 g, 6 mmol), HOBT (810 mg, 6 mmol) and N,N-diisopropylethylamine (1.6 g, 12 mmol), followed by 1-(3-dimethylaminopropyl)-3-ethylcarbodiimide hydrochloride (1.4 g, 73 mmol). After stirring for 20 hours, the solution was diluted with ethyl acetate (300 mL) and washed three times with 1N citric acid (150 mL), once with water (150 mL), and twice with saturated aqueous sodium bicarbonate. The organic phase was then dried ($MgSO_4$), filtered and concentrated in vacuo. The residue was chromatographed over silica gel, eluting with a step gradient of ethyl acetate:hexanes (1:4) through ethyl acetate. The product containing fractions (based on TLC) were combined and concentrated to give 2.4 g (60%) of a thick oil.

$^1$H NMR

FD-MS, m/e 668 ($MH^+$)

H) Preparation of $EtSO_2$-D-Phe-Pro-Agm.HCl

A stirring suspension of $EtSO_2$-D-Phe-Pro-Agm($Boc$)$_2$ (1.6 g, 2.4 mmol) in anisole (1 mL) was dissolved in trifluoroacetic acid (20 mL) and allowed to stir for 1 hour at room temperature. The solvent was then removed in vacuo and the residue was partitioned between water (100 mL) and diethyl ether (50 mL). The aqueous phase was washed again with diethyl ether (50 mL) and then partially concentrated and lyophilized to yield 1.4 g of crude trifluoroacetate salt. Half of this material was then dissolved in water and purified by RPHPLC (method 1; 98/2 (A/B); ramp to 50/50 (A/B), 60 minutes) to give 490 mg (81%) of white powder.

1H NMR

FD-MS, m/e 467 ($M^+$)

Analysis for $C_{21}H_{34}N_6O_4S.HCl.H_2O$: Calc: C, 48.41; H, 7.16; N, 16.13; Cl, 6.80; Found: C, 48.01; H, 6.81; N, 16.15; Cl, 6.97.

EXAMPLE 2

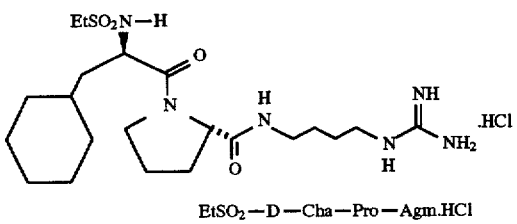

EtSO$_2$—D—Cha—Pro—Agm.HCl

A) Preparation of Boc-D-Cha-Pro-OBn

By a method substantially equivalent to that described in Example 1-A, Boc-D-Cha-Pro-OBn was prepared from Boc-D-Cha-OH and Pro-OBn.HCl in 91% yield (109 g).

FD-MS, m/e 458 (M$^+$)

B) Preparation of D-Cha-Pro-OBn.TFA

By a method substantially equivalent to that described in Example 1-B, D-Cha-Pro-OBn.TFA was prepared (116% of theoretical yield, 130 g).

$^1$H NMR

FD-MS, m/e 359 (M$^+$)

C) Preparation of EtSO$_2$-D-Cha-Pro-OBn

By a method substantially equivalent to that described in Example 1-C, EtSO$_2$-D-Cha-Pro-OBn was prepared (20% yield, 2.3 g).

$^1$H NMR

FD-MS, m/e 450 (M$^+$)

Analysis for C$_{23}$H$_{34}$N$_2$O$_5$S: Calc: C, 61.31; H, 7.61; N, 6.22; Found: C, 61.55; H, 7.59; N, 6.28.

D) Preparation of EtSO$_2$-D-Cha-Pro-OH

By a method substantially equivalent to that described in Example 1-D, EtSO$_2$-D-Cha-Pro-OH was prepared (48% yield, 0.78 g).

$^1$H NMR

FD-MS, m/e 361 (M$^+$)

E) Preparation of EtSO$_2$-D-Cha-Pro-Agm(Boc)$_2$

By a method substantially equivalent to that described in Example 1-G, 400 mg (40%) of EtSO$_2$-D-Cha-Pro-Agm(Boc)$_2$ were prepared from EtSO$_2$-D-Cha-Pro-OH and N$^g$-N$^{g'}$-di-Boc-Agm.

$^1$H NMR

FD-MS, m/e 674 (MH$^+$)

F) Preparation of EtSO$_2$-D-Cha-Pro-Agm.HCl

By a method substantially equivalent to that described in Example 1-H, EtSO$_2$-D-Cha-Pro-Agm.HCl was prepared (45% yield, 100 mg). The product was purified by RPHPLC (method 1, 98/2 (A/B), ramp to 50/50 (A/B), 60 minutes).

$^1$H NMR

FD-MS, m/e 473 (M$^+$)

Analysis for C$_{21}$H$_{40}$N$_6$O$_4$S.1.2HCl.H$_2$O: Calc: C, 47.20; H, 8.15; N, 15.73; Cl, 7.96; Found: C, 47.47; H, 7.84; N, 16.10; Cl, 7.80.

EXAMPLE 3

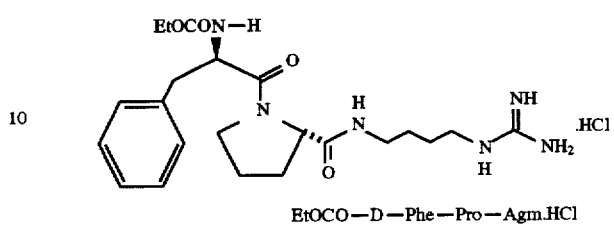

EtOCO—D—Phe—Pro—Agm.HCl

A) Preparation of EtOCO-D-Phe-Pro-OH

By methods substantially equivalent to those described in Examples 1-C and 1-D using ethyl chloroformate in place of ethanesulfonyl chloride, 6.59 g (92%) of EtOCO-D-Phe-Pro-OH were prepared.

$^1$H NMR

FD-MS, m/e 335 (M$^+$)

Analysis for C$_{17}$H$_{22}$N$_2$O$_5$: Calc: C, 61.07; H, 6.63; N, 8.38; Found: C, 60.88; H, 6.72; N, 8.14.

B) Preparation of EtOCO-D-Phe-Pro-Agm.HCl

By a method substantially equivalent to that described in Example 1-G, 2.1 g (54%) of EtOCO-D-Phe-Pro-Agm(Boc)$_2$ were prepared from EtOCO-D-Phe-Pro-OH and N$^g$-N$^{g'}$-di-Boc-Agm. Then by a method substantially equivalent to that described in Example 1-H, 390 mg (77%) of EtOCO-D-Phe-Pro-Agm.HCl were prepared. The product was purified by RPHPLC (method 1, 98/2 (A/B), ramp to 50/50 (A/B), 60 minutes).

$^1$H NMR

FD-MS, m/e 447 (M$^+$)

Analysis for C$_{22}$H$_{34}$N$_6$O$_4$.0.9HCl.0.2TFA.H$_2$O: Calc: C, 51.70; H, 7.22; N, 16.15; Cl, 6.13; Found: C, 51.73; H, 7.20; N, 16.54; Cl, 6.36.

EXAMPLE 4

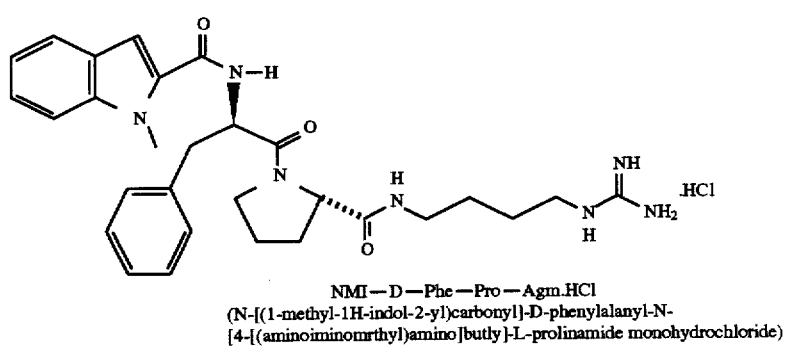

NMI—D—Phe—Pro—Agm.HCl
(N-[(1-methyl-1H-indol-2-yl)carbonyl]-D-phenylalanyl-N-[4-[(aminoiminomrthyl)amino]butly]-L-prolinamide monohydrochloride)

A) Preparation of NMI-D-Phe-Pro-OH

To a solution of N-methylindole-2-carboxylic acid (2.6 g, 14.9 mmol) in dry tetrahydrofuran (45 mL) was added pentafluorophenol (3 g, 16.5 mmol), followed by 1-(3-dimethylaminopropyl)-3-ethylcarbodiimide (3.2 g, 16.5 mmol). The mixture was allowed to stir at reflux for 3.5 hours and then cooled to room temperature. To this mixture was added a solution of D-Phe-Pro-OBn. TFA (7 g, 14.9 mmol) and N,N-diisopropylethylamine (4 g, 30 mmol) in tetrahydrofuran (25 mL). After stirring for an additional 2 hours, the solvents were removed in vacuo and the residue was dissolved in ethyl acetate (500 mL), then washed three times with 0.1N aqueous sodium bisulfate (250 mL) and three times with 1N aqueous potassium carbonate (250 mL). The organic phase was dried ($Na_2SO_4$), filtered, and concentrated in vacuo to give 6.5 g of amorphous solid (a mixture of the desired product, contaminated with pentafluorophenol). This crude product was then hydrolyzed by a method substantially equivalent to that described in Example 1-D to yield 3.8 g (62%) of an off white solid.

$^1$H NMR
FD-MS, m/e 419 ($M^+$)

B) Preparation of NMI-D-Phe-Pro-Agm.HCl

By a method substantially equivalent to that described in Example 1-G, 900 mg (20%) of NMI-D-Phe-Pro-Agm $(Boc)_2$ were prepared. Then, by a method substantially equivalent to that described in Example 1-H, 144 mg (31%) of NMI-D-Phe-Pro-Agm.HCl were prepared. The crude product was dissolved in glacial acetic acid and purified by RPHPLC (method 1, 90/10 (A/B), ramp to 40/60 (A/B), 80 minutes).

$^1$H NMR
FD-MS, m/e 532 ($M^+$)

Analysis for $C_{25}H_{37}N_7O_3 \cdot 0.9HCl \cdot 0.6TFA \cdot 0.5H_2O$: Calc: C, 56.46; H, 6.29; N, 15.27; Cl, 4.97; Found: C, 56.77; H, 6.58; N, 15.35; Cl, 5.28.

EXAMPLE 5

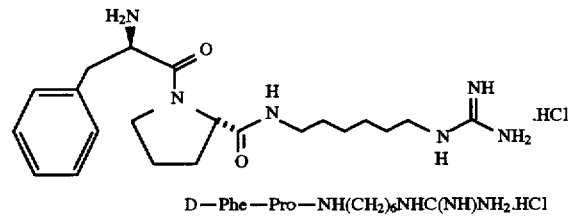

D—Phe—Pro—NH(CH$_2$)$_6$NHC(NH)NH$_2$.HCl

A) Preparation of Boc-D-Phe-Pro-OH

To a solution of Boc-D-Phe-Pro-OBn (145 g, 320 mmol) in p-dioxane (660 mL) was added a solution of lithium hydroxide monohydrate (54 g, 1,280 mmol) in water (330 mL) with vigorous stirring. After 4 hours, the solution was concentrated in vacuo to about one-fourth the original volume and diluted with water (350 mL) and 0.1N sodium hydroxide (100 mL). The aqueous phase was washed three times with diethyl ether (250 mL) and then acidified to pH 3 with solid citric acid which caused a precipitate to form. The solid was filtered, washed twice with water, and then dried under high vacuum, to yield 91 g (78%) of a white solid.

$^1$H NMR
FD MS, m/e 363 ($M^+$)

B) Preparation of $N^g,N^{g'}$-di-Boc-6-aminohexylguanidine

By a method substantially equivalent to that described in Example 1-F, 4.7 g (66%) of $N^g,N^{g'}$-di-Boc-6-aminohexylguanidine were prepared from 1,6-hexanediamine.

C) Preparation of Boc-D-Phe-Pro-NH(CH$_2$)$_6$NHC(NBoc)NH(Boc)

By a method substantially equivalent to that described in Example 1-G, 1.3 g (62%) of Boc-D-Phe-Pro-NH(CH$_2$)$_6$NHC(NBoc)NH(Boc) were prepared from Boc-D-Phe-Pro-OH and $N^g,N^{g'}$-di-Boc-6-aminohexylguanidine.

$^1$H NMR
FD-MS, m/e 703 ($M^+$)

D) Preparation of D-Phe-Pro-NH(CH$_2$)$_6$NHC(NH)NH$_2$.HCl

By a method substantially equivalent to that described in Example 1-H, approximately 100 mg of D-Phe-Pro-NH(CH$_2$)$_6$NHC(NH)NH$_2$.HCl were prepared.

FD-MS, m/e 389 ($M^+$)

Analysis for $C_{21}H_{34}N_6O_2 \cdot 0.9HCl \cdot 0.9TFA \cdot 0.5H_2O$: Calc: C, 49.97; H, 6.95; N, 15.34; Found: C, 49.60; H, 7.13; N, 15.23.

EXAMPLE 6

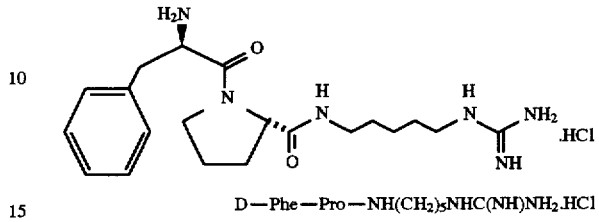

D—Phe—Pro—NH(CH$_2$)$_5$NHC(NH)NH$_2$.HCl

A) Preparation of $N^g,N^{g'}$-di-Boc-5-aminopentylguanidine

By a method substantially equivalent to that described in Example 1-F, 1.73 g (72%) of $N^g,N^{g'}$-di-Boc-5-aminopentylguanidine were prepared from 1,5-pentanediamine.

FD-MS, m/e 345 ($M^+$)
$^1$H NMR

B) Preparation of Boc-D-Phe-Pro-NH(CH$_2$)$_5$NHC(NBoc)NH(Boc)

By a method substantially equivalent to that described in Example 1-G, 1.9 g (92%) of Boc-D-Phe-Pro-NH(CH$_2$)$_5$NHC(NBoc)NH(Boc) were prepared from Boc-D-Phe-Pro-OH and $N^g,N^{g'}$-di-Boc-5-aminopentylguanidine.

$^1$H NMR
FD-MS, m/e 689 ($M^+$)

C) Preparation of D-Phe-Pro-NH(CH$_2$)$_5$NHC(NH)NH$_2$.HCl

By a method substantially equivalent to that described in Example 1-H, approximately 100 mg of D-Phe-Pro-NH(CH$_2$)$_5$NHC(NH)NH$_2$.HCl were prepared. The product was purified by RPHPLC (method 1, 98/2 (A/B), ramp to 40/60 (A/B), 40 minutes).

FD-MS, m/e 389 ($M^+$)

Analysis for $C_{20}H_{32}N_6O_2 \cdot 0.9HCl \cdot 0.9TFA \cdot 0.7H_2O$: Calc: C, 48.71; H, 6.79; N, 15.63; Found: C, 48.34; H, 6.68; N, 16.01.

EXAMPLE 7

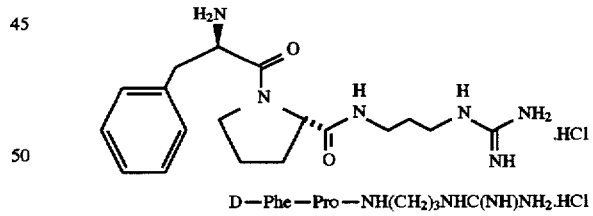

D—Phe—Pro—NH(CH$_2$)$_3$NHC(NH)NH$_2$.HCl

A) Preparation of Boc-D-Phe-Pro-NH(CH$_2$)$_3$NHC(NBoc)NH(Boc)

To a solution of 1,3-diaminopropane (2.2 g, 30 mmol) in dimethylformamide (25 mL) was added a solution of N,N'-di-Boc-S-methylisothiourea (2.9 g, 10 mmol) in dimethylformamide (25 mL). After stirring for 1 hour, the mixture was diluted with dichloromethane (400 mL) and washed twice with a mixture of saturated aqueous sodium bicarbonate and saturated aqueous sodium chloride (200 mL), and once with saturated aqueous sodium chloride (250 mL). The organic phase was dried ($MgSO_4$), filtered, and partially concentrated in vacuo to a volume of about 200 mL.

To this solution was then added Boc-D-Phe-Pro-OH (3.6 g, 10 mmol), HOBT (1.3 g, 10 mmol) and N,N- diisopropylethylamine (1.3 g, 10 mmol), followed by 1-(3-dimethylaminopropyl)-3-ethylcarbodiimide.HCl (2.1 g, 11 mmol). After stirring for 16 hours, the solvents were removed in vacuo and the residue was taken up in ethyl acetate (250 mL). The organic phase was washed three times with 1N citric acid (200 mL), once with water (100 mL), twice with saturated aqueous sodium bicarbonate (200 mL) and once with saturated aqueous sodium chloride. The organic phase was then dried (MgSO$_4$), filtered and concentrated in vacuo. The residue was then chromatographed over silica gel, eluting with a step gradient of ethyl acetate/hexanes (1:4) through ethyl acetate. The product containing fractions (judged by TLC) were concentrated to yield 2.6 g (40%) of thick colorless oil.

$^1$H NMR

FD-MS, m/e 661 (M$^+$)

B) Preparation of D-Phe-Pro-NH(CH$_2$)$_3$NHC(NH)NH$_2$.HCl

By a method substantially equivalent to that described in Example 1-H, 460 mg (71%) of D-Phe-Pro-NH(CH$_2$)$_3$NHC(NH)NH$_2$.HCl were prepared. The product was purified by RPHPLC (method 1, 98/2 (A/B), ramp to 40/60 (A/B), 40 minutes).

$^1$H NMR

FD-MS, m/e 361 (M$^+$)

Analysis for C$_{18}$H$_{28}$N$_6$O$_2$.HCl.1.1TFA.1.1H$_2$O: Calc: C, 44.66; H, 6.20; N, 15.47; Found: C, 44.69; H, 6.10; N, 15.19.

EXAMPLE 8

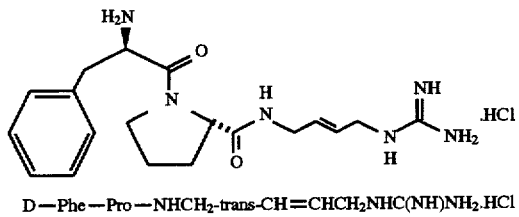

D—Phe—Pro—NHCH$_2$-trans-CH=CHCH$_2$NHC(NH)NH$_2$.HCl

A) Preparation of N$^g$,N$^{g'}$-di-Boc-4-amino-trans-2-butenylguanidine

By a method substantially equivalent to that described in Example 1-F, 2.4 g (42%) of N$^g$,N$^{g'}$-di-Boc-4-amino-trans-2-butenylguanidine were prepared from 1,4-diamino-trans-2-butene.

B) Preparation of Boc-D-Phe-Pro-NHCH$_2$-trans-CH=CHCH$_2$NHC(NBoc)NHBoc

By a method substantially equivalent to that described in Example 1-G, 2.7 g (55%) of Boc-D-Phe-Pro-NHCH$_2$-trans-CH=CHCH$_2$NHC(NBoc)NHBoc were prepared from Boc-D-Phe-Pro-OH and N$^g$,N$^{g'}$-di-Boc-4-amino-trans-2-butenylguanidine.

$^1$H NMR

FD-MS, m/e 673 (M$^+$)

C) Preparation of D-Phe-Pro-NHCH$_2$-trans-CH=CHCH$_2$NHC(NH)NH$_2$.HCl

By a method substantially equivalent to that described in Example 1-H, approximately 100 mg of D-Phe-Pro-NHCH$_2$-trans-CH=CHCH$_2$NHC(NH)NH$_2$.HCl were prepared. The product was purified by RPHPLC (method 1, 98/2 (A/B), ramp to 40/60 (A/B), 40 minutes).

$^1$H NMR

FD-MS, m/e 373 (M$^+$)

Analysis for C$_{19}$H$_{28}$N$_6$O$_2$.HCl.0.5TFA.2.5H$_2$O: Calc: C, 47.01; H, 6.81; N, 16.45; Found: C, 47.36; H, 6.53; N, 16.70.

EXAMPLE 9

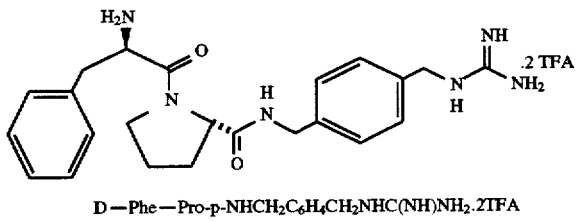

D—Phe—Pro-p-NHCH$_2$C$_6$H$_4$CH$_2$NHC(NH)NH$_2$.2TFA

A) Preparation of p-H$_2$NCH$_2$C$_6$H$_4$CH$_2$NHC(NBoc)NHBoc

By a method substantially equivalent to that described in Example 1-F, 2.3 g (42%) of p-H$_2$NCH$_2$C$_6$H$_4$CH$_2$NHC(NBoc)NHBoc were prepared from p-xylenediamine.

$^1$H NMR

B) Preparation of Boc-D-Phe-Pro-p-NHCH$_2$-C$_6$H$_4$CH$_2$NHC(NBoc)NHBoc

By a method substantially equivalent to that described in Example 1-G, 2.8 g (63%) of Boc-D-Phe-Pro-p-NHCH$_2$-C$_6$H$_4$CH$_2$NHC(NBoc)NHBoc were prepared from Boc-D-Phe-Pro-OH and p-H$_2$NCH$_2$C$_6$H$_4$CH$_2$NHC(NBoc)NHBoc.

$^1$H NMR

FD-MS, m/e 723 (M$^+$)

C) Preparation of D-Phe-Pro-p-NHCH$_2$-C$_6$H$_4$CH$_2$NHC(NH)NH$_2$.2TFA

By a method substantially equivalent to that described in Example 1-H, 725 mg (81%) of the title bis-TFA salt were prepared and was not purified further by RPHPLC.

$^1$H NMR

FD-MS, m/e 423 (M$^+$)

Analysis for C$_{23}$H$_{30}$N$_6$O$_2$.2.1TFA.H$_2$O: Calc: C, 48.05; H, 5.05; N, 12.36; Found: C, 48.06; H, 4.85; N, 12.28.

EXAMPLE 10

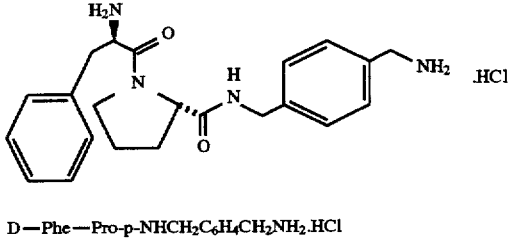

D—Phe—Pro-p-NHCH$_2$C$_6$H$_4$CH$_2$NH$_2$.HCl

A) Preparation of N-Boc-p-(aminomethyl)benzylamine

To a stirring solution of p-xylenediamine (10 g, 73 mmol) in dimethylformamide/water (1:1, 100 mL) was added di-t-butyl dicarbonate (8 g, 37 mmol). After stirring for 20 hours, the mixture was concentrated in vacuo and the residue was partitioned between diethyl ether (200 mL) and 1N citric acid (200 mL). The aqueous phase was washed again with diethyl ether (200 mL), and then basified with solid sodium bicarbonate and saturated with solid sodium chloride. The aqueous phase was then extracted four times with ethyl acetate (200 mL). The combined ethyl acetate extracts were dried (MgSO$_4$), filtered and concentrated to give 2.1 g (24%) of a thick oil.

$^1$H NMR

FD-MS, m/e 237 (MH$^+$)

Analysis for C$_{13}$H$_{20}$N$_2$O$_2$: Calc: C, 66.07; H, 8.53; N, 11.85; Found: C, 66.33; H, 8.44; N, 12.11.

B) Preparation of Boc-D-Phe-Pro-p-NHCH$_2$C$_6$H$_4$CH$_2$NHBoc

By a method substantially equivalent to that described in Example 1-G, 1.1 g (63%) of Boc-D-Phe-Pro-p-NHCH$_2$-

$C_6H_4CH_2NHBoc$ were prepared from Boc-D-Phe-Pro-OH and N-Boc-p-(aminomethyl)benzyl amine.

$^1$H NMR

FD-MS, m/e 581 (M$^+$)

Analysis for $C_{32}H_{44}N_4O_6$: Calc: C, 66.19; H, 7.64; N, 9.65; Found: C, 65.99; H, 7.63; N, 9.42.

C) Preparation of D-Phe-Pro-p-NHCH$_2$C$_6$H$_4$CH$_2$NH$_2$.HCl

By a method substantially equivalent to that described in Example 1-H, about 100 mg of D-Phe-Pro-p-NHCH$_2$-C$_6$H$_4$CH$_2$NH$_2$.HCl were prepared. The product was purified by RPHPLC (method 1, 98/2 (A/B), ramp to 40/60 (A/B), 40 minutes).

$^1$H NMR

FD-MS, m/e 381 (M$^+$)

Analysis for $C_{22}H_{28}N_4O_2$.HCl.1.1TFA.H$_2$O: Calc: C, 51.87; H, 5.77; N 10.00; Found: C, 51.78; H, 5.88; N 10.28.

EXAMPLE 11

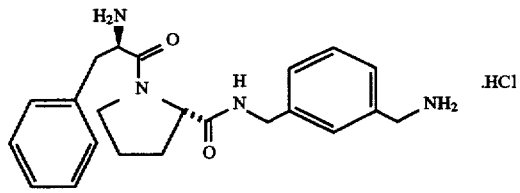

D—Phe—Pro-m-NHCH$_2$C$_6$H$_4$CH$_2$NH$_2$.HCl

A) Preparation of N-Boc-m-(aminomethyl)benzylamine

By a procedure substantially equivalent to that described in Example 10-A, 2.6 g (30%) of N-Boc-m-(aminomethyl)benzylamine were prepared from m-xylenediamine.

$^1$H NMR

FD-MS, m/e 237 (MH$^+$)

Analysis for $C_{13}H_{20}N_2O_2$: Calc: C, 66.07; H, 8.53; N, 11.85; Found: C, 65.81; H, 8.48; N, 11.98.

B) Preparation of Boc-D-Phe-Pro-m-NHCH$_2$C$_6$H$_4$CH$_2$NHBoc

By a method substantially equivalent to that described in Example 1-G, 1.6 g (95%) of Boc-D-Phe-Pro-m-NHCH$_2$-C$_6$H$_4$CH$_2$NHBoc were prepared from Boc-D-Phe-Pro-OH and N-Boc-m-(aminomethyl)benzylamine.

$^1$H NMR

FD-MS, m/e 581 (M$^+$)

C) Preparation of D-Phe-Pro-m-NHCH$_2$C$_6$H$_4$CH$_2$NH$_2$.HCl

By a method substantially equivalent to that described in Example 1-H, about 100 mg of D-Phe-Pro-m-NHCH$_2$-C$_6$H$_4$CH$_2$NH$_2$.HCl were prepared.

$^1$H NMR

FD-MS, m/e 381 (M$^+$)

Analysis for $C_{22}H_{28}N_4O_2$.HCl.TFA.H$_2$O: Calc: C, 52.51; H, 5.87; N 10.21; Found: C, 52.13; H, 6.21; N 10.48.

EXAMPLE 12

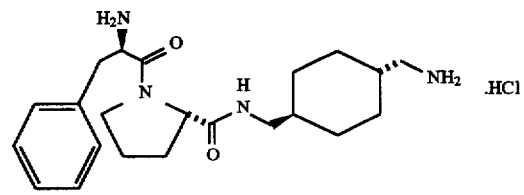

D—Phe—Pro—NHCH$_2$-trans-4-(aminomethyl)cyclohexane.HCl

A) Preparation of N-Boc-trans-4-(aminomethyl) cyclohexanecarboxylic acid

To a solution of trans-4-(aminomethyl) cyclohexanecarboxylic acid (50 g, 318 mmol) in 1N sodium hydroxide (334 mL, 334 mmol) and t-butanol (400 mL) was added a solution of di-t-butyl dicarbonate (73 g, 334 mmol) in tetrahydrofuran (50 mL). After stirring for 20 hours, the solvents were removed in vacuo and the residue was partitioned between water (500 mL) and diethyl ether (250 mL). The aqueous phase was washed again with diethyl ether (250 mL) and then acidified with solid citric acid, which resulted in the formation of a white precipitate. The solid was filtered, washed twice with water (100 mL) and dried in vacuo to yield 48 g (59%) of white powder.

$^1$H NMR

B) Preparation of HOCH$_2$-trans-4-(N-Boc-aminomethyl) cyclohexane

To a stirring solution of N-Boc-trans-4-(aminomethyl) cyclohexanecarboxylic acid (15 g, 58 mmol) in tetrahydrofuran (150 mL) at 0° C., was added N-methylmorpholine (5.9 g, 58 mmol), followed by ethyl chloroformate (6.3 g, 58 mmol). After stirring for 30 minutes, sodium borohydride (6.5 g, 175 mmol) was added, and then methanol (300 mL) was added via an addition funnel over 5 minutes. The mixture was allowed to stir for 1 hour and then the solvents were removed in vacuo. The residue was dissolved in ethyl acetate (500 mL) and washed twice with 1N citric acid (250 mL), once with water (100 mL), twice with saturated aqueous sodium bicarbonate (250 mL) and once with saturated aqueous sodium chloride (250 mL). The organic phase was dried (MgSO$_4$), filtered and concentrated to give 13 g (91%) of the title compound.

$^1$H NMR

C) Preparation of NH$_2$CH$_2$-trans-4-(N-Boc-aminomethyl) cyclohexane

To a stirring solution of HOCH$_2$-trans-4-(N-Boc-aminomethyl)cyclohexane (13 g, 53 mmol) and triphenylphosphine (21 g, 80 mmol) in tetrahydrofuran (300 mL) was added diethyl azodicarboxylate (13.9 g, 80 mmol), followed by a solution of diphenylphosphoryl azide (22 g, 80 mmol) in tetrahydrofuran (100 mL). After stirring for 16 hours, the solvents were removed in vacuo and the residue was chromatographed over silica gel, eluting with a step gradient of ethyl acetate/hexanes (1:3) through ethyl acetate/hexanes (3:1). The product containing fractions (judged by TLC), were combined and concentrated to give 17.4 g of crude product (contaminated with higher R$_f$ compound). The crude azide was dissolved in methanol (200 mL) and this solution was added to a stirring suspension of finely ground Na$_2$S.9H$_2$O (51 g, 212 mmol) and triethylamine (1 g, 11 mmol) in methanol (100 mL). The resulting mixture was heated to reflux (16 hours), then cooled to room temperature and the solvents were removed in vacuo. The residue was diluted with water (250 mL) and acidified with solid citric acid. The aqueous phase was washed twice with ethyl acetate (250 mL), basified with solid sodium bicarbonate, and saturated with solid sodium chloride. The aqueous phase was then extracted three times with ethyl acetate (200 mL) and the combined extracts were dried (MgSO$_4$), filtered and concentrated to give 6.4 g (45%) of a thick oil.

$^1$H NMR

D) Preparation of N-Boc-D-Phe-Pro-NHCH$_2$-trans-4-(N-Boc-aminomethyl)cyclohexane By a method substantially equivalent to that described in Example 1-G, 4.5 g (74%) of N-Boc-D-Phe-Pro-NHCH$_2$-trans-4-(N-Boc-aminomethyl)cyclohexane were prepared from Boc-D-Phe-Pro-OH and NH$_2$CH$_2$-trans-4-(N-Boc-aminomethyl)cyclohexane.

$^1$H NMR

FD-MS, m/e 587 (M$^+$)

E) Preparation of D-Phe-Pro-NHCH$_2$-trans-4-(aminomethyl)cyclohexane.HCl

By a method substantially equivalent to that described in Example 1-H, 588 mg (75%) of D-Phe-Pro-NHCH$_2$-trans-4-(aminomethyl)cyclohexane.HCl were prepared. In this case, the analytical RPHPLC of the intermediate TFA salt was very clean, but the salt was hygroscopic. So the salt was dissolved in 0.1N HCl (20 mL), the pH was adjusted to 5, and the sample was lyophilized again to yield the stable white solid, hydrochloride salt.

$^1$H NMR

FD-MS, m/e 387 (M$^+$)

Analysis for C$_{22}$H$_{34}$N$_4$O$_2$.HCl.TFA.2H$_2$O: Calc: C, 50.30; H, 7.04; N, 9.78; Found: C, 50.44; H, 7.20; N, 9.62.

EXAMPLE 13

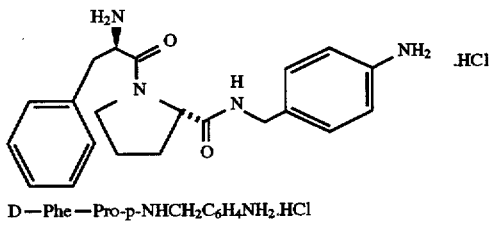

D—Phe—Pro-p-NHCH$_2$C$_6$H$_4$NH$_2$.HCl

A) Preparation of Boc-D-Phe-Pro-p-NHCH$_2$C$_6$H$_4$NH$_2$

By a method substantially equivalent to that described in Example 1-G, 8 g of Boc-D-Phe-Pro-p-NHCH$_2$C$_6$H$_4$NO$_2$ were prepared from Boc-D-Phe-Pro-OH and p-NO$_2$-benzylamine.HCl. The intermediate was dissolved in ethanol (250 mL) and heated to reflux. To this stirring solution was added a solution of Na$_2$S$_2$O$_4$ (12.3 g, 70 mmol) in water (125 mL). After stirring at reflux for 2 hours, the solvents were removed in vacuo and the residue was partitioned between ethyl acetate (250 mL) and water (250 mL). The aqueous phase was extracted again with ethyl acetate (250 mL) and the combined organic phase was dried (MgSO$_4$), filtered, and concentrated in vacuo to give 2.4 g (21%) of a light yellow solid.

$^1$H NMR

FD-MS, m/e 466 (M$^+$)

Analysis for C$_{26}$H$_{34}$N$_4$O$_4$: Calc: C, 66.93; H, 7.34; N, 12.01; Found: C, 66.69; H, 7.32; N, 12.28.

B) Preparation of D-Phe-Pro-p-NHCH$_2$C$_6$H$_4$NH$_2$.HCl

By a method substantially equivalent to that described in Example 1-H, 180 mg (60%) of D-Phe-Pro-p-NHCH$_2$-C$_6$H$_4$NH$_2$.HCl were prepared. The product was purified by RPHPLC (method 1, 98/2 (A/B), ramp to 60/40 (A/B), 60 minutes).

$^1$H NMR

FD-MS, m/e 366 (M$^+$)

Analysis for C$_{21}$H$_{26}$N$_4$O$_2$.HCl.0.6TFA.0.5H$_2$O: Calc: C, 55.51; H, 6.00; N, 11.66; Found: C, 55.16; H, 6.14; N, 11.57.

EXAMPLE 14

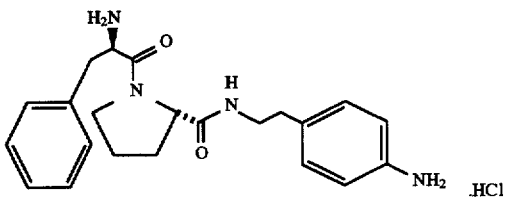

D—Phe—Pro-p-NHCH$_2$CH$_2$C$_6$H$_4$NH$_2$.HCl

A) Preparation of Boc-D-Phe-Pro-p-NHCH$_2$CH$_2$C$_6$H$_4$NH$_2$

By a method substantially equivalent to that described in Example 13-A, 3 g (23%) of Boc-D-Phe-Pro-p-NHCH$_2$CH$_2$-C$_6$H$_4$NH$_2$ were prepared from Boc-D-Phe-Pro-OH and p-NO$_2$-phenethylamine.HCl.

$^1$H NMR

FD-MS, m/e 480 (M$^+$)

Analysis for C$_{27}$H$_{36}$N$_4$O$_4$: Calc: C, 67.48; H, 7.55; N, 11.66; Found: C, 67.30; H, 7.54; N, 12.34.

B) Preparation of D-Phe-Pro-p-NHCH$_2$CH$_2$C$_6$H$_4$NH$_2$.HCl

By a method substantially equivalent to that described in Example 1-H, 175 mg (58%) of D-Phe-Pro-p-NHCH$_2$CH$_2$-C$_6$H$_4$NH$_2$.HCl were prepared. The product was purified by RPHPLC (method 1, 98/2 (A/B), ramp to 60/40 (A/B), 60 minutes).

$^1$H NMR

FD-MS, m/e 380 (M$^+$)

Analysis for C$_{22}$H$_{28}$N$_4$O$_2$.HCl.0.7TFA.0.7H$_2$O: Calc: C, 55.18; H, 6.15; N, 11.00; Found: C, 55.12; H, 6.18; N, 10.99.

EXAMPLE 15

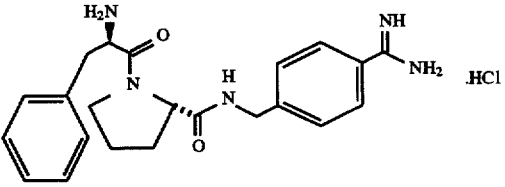

D—Phe—Pro-p-NHCH$_2$C$_6$H$_4$C(NH) NH$_2$.HCl
(D-phenylalanyl-N-[[4-(aminoiminomethyl)phenyl]methyl]-L-prolinamide hydrochloride)

A) Preparation of p-(aminomethyl)benzonitrile.TFA

To a stirring suspension of sodium hydride (2.2 g, 56 mmol, 60% dispersion in oil) in tetrahydrofuran (100 mL) was added 4-(bromomethyl)benzonitrile (10 g, 51 mmol). To this mixture was added slowly via an addition funnel a solution of di-t-butyl iminodicarboxylate (12.2 g, 56 mmol). After stirring for 16 hours, the mixture was diluted with diethyl ether (300 mL) and washed twice with water (150 mL). The organic phase was then dried (MgSO$_4$), filtered and concentrated. The resulting solid was then dissolved in a minimum amount of dichloromethane. Anisole (10 mL) was added, and the solution was cooled to 0° C. The solution was then diluted with trifluoroacetic acid (200 mL) and allowed to stir for 1 hour. The solvent was then removed in vacuo and the oily residue was stirred vigorously with diethyl ether (100 mL) and after a few minutes, the product solidified. The precipitate was filtered, washed with diethyl ether, and dried in vacuo to give 11.3 g (90%) of white powder.

IR

¹H NMR
FD-MS, m/e 132 (M⁺)

B) Preparation of Boc-D-Phe-Pro-p-NHCH₂C₆H₄CN

By a method substantially equivalent to that described in Example 1-G, 7.4 g (78%) of Boc-D-Phe-Pro-p-NHCH₂C₆H₄CN were prepared from Boc-D-Phe-Pro-OH and p-(aminomethyl)benzonitrile.TFA. In this case, the product was purified by recrystallization from diethyl ether.

IR
¹H NMR
FD-MS, m/e 476 (M⁺)

C) Preparation of Boc-D-Phe-Pro-p-NHCH₂C₆H₄C(NH)NH₂

Hydrogen sulfide gas was bubbled through a solution of Boc-D-Phe-Pro-p-NHCH₂C₆H₄CN (2 g, 4.2 mmol) in pyridine (25 mL) and triethylamine (2.5 mL) for 30 minutes. The reaction vessel was then sealed and allowed to stand at room temperature for 2 days. The solution was then diluted with water (100 mL) and extracted twice with ethyl acetate (200 mL). The combined organic phase was washed twice with saturated aqueous sodium chloride, dried (MgSO₄), filtered and concentrated in vacuo.

The residue was dissolved in acetone (50 mL), methyl iodide (10 mL) was added, and the solution was heated to reflux (2 hours). The solvents were removed in vacuo, the residue was dissolved in methanol (20 mL), NH₄OAc (712 mg, 9.2 mmol) was added, and the solution was heated to reflux (12 hours). The solvent was again removed in vacuo, the residue was dissolved in 1N citric acid (100 mL) and the aqueous phase was washed twice with ethyl acetate (200 mL), then basified with solid sodium bicarbonate, saturated with solid sodium chloride, and extracted twice with ethyl acetate (200 mL). The combined ethyl acetate extracts were dried (MgSO₄), filtered and concentrated to give 1.4 g (67%) of thick oil.

¹H NMR
FD-MS, m/e 494 (M⁺)

D) Preparation of D-Phe-Pro-p-NHCH₂C₆H₄C(NH)NH₂.HCl

By a method substantially equivalent to that described in Example 1-H, 7.7 g (57%) of D-Phe-Pro-p-NHCH₂C₆H₄C(NH)NH₂.HCl were prepared. The product was purified by RPHPLC (method 3, 98/2 (A/B), ramp to 70/30 (A/B), 300 minutes).

¹H NMR
FD-MS, m/e 394 (M⁺)

Analysis for C₂₂H₂₇N₅O₂.HCl.1.4TFA.0.5H₂O: Calc: C, 49.76; H, 5.12; N, 11.70; Found: C, 49.75; H, 5.19; N, 11.58.

EXAMPLE 16

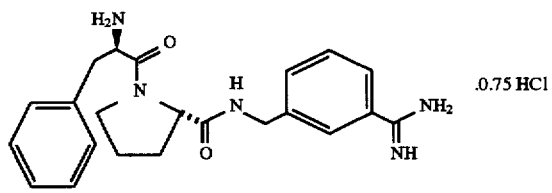

D—Phe—Pro-m-NHCH₂C₆H₄C(NH)NH₂.0.75HCl

A) Preparation of m-(aminomethyl)benzonitrile.TFA

By a method substantially equivalent to that described in Example 15-A, 10.8 g (86%) of m-(aminomethyl)benzonitrile.TFA were prepared from m-(bromomethyl)benzonitrile.

IR
¹H NMR
FD-MS, m/e 132 (M⁺)

B) Preparation of Boc-D-Phe-Pro-m-NHCH₂C₆H₄CN

By a method substantially equivalent to that described in Example 1-G, 7.5 g (79%) of Boc-D-Phe-Pro-m-NHCH₂C₆H₄CN were prepared from Boc-D-Phe-Pro-OH and m-(aminomethyl)benzonitrile.TFA. In this case, the product was purified by recrystallization from diethyl ether.

IR
¹H NMR
FD-MS, m/e 476 (M⁺)

Analysis for C₂₇H₃₂N₄O₄: Calc: C, 68.05; H, 6.77; N, 11.76; Found: C, 68.27; H, 6.82; N, 11.96.

C) Preparation of Boc-D-Phe-Pro-m-NHCH₂C₆H₄C(NH)NH₂

By a method substantially equivalent to that described in Example 15-C, 1.1 g (53%) of Boc-D-Phe-Pro-m-NHCH₂C₆H₄C(NH)NH₂ were prepared.

FD-MS, m/e 494 (M⁺)

D) Preparation of D-Phe-Pro-m-NHCH₂C₆H₄C(NH)NH₂.0.75HCl

By a method substantially equivalent to that described in Example 1-G, 0.65 g (63%) of D-Phe-Pro-m-NHCH₂C₆H₄C(NH)NH₂.0.75 HCl were prepared. The product was purified by RPHPLC (method 2, 98/2 (A/B), ramp to 75/25 (A/B), 120 minutes).

FD-MS, m/e 394 (M⁺)

Analysis for C₂₂H₂₇N₅O₂.0.75HCl.1.2TFA.0.5H₂O: Calc. C, 51.72; H, 5.33; H, 12.36; Cl, 4.69; Found: C, 51.79; H, 4.93; N, 11.96; Cl, 4.82.

EXAMPLE 17

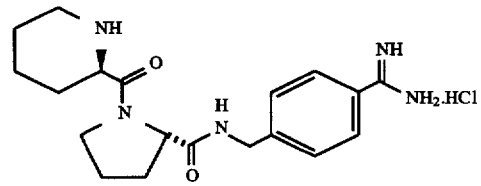

D-hPro—Pro-p-NHCH₂C₆H₄C(NH)NH₂.HCl
(D-homoprolyl-N-[[4-(aminoiminomethyl)phenyl]methyl]-L-prolinamide hydrochloride)

A) Preparation of Cbz-D-hPro-OH

D-hPro-OH (5.0 g, 38.7 mmol) was dissolved in tetrahydrofuran (100 mL) and water (30 mL). The pH of the solution was adjusted to 9.5 with 2N sodium hydroxide and benzyl chloroformate (5.5 mL, 38.7 mmol) was added dropwise and the pH maintained at 9.5 with 2N sodium hydroxide. The reaction was stirred for an additional 1 hour at room temperature. The organic solvent was evaporated in vacuo, diethyl ether (100 mL) and water (50 mL) was added to the residue. The aqueous layer separated, the pH of the solution was adjusted to 2.8 with 3N hydrochloric acid and ethyl acetate (150 mL) was added. The organic layer was separated and dried (MgSO₄); the filtrate was concentrated in vacuo to give 9.6 g (95%) of a clear oil.

¹H NMR
FD-MS, m/e 264 (MH⁺)

B) Preparation of Cbz-D-hPro-Pro-OH

Cbz-D-hPro-OH (9.5 g, 36 mmol) was dissolved in ethyl acetate (100 mL) and the solution cooled to 0° C. Added to the solution was 2,4,5-trichlorophenol (7.1 g, 36 mmol) and 1,3-dicyclohexylcarbodiimide (7.4 g, 36 mmol). The reaction was stirred for 1 hour at 0° C. and 1 hour at room temperature. The precipitate was filtered and the filtrate concentrated in vacuo to an oil. The oil was dissolved in pyridine (100 mL), Pro-OH (4.2 g, 36 mmol), and triethylamine (5.0 mL, 36 mmol) were added. The reaction was stirred at room temperature (24 hours). The reaction solvent was removed in vacuo to an oil. The residue was dissolved in water (100 mL), diethyl ether (50 mL) was added and the pH adjusted to 9.5 with 2N sodium hydroxide. The aqueous layer extracted twice with diethyl ether. The aqueous layer separated, the pH adjusted to 2.8 with 3N hydrochloric acid and ethyl acetate (150 mL) was added. The organic layer was separated, dried ($MgSO_4$), and the filtrate evaporated in vacuo to an amorphous solid (11.4 g, 88%).

FD-MS 361 ($M^+$);

Analysis for $C_{19}H_{24}N_2O_5$: Calc: C, 63.32; H, 6.71; N, 7.77; Found: C, 63.42; H, 6.84; N, 7.96.

C) Preparation of Cbz-D-hPro-Pro-p-$NHCH_2C_6H_4CN$

By a method substantially equivalent to that described in Example 1-G, 2.2 g (84%) of Cbz-D-hPro-Pro-p-$NHCH_2C_6H_4CN$ were prepared from Cbz-D-hPro-Pro-OH and p-$NH_2CH_2C_6H_4CN$.TFA.

$^1$H NMR

FD-MS, m/e 474 ($M^+$)

Analysis for $C_{27}H_{30}N_4O_4$: Calc: C, 68.34; H, 6.37; N, 11.81; Found: C, 68.36; H, 6.47; N, 11.57.

D) Preparation of D-hPro-Pro-p-$NHCH_2C_6H_4C(NH)NH_2$.HCl

By a method substantially equivalent to that described in Example 15-C, Cbz-hPro-Pro-p-$NHCH_2C_6H_4C(NH)NH_2$ (28 mmol, theoretical) was prepared. This crude material was then dissolved in acetic acid (350 mL) and HBr gas was bubbled through the solution for 30 minutes. After stirring for an additional 1 hour, the solvent was removed in vacuo and the residue was dissolved in water (200 mL) and washed twice with ethyl acetate (100 mL). The aqueous phase was then adjusted to pH 4 with ion exchange resin (Bio Rad AG1-X8, in basic form) and lyophilized to give a fluffy white solid. The product was then redissolved in water (25 mL) and purified by preparative RPHPLC (method 3, 98/2 (A/B), ramp to 70/30 (A/B), 300 minutes) to give 5 g (41%) of hPro-Pro-p-$NHCH_2C_6H_4C(NH)NH_2$.0.9HCl.0.9HBr.0.5$H_2O$.

$^1$H NMR

FD-MS, m/e 357 ($M^+$)

Analysis for $C_{19}H_{27}N_5O_2$.0.9HCl.0.9HBr.0.5$H_2O$: Calc: C, 48.34; H, 6.36; N, 14.83; Cl, 6.76; Br, 15.23; Found: C, 48.66; H, 6.36; N, 14.62; Cl, 7.14; Br, 14.90.

EXAMPLE 18

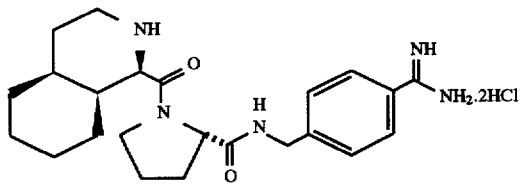

1-Piq-Pro-p-$NHCH_2C_6H_4C(NH)NH_2$.2HCl
(N-[[4-(aminoiminomethyl)phenyl]methyl]-1-[[(4aS,8aS)-decahydro-1(R)-isoquinolinyl]carbonyl]-L-prolinamide dihydrochloride)

A) Preparation of Cbz-D-1-Piq-Pro-OH

A solution of 1-isoquinolinecarboxylic acid (50 g, 0.288 mol) in EtOH (150 mL) and 60 mL of 5N HCl was reduced over 5% Rh/$Al_2O_3$ (14 g) at 52 bar (750 psi) of hydrogen in a high pressure apparatus at 50° C. for 17 hours. The reaction mixture was filtered through a pad of diatomaceous earth, and the filtrate was concentrated in vacuo. The solid was triturated with water, filtered and dried to give DL-perhydro-1-isoquinolinecarboxylic acid (DL-1-Piq-OH) (30 g, 48%) FD-MS 184 ($MH^+$).

DL-1-Piq-OH (30.2 g, 137 mmol) was dissolved in tetrahydrofuran (150 mL) and water (150 mL). The pH of the solution was adjusted to 9.8 with 5N NaOH, and benzyl chloroformate (21.6 mL, 151 mmol) was added dropwise and the pH maintained at 9.5 with 2N NaOH. The reaction was stirred for an additional 2 hours at room temperature. The organic solvent was evaporated in vacuo, and diethyl ether (150 mL) and water (50 mL) were added to the residue. The aqueous layer was separated, the pH of the solution was adjusted to 2.5 with 5N HCl, and ethyl acetate (200 mL) was added. The organic layer was separated and dried ($MgSO_4$) and the filtrate was concentrated in vacuo to give a clear oil. The oil was dissolved in diethyl ether (150 mL) and the solution allowed to stand at room temperature (24 hours). The precipitate was filtered and dried to give 2-Cbz-DL-perhydro-1-isoquinolinecarboxylic acid (Cbz-DL-1-Piq-OH) (32 g, 75%) FD-MS 318 ($MH^+$).

Cbz-DL-1-Piq-OH (31.8 g, 100 mmol) was dissolved in DMF (100 mL) and cooled to 0° C. To the reaction was added proline t-butyl ester (17.1 g, 100 mmol), 1-hydroxybenzotriazole (13.5 g, 100 mmol), and DCC (20.6 g, 100 mmol). The reaction was stirred for 3 hours at 0° C. and 24 hours at room temperature. The reaction precipitate was filtered and the filtrate concentrated in vacuo to an oil. The oil was dissolved in EtOAc (200 mL) and water (100 mL). The organic layer was separated, and washed sequentially with 1N $NaHCO_3$, water, 1.5N citric acid, and water. The organic layer was dried ($MgSO_4$), and the filtrate evaporated to an oil which was dried to give 2-Cbz-DL-perhydro-1-isoquinolinecarbonyl-L-prolyl t-butyl ester (Cbz-DL-1-Piq-Pro-O-t-Bu) (47.0 g, 100%) FAB-MS 470 ($MH^+$).

Cbz-DL-1-Piq-Pro-O-t-Bu (47.0 g, 100 mmol) was placed in a round bottom flask containing trifluoroacetic acid (100 mL), $CH_2Cl_2$ (35 mL), anisole (5 mL) and stirred at room temperature (1 hour). The reaction was concentrated in vacuo without heating, and diethyl ether (100 mL) and water (100 mL) were added. The pH of the solution was adjusted to 9.8 with 5N NaOH. The aqueous layer was separated, the pH of the solution was adjusted to 2.5 with 5N HCl, and ethyl acetate (200 mL) was added. The organic layer was separated and dried ($MgSO_4$) and the filtrate was concentrated in vacuo to give a clear oil. The oil was dissolved in diethyl ether (700 mL) and (L)-(-)-α-methylbenzylamine added to the solution. The solution was allowed to stand at room temperature for 5 days. The resulting solid was filtered and washed with diethyl ether. The filtrate was washed with 1.5N citric acid, and water. The organic layer was dried ($MgSO_4$), and the filtrate evaporated to an oil. The oil was dissolved in diethyl ether (400 mL) and allowed to stand at room temperature (48 hours). The resulting solid was filtered, washed with diethyl ether, and dried to give 2-Cbz-D-perhydro-1-isoquinolinecarbonyl-L-proline (Cbz-D-1-Piq-Pro-OH) (5.86 g, 36%) FAB-MS 415 ($MH^+$); $[α]_D=-34.2°$ (C=0.5, MeOH).

B) Preparation of N-Boc-p-(aminomethyl)benzonitrile

To a stirring suspension of sodium hydride (4.6 g, 115 mmol, 60% dispersion in oil) in tetrahydrofuran (150 mL) was added 4-(bromomethyl)benzonitrile (20.5 g, 105 mmol). To this mixture was added (slowly via an addition funnel) a solution of di-t-butyl iminodicarboxylate (25 g, 115 mmol). After stirring for 16 hours, the mixture was diluted with diethyl ether (500 mL) and washed twice with water (250 mL). The organic phase was then dried (MgSO₄), filtered and concentrated to give 40.2 g of crude solid.

The resulting solid (28.3 g, 85 mmol) was then dissolved in tetrahydrofuran (150 mL) and a solution of sodium hydroxide (3.4 g, 85 mmol) in methanol (300 mL) was added. After stirring overnight, the solution was concentrated to about one-half volume and water was added to promote precipitation of the product. The precipitate was filtered and dried in vacuo to give 18.5 g (94%) of a white solid.

IR
¹H NMR
FD-MS, m/e 232 (M⁺)
Analysis for $C_{13}H_{16}N_2O_2$: Calc: C, 67.22; H, 6.94; N, 12.06; Found: C, 67.19; H, 7.16; N, 11.82.

C) Preparation of p-(BocNHCH₂)C₆H₄C(NH)NHCbz

By a method substantially equivalent to that described in Example 15-C, N-Boc-p-(aminomethyl)benzonitrile (32.7 g, 140 mmol) was elaborated to p-(BocNHCH₂)C₆H₄C(NH)NH₂. The residue from this procedure was dissolved in dimethylformamide (700 mL) and N,N-diisopropylethylamine (72 g, 560 mmol) was added. To this stirring solution was added dropwise benzyl chloroformate (48 g, 280 mmol). After stirring for 16 hours, water (100 mL) was added and then the solvents were removed in vacuo. The residue was partitioned between water (250 mL) and ethyl acetate (500 mL). The phases were separated and the organic phase was washed three times with saturated aqueous ammonium chloride (250 mL), once with water (200 mL) and twice with saturated aqueous sodium bicarbonate (250 mL). The organic phase was then dried (MgSO₄), filtered and concentrated and the product was recrystallized from diethyl ether to give 14 g (26%) of white solid.

¹H NMR
FD-MS, m/e 384 (M⁺)

D) Preparation of p-H₂NCH₂C₆H₄C(NH)NHCbz.2HCl

To a solution of p-(BocNHCH₂)C₆H₄C(NH)NHCbz (11 g, 28.7 mmol) in dichloromethane (125 mL) at 0° C., was added anisole (10 mL) followed by trifluoroacetic acid (125 mL). After stirring for 2 hours, the solvents were removed in vacuo and the residue was dissolved in 1N hydrochloric acid (50 mL) and washed twice with diethyl ether (50 mL). The pH was adjusted to 3 with ion exchange resin (Bio Rad AG1-X8, in basic form) and the solution was lyophilized to give 9.2 g (90%) of white powder.

¹H NMR
FD-MS, m/e 284 (M⁺)

E) Preparation of Cbz-1-Piq-Pro-p-NHCH₂C₆H₄C(NH)NHCbz

By a method substantially equivalent to that described in Example 1-G, 4.4 g (79%) of Cbz-1-Piq-Pro-p-NHCH₂C₆H₄C(NH)NHCbz were prepared from Cbz-1-Piq-Pro-OH and p-H₂NCH₂C₆H₄C(NH)NHCbz.2HCl. In this case, the reaction was performed in dimethylformamide due to solubility problems with p-H₂NCH₂C₆H₄C(NH)NHCbz.2HCl.

¹H NMR
FD-MS, m/e 681 (MH⁺)
Analysis for $C_{39}H_{45}N_5O_6$: Calc: C, 68.91; H, 6.67; N, 10.30; Found: C, 68.71; H, 6.93; N, 10.38.

F) Preparation of 1-Piq-Pro-p-NHCH₂C₆H₄C(NH)NH₂.2HCl

To a solution of Cbz-1-Piq-Pro-p-NHCH₂C₆H₄C(NH)NHCbz (4.2 g, 6.1 mmol) in ethanol (200 mL), was added 1N hydrochloric acid (18.3 mL, 18.3 mmol) and water (100 mL). To this stirring solution was added 5% Pd/C (1 g), and hydrogen gas was bubbled through the solution for a period of 2 hours. The mixture was then flushed with nitrogen, and then filtered through a pad of diatomaceous earth. The filtrate was then concentrated in vacuo, redissolved in water (25 mL) and purified by RPHPLC (method 2, 98/2 (A/B), ramp to 60/40 (A/B), 300 minutes), to give 1.3 g (53%) of 1-Piq-Pro-p-NHCH₂C₆H₄C(NH)NH₂.2HCl.

¹H NMR
FD-MS, m/e 412 (M⁺)
Analysis for $C_{23}H_{33}N_5O_2 \cdot 1.9HCl \cdot 2.5H_2O$: Calc: C, 52.53; H, 7.65; N, 13.32; Cl, 12.81; Found: C, 52.63; H, 7.36; N, 13.47; Cl, 12.95.

EXAMPLE 19

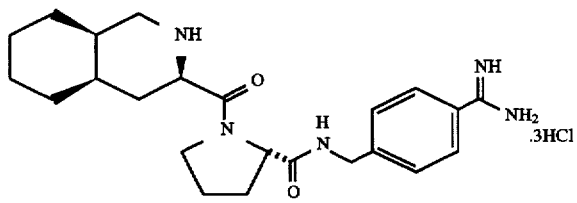

D-3-Piq-Pro-p-NHCH₂C₆H₄C(NH)NH₂.3HCl

A) Preparation of Cbz-D-3-Piq-Pro-OH

D-Phenylalanine (50 g, 302 mmol) was reacted with a 37% solution of formaldehyde (120 mL) and concentrated HCl (380 mL) at reflux. After 30 minutes an additional 50 mL of formaldehyde was added and reaction continued for 3 hours. The reaction cooled to −10° C. and the precipitate was filtered. The solid was dried in vacuo to give D-1,2,3,4-tetrahydro-3-isoquinolinecarboxylic acid (24.2 g, 45%) FD-MS 178 (MH⁺).

A solution of D-1,2,3,4-tetrahydro-3-isoquinolinecarboxylic acid (17 g, 96 mmol) in water (200 mL) and 20 mL of 5N HCl was hydrogenated over 5% Rh/Al₂O₃ (8.5 g) at 138 bar (2000 psi) in a high pressure apparatus at 120° C. for 16 hours. The reaction mixture was filtered through a pad of diatomaceous earth and the filtrate was freeze-dried to give D-perhydro-3-isoquinolinecarboxylic acid (D-3-Piq-OH) (21 g, 100%) FD-MS 184 (MH⁺).

D-3-Piq-OH (21.0 g, 95.8 mmol) was dissolved in tetrahydrofuran (75 mL) and water (50 mL). The pH of the solution was adjusted to 10.0 with 5N NaOH, and benzyl chloroformate (16.4 mL, 115 mmol) was added dropwise and the pH maintained at 9.5 with 2N NaOH. The reaction was stirred for an additional 1 hour at room temperature. The organic solvent was evaporated in vacuo, and diethyl ether (100 mL) and water (50 mL) were added to the residue. The aqueous layer was separated, the pH of the solution was adjusted to 3.0 with 3N HCl, and ethyl acetate (250 mL) was added. The organic layer was separated and dried (MgSO₄). The filtrate was concentrated in vacuo to give a clear oil of 2-Cbz-D-perhydro-3-isoquinolinecarboxylic acid (Cbz-D-3-Piq-OH) (25.8 g, 85%) FD-MS 318 (MH⁺).

Cbz-D-3-Piq-OH (17.2 g, 54 mmol) was dissolved in DMF (50 mL) and cooled to 0° C. To the reaction was added proline t-butyl ester (9.2 g, 54 mmol), 1-hydroxybenzotriazole (7.3 g, 54 mmol), and DCC (11.1 g, 54 mmol). The reaction was stirred for 3 hours at 0° C. and 24 hours at room temperature. The reaction precipitate was filtered and the filtrate concentrated in vacuo to an oil. The oil was dissolved in EtOAc (200 mL) and water (100 mL). The organic layer was separated, and washed sequentially with 1N NaHCO₃, water, 1.5N citric acid, and water. The organic layer was dried (MgSO₄), and the filtrate evaporated to an oil which was dried to give 2-Cbz-D-perhydro-3-isoquinolinecarbonyl-L-proline t-butyl ester (Cbz-D-3-Piq-Pro-O-Bu) (23.8 g, 94%) FAB-MS 471 (MH⁺).

Cbz-D-3-Piq-Pro-O-t-Bu (31.2 g, 66.3 mmol) was placed in a round bottom flask containing trifluoroacetic acid (100 mL), anisole (5 mL), and stirred at room temperature (1 hour). The reaction was concentrated in vacuo without heating, and diethyl ether (150 mL), and water (100 mL) were added. The pH of the solution was adjusted to 9.8 with 5N NaOH. The aqueous layer was separated, the pH of the solution was adjusted to 2.8 with 3N HCl, and ethyl acetate (200 mL) was added. The organic layer was separated, dried (MgSO₄), and filtered. The filtrate was concentrated in vacuo to give a clear oil. The oil was dissolved in diethyl ether (300 mL) and the solution was allowed to stand at room temperature (24 hours). The resulting solid was filtered, washed with diethyl ether, and dried to give 2-Cbz-perhydro-3-isoquinolinecarbonyl-L-proline (Cbz-D-3-Piq-Pro-OH) (13.5 g, 49%) FAB-MS 415 (MH⁺).

Analysis for $C_{23}H_{30}N_2O_5$: Calc: C, 66.65; H, 7.29; N, 6.76; Found: C, 66.90, H, 7.33, N, 6.81.

B) Preparation of Cbz-D-3-Piq-Pro-p-NHCH₂C₆H₄C(NH)NHCbz

By a method substantially equivalent to that described in Example 18-E, 1.6 g (49%) of Cbz-D-3-Piq-Pro-p-NHCH₂C₆H₄C(NH)NHCbz were prepared from Cbz-D-3-Piq-Pro-OH and p-H2NCH₂C₆H₄C(NH)NHCbz.2HCl.

FD-MS, m/e 680 (M⁺)

C) Preparation of D-3-Piq-Pro-D-NHCH₂C₆H₄C(NH)NH₂.3HCl

By a method substantially equivalent to that described in Example 17-C, 150 mg of D-3-Piq-Pro-p-NHCH₂C₆H₄C(NH)NH₂.3HCl were prepared. The product was purified by RPHPLC (method 2, 98/2 (A/B), ramp to 60/40 (A/B), 240 minutes).

¹H NMR
FD-MS, m/e 412 (M⁺)

Analysis for $C_{23}H_{33}N_5O_2 \cdot 3HCl \cdot 0.5H_2O$: Calc: C, 52.13; H, 7.04; N, 13.22; Found: C, 52.35; H, 7.23; N, 12.95.

EXAMPLE 20 genated on a Parr shaker for 8 hours (4.1 bar, 60 psi). The solution was filtered and the solvent was removed in vacuo. The residue was dissolved triturated with diethyl ether and 18.8 g (73%) of an off white solid (cis-Ohi-OEt.HCl) were collected by filtration.

By a method substantially equivalent to that described in Example 1-A, 13.5 g (93%) of Cbz-D-hPro-cis-Ohi-OEt were prepared from Cbz-D-hPro-OH and cis-Ohi-OEt.HCl.

¹H NMR
FD-MS, m/e 442 (M⁺)

Analysis for $C_{25}H_{34}N_2O_5$: Calc: C, 67.85; H, 7.74; N, 6.33; Found: C, 67.59; H, 7.72; N, 6.48.

By a method substantially equivalent to that described in Example 1-D, 12.5 g (102%) of Cbz-D-hPro-cis-Ohi-OH were prepared.

¹H NMR
FD-MS, m/e 414 (M⁺)

Analysis for $C_{23}H_{30}N_2O_5$: Calc: C, 66.65; H, 7.29; N, 6.76; Found: C, 66.46; H, 7.30; N, 6.86.

B) Preparation of Cbz-D-hPro-Ohi-p-NHCH₂C₆H₄C(NH)NHCbz

By a method substantially equivalent to that described in Example 18-E, 3.3 g (67%) of Cbz-D-hPro-Ohi-p-NHCH₂C₆H₄C(NH)NHCbz were prepared from Cbz-D-hPro-Ohi-OH and p-H₂NCH₂C₆H₄C(NH)NHCbz.2HCl.

¹H NMR
FD-MS, m/e 681 (MH⁺)

C) Preparation of D-hPro-Ohi-p-NHCH₂C₆H₄C(NH)NH₂.3HCl

By a method substantially equivalent to that described in Example 18-F, 2.2 g (66%) of D-hPro-Ohi-D-NHCH₂-C₆H₄C(NH)NH₂.3HCl were prepared. The product was purified by RPHPLC (method 2, 98/2 (A/B), ramp to 60/40 (A/B), 3000 minutes).

¹H NMR
FD-MS, m/e 412 (M⁺)

Analysis for $C_{23}H_{33}N_5O_2 \cdot 3HCl \cdot 0.5H_2O$: Calc: C, 52.13; H, 7.04; N, 13.22; Found: C, 51.98; H, 7.04; N 13.35.

EXAMPLE 21

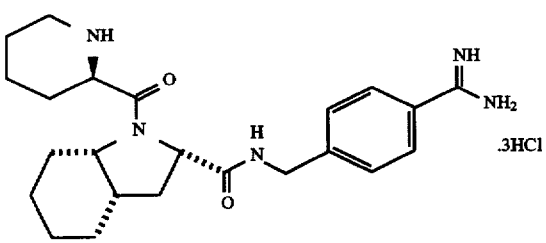

D-hPro—Ohi-p-NHCH₂C₆H₄C(NH)NH₂.3HCl
((S-cis)-N-[[4-(aminoiminomethyl)phenyl]methyl]-octahydro-1-D-homoprolyl-1H-indole-2-carboxamide trihydrochloride)

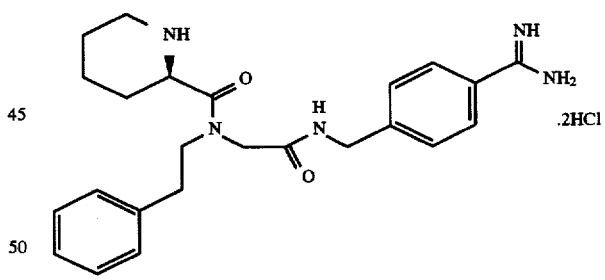

D-hPro—N(PhCH₂CH₂)Gly-p-NHCH₂C₆H₄C(NH)NH₂.2HCl
(D-homoprolyl-N(α)-(2-phenylethyl)-N-[[4-(aminoiminomethyl)phenyl]methyl]glycinamide dihydrochloride)

A) Preparation of Cbz-D-hPro-Ohi-OH

HCl gas was bubbled through a stirring suspension of (S)-indoline-2-carboxylic acid (20 g, 110 mmol) in ethanol (500 mL). When the acid was completely dissolved, the solution was brought to reflux. After 16 hours, the solution was cooled and the solvent removed in vacuo. The residue was triturated with diethyl ether and the resulting off-white solid was collected by filtration, washed with hexanes and dried overnight in a vacuum oven at 30° C. to give (S)-indoline-2-carboxylic acid ethyl ester.HCl (25.7 g, 78%).

The solid was dissolved in ethanol (800 mL), 5% Pd/C (25 g) was added, and the resulting suspension was hydro- A) Preparation of Cbz-D-hPro-N(PhCH₂CH₂)Gly-OH To a solution of phenethylamine (58 mL, 461 mmol) and triethylamine (21 mL, 154 mmol) in ethanol (200 mL) at 0° C. was added a solution of t-butyl bromoacetate (30 g, 154 mmol) in ethanol (50 mL) over 1 hour. The cold bath was left unattended and the solution was allowed to warm to room temperature. After stirring overnight, the solvents were removed in vacuo and the residue was dissolved in 1N citric acid. The aqueous solution was washed twice with diethyl ether, basified with solid sodium bicarbonate, and then extracted three times with ethyl acetate (200 mL). The combined ethyl acetate extracts were dried (MgSO₄), filtered and allowed to stand for 24 hours. The resulting precipitate was filtered, washed with diethyl ether, and dried to give 10.5 g of white solid. The mother liquor was concentrated to a volume of about 100 mL and then diluted with diethyl ether (400 mL). After standing for 30 minutes, the solution was filtered to yield an additional 23.5 g of white solid for a combined total of 34 g (94%) of N(PhCH₂CH₂)Gly-O-t-Bu.

¹H-NMR

FD-MS, m/e 235 (M⁺)

By a method substantially equivalent to that described in Example 1-A, 10.8 g (56%) of Cbz-D-hPro-N(PhCH₂CH₂) Gly-O-t-Bu were prepared from Cbz-D-hPro-OH and N(PhCH₂CH₂)Gly-O-t-Bu.

¹H NMR

FD-MS, m/e 480 (M⁺)

Analysis for C₂₈H₃₆N₂O₅: Calc: C, 69.98; H, 7.55; N, 5.83; Found: C, 69.68; H, 7.56; N, 5.77.

By a method substantially equivalent to that described in Example 18-A, for the deprotection of Cbz-DL-1-Piq-Pro-O-t-Bu, 9.2 g (100%) of Cbz-D-hPro-N(PhCH₂CH₂)Gly-OH were prepared.

¹H NMR

FD-MS, m/e 425 (M⁺)

Analysis for C₂₄H₂₈N₂O₅: Calc: C, 67.91; H, 6.65; N, 6.60; Found: C, 68.19; H, 6.68; N, 6.71.

B) Preparation of Cbz-D-hPro-N(PhCH₂CH₂)Gly-p-NHCH₂-C₆H₄C(NH)NHCbz

By a method substantially equivalent to that described in Example 18-E, 3.2 g (55%) of Cbz-D-hPro-N(PhCH₂CH₂) Gly-p-NHCH₂C₆H₄C(NH)NHCbz were prepared from Cbz-D-hPro-N(PhCH₂CH₂)Gly-OH and p-H₂NCH₂C₆H₄C (NH)NHCbz.2HCl.

¹H NMR

FD-MS, m/e 690 (M⁺)

Analysis for C₄₀H₄₃N₅O₆: Calc: C, 69.65; H, 6.28; N, 10.15; Found: C, 69.80; H, 6.46; N, 10.14.

C) Preparation of D-hPro-N(PhCH₂CH₂)Gly-p-NHCH₂-C₆H₄C(NH)NH₂.2HCl

By a method substantially equivalent to that described in Example 19-F, 770 mg (54%) of D-hPro-N(PhCH₂CH₂) Gly-p-NHCH₂C₆H₄C(NH)NH₂.2HCl were prepared. The product was purified by RPHPLC (method 2, 98/2 (A/B), ramp to 85/15 (A/B), 120 minutes).

¹H NMR

FD-MS, m/e 423 (MH⁺)

Analysis for C₂₄H₃₁N₅O₂.2HCl: Calc: C, 58.30; H, 6.73; N, 14.16; Found: C, 58.05; H, 6.60; N, 14.28.

EXAMPLE 22

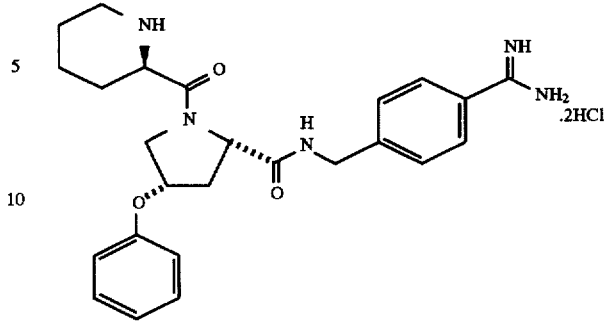

D-hPro—Pro(4-cis-PhO)-p-NHCH₂C₆H₄C(NH)NH₂.2HCl
(cis-D-homoprolyl-N-[[4-(aminoiminomethyl)-phenyl]methyl]-4-phenoxy-L-prolinamide dihydrochloride)

A) Preparation of Cbz-D-hPro-Pro(4-cis-PhO)-OH

To a solution of Cbz-Pro(4-trans-OH)-Et (58.8 g, 200 mmol), triphenylphosphine (65.6 g, 250 mmol), and phenol (23.5 g, 250 mmol) in tetrahydrofuran (500 mL) at 0° C., was added (dropwise over 1 hour) a solution of diethyl azodicarboxylate (40 mL, 250 mmol) in tetrahydrofuran (50 mL). The cold bath was then removed and the solution was allowed to warm to room temperature (16 hours). The solvent was then removed in vacuo and the remaining amber syrup was triturated with diethyl ether. The white solid was removed by filtration and the filtrate was concentrated. The residue was then chromatographed over silica gel (1 Kg), eluting with a step gradient from hexanes through 1:1 ethyl acetate/hexanes. The fractions containing pure product (as judged by TLC) were combined and concentrated in vacuo to give 36.3 g (50%) of Cbz-Pro(4-cis-phenoxy)-OEt as a colorless syrup.

¹H NMR

FD-MS, m/e 369 (M⁺)

Analysis for C₂₁H₂₃NO₅: Calc: C, 68.28; H, 6.28; N, 3.79; Found: C, 68.38; H, 6.30; N, 3.89.

To a solution of Cbz-Pro(4-cis-phenoxy)-OEt (25 g, 67.7 mmol) in ethanol (400 mL) was added 5% Pd/C (5 g). After bubbling hydrogen through the solution for 3 hours, the solution was filtered through a pad of diatomaceous earth, 3 mL of concentrated hydrochloric acid were added, and the solution was concentrated in vacuo. The residue was suspended in diethyl ether with vigorous stirring and then filtered and dried to give 14.2 g (77%) of Pro(4-cis-phenoxy) -OEt.HCl as a white solid.

¹H NMR

FD-MS, m/e 235 (M⁺)

Analysis for C₁₃H₁₈NO₃Cl: Calc: C, 57.46; H, 6.68; N, 5.15; Found: C, 57.68; H, 6.78; N, 5.18.

By a method substantially equivalent to that described in Example 1-A, 19.4 g (100%) of Cbz-D-hPro-Pro(4-cis-phenoxy)-OEt were prepared from Cbz-D-hPro-OH and Pro(4-cis-phenoxy)-OEt.HCl.

¹H NMR

FD-MS, m/e 480 (M⁺)

Analysis for C₂₇H₃₂N₂O₆: Calc: C, 67.48; H, 6.71; N, 5.83; Found: C, 67.71; H, 6.79; N, 5.89.

By a method substantially equivalent to that described in Example 1-D, 16 g (100%) of Cbz-D-hPro-Pro(4-cis-phenoxy)-OH were prepared.

¹H NMR

FD-MS, m/e 452 (M⁺)

Analysis for C₂₅H₂₈N₂O₆: Calc: C, 66.36; H, 6.24; N, 6.19; Found: C, 66.22; H, 6.18; N, 6.17.

B) Preparation of Cbz-D-hPro-Pro(4-cis-PhO)-p-NHCH₂-C₆H₄C(NH)NHCbz

By a method substantially equivalent to that described in Example 18-E, 4.55 g (75%) of Cbz-D-hPro-Pro(4-cis-PhO)-p-NHCH₂C₆H₄C(NH)NHCbz were prepared from Cbz-D-hPro-Pro(4-cis-PhO)-OH and p-H₂NCH₂C₆H₄C(NH)NHCbz.2HCl.

¹H NMR
FD-MS, m/e 718 (M⁺)

C) Preparation of D-hPro-Pro(4-cis-PhO)-p-NHCH₂-C₆H₄C(NH)NH₂.2HCl

By a method substantially equivalent to that described in Example 18-F, 873 mg (40%) of D-hPro-Pro(4-cis-PhO)-p-NHCH₂C₆H₄C(NH)NH₂.2HCl were prepared. The product was purified by RPHPLC (method 2, 98/2 (A/B), ramp to 85/15 (A/B), 120 minutes).

¹H NMR
FD-MS, m/e 451 (MH⁺)

Analysis for C₂₅H₃₁N₅O₃.2HCl: Calc: C, 57.47; H, 6.37; N, 13.40; Found: C, 57.22; H, 6.29; N, 13.47.

EXAMPLE 23

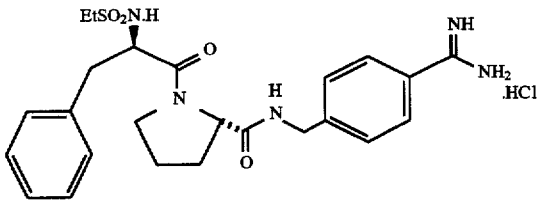

EtSO₂—D—Phe—Pro-p-NHCH₂C₆H₄C(NH)NH₂.HCl
(N-(ethylsulfonyl)-D-phenylalanyl-N-[[4-(aminoiminomethyl)phenyl]]methyl]-L-prolinamide hydrochloride)

A) Preparation of p-NH₂CH₂-C₆H₄CN.HCl

HCl gas was bubbled through a stirring solution of N-Boc-p-aminomethylbenzonitrile (15 g, 64.6 mmol) in ethyl acetate (400 mL) at 0° C. for 10 minutes. The cold bath was removed and after stirring for 1.5 hours, the solvent was removed in vacuo and the residue was suspended in diethyl ether, filtered, washed with diethyl ether and dried to give 10.1 g (93%) of white solid.

IR
¹H NMR
FD-MS, m/e 132 (M⁺)

Analysis for C₈H₉N₂Cl: Calc: C, 56.98; H, 5.38; N, 16.61; Cl, 21.02; Found: C, 56.36; H, 5.46; N, 16.22; Cl, 21.31.

B) Preparation of EtSO₂-D-Phe-Pro-p-NHCH₂-C₆H₄CN

By a method substantially equivalent to that described in Example 1-G, 1.5 g (80%) of EtSO₂-D-Phe-Pro-p-NHCH₂-C₆H₄CN were prepared from EtSO₂-D-Phe-Pro-OH and p-NH₂CH₂-C₆H₄CN.HCl.

IR
¹H NMR
FD-MS, m/e 468 (M⁺)

Analysis for C₂₄H₂₈N₄O₄S: Calc: C, 61.52; H, 6.02; N, 11.90; Found: C, 61.23; H, 6.13; N, 11.80.

C) Preparation of EtSO₂-D-Phe-Pro-p-NHCH₂-C₆H₄C(=NOH)NH₂.HCl

To a solution of EtSO₂-D-Phe-Pro-p-NHCH₂-C₆H₄CN (1 g, 2.1 mmol) in absolute ethanol (35 mL) was added N,N-diisopropylethylamine (0.47 mL, 2.7 mmol) followed by hydroxylamine hydrochloride (185 mg, 2.7 mmol) and the solution was brought to reflux. After 16 hours, the solution was cooled and the solvents were removed in vacuo. 250 mg of this material were taken on to the next step and the remaining material was purified by RPHPLC (method 1, 90/10 (A/B); ramp to 60/40 (A/B) over 200 minutes).

IR
¹H NMR
FD-MS, m/e 501 (M⁺)

Analysis for C₂₄H₃₁N₅O₅S.1.2HCl.H₂O: Calc: C, 51.17; H, 6.12; N, 12.42; Cl, 7.55; Found: C, 51.04; H, 5.81; N, 12.39; Cl, 7.18.

D) Preparation of EtSO₂-D-Phe-Pro-p-NHCH₂-C₆H₄C(=NH)NH₂.HCl

To a solution of EtSO₂-D-Phe-Pro-p-NHCH₂-C₆H₄C(=NOH)NH₂.HCl (250 mg, 0.52 mmol) in ethanol (40 mL) and water (19 mL) was added 1N HCl (1 mL) followed by 5% Pd on carbon (250 mg). The stirring suspension was placed under an atmosphere of hydrogen for 18 hours and was then filtered, concentrated and purified by RPHPLC (method 1, 90/10 (A/B), ramp to 60/40 (A/B) over 200 minutes) to give 140 mg (52%) of EtSO₂-D-Phe-Pro-p-NHCH₂-C₆H₄C(=NH)NH₂.HCl.

¹H NMR
FD-MS, m/e 486 (M⁺)

Analysis for C₂₄H₃₁N₅O₄S.HCl.1.5H₂O: Calc: C, 52.50; H, 6.42; N, 12.75; Found: C, 52.56; H, 6.19; N, 12.59.

Another 5 g of product were prepared by the methods described in Example 15 and purified by RPHPLC (method 3; 98/2 (A/B), 60 minutes, ramp to 60/40 (A/B) 300 minutes).

EXAMPLE 24

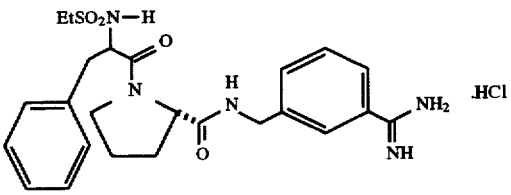

EtSO₂—D—Phe—Pro-m-NHCH₂—C₆H₄C(=NH)NH₂.HCl

A) Preparation of EtSO₂-D-Phe-Pro-m-NHCH₂-C₆H₄C(=NOH)NH₂

By methods substantially equivalent to those described in Example 23, EtSO₂-D-Phe-Pro-m-NHCH₂-C₆H₄C(=NOH)NH₂ was prepared using m-BrCH₂-C₆H₄CN in place of p-BrCH₂—C₆H₄CN. 140 mg (13%) of this crystalline intermediate was held back and the rest of the material was taken on to step B.

¹H NMR
FD-MS, m/e 502 (M⁺)

Analysis for C₂₄H₃₁N₅O₅S: Calc: C, 57.47; H, 6.23; N, 13.96; Found: C, 57.28; H, 6.21; N, 13.66.

B) Preparation of EtSO₂-D-Phe-Pro-m-NHCH₂-C₆H₄C(=NH)NH₂.HCl

By a method substantially equivalent to that described in Examples 23-C and 23-D, 0.27 g (28%, 2 steps) of EtSO₂-D-Phe-Pro-m-NHCH₂-C₆H₄C(=NH)NH₂.HCl were prepared.

¹H NMR
FD-MS, m/e 486 (M⁺)

Analysis for C₂₄H₃₁N₅O₄S.1.1HCl.2H₂O: Calc: C, 51.32; H, 6.48; N, 12.47; Cl, 6.94; Found: C, 51.33; H, 6.09; N, 12.20; Cl, 6.66.

EXAMPLE 25

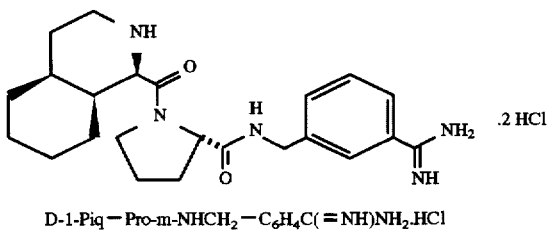

D-1-Piq—Pro-m-NHCH$_2$—C$_6$H$_4$C(=NH)NH$_2$.HCl

By a method substantially equivalent to that described in Example 23, 0.86 g of D-1-Piq-Pro-m-NHCH$_2$-C$_6$H$_4$C(=NH)NH$_2$.HCl were prepared from Cbz-D-1-Piq-Pro-OH and m-NH$_2$CH$_2$-C$_6$H$_4$CN.HCl.

$^1$H NMR

FD-MS, m/e 412 (M$^+$)

Analysis for C$_{23}$H$_{33}$N$_5$O$_2$.2.5HCl.0.5H$_2$O: Calc: C, 53.99; H, 7.19; N, 13.69; Found: C, 54.19; H, 7.02; N, 13.81.

EXAMPLE 26

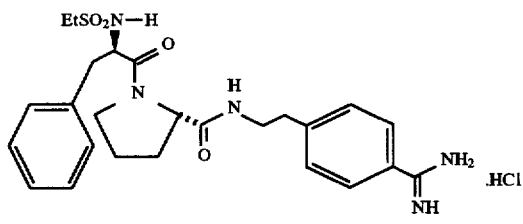

EtSO$_2$—D—Phe—Pro-p-NHCH$_2$CH$_2$—C$_6$H$_4$C(=NH)NH$_2$.HCl

A) Preparation of methyl p-cyano-trans-cinnamate

To a stirring suspension of NaH (6.1 g of 60% oil suspension, 153 mmol) and p-cyanobenzaldehyde (20 g, 153 mmol) in tetrahydrofuran (250 mL) at 0° C. was added via addition funnel a solution of trimethyl phosphonoacetate (28 g, 153 mmol) in tetrahydrofuran (50 mL). After stirring for 48 hours, the solvent was removed in vacuo and the crude residue was dissolved in ethyl acetate (500 mL). The ethyl acetate solution was washed once with water, three times with saturated aqueous NaHSO$_3$ and once with brine. The organic phase was then dried with MgSO$_4$, filtered and concentrated in vacuo to give 28 g (98%) of a white solid.

IR $^1$H NMR

FD-MS, m/e 187 (M$^+$)

B) Preparation of methyl p-cyano-dihydrocinnamate

To a solution of methyl p-cyano-trans-cinnamate (13.6 g, 73 mmol) in toluene (485 mL) was added 5% Pd/BaSO$_4$ (2.7 g). After 9 hours under hydrogen gas at 4 bar (60 psi), the solution was filtered, concentrated in vacuo and chromatographed over silica gel, eluting with a step gradient of hexanes through 30% ethyl acetate/hexanes. The product containing fractions were combined and concentrated to give 10.6 g (77%) of colorless oil.

IR $^1$H NMR

FD-MS, m/e 189 (M$^+$)

C) Preparation of p-cyano-dihydrocinnamic acid

By methods substantially equivalent to those described in Example 1-D, using 1.1 equivalent of LiOH.H$_2$O, 5.1 g (58%) of p-cyano-dihydrocinnamic acid were prepared from methyl p-cyano-dihydrocinnamate.

IR $^1$H NMR

FD-MS, m/e 175 (M$^+$)

D) Preparation of Boc-P-NHCH$_2$CH$_2$-C$_6$H$_4$CN

To a solution of P-cyano-dihydrocinnamic acid (6.7 g, 38.2 mmol) and triethylamine (5.9 mL, 42 mmol) in t-butanol (150 mL) was added diphenylphosphoryl azide (11.6 g, 42 mmol) and the solution was brought to reflux. After stirring overnight, the solution was cooled and the solvent was removed in vacuo. The residue was dissolved in ethyl acetate and washed three times with 1N citric acid, once with brine, twice with saturated aqueous NaHCO$_3$, and then dried (MgSO$_4$), filtered and concentrated in vacuo. The residue was then chromatographed over silica gel, eluting with 10% ethyl acetate/hexanes through 50% ethyl acetate/hexanes. The product containing fractions as judged by TLC were combined and concentrated to give 5.4 g (57%) of white solid.

IR $^1$H NMR

FD-MS, m/e 246 (M$^+$)

Analysis for C$_{14}$H$_{18}$N$_2$O$_2$: Calc: C, 68.27; H, 7.37; N, 11.37; Found: C, 68.39; H, 7.50; N, 11.40.

E) Preparation of p-NH$_2$CH$_2$CH$_2$-C$_6$H$_4$CN.HCl

By methods substantially equivalent to those described in Example 23-A, 3.6 g (98%) of p-NH$_2$CH$_2$CH$_2$-C$_6$H$_4$CN.HCl were prepared.

$^1$H NMR

FD-MS, m/e 147 (MH$^+$)

Analysis for C$_9$H$_{11}$N$_2$Cl: Calc: C, 59.18; H, 6.07; N, 15.34; Cl, 19.41; Found: C, 58.90; H, 6.16; N, 15.20; Cl, 19.30.

F) Preparation of EtSO$_2$-D-Phe-Pro-p-NHCH$_2$CH$_2$-C$_6$H$_4$CN

By methods substantially equivalent to those described in Example 1-G, 1.5 g of EtSO$_2$-D-Phe-Pro-p-NHCH$_2$CH$_2$-C$_6$H$_4$CN were prepared from EtSO$_2$-D-Phe-Pro-OH and p-NH$_2$CH$_2$CH$_2$-C$_6$H$_4$CN.HCl.

IR $^1$H NMR

FD-MS, m/e 482 (M$^+$)

G) Preparation of EtSO$_2$-D-Phe-Pro-p-NHCH$_2$CH$_2$-C$_6$H$_4$C(=NOH)NH$_2$.HCl To a stirring solution of EtSO$_2$-D-Phe-Pro-p-NHCH$_2$CH$_2$-C$_6$H$_4$CN (1 g, 2.07 mmol) and N,N-diisopropylethylamine (0.45 mL, 2.59 mmol) was added hydroxylamine hydrochloride (180 mg, 2.59 mmol) and the solution was brought to reflux. After 18 hours, the solution was cooled, the solvent was removed in vacuo and the residue was dissolved in acetic acid (15 mL) and purified by RPHPLC (Method 2, 90/10 (A/B); ramp to 60/40 (A/B) over 200 minutes). The fractions containing pure EtSO$_2$-D-Phe-Pro-p-NHCH$_2$CH$_2$-C$_6$H$_4$C(=NOH)NH$_2$.HCl as determined by analytical RPHPLC were combined and pH adjusted as described above and lyophilized to give 0.35 g (31%) of EtSO$_2$-D-Phe-Pro-p-NHCH$_2$CH$_2$-C$_6$H$_4$C(=NOH)NH$_2$.HCl.

$^1$H NMR

FD-MS, m/e 516 (M$^+$)

Analysis for C$_{25}$H$_{33}$N$_5$O$_5$S.HCl.H$_2$O: Calc: C, 52.67; H, 6.36; N, 12.28; Cl, 6.22; Found: C, 52.40; H, 6.10; N, 12.25; Cl, 6.51.

G) Preparation of EtSO$_2$-D-Phe-Pro-p-NHCH$_2$CH$_2$-C$_6$H$_4$C(=NH)NH$_2$.HCl By a method substantially equivalent to that described in Example 23-D, 0.098 g (50%) of EtSO$_2$-D-Phe-Pro-p-NHCH$_2$CH$_2$-C$_6$H$_4$C(=NH)NH$_2$.HCl were prepared from EtSO$_2$-D-Phe-Pro-p-NHCH$_2$CH$_2$-C$_6$H$_4$C(=NOH)NH$_2$.HCl.

$^1$H NMR

FD-MS, m/e 500 (M⁺)

Analysis for $C_{25}H_{33}N_5O_4S \cdot 2.6HCl \cdot H_2O$: Calc: C, 49.03; H, 6.19; N, 11.44; Found: C, 48.87; H, 5.79; N, 11.15.

EXAMPLE 27

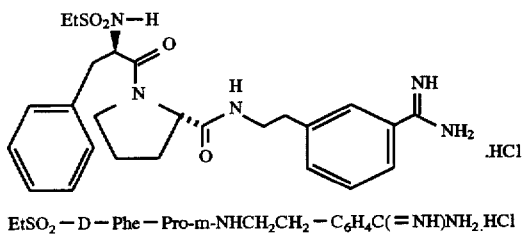

EtSO₂—D—Phe—Pro-m-NHCH₂CH₂—C₆H₄C(=NH)NH₂.HCl

A) Preparation of EtSO₂-D-Phe-Pro-m-NHCH₂CH₂-C₆H₄C(=NOH)NH₂

By a method substantially equivalent to that described in Examples 26-A through 26-E and 24-A, 0.15 g of EtSO₂-D-Phe-Pro-m-NHCH₂CH₂-C₆H₄C(=NOH)NH₂ were prepared from m-cyanobenzaldehyde.

¹H NMR

FD-MS, m/e 516 (M⁺)

Analysis for $C_{25}H_{33}N_5O_5S$: Calc: C, 58.23; H, 6.45; N, 13.50; Found: C, 57.99; H, 6.57; N, 13.28.

B) Preparation of EtSO₂-D-Phe-Pro-m-NHCH₂CH₂-C₆H₄C(=NH)NH₂.HCl

By a method substantially equivalent to that described in Example 24-B, 0.21 g (20%) of EtSO₂-D-Phe-Pro-m-NHCH₂CH₂-C₆H₄C(=NH)NH₂.HCl were prepared from EtSO₂-D-Phe-Pro-m-NHCH₂CH₂-C₆H₄C(=NOH)NH₂.

¹H NMR

FD-MS, m/e 500 (M⁺)

Analysis for $C_{25}H_{33}N_5O_4S \cdot 2.1HCl \cdot 0.7H_2O$ Calc: C, 51.00; H, 6.25; N, 11.89; Found: C, 50.79; H, 5.86; N, 11.54.

EXAMPLE 28

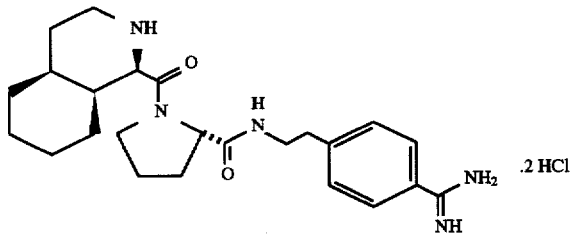

D-1-Piq—Pro-p-NHCH₂CH₂—C₆H₄C(=NH)NH₂.2HCl

By a method substantially equivalent to that described in Example 23, 0.85 g of 1-Piq-Pro-p-NHCH₂CH₂-C₆H₄C(=NH)NH₂.2HCl were prepared from Cbz-D-1-Piq-Pro-OH and p-NH₂CH₂CH₂-C₆H₄CN.HCl.

¹H NMR

FD-MS, m/e 426 (M⁺)

Analysis for $C_{24}H_{35}N_5O_2 \cdot 2HCl \cdot 2H_2O$: Calc: C, 53.93; H, 7.73; N, 13.10; Found: C, 53.94; H, 7.60; N, 13.06.

EXAMPLE 29

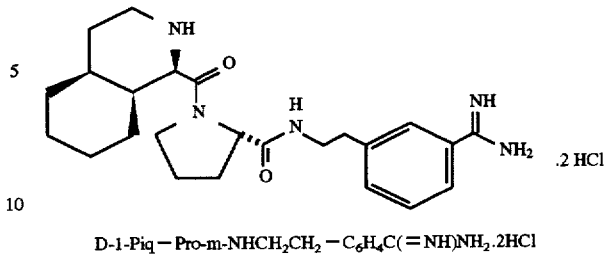

D-1-Piq—Pro-m-NHCH₂CH₂—C₆H₄C(=NH)NH₂.2HCl

By a method substantially equivalent to that described in Example 23, 0.8 g of 1-Piq-Pro-m-NHCH₂CH₂-C₆H₄C(=NH)NH₂.2HCl were prepared from Cbz-D-1-Piq-Pro-OH and m-NH₂CH₂CH₂-C₆H₄CN.HCl.

¹H NMR

FD-MS, m/e 426 (M⁺)

Analysis for $C_{24}H_{35}N_5O_2 \cdot 2HCl \cdot 2H_2O$: Calc: C, 53.93; H, 7.73; N, 13.10; Found: C, 53.62; H, 7.57; N, 13.18.

EXAMPLE 30

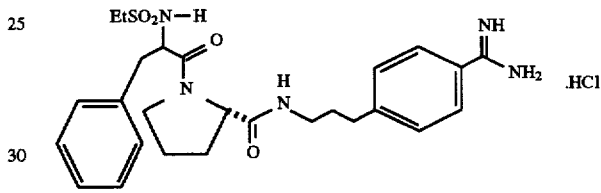

EtSO₂—D—Phe—Pro-p-NHCH₂CH₂CH₂—C₆H₄C(=NH)NH₂.HCl

A) Preparation of p-HOCH₂CH₂CH₂-C₆H₄CN

To a stirring solution of methyl p-cyano-dihydrocinnamate (10 g, 53 mmol) in tetrahydrofuran (150 mL) was added LiBH₄ (1.15 g, 53 mmol) and the solution was heated to reflux. After 2 hours, the solution was cooled, and sodium phosphate buffer (pH 7) was added dropwise. After gas evolution was complete, ethyl acetate and water were added and the layers were separated. The aqueous phase was extracted once with ethyl acetate and the combined ethyl acetate phases were washed with brine, then dried with MgSO₄, filtered and concentrated to give 8.1 g (95%) of a thick colorless oil.

IR

¹H NMR

FD-MS, m/e 161 (M⁺)

B) Preparation of p-BrCH₂CH₂CH₂-C₆H₄CN

To a stirring solution of p-HOCH₂CH₂CH₂-C₆H₄CN (8.1 g, 50 mmol) in tetrahydrofuran (100 mL) was added triphenylphosphine (14.4 g, 55 mmol) followed by carbon tetrabromide (18.2 g, 55 mmol). After stirring for 18 hours, the solvent was removed in vacuo and the residue was chromatographed over silica gel eluting with a step gradient of hexanes through 20% ethyl acetate/hexanes. The product containing fractions as judged by TLC were combined and concentrated to give 7.3 g (65%) of a thick colorless oil.

IR

¹H NMR

FD-MS, m/e 223 (M⁺)

Analysis for $C_{10}H_{10}BrN$: Calc: C, 53.60; H, 4.50; N, 6.25; Found: C, 53.90; H, 4.67; N, 6.24.

C) Preparation of p-Boc₂NCH₂CH₂CH₂-C₆H₄CN

To a stirring suspension of NaH (1.4 g of 60% oil dispersion, 34 mmol) in DMF (100 mL) was added dropwise a solution of di-t-butyl iminodicarboxylate (7.4 g, 34 mmol)

in DMF (20 mL) via an addition funnel. After gas evolution was complete, a solution of p-BrCH$_2$CH$_2$CH$_2$-C$_6$H$_4$CN (7 g, 31 mmol) in DMF was added via an addition funnel and the solution was heated to 70° C. After stirring for 12 hours, the solution was cooled and the solvent was removed in vacuo. The residue was dissolved in diethyl ether and washed three times with water. The organic phase was dried with MgSO$_4$, filtered and concentrated and the residue was chromatographed over silica gel, eluting with hexanes through 20% ethyl acetate/hexanes. The product containing fractions were combined and concentrated to give 9.38 g (84%) of white solid.

IR
$^1$H NMR
FD-MS, m/e 361 (M$^+$)
Analysis for C$_{20}$H$_{28}$N$_2$O$_4$: Calc: C, 66.64; H, 7.83; N, 7.77; Found: C, 66.40; H, 7.81; N, 7.57.

D) Preparation of p-NH$_2$CH$_2$CH$_2$CH$_2$-C$_6$H$_4$CN.HCl

By methods substantially equivalent to those described in Example 23-A, 4.3 g (84%) of p-NH$_2$CH$_2$CH$_2$CH$_2$-C$_6$H$_4$CN.HCl were prepared.

IR
$^1$H NMR
FD-MS, m/e 160 (M$^+$)

E) Preparation of EtSO$_2$-D-Phe-Pro-p-NHCH$_2$CH$_2$CH$_2$-C$_6$H$_4$C(=NOH)NH$_2$.HCl By methods substantially equivalent to those described in Examples 1-G and 26-G, 0.32 g of EtSO$_2$-D-Phe-Pro-p-NHCH$_2$CH$_2$CH$_2$-C$_6$H$_4$C(=NOH)NH$_2$.HCl were prepared from EtSO$_2$-D-Phe-Pro-OH and p-NHCH$_2$CH$_2$CH$_2$—C$_6$H$_4$CN.HCl.

$^1$H NMR
FD-MS, m/e 530 (M$^+$)
Analysis for C$_{26}$H$_{35}$N$_5$O$_5$S.1.2HCl.H$_2$O: Calc: C, 52.88; H, 6.51; N, 11.84; Found: C, 52.71; H, 6.26; N, 11.76.

F) Preparation of EtSO$_2$-D-Phe-Pro-p-NHCH$_2$CH$_2$CH$_2$-C$_6$H$_4$C(=NH)NH$_2$.HCl By a method substantially equivalent to that described in Example 23-D, 0.13 g (67%) of EtSO$_2$-D-Phe-Pro-p-NHCH$_2$CH$_2$CH$_2$-C$_6$H$_4$C(=NH)NH$_2$.HCl were prepared from EtSO$_2$-D-Phe-Pro-p-NHCH$_2$CH$_2$CH$_2$-C$_6$H$_4$C(=NOH)NH$_2$.HCl.

$^1$H NMR
FD-MS, m/e 514 (M$^+$)
Analysis for C$_{26}$H$_{35}$N$_5$O$_4$S.1.5HCl.2H$_2$O: Calc: C, 51.67; H, 6.75; N, 11.59; Found: C, 51.36; H, 6.46; N, 11.28.

EXAMPLE 31

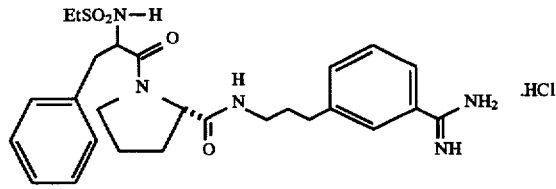

EtSO$_2$—D—Phe—Pro-m-NHCH$_2$CH$_2$CH$_2$—C$_6$H$_4$C(=NH)NH$_2$.HCl

A) Preparation of EtSO$_2$-D-Phe-Pro-m-NHCH$_2$CH$_2$CH$_2$-C$_6$H$_4$C(=NOH)NH$_2$.HCl By methods substantially equivalent to those described in Examples 1-G and 26-G, 0.32 g of EtSO$_2$-D-Phe-Pro-m-NHCH$_2$CH$_2$CH$_2$-C$_6$H$_4$C(=NOH)NH$_2$.HCl were prepared from m-cyanodihydrocinnamic acid.

$^1$H NMR
FD-MS, m/e 530 (M$^+$)
Analysis for C$_{26}$H$_{35}$N$_5$O$_5$S.HCl.1.1H$_2$O: Calc: C, 53.30; H, 6.57; N, 11.95; Cl, 6.05; Found: C, 52.97; H, 6.19; N, 11.96; Cl, 6.13.

B) Preparation of EtSO$_2$-D-Phe-Pro-m-NHCH$_2$CH$_2$CH$_2$-C$_6$H$_4$C(=NH)NH$_2$.HCl By a method substantially equivalent to that described in Example 23-D, 0.12 g (62%) of EtSO$_2$-D-Phe-Pro-m-NHCH$_2$CH$_2$CH$_2$-C$_6$H$_4$C(=NH)NH$_2$.HCl were prepared from EtSO$_2$-D-Phe-Pro-m-NHCH$_2$CH$_2$CH$_2$-C$_6$H$_4$C(=NOH)NH$_2$.HCl.

$^1$H NMR
FD-MS, m/e 514 (M$^+$)
Analysis for C$_{26}$H$_{35}$N$_5$O$_4$S.1.5HCl.H$_2$O: Calc: C, 53.26; H, 6.62; N, 11.94; Found: C, 53.19; H, 6.25; N, 12.00.

EXAMPLE 32

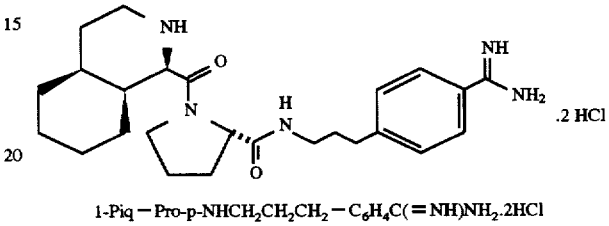

1-Piq—Pro-p-NHCH$_2$CH$_2$—C$_6$H$_4$C(=NH)NH$_2$.2HCl

By a method substantially equivalent to that described in Example 23, 0.66 g (48%) of 1-Piq-Pro-p-NHCH$_2$CH$_2$CH$_2$-C$_6$H$_4$C(=NH)NH$_2$.HCl were prepared from 1-Piq-Pro-OH and p-NH$_2$CH$_2$CH$_2$CH$_2$-C$_6$H$_4$CN.HCl.

$^1$H NMR
FD-MS, m/e 440 (M$^+$)
Analysis for C$_{25}$H$_{37}$N$_5$O$_2$.2.1HCl.H$_2$O: Calc: C, 56.21; H, 7.75; N, 13.11; Found: C, 56.36; H, 7.44; N, 12.79.

EXAMPLE 33

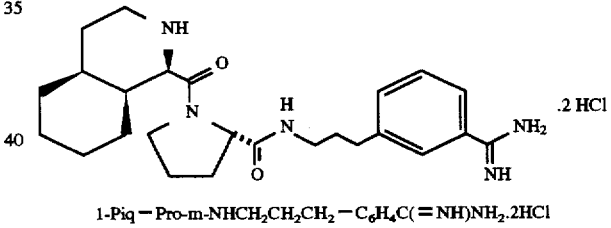

1-Piq—Pro-m-NHCH$_2$CH$_2$CH$_2$—C$_6$H$_4$C(=NH)NH$_2$.2HCl

By a method substantially equivalent to that described in Example 23, 0.64 (46%) of 1-Piq-Pro-m-NHCH$_2$CH$_2$CH$_2$-C$_6$H$_4$C(=NH)NH$_2$.HCl were prepared from 1-Piq-Pro-OH and m-NH$_2$CH$_2$CH$_2$CH$_2$-C$_6$H$_4$CN.HCl.

$^1$H NMR
FD-MS, m/e 440 (M$^+$)
Analysis for C$_{25}$H$_{37}$N$_5$O$_2$.2HCl.H$_2$O: Calc: C, 56.60; H, 7.79; N, 13.20; Found: C, 56.92; H, 7.55; N, 13.26.

EXAMPLE 34

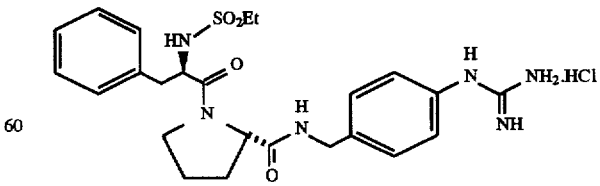

EtSO$_2$—D—Phe—Pro-p-NHCH$_2$C$_6$H$_4$NHC(NH)NH$_2$.HCl

A) Preparation of Boc-p-NHCH$_2$C$_6$H$_4$NO$_2$

To a stirring solution of 4-nitrobenzylamine hydrochloride (15 g, 79 mmol) and N,N-diisopropylethylamine (14 mL, 79 mmol) in dichloromethane (200 mL) was added di-t-butyl dicarbonate (17 g, 79 mmol). After 48 h, the solvent was removed in vacuo and the residue was dissolved in ethyl acetate (500 mL) and washed twice with 1M citric acid, once with water, and once with saturated aqueous NaHCO₃. The organic phase was dried with MgSO₄, filtered and concentrated in vacuo to give an off white solid which was recrystallized from chloroform/hexanes. Three crops were combined, washed with hexanes and dried in vacuo to give 11.5 g (58%) of a white solid.

IR
¹H NMR
FD-MS, m/e 252 (M⁺)

Analysis for $C_{12}H_{16}N_2O_4$: Calc: C, 57.13; H, 6.39; N, 11.10; Found: C, 57.27; H, 6.60; N, 11.13.

B) Preparation of p-BocNHCH₂C₆H₄NH₂

To a stirring solution of p-BocNHCH₂C₆H₄NO₂ (7.5 g, 29.7 mmol) and NiCl₂.6H₂O (17.7 g, 74.3 mmol) in methanol (150 mL) at 0° C. was added NaBH₄ (5.6 g, 149 mmol) in small portions over 30 min. After complete addition of NaBH₄ and 15 min, the solvent was evaporated in vacuo and the residue was dissolved in conc. ammonium hydroxide and extracted twice with dichloromethane. The combined organic extracts were washed with brine, dried with MgSO₄, filtered and concentrated in vacuo to give 6.4 g (97%) of a white solid.

IR
¹H NMR
FD-MS, m/e 222 (M⁺)

Analysis for $C_{12}H_{18}N_2O_2$: Calc: C, 64.84; H, 8.16; N, 12.60; Found: C, 65.10; H, 8.42; N, 12.76.

C) Preparation of N,N'-di-Cbz-S-methylisothiourea

To a stirring suspension of bis-S-methylisothiourea sulfate (20 g, 144 mmol) in dichloromethane (200 mL), was added 5N sodium hydroxide (16 mL). The solution was cooled to 0° C. and benzyl chloroformate (41 mL, 288 mmol) was added dropwise. At the same time, 2N sodium hydroxide was added at a rate which kept the pH of the solution at approximately 11. The cold bath was then removed and after warming to room temperature, the phases were separated and the aqueous phase was extracted with dichloromethane (250 mL). The combined organic phases were then washed twice with 0.1N HCl (250 mL) and once with brine (250 mL). The organic phase was then dried with MgSO₄, filtered and concentrated in vacuo to give 41 g (79%) of a thick, colorless syrup.

¹H NMR

D) Preparation of p-BocNHCH₂C₆H₄NHC(NCbz)NHCbz

To a stirring solution of p-BocNHCH₂C₆H₄NH₂ (5 g, 22.5 mmol) in tetrahydrofuran (50 mL) was added N,N'-di-Cbz-S-methylisothiourea (8.9 g, 24.7 mmol). After 48 h, the solvent was removed in vacuo and the residue was dissolved in chloroform. Silica gel was added and the solvent was removed in vacuo to give an off white powder which was then dry loaded onto a silica gel column. The column was then eluted with a step gradient of 5% ethyl acetate/hexanes through 30% ethyl acetate/hexanes. The product containing fractions (determined by TLC) were combined and concentrated in vacuo to give 7.6 g (63%) of a white solid.

IR
¹H NMR
FD-MS, m/e 532 (M⁺)

Analysis for $C_{29}H_{32}N_4O_6$: Calc: C, 65.40; H, 6.06; N, 10.52; Found: C, 65.66; H, 6.35; N, 10.59.

E) Preparation of HCl.p-NH₂CH₂C₆H₄NHC(NCbz)NHCbz

By a method substantially equivalent to that described in example 23-A, 4.7 g (89%) of HCl.p-NH₂CH₂C₆H₄NHC(NCbz)NHCbz, a white solid, was prepared from p-BocNHCH₂C₆H₄NHC(NCbz)NHCbz.

IR
¹H NMR
FD-MS, m/e 433 (MH⁺)

F) Preparation of EtSO₂-D-Phe-Pro-p-NHCH₂C₆H₄NHC(NH)NH₂.HCl

By methods substantially equivalent to those described in example 1-G and example 18-F, 1.1 g of EtSO₂-D-Phe-Pro-p-NHCH₂C₆H₄NHC(NH)NH₂.HCl was prepared from EtSO₂-D-Phe-ProOH and HCl.p-NH₂CH₂C₆H₄NHC(NCbz)NHCbz.

IR
¹H NMR
FD-MS, m/e 501 (M⁺)

Analysis for $C_{24}H_{32}N_6O_4S.HCl.H_2O$: Calc: C, 51.73; H, 6.36; N, 15.14; Found: C, 52.32; H, 5.99; N, 14.79.

EXAMPLE 35

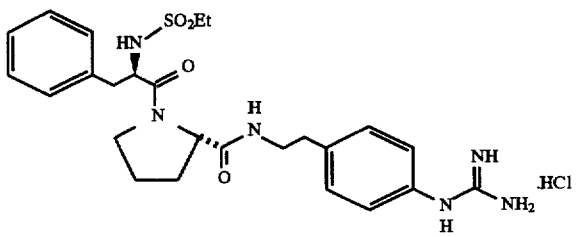

EtSO₂—D—Phe—Pro-p-NHCH₂CH₂C₆H₄NHC(NH)NH₂.HCl

By methods substantially equivalent to those described in example 34, 1.8 g of EtSO₂-D-Phe-Pro-p-NHCH₂CH₂C₆H₄CNH(NH)NH₂.HCl was prepared from 4-nitrophenethylamine.HCl.

IR
¹H NMR
FD-MS, m/e 515 (MH⁺)

HRMS (FAB), m/e calcd. for $C_{25}H_{35}N_6O_4S$: 515.2441 Found: 515.2483

EXAMPLE 36

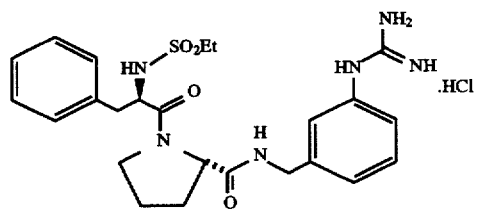

EtSO₂—D—Phe—Pro-m-NHCH₂C₆H₄NHC(NH)NH₂.HCl

By methods substantially equivalent to those described in examples 30-C and 34-B through 34-F, 1.8 g of EtSO₂-D-Phe-Pro-m-NHCH₂ C₆H₄NHC(NH)NH₂.HCl was prepared from 3-nitrobenzyl bromide.

IR
¹H NMR
FD-MS, m/e 501 (MH⁺)

HRMS (FAB), m/e calcd. for $C_{24}H_{33}N_6O_4S$: 501.2284 Found: 501.2280

EXAMPLE 37

EtSO₂—D—Phe—Pro-m-NHCH₂CH₂C₆H₄NHC(NH)NH₂.HCl

By methods substantially equivalent to those described in examples 26-D, 26-B (using 5% Pd/C in place of Pd/BaSO₄ and ethyl acetate in place of toluene), and 34-D through 34-F, 0.85 g of EtSO₂-D-Phe-Pro-m-NHCH₂CH₂C₆H₄NHC(NH)NH₂.HCl was prepared from 3-nitrocinnamic acid.

¹H NMR

FD-MS, m/e 515 (MH⁺)

Analysis for $C_{25}H_{34}N_6O_4S.2.2HCl.0.5H_2O$: Calc: C, 49.73; H, 6.21; N, 13.92; Found: C, 49.45; H, 5.82; N, 13.55.

EXAMPLE 38

D-1-Piq—Pro-p-NHCH₂C₆H₄NHC(NH)NH₂.2HCl

By methods substantially equivalent to those described in example 34, 0.94 g of D-1-Piq-Pro-p-NHCH₂C₆H₄NHC(NH)NH₂.2HCl was prepared. The final product was purified by RPHPLC (method 2, 98/2 (A/B), ramp to 70/30 (A/B), 180 min.

¹H NMR

FD-MS, m/e 427 (MH⁺)

Analysis for $C_{23}H_{34}N_6O_2.2HCl$: Calc: C, 55.31; H, 7.26; N, 16.82; Cl, 14.20; Found: C, 55.05; H, 7.23; N, 16.55; Cl, 14.24.

EXAMPLE 39

D-1-Piq—Pro-p-NHCH₂CH₂C₆H₄NHC(NH)NH₂.2HCl

By methods substantially equivalent to those described in example 35, 1.03 g of D-1-Piq-Pro-p-NHCH₂CH₂C₆H₄NHC(NH)NH₂.2HCl was prepared. The final product was purified by RPHPLC (method 2, 98/2 (A/B), ramp to 70/30 (A/B), 180 min.

¹H NMR

FD-MS, m/e 441 (M⁺)

Analysis for $C_{24}H_{36}N_6O_2.2HCl.1.5H_2O$: Calc: C, 53.33; H, 7.65; N, 15.55; Cl, 13.12; Found: C, 53.41; H, 7.45; N, 15.37; Cl, 13.48.

EXAMPLE 40

D-1-Piq—Pro-m-NHCH₂C₆H₄NHC(NH)NH₂.2HCl

By methods substantially equivalent to those described in example 36, 1.04 g of D-1-Piq-Pro-m-NHCH₂C₆H₄NHC(NH)NH₂.2HCl was prepared. The final product was purified by RPHPLC (method 2, 98/2 (A/B), ramp to 70/30 (A/B), 180 min.

¹H NMR

FD-MS, m/e 427 (M⁺)

Analysis for $C_{23}H_{34}N_6O_2.2HCl.H_2O$: Calc: C, 53.38; H, 7.40; N, 16.24; Cl, 13.70; Found: C, 53.25; H, 7.50; N, 16.23; Cl, 13.88.

EXAMPLE 41

D-1-Piq—Pro-m-NHCH₂CH₂C₆H₄NHC(NH)NH₂.2HCl

By methods substantially equivalent to those described in example 37, 0.96 g D-1-Piq-Pro-m-NHCH₂CH₂C₆H₄NHC(NH)NH₂.2HCl of was prepared. The final product was purified by RPHPLC (method 2, 98/2 (A/B), ramp to 70/30 (A/B), 180 min.

¹H NMR

FD-MS, m/e 441 (M⁺)

Analysis for $C_{24}H_{36}N_6O_2.2.1HCl.1.5H_2O$: Calc: C, 52.97; H, 7.61; N, 15.44; Cl, 13.68; Found: C, 52.80; H, 7.57; N, 15.46; Cl, 13.35.

EXAMPLE 42

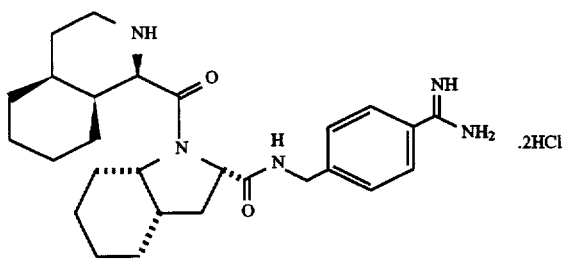

D-1-Piq-cis-Ohi-p-NHCH$_2$C$_6$H$_4$C(NH)NH$_2$.2HCl

A) Preparation of Cbz-DL-1-Piq-cis-Ohi-OEt

By a method substantially equivalent to that described in Example 1-A, 16.6 g (100%) of Cbz-DL-1-Piq-cis-Ohi-OEt was prepared from Cbz-DL-1-Piq-OH and cis-Ohi-OEt.HCl.

$^1$H NMR

FD-MS, m/e 496 (M$^+$)

Analysis for C$_{29}$H$_{40}$N$_2$O$_5$: Calc: C, 70.13; H, 8.12; N, 5.64; Found: C, 69.96; H, 8.23; N, 5.73.

B) Preparation of Cbz-D-1-Piq-cis-Ohi-p-NHCH$_2$C$_6$H$_4$C(NH)NHCbz

By methods substantially equivalent to those described in Example 1-D and 18-E, Cbz-D-1-Piq-cis-Ohi-p-NHCH$_2$C$_6$H$_4$C(NH)NHCbz and Cbz-L-1-Piq-cis-Ohi-p-NHCH$_2$C$_6$H$_4$C(NH)NHCbz were prepared from Cbz-D,L-1-Piq-Pro-OH and p-H$_2$NCH$_2$C$_6$H$_4$C(NH)NHCbz.2HCl. These diastereomers were separated by silica gel chromatography using an ethyl acetate/hexanes gradient. The fractions containing the leading diastereomer (R$_f$=0.31, ethyl acetate) were pooled and concentrated to give 1.3 g of Cbz-L-1-Piq-cis-Ohi-p-NHCH$_2$C$_6$H$_4$C(NH)NHCbz. The fractions containing the trailing diastereomer (R$_f$=0.19, ethyl acetate) were pooled and concentrated to give 1.5 g of Cbz-D-i-Piq-cis-Ohi-p-NHCH$_2$C$_6$H$_4$C(NH)NHCbz as a white foam.

$^1$H NMR

FD-MS, m/e 735 (MH$^+$)

Analysis for C$_{43}$H$_{51}$N$_5$O$_6$: Calc: C, 70.37; H, 7.00; N, 9.54; Found: C, 70.20; H, 7.22; N, 9.36.

C) Preparation of D-1-Piq-cis-Ohi-p-NHCH$_2$C$_6$H$_4$C(NH)NH$_2$.2HCl

By a method substantially equivalent to that described in Example 18-F, 0.61 g (63%) of D-1-Piq-cis-Ohi-p-NHCH$_2$C$_6$H$_4$ C(NH)NH$_2$.2HCl were prepared from Cbz-D-1-Piq-cis-Ohi-p-NHCH$_2$C$_6$H$_4$C(NH)NHCbz. The HPLC gradient used in this case was a ramp of 98/2 A/B to 70/30 A/B over 120 minutes.

$^1$H NMR

FAB-MS, m/e 466.4 (MH$^+$)

Analysis for C$_{27}$H$_{39}$N$_5$O$_2$.2HCl.1H$_2$O: Calc: C, 58.27; H, 7.79; N, 12.58; Found: C, 58.66; H, 7.56; N, 12.78.

EXAMPLE 43

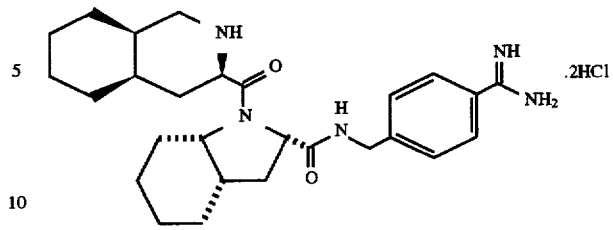

D-3-Piq-cis-Ohi-p-NHCH$_2$C$_6$H$_4$C(NH)NH$_2$.2HCl

A) Preparation of D-3-Piq-cis-Ohi-p-NHCH$_2$C$_6$H$_4$C(NH) NH$_2$.2HCl

By methods substantially equivalent to those described in Example 1-A, 1-D, 18-E, and 18-F, 1.3 g of 3-Piq-cis-Ohi-P-NHCH$_2$C$_6$H$_4$C(NH)NH$_2$.2HCl was prepared. The HPLC gradient used in this case was a ramp of 98/2 A/B to 70/30 A/B over 120 minutes.

$^1$H NMR

FAB-MS, m/e 466.4 (MH$^+$)

Analysis for C$_{27}$H$_{39}$N$_5$O$_2$.2HCl: Calc: C, 60.22; H, 7.67; N, 13.00; Found: C, 59.95; H, 7.73; N, 12.89.

EXAMPLE 44

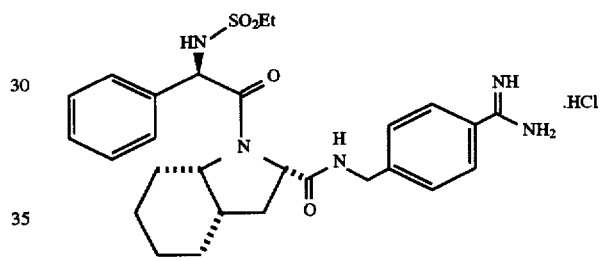

EtSO$_2$—Phg-cis-Ohi-p-NHCH$_2$C$_6$H$_4$C(NH)NH$_2$.HCl
((S-cis)-N-[[4-(amino iminomethyl)phenyl]methyl]-1-[N-(ethylsulfonyl)-D-phenylglycyl]-1H-indole-2-carboxamide hydrochloride)

A) Preparation of Boc-D-Phg-cis-Ohi-OEt

By a method substantially equivalent to that described in Example 1-A, 14.9 g (58%) of Boc-D-Phg-cis-Ohi-OEt was prepared from Boc-D-Phg-OH and (S)-cis-octahydroindole-2-carboxylic acid ethyl ester.HCl.

$^1$H NMR

FD-MS, m/e 430 (M$^+$)

Analysis for C$_{24}$H$_{34}$N$_2$O$_5$: Calc: C, 66.95; H, 7.96; N, 6.51; Found: C, 66.69; H, 8.02; N, 6.40.

B) Preparation of D-Phg-cis-Ohi-OEt.HCl

To a cold (0° C.), stirring solution of Boc-D-Phg-cis-Ohi-OEt in ethyl acetate was bubbled HCl gas for 10 min. After stirring for 2 h while warming to room temperature, the solvent was removed in vacuo. The resulting solid was suspended in diethyl ether and subsequently isolated by filtration to give 10.7 g (97%) of D-Phg-cis-Ohi-OEt.HCl.

$^1$H NMR

FD-MS, m/e 331 (M$^+$)

Analysis for C$_{19}$H$_{27}$N$_2$O$_3$Cl: Calc: C, 62.20; H, 7.41; N, 7.64; Found: C, 62.42; H, 7.36; N, 7.85.

C) Preparation of EtSO$_2$-D-Phg-cis-Ohi-OEt

To a solution of D-Phg-cis-Ohi-OEt.HCl (10 g, 27 mmol) and N,N-diisopropylethylamine (10.7 mL, 61 mmol) in THF (200 mL) at −78° C., was added dropwise via an addition funnel a solution of ethanesulfonyl chloride (3.9 g, 30 mmol) in THF (20 mL). The cold bath was then left unattended and the solution warmed slowly to room temperature. After about 18 h, the solution was concentrated in vacuo. The residue was dissolved in ethyl acetate (200 mL), washed twice each with 1N citric acid (200 mL), saturated aqueous NaHCO$_3$ (200 mL) and brine (200 mL). The organic phase was then dried with MgSO$_4$, filtered, and concentrated in vacuo to give 11.2 g (97%) of a yellow foam.

$^1$H NMR

FD-MS, m/e 422 (M$^+$)

Analysis for C$_{21}$H$_{30}$N$_2$O$_5$S: Calc: C, 59.69; H, 7.16; N, 6.63; Found: C, 59.94; H, 7.08; N, 6.78.

D) Preparation of EtSO$_2$-Phg-cis-Ohi-p-NHCH$_2$C$_6$H$_4$C(NH)NH$_2$.HCl

By methods substantially equivalent to those described in Examples 1-D, 18-E and 18-F, 0.62 g of EtSO$_2$-Phg-cis-Ohi-p-NHCH$_2$C$_6$H$_4$C(NH)NH$_2$.2HCl were obtained. The HPLC gradient used in this case was a ramp of 90/10 A/B to 60/40 A/B over 120 minutes.

$^1$H NMR

FAB-MS, m/e 526.3 (MH$^+$)

Analysis for C$_{27}$H$_{35}$N$_5$O$_4$S.HCl: Calc: C, 57.69; H, 6.45; N, 12.46; Found: C, 57.47; H, 6.48; N, 12.20.

EXAMPLE 45

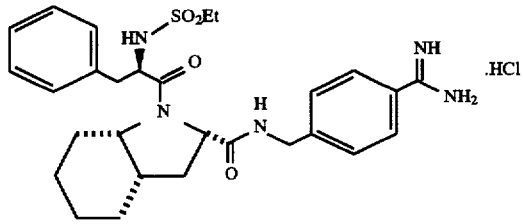

EtSO$_2$—Phe-cis-Ohi-p-NHCH$_2$C$_6$H$_4$C(NH)NH$_2$.HCl
((S-cis)-N-[[4-(aminoiminomethyl)phenyl]methyl]-1-[N-(ethylsulfonyl)-D-phenylalanyl]-1H-indole-2-carboxamide hydrochloride)

A) Preparation of EtSO$_2$-Phe-cis-Ohi-p-NHCH$_2$C$_6$H$_4$C(NH)NH$_2$.2HCl

By methods substantially equivalent to those described in Example 44, 1.5 g EtSO$_2$-Phe-cis-Ohi-p-NHCH$_2$C$_6$H$_4$C(NH)NH$_2$.HCl were prepared from Boc-D-Phe-OH.

$^1$H NMR

FAB-MS, m/e 540.3 (MH$^+$)

Analysis for C$_{28}$H$_{37}$N$_5$O$_4$S.HCl.H$_2$O: Calc: C, 56.51; H, 6.94; N, 11.77; Found: C, 56.24; H, 6.55; N, 11.72.

EXAMPLE 46

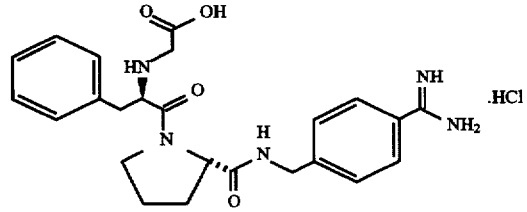

HOOCCH$_2$—D—Phe—Pro-p-NHCH$_2$C$_6$H$_4$C(NH)NH$_2$.HCl
(N-(carboxymethyl)-D-phenylalanyl-N-[[4-(aminoiminomethyl)phenyl]methyl]-L-prolinamide hydrochloride)

A) Preparation N-(t-BuOOCCH$_2$)-N-Boc-D-Phe-Pro-OBn

To a solution of D-Phe-Pro-OBn.HCl (20 g, 51 mmol) in DMF (100 mL) was added t-butyl bromoacetate (9.9 g, 56 mmol) in one portion and N,N-diisopropylethylamine (17.4 mL, 101 mmol) dropwise over 30 min. This mixture was allowed to stir for 18 hrs at room temperature. Di-t-butyl dicarbonate (16.6 g, 76 mmol) and N,N-diisopropylethylamine (13.2 mL, 76 mmol) were then added in one portion and the reaction was allowed to stir an additional 24 h. The solvent was removed in vacuo and the residue was partitioned between ethyl acetate (1 L) and 1M aqueous citric acid (500 mL). The layers were separated and the organic phase was washed once with 1M aqueous citric acid, twice with saturated aqueous sodium bicarbonate, and once with brine (500 mL each). The organic phase was dried (Na$_2$SO$_4$), filtered, and concentrated in vacuo. The amber oil was purified by silica gel chromatography eluting with a ethyl acetate/hexanes gradient (hexanes to 30% ethyl acetate/hexanes). Fractions containing product were combined and concentrated to give 19.0 g (66%) as a colorless oil which slowly crystallized upon standing.

$^1$H NMR

FD-MS, m/e 566 (M$^+$)

Analysis for C$_{32}$H$_{42}$N$_2$O$_7$: Calc: C, 67.82; H, 7.47; N, 4.94; Found: C, 68.06; H, 7.33; N, 5.17.

B) Preparation of N-(t-BuOOCCH$_2$)-N-Boc-D-Phe-Pro-OH

To a solution of N-(t-BuOOCCH$_2$)-N-Boc-D-Phe-Pro-OBn (18.5 g, 33 mmol) in ethyl acetate (250 mL) was added 5% Pd/C catalyst (5 g). This solution was degassed in vacuo several times and placed under an atmosphere of hydrogen for 2 h with stirring. The balloon was removed, diatomaceous earth was added and the slurry was filtered over a pad of diatomaceous earth. The filtrate was concentrated in vacuo to give 13.2 g (84%) of a white foam.

$^1$H NMR

FD-MS, m/e 476 (M$^+$)

Analysis for C$_{25}$H$_{36}$N$_2$O$_7$: Calc: C, 63.01; H, 7.61; N, 5.88; Found: C, 63.23; H, 7.73; N, 5.59.

C) Preparation of N-(t-BuOOCCH$_2$)-N-Boc-D-Phe-Pro-p-NHCH$_2$C$_6$H$_4$C(NH)NHCbz By a method substantially equivalent to Example 18-E, 2.7 g (90%) of N-(t-BuOOCCH$_2$)-N-Boc-D-Phe-Pro-p-NHCH$_2$C$_6$H$_4$C(NH)NHCbz was prepared from N-(t-BuOOCCH$_2$)-N-Boc-D-Phe-Pro-OH and p-H$_2$NCH$_2$C$_6$H$_4$C(NH)NHCbz.2HCl.

$^1$H NMR

FD-MS, m/e 743 (MH$^+$)

Analysis for C$_{41}$H$_{51}$N$_5$O$_8$: Calc: C, 66.38; H, 6.93; N, 9.44; Found: C, 66.08; H, 6.92; N, 9.16.

D) Preparation of HOOCCH$_2$-D-Phe-Pro-p-NHCH$_2$C$_6$H$_4$C(NH)NH$_2$.HCl

To a cooled (0° C.) solution of N-(t-BuOOCCH$_2$)-N-Boc-D-Phe-Pro-P-NHCH$_2$C$_6$H$_4$C(NH)NHCbz (2.2 g, 3 mmol) in dioxane (100 mL) was bubbled HCl gas for 10 minutes. After stirring for 3 h while warming to room temperature, the dioxane was removed in vacuo. The residue was dissolved in a mixture of absolute ethanol (150 mL), water (75 mL) and 1N HCl (6 mL). To this was added 5% Pd/C (1 g). After degassing using vacuum, this mixture was placed under a hydrogen atmosphere for 16 h while stirring at room temperature. Diatomaceous earth was added and the resulting slurry was filtered over a pad of diatomaceous earth. The filtrate was concentrated in vacuo to a residue and this was immediately purified by HPLC Method 2 (98/2 A/B to 70/30 A/B ramp over 2 hrs). Fractions containing pure product were pooled and lyophilized to give 1.1 g (72%) of a white solid.

$^1$H NMR

FAB-MS, m/e 452.3 (MH$^+$)

Analysis for C$_{24}$H$_{29}$N$_5$O$_4$.2HCl: Calc: C, 54.97; H, 5.96; N, 13.35; Found: C, 55.21; H, 6.11; N, 13.39.

EXAMPLE 47

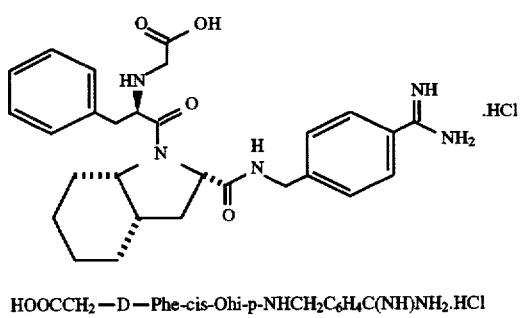

HOOCCH₂—D—Phe-cis-Ohi-p-NHCH₂C₆H₄C(NH)NH₂.HCl

A) Preparation t-BuOOCCH₂-D-Phe-cis-Ohi-OEt

To a solution of D-Phe-cis-Ohi-OEt.HCl (30 g, 79 mmol) in acetonitrile (400 mL) was added N,N-diisopropylethylamine (41 mL, 236 mmol) and t-butyl bromoacetate (14 mL, 87 mmol). This solution was warmed to 50° C. and maintained there for 3 h. After cooling to room temperature, the solution was concentrated in vacuo. The residue was dissolved in ethyl acetate (300 mL) and this solution was washed twice with saturated aqueous ammonium chloride (200 mL), twice with saturated aqueous sodium bicarbonate (200 mL), and twice with brine (200 mL). The organic layer was dried (MgSO₄), filtered, and concentrated in vacuo to give an orange oil which was purified by silica gel chromatography eluting with a gradient of hexanes to 1:1 hexanes/ethyl acetate. Fractions containing product (as judged by TLC) were combined and concentrated to give 33.2 g (92%) of a colorless oil.

¹H NMR

FD-MS, m/e 458 (M⁺)

Analysis for C₂₆H₃₈N₂O₅: Calc: C, 68.10; H, 8.35; N, 6.11; Found: C, 68.37; H, 8.47; N, 5.90.

B) Preparation of N-(t-BuOOCCH₂)-N-Boc-D-Phe-cis-Ohi-OH

To a solution of t-BuOOCCH₂-D-Phe-cis-Ohi-OEt (30 g, 65 mmol) in THF (200 mL) was added N,N-diisopropylethylamine (17 mL, 98 mmol) and di-t-butyl dicarbonate (15.7 g, 72 mmol). This solution was brought to gentle reflux and maintained for 16 hrs. Heating was discontinued, and once cool, the solution was concentrated in vacuo. The residue was dissolved in ethyl acetate (400 mL) and washed twice with 1.0M citric acid (200 mL), twice with saturated aqueous sodium bicarbonate (200 mL), and twice with brine (200 mL). The organic solution was dried (MgSO₄), filtered, and concentrated in vacuo to give a yellow oil. A portion of this oil (24.8 g, 44 mmol) was dissolved in 300 mL of dioxane. To this was added a solution consisting of 2.05 g LiOH.H₂O (49 mmol) in 150 mL water. This mixture was allowed to stir for 5 hrs at room temp at which time 100 mL of saturated aqueous ammonium chloride was added. Solvents were removed in vacuo and the residue was partitioned between saturated aqueous sodium bicarbonate and diethyl ether. The layers were separated and the aqueous layer was acidified to pH 3 with citric acid. The acidic aqueous solution was extracted 3 times with diethyl ether (200 mL) and these were combined, dried (MgSO₄), filtered and concentrated to give 24.3 g of N-(t-BuOOCCH₂)-N-Boc-D-Phe-cis-Ohi-OH as a white foam.

¹H NMR

FD-MS, m/e 530 (M⁺)

Analysis for C₂₉H₄₂N₂O₇: Calc: C, 65.64; H, 7.98; N, 5.28; Found: C, 65.39; H, 8.04; N, 5.39.

C) Preparation of HOOCCH₂-D-Phe-cis-Ohi-p-NHCH₂C₆H₄C(NH)NH₂.HCl

By methods substantially equivalent to those described in Example 18-E and 46-D, 1.2 g (67%) of HOOCCH₂-D-Phe-cis-Ohi-p-NHCH₂C₆H₄C(NH)NH₂.HCl were obtained.

¹H NMR

FAB-MS, m/e 506.3 (MH⁺)

Analysis for C₂₈H₃₅N₅O₄.2HCl.H₂O: Calc: C, 57.24; H, 6.52; N, 11.92; Found: C, 57.40; H, 6.30; N, 11.69.

EXAMPLE 48

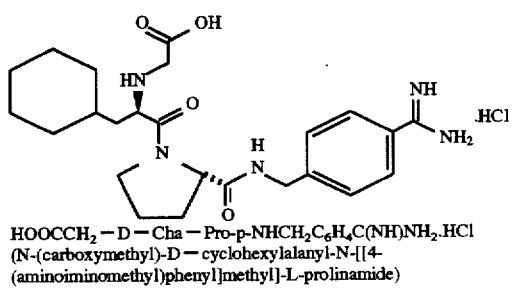

HOOCCH₂—D—Cha—Pro-p-NHCH₂C₆H₄C(NH)NH₂.HCl
(N-(carboxymethyl)-D—cyclohexylalanyl-N-[[4-(aminoiminomethyl)phenyl]methyl]-L-prolinamide)

A) Preparation of HOOCCH₂-D-Cha-Pro-p-NHCH₂C₆H₄C(NH)NH₂.HCl

By methods substantially equivalent to those described in Example 46, 0.92 g of HOOCCH₂-D-Cha-Pro-p-NHCH₂C₆H₄C(NH)NH₂.HCl were prepared.

¹H NMR

FD-MS, m/e 458 (M⁺)

Analysis for C₂₄H₃₅N₅O₄.HCl.0.5H₂O: Calc: C, 57.30; H, 7.41; N, 13.92; Found: C, 57.52; H, 7.29; N, 13.83.

EXAMPLE 49

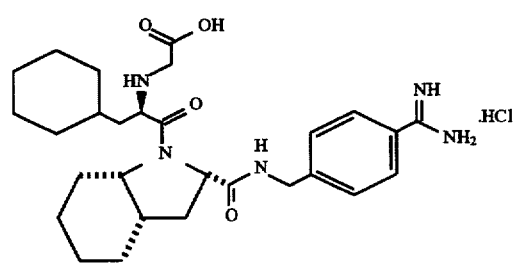

HOOCCH₂—D—Cha-cis-Ohi-p-NHCH₂C₆H₄C(NH)NH₂.HCl
((S—cis)-N- [[4-(aminoiminomethyl)phenyl]methyl]-1-[N-(carboxymethyl)-D-cyclohexylalanyl-1H-indole-2-carboxamide hydrochloride)

A) Preparation of HOOCCH₂-D-Phe-cis-Ohi-p-NHCH₂C₆H₄C(NH)NH₂.HCl

By methods substantially equivalent to those described in Example 1-A and 1-D, 18-E, 44-B, 47-A(using benzyl bromoacetate) and 18-F, 0.75 g of HOOCCH₂-D-Cha-cis-Ohi-p-NHCH₂C₆H₄C(NH)NH₂.HCl were obtained starting from Boc-D-Cha and cis-Ohi-OEt.HCl. HPLC Method 2 was used in the purification of this material using a gradient of 98/2 A/B to 70/30 A/B over 3 h.

¹H NMR

FAB-MS, m/e 512.3 (MH⁺)

Analysis for C₂₈H₄₁N₅O₄.HCl: Calc: C, 61.36; H, 7.72; N, 12.78; Found: C, 61.08; H, 7.47; N, 12.53.

EXAMPLE 50

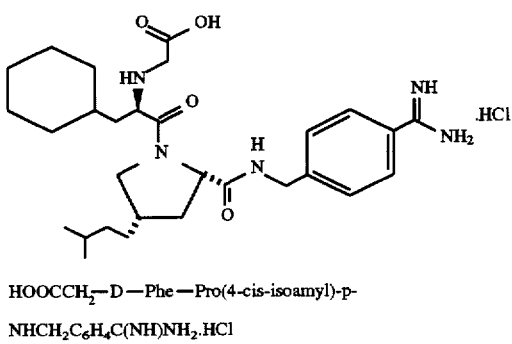

HOOCCH₂—D—Phe—Pro(4-cis-isoamyl)-p-
NHCH₂C₆H₄C(NH)NH₂·HCl

A) Preparation of Cbz-Pro(4-trans-OH)-OEt

To a solution of Cbz-Pro(4-trans-OH)-OH (33 g, 124 mmol) in ethanol (500 mL) was added p-toluenesulfonic acid (1 g) and the solution was heated to reflux. After 16 h, the solution was cooled to room temperature, and the solvent was removed in vacuo. The residue was dissolved in ethyl acetate (400 mL) and washed twice with saturated aqueous NaHCO₃, and twice with a saturated aqueous sodium chloride solution. The ethyl acetate solution was dried with MgSO₄, filtered and concentrated in vacuo to give 34.5 g (95%) of a colorless oil.

¹H NMR
FD-MS, m/e 293 (M⁺)

Analysis for C₁₅H₁₉NO₅: Calc: C, 61.42; H, 6.53; N, 4.77; Found: C, 61.20; H, 6.65; N, 4.73.

B) Preparation of Cbz-Pro(4-oxo)-OEt

Cbz-Pro(4-trans-OH)-OEt (32.7 g, 111 mmol) was dissolved in dichloromethane (500 mL) with mechanical stirring in a 1 L round bottom flask. To this solution was added 3 Å molecular sieves (100 g) and pyridinium chlorochromate (60 g, 278 mmol), in portions small enough to maintain efficient stirring. After stirring for 12 h at room temperature, diethyl ether (200 mL) was added and the black slurry was decanted from a tarry residue and flushed through a column of silica gel (200 g). The residue was washed twice with dichloromethane (200 mL) and the combined washings were also passed through the silica plug. The filtrate was flushed through a silica gel column with 1:1 ethyl acetate/hexanes (4 L) and 500 mL fractions were collected. All fractions containing product, as judged by TLC, were combined and concentrated in vacuo to give 23.8 g (74%) of a colorless oil.

¹H NMR
FD-MS, m/e 291 (M⁺)

Analysis for C₁₅H₁₇NO₅: Calc: C, 61.85; H, 5.88; N, 4.81; Found: C, 61.57; H, 5.82; N, 4.71.

C) Preparation of Cbz-Pro(4-isobutylmethylidene)-OEt

Potassium t-butoxide (34 g, 288 mmol) was suspended in tetrahydrofuran (800 mL) in an oven dried 2-neck 2 L round bottom flask equipped with a nitrogen inlet, magnetic stir bar, and addition funnel. To this suspension was added, in several portions, isoamyltriphenylphosphonium bromide (120 g, 288 mmol). After stirring for 30 min, a solution of Cbz-Pro(4-oxo)-OEt (70 g, 240 mmol) in tetrahydrofuran (150 mL) was added dropwise via an addition funnel over a 1 h period. After stirring for an additional 2 h, saturated aqueous NH₄Cl (100 mL) was added. This solution was diluted with ethyl acetate (750 mL) and the layers were separated. The organic layer was washed two times with 1N citric acid, twice with saturated aqueous NaHCO₃, and twice with a saturated aqueous sodium chloride solution. The organic solution was dried with MgSO₄, filtered and concentrated to give a yellow oil. This oil was purified by flash chromatography over silica gel, eluting with 2:1 hexanes/ethyl acetate. Fractions containing product (as judged by TLC) were combined and concentrated in vacuo to give 37 g (45%) of a colorless oil.

¹H NMR
FD-MS, m/e 345 (M⁺)

Analysis for C₂₀H₂₇NO₄: Calc: C, 69.54; H, 7.88; N, 4.05; Found: C, 69.74; H, 7.85; N, 3.99.

D) Preparation of Pro(4-cis-isoamyl)-OEt·HCl

To a solution of Cbz-Pro(4-isobutylmethylidene)-OEt (37 g, 107 mmol) in ethanol (500 mL) was added 5% Pd/C (5 g). Nitrogen gas was bubbled through this solution for 5 min and then hydrogen gas was bubbled through for 3 h. The solution was filtered through a pad of diatomaceous earth. Hydrogen chloride gas was then bubbled through the solution until saturation, and then the solution was concentrated in vacuo to give 26 g (97%) of amber oil.

¹H NMR
FD-MS, m/e 214 (M⁺)

Analysis for C₁₂H₂₄ClNO₂: Calc: C, 57.70; H, 9.68; N, 5.61; Found: C, 57.46; H, 9.50; N, 5.82.

E) Preparation of HOOCCH₂-D-Phe-Pro(4-cis-isoamyl)-p-NHCH₂C₆H₄C(NH)NH₂·HCl

By methods substantially equivalent to those described in Example 1-A and 1-D, 18-E, 44-B, 47-A(using benzyl bromoacetate) and 18-F, 0.27 g of HOOCCH₂-D-Phe-Pro(4-cis-isoamyl)-p-NHCH₂C₆H₄C(NH)NH₂·HCl were obtained starting from Boc-D-Cha and Pro(4-cis-isoamyl)-OEt·HCl. HPLC Method 2 was used in the purification of this material using a gradient of 98/2 A/B to 50/50 A/B over 3 h.

¹H NMR
FAB-MS, m/e 528.4 (MH⁺)

Analysis for C₂₉H₄₅N₅O₄·1.9HCl: Calc: C, 58.34; H, 7.92; N, 11.73; Cl, 11.28; Found: C, 58.30; H, 7.85; N, 11.83; Cl, 11.27.

EXAMPLE 51

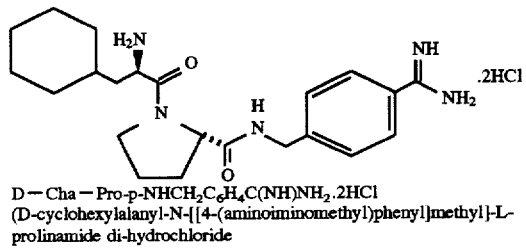

D—Cha—Pro-p-NHCH₂C₆H₄C(NH)NH₂·2HCl
(D-cyclohexylalanyl-N-{[4-(aminoiminomethyl)phenyl]methyl}-L-prolinamide di-hydrochloride A) Preparation of Boc-D-Cha-Pro-p-NHCH₂C₆H₄C(NH)NHCbz By methods substantially equivalent to those described in Examples 1-A, 46-E, and 18-E, 32.5 g (94%) of Boc-D-Cha-Pro-p-NHCH₂C₆H₄C(NH)NHCbz was prepared starting from Boc-D-Cha-Pro-OH.

¹H NMR
FD-MS, m/e 634 (M⁺)

Analysis for C₃₅H₄₇N₅O₆: Calc: C, 66.33; H, 7.47; N, 11.05; Found: C, 66.30; H, 7.47; N, 11.26.

B) Preparation of D-Cha-Pro-p-NHCH₂C₆H₄C(NH)NHCbz·2HCl

By a method substantially equivalent to that described in Example 23-A, 9.6 g (101%) of D-Cha-Pro-p-NHCH₂C₆H₄C(NH)NHCbz·2HCl was prepared from Boc-D-Cha-Pro-p-NHCH₂C₆H₄C(NH)NHCbz.

¹H NMR
FD-MS, m/e 534 (M⁺)

Analysis for C₃₀H₄₁N₅O₄Cl₂: Calc: C, 59.40; H, 6.81; N, 11.54; Cl, 11.69; Found: C, 59.54; H, 6.80; N, 11.77; Cl, 11.21.

C) Preparation of D-Cha-Pro-p-NHCH$_2$C$_6$H$_4$C(NH)NH$_2$.2HCl

By a method substantially equivalent to that described in Example 18-F, 0.74 g (62%) of D-Cha-Pro-p-NHCH$_2$C$_6$H$_4$C(NH)NH$_2$.2HCl was prepared. HPLC Method 2 was used in the purification of this material using a gradient of 98/2 A/B to 75/25 A/B over 2.5 hrs.

$^1$H NMR

FAB-MS, m/e 400.3 (M$^+$)

Analysis for C$_{22}$H$_{33}$N$_5$O$_2$.2.1HCl: Calc: C, 55.50; H, 7.43; N, 14.71; Cl, 15.64; Found: C, 55.64; H, 7.50; N, 14.65; Cl, 15.81.

EXAMPLE 52

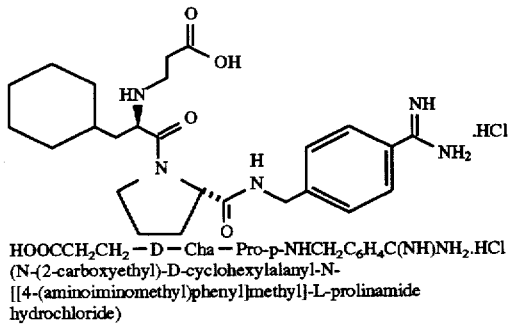

HOOCCH$_2$CH$_2$—D—Cha—Pro-p-NHCH$_2$C$_6$H$_4$C(NH)NH$_2$.HCl
(N-(2-carboxyethyl)-D-cyclohexylalanyl-N-[[4-(aminoiminomethyl)phenyl]methyl]-L-prolinamide hydrochloride)

A) Preparation of HOOCCH$_2$CH$_2$-D-Cha-Pro-p-NHCH$_2$C$_6$H$_4$C(NH)NH$_2$.HCl D-Cha-Pro-p-NHCH$_2$C$_6$H$_4$C(NH)NHCbz.2HCl (2.5 g, 4.1 mmol) was suspended in EtOAc (100 mL) with stirring. A solution of 1M KHCO$_3$ (100 mL) was added to the suspension and the mixture was stirred until all solid had dissolved. The mixture was transferred to a separatory funnel and the layers separated. The organic layer was dried (MgSO$_4$), filtered and concentrated in vacuo to give 1.24 g of the free base as a white solid. This solid was dissolved in EtOH (100 mL). Benzyl acrylate (0.41 g, 2.6 mmol) was added and the solution was stirred for 2 days at room temperature. Then, to this solution was added water (50 mL), 1N HCl (4.6 mL) and 5% Pd/C (0.5 g) and the stirring suspension was degassed and placed under an atmosphere of hydrogen. After 16 h, diatomaceous earth was added and the slurry was filtered over a pad of diatomaceous earth. The filtrate was concentrated to a volume of 25 mL in vacuo and purified by preparative RPHPLC method 2, using a gradient of 98/2 A/B to 75/25 A/B over 2.5 h. Fractions containing pure product (as judged by analytical HPLC) were pooled, concentrated and lyophilized to give 0.27 g (23%) of HOOCCH$_2$CH$_2$-D-Cha-Pro-p-NHCH$_2$C$_6$H$_4$C(NH)NH$_2$.HCl.

$^1$H NMR

FAB-MS, m/e 472.4 (MH$^+$)

Analysis for C$_{25}$H$_{37}$N$_5$O$_4$.1.9HCl: Calc: C, 55.50; H, 7.25; N, 12.94; Cl, 12.45; Found: C, 55.26; H, 7.26; N, 13.21; Cl, 12.85.

EXAMPLE 53

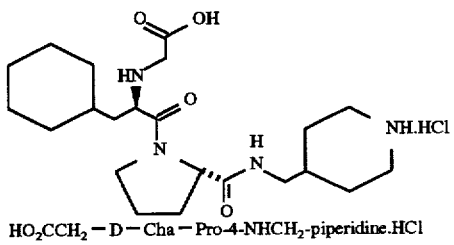

HO$_2$CCH$_2$—D—Cha—Pro-4-NHCH$_2$-piperidine.HCl

A) Preparation of Boc-4-(aminomethyl)pyridine

By a method substantially equivalent to that described in example 34-A, 19 g (87%) of Boc-4-(aminomethyl)pyridine was prepared from 4-(aminomethyl)pyridine.

$^1$H NMR

B) Preparation of 4-BocNHCH$_2$-N-Cbz-piperidine

4-BocNHCH$_2$-pyridine (10 g, 48 mmol) was dissolved in ethanol (280 mL) and 5% Rh/C (10 g) was added. The suspension was shaken under an atmosphere of hydrogen (4.1 bar, 60 psi) at 60° C. overnight. The catalyst was then filtered off and the solution was concentrated in vacuo to give 9.0 g of a gray solid. A 3.2 g portion of the solid was dissolved in tetrahydrofuran (75 mL) and an aqueous solution (75 mL) of potassium carbonate (4.2 g, 30 mmol) was added. To this stirring solution was added benzyl chloroformate (2.3 mL, 16 mmol). After 15 min, the solution was concentrated in vacuo to about ½ the original volume and then diluted with ethyl acetate. The organic phase was separated and washed with brine, then dried (MgSO$_4$), filtered and concentrated in vacuo to give 4.6 g (76%) of a white solid.

$^1$H NMR

FD-MS, m/e 349 (M$^+$)

C) Preparation of 4-NH$_2$CH$_2$—N-Cbz-piperidine.HCl

By a method substantially equivalent to that described in example 23-A, 3 g (84%) of 4-NH$_2$CH$_2$—N-Cbz-piperidine.HCl was prepared from 4-BocNHCH$_2$—N-Cbz-piperidine.

IR $^1$H NMR

FD-MS, m/e 249 (MH$^+$)

D) Preparation of N-(t-BuO$_2$CCH$_2$)-N-Boc-D-Cha-Pro-OH

N-(t-BuO$_2$CCH$_2$)-N-Boc-D-Phe-Pro-OH (13 g, 27 mmol) was dissolved in ethanol (750 mL) and PtO$_2$ (13 g) was added. The suspension was shaken under an atmosphere of hydrogen at 4.1 bar (60 psi) at 40° C. for 16 h. The catalyst was then filtered off and the filtrate was concentrated in vacuo to give 11.7 g (90%) of a white foam.

IR $^1$H NMR

FD-MS, m/e 483 (M$^+$)

Analysis for C$_{25}$H$_{42}$N$_2$O$_7$: Calc: C, 62.22; H, 8.77; N, 5.80; Found: C, 62.99; H, 8.96; N, 5.48.

E) Preparation of HO$_2$CCH$_2$-D-Cha-Pro-4-NHCH$_2$-piperidine.HCl

By methods substantially equivalent to those described in example 1-G and example 46-D, 1.1 g of HO$_2$CCH$_2$-D-Cha-Pro-4-NHCH$_2$-piperidine.HCl was prepared from N-(t-BuO$_2$CCH$_2$)-N-Boc-D-Cha-Pro-OH and HCl.4-NH$_2$CH$_2$-N-Cbz-piperidine. The product was purified by RPHPLC method 2, ramping from 98/2 (A/B) through 70/30 (A/B) over 2 h.

IR $^1$H NMR

FD-MS, m/e 423 (M$^+$)

Analysis for C$_{22}$H$_{38}$N$_4$O$_4$.2HCl.1.5H$_2$O: Calc: C, 50.57; H, 8.29; N, 10.72; Found: C, 50.31; H, 8.46; N, 10.93.

EXAMPLE 54

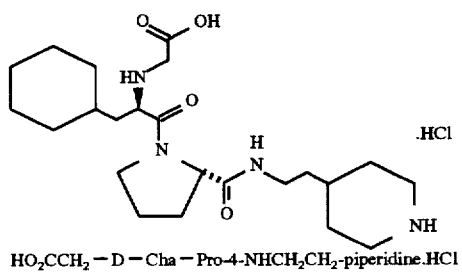

HO₂CCH₂—D—Cha—Pro-4-NHCH₂CH₂-piperidine.HCl

Preparation of HO₂CCH₂-D-Cha-Pro-4-NHCH₂CH₂-piperidine.HCl

By methods substantially equivalent to those described in example 52, 0.59 g of HO₂CCH₂-D-Cha-Pro-4-NHCH₂CH₂-piperidine.HCl was prepared from 4-aminoethylpyridine. The product was purified by RPHPLC method 2, ramping from 98/2 (A/B) through 70/30 (A/B) over 2 h.

IR
¹H NMR
FD-MS, m/e 437 (M⁺)

Analysis for $C_{23}H_{40}N_4O_4 \cdot 2.5HCl \cdot 1.5H_2O$: Calc: C, 49.80; H, 8.27; N, 10.10; Found: C, 49.95; H, 8.08; N, 10.34.

EXAMPLE 55

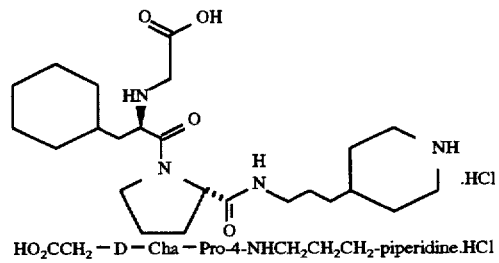

HO₂CCH₂—D—Cha—Pro-4-NHCH₂CH₂CH₂-piperidine.HCl

A) Preparation of 4-hydroxypropyl-N-Cbz-piperidine

By methods substantially equivalent to those described in example 53-B, 28 g (67%) of 4-hydroxypropyl-N-Cbz-piperidine was prepared from 4-hydroxypropylpyridine.

¹H NMR

B) Preparation of 4-(NH₂CH₂CH₂CH₂)-N-Cbz-piperidine.HCl

By methods substantially equivalent to those described in examples 30-B, 30-C and 30-D, 7.3 g of 4-(NH₂CH₂CH₂CH₂)-N-Cbz-piperidine.HCl were prepared from 4-hydroxypropyl-N-Cbz-piperidine.

¹H NMR
FD-MS, m/e 276 (M⁺)

C) Preparation of HO₂CCH₂-D-Cha-Pro-4-NHCH₂CH₂CH₂-piperidine.HCl

By methods substantially equivalent to those described in example 53-D and 53-E, 0.39 g of HO₂CCH₂-D-Cha-Pro-4-NHCH₂CH₂CH₂-piperidine.HCl was prepared from N-(t-BuO₂CCH₂)—N-Boc-D-Cha-Pro-OH and 4-aminopropyl-N-Cbz-piperidine.HCl. The product was purified by RPHPLC method 2, ramping from 98/2 (A/B) through 70/30 (A/B) over 2 h.

IR
¹H NMR
IS-MS, m/e 451.4 (MH⁺)

Analysis for $C_{24}H_{42}N_4O_4 \cdot 2HCl \cdot H_2O$: Calc: C, 53.23; H, 8.56; N, 10.35; Found: C, 53.43; H, 8.63; N, 10.19.

EXAMPLE 56

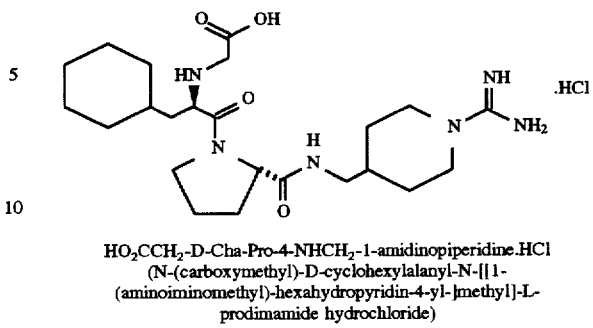

HO₂CCH₂-D-Cha-Pro-4-NHCH₂-1-amidinopiperidine.HCl
(N-(carboxymethyl)-D-cyclohexylalanyl-N-[[1-(aminoiminomethyl)-hexahydropyridin-4-yl-]methyl]-L-prodinamide hydrochloride)

Preparation of HO₂CCH₂-D-Cha-Pro-4-NHCH₂-1-amidinopiperidine.HCl

By methods substantially equivalent to those described in examples 34-D, 23-A, 1-G (using N-(t-BuO₂CCH₂)-N-Boc-D-Cha-Pro-OH), 18-E, and 1-H, 0.35 g of HO₂CCH₂-D-Cha-Pro-4-NHCH₂-1-amidinopiperidine.HCl was prepared from 4-BocNHCH₂piperidine. The final product was purified by RPHPLC method 2 (98/2 (A/B) ramp to 75/25 (A/B), 150 min).

IR
¹H NMR
FAB-MS, m/e 465 (MH⁺)

Analysis for $C_{23}H_{40}N_6O_4 \cdot 2HCl$: Calc: C, 51.39; H, 7.88; N, 15.63; Cl, 13.19; Found: C, 51.66; H, 7.98; N, 15.80; Cl, 13.48.

EXAMPLE 57

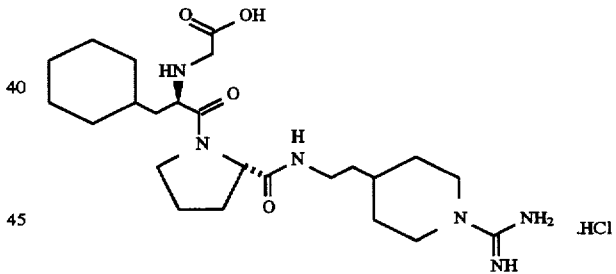

HO₂CCH₂-D-Cha-Pro-4-NHCH₂CH₂-1-amidinopiperidine.HCl

Preparation of HO₂CCH₂-D-Cha-Pro-4-NHCH₂CH₂-1-amidinopiperidine.HCl

By methods substantially equivalent to those described in examples 34-D, 23-A, 1-G (using N-(t-BuO₂CCH₂)-N-Boc-D-Cha-Pro-OH), 18-E, and 1-H, 0.34 g of HO₂CCH₂-D-Cha-Pro-4-NHCH₂CH₂-1-amidinopiperidine.HCl were prepared from 4-BocNHCH₂CH₂-piperidine. The final product was purified by RPHPLC method 2 (98/2 (A/B) ramp to 75/25 (A/B), 150 min).

IR
¹H NMR
FAB-MS, m/e 479.4 (MH⁺)

Analysis for $C_{24}H_{42}N_6O_4 \cdot 2HCl$: Calc: C, 52.26; H, 8.07; N, 15.24; Cl, 12.86; Found: C, 52.56; H, 8.15; N, 15.37; Cl, 13.07.

EXAMPLE 58

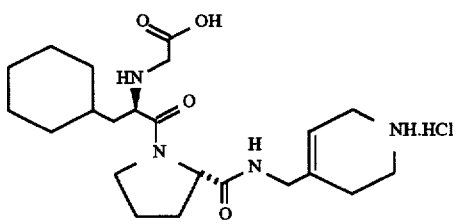

HO$_2$CCH$_2$-D-Cha-Pro-4-NHCH$_2$-3,4-dehydro-piperidine.HCl

A) Preparation of 4-BocNHCH$_2$-N-methyl-pyridinium iodide

To a stirring solution of 4-BocNHCH$_2$-pyridine (20 g, 96 mmol) in acetonitrile (200 mL) was added iodomethane (8.9 mL, 144 mmol). After 16 h, the solution was concentrated in vacuo to give 33.8 g (96%) of a thick light yellow oil.

FD-MS, m/e 223.1 (M+)

B) Preparation of 4-BocNHCH$_2$-N-Fmoc-3,4-dehydro-piperidine

To a stirring solution of 4-BocNHCH$_2$-N-methyl-pyridinium iodide (7.7 g, 34 mmol) in 1,2-dichloroethane (100 mL) was added 1,8-bis(dimethylamino)naphthalene (1.5 g, 6.8 mmol) followed by 2-chloroethyl chloroformate (5.3 g, 37 mL). The solution was heated to reflux and after 2 h, the solution was cooled to room temperature and the solvent was removed in vacuo and the residue was quickly flushed through a column of silica gel with 20% ethyl acetate/hexanes. The organic solvents were removed in vacuo and the residue was dissolved in methanol (300 mL) and heated to reflux for 20 min. Saturated aqueous NaHCO$_3$ (100 mL) was then added and the solvents were removed in vacuo. The residue was dissolved in water (200 mL) and washed twice with hexanes, then saturated with solid NaCl and extracted several times with ethyl acetate. The combined ethyl acetate extracts were dried (MgSO$_4$), filtered, and concentrated in vacuo to give a light yellow oil which was dissolved in dichloromethane (75 mL). To this stirring solution was then added N,N-diisopropylethylamine (2.1 mL, 12.2 mmol) followed by 9-fluorenylmethyl chloroformate (3.2 g, 12.2 mmol). After 2 h, the solvent was removed in vacuo and the residue was dissolved in ethyl acetate (250 mL) and washed twice with 1N citric acid, once with brine, twice with saturated aqueous NaHCO$_3$ and finally once with brine. The organic phase was then dried (MgSO$_4$), filtered and concentrated in vacuo and the residue was chromatographed over a silica gel column, eluting with a step gradient of 5% ethyl acetate/hexanes through 50% ethyl acetate/hexanes. The product containing fractions (judged by TLC) were combined and concentrated to give 4 g (27%) of a white solid.

IR $^1$H NMR

FD-MS, m/e 435 (M$^+$)

C) Preparation of N-(t-BuO$_2$CCH$_2$)-N-Boc-D-Cha-Pro-4-NHCH$_2$-N-Fmoc-3,4-dehydro-piperidine By methods substantially equivalent to those described in examples 23-A and 1-G (using N-(t-BuO$_2$CCH$_2$)-N-Boc-D-Cha-Pro-OH), 2.5 g of N-(t-BuO$_2$CCH$_2$)-N-Boc-D-Cha-Pro-4-NHCH$_2$-N-Fmoc-3,4-dehydro-piperidine was prepared from 4-BocNHCH$_2$-N-Fmoc-3,4-dehydro-piperidine.

IR $^1$H NMR

FD-MS, m/e 799 (M$^+$)

D) Preparation of N-(t-BuO$_2$CCH$_2$)-N-Boc-D-Cha-Pro-4-NHCH$_2$-3,4-dehydro-piperidine N-(t-BuO$_2$CCH$_2$)-N-Boc-D-Cha-Pro-4-NHCH$_2$-N-Fmoc-3,4-dehydro-piperidine (1.5 g, 1.9 mmol) was dissolved in morpholine (25 mL) and after stirring for 5 h, the solvent was evaporated in vacuo. The residue was dissolved in ethyl acetate and washed twice with saturated aqueous NaHCO$_3$, dried (MgSO$_4$), filtered and concentrated in vacuo. The residue was then dissolved in a small volume of chloroform and chromatographed over silica gel, eluting with a gradient of 5% to 10% A/B (A=9:1 methanol/conc. NH$_4$OH; B=chloroform). The product containing fractions as judged by TLC were combined and concentrated in vacuo to give 890 mg (82%) of white solid.

$^1$H NMR

FD-MS, m/e 576 (MH$^+$)

E) Preparation of HO$_2$CCH$_2$-D-Cha-Pro-4-NHCH$_2$-3,4-dehydro-piperidine.HCl

HCl gas was bubbled through a solution of N-(t-BuO$_2$CCH$_2$)—N-Boc-D-Cha-Pro-4-NHCH$_2$-3,4-dehydro-piperidine (820 mg, 1.4 mmol) and anisole (1 mL) in dioxane (25 mL) at 0° C. for 10 min. After stirring for 12 h, the solvent was removed in vacuo and the residue was dissolved in water (50 mL) and washed twice with diethyl ether. The aqueous phase was then concentrated to a volume of about 20 mL in vacuo and purified by RPHPLC (Method 2, 98/2 (A/B) through 70/30 (A/B), 2 h). The product containing fractions as judged by analytical RPHPLC were combined, partially concentrated in vacuo and lyophilized to give 442 mg (68%) of white solid.

IR $^1$H NMR

FD-MS, m/e 423 (MH$^+$)

Analysis for C$_{22}$H$_{36}$N$_4$O$_4$.2HCl.1.5H$_2$O: Calc: C, 50.57; H, 8.29; N, 10.72; Found: C, 50.31; H, 8.46; N, 10.93.

EXAMPLE 59

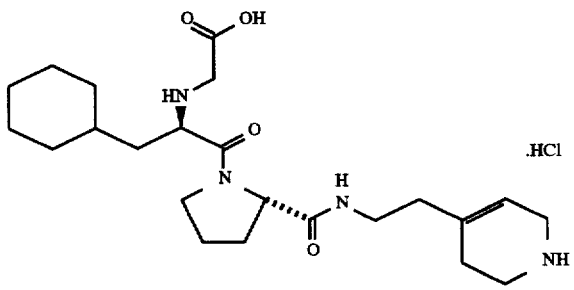

HO$_2$CCH$_2$-D-Cha-Pro-4-NHCH$_2$CH$_2$-3,4,-dehydro-piperidine.HCl

Preparation of HO$_2$CCH$_2$-D-Cha-Pro-4-NHCH$_2$CH$_2$-3,4-dehydro-piperidine.HCl By methods substantially equivalent to those described in example 58, 73 mg of HO$_2$CCH$_2$-D-Cha-Pro-4-NHCH$_2$CH$_2$-3,4-dehydro-piperidine.HCl was prepared from 4-BocNHCH$_2$CH$_2$-pyridine. The final product was purified by RPHPLC method 2 (98/2 (A/B) through 70/30 (A/B), 2 h).

IR $^1$H NMR

IS-MS, m/e 435.2 (MH$^+$)

Analysis for C$_{23}$H$_{38}$N$_4$O$_4$.2.3HCl.3H$_2$O: Calc: C, 48.26; H, 8.15; N, 9.79; Cl, 14.24; Found: C, 48.31; H, 7.93; N, 9.66; Cl, 14.56.

EXAMPLE 60

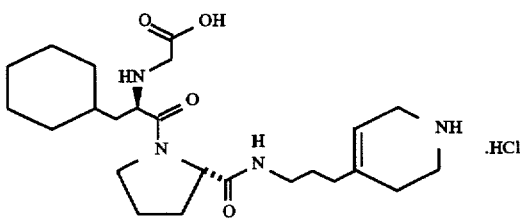

HO$_2$CCH$_2$-D-Cha-Pro-4-NHCH$_2$CH$_2$CH$_2$-3,4-dehydro-piperidine.HCl

Preparation of HO$_2$CCH$_2$-D-Cha-Pro-4-NHCH$_2$CH$_2$CH$_2$-3,4-dehydro-piperidine.HCl By methods substantially equivalent to those described in example 58, 205 mg of HO$_2$CCH$_2$-D-Cha-Pro-4-NHCH$_2$CH$_2$CH$_2$-3,4-dehydro-piperidine.HCl was prepared from 4-BocNHCH$_2$CH$_2$CH$_2$-pyridine.

IR
$^1$H NMR
IS-MS, m/e 449.2 (MH$^+$)

Analysis for C$_{24}$H$_{40}$N$_4$O$_4$.2.3 HCl.H$_2$O: Calc: C, 52.37; H, 3.11; N, 10.18; Found: C, 51.64; H, 7.72; N, 10.31; Cl, 14.69.

EXAMPLE 61

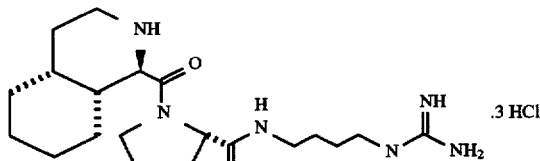

(1R, 4aR, 8aR)-1-Piq-Pro-Agm.3HCl
(N-[4-[(aminoiminomethyl)amino]butyl]-1-[[(4aR, 8aR)-decahydro-1(R)-isoquinolinyl]carbonyl]-1-prolinamide trihydrochloride)

The R$_f$ values in this example were determined by silica gel thin layer chromotography (Kieselgel 60 F-254) in the following systems (v/v):

(A) Chloroform:Methanol:Acetic Acid 135:15:1

(B) Ethyl acetate:Acetic Acid:Absolute Ethanol 90:10:10

(c) Ethyl acetate:Hexane (70:30)

(D) Chloroform

A) N-Methoxycarbonylphenethylamine

To a stirred solution of phenethylamine (75.2 mL, 0.6 mol) and triethylamine (83 mL, 0.6 mol) in THF (500 mL) was added slowly methyl chloroformate 46.2 mL, 0.6 mol) dissolved in THF (50 mL). After the reaction was stirred for an additional 1 h at room temperature, diethyl ether (2 L) and 1N HCl (800 mL) were added. The organic layer was washed with water, dried (MgSO$_4$), filtered, and the filtrate was concentrated in vacuo to give a clear oil of pure title compound (102 g, 95%).

B) 2-Methoxycarbonyl-DL-1,2,3,4-tetrahydoisoquinoline-1-carboxylic acid

To a solution of N-methoxycarbonyl phenethylamine (102 g, 0.57 mol) in trifluoroacetic acid (300 mL) was added glyoxylic acid (63 g, 0.68 mol), and the mixture was heated to reflux temperature. After 4 h at reflux the reaction was cooled to room temperature, solvent removed in vacuo, and diethyl ether (800 mL)/water (100 mL) was added to the residue. The reaction mixture pH was raised to 12 with 5N NaOH and the aqueous layer separated. To the aqueous layer was added diethyl ether (500 mL), and the solution was acidified to pH 2.5 with 5N HCl. The organic layer was separated, dried (MgSO$_4$), filtered, and the filtrate was concentrated in vacuo to afford an oil of pure title compound (107 g, 80%); FAB-MS 236 (MH$^+$).

C) 2-Methoxycarbonyl-DL-1,2,3,4-tetrahydoisoquinoline-1-carboxylic acid t-butyl ester To a stirred, cooled (0° C.), solution of 2-methoxycarbonyl-DL-1,2,3,4-tetrahydoisoquinoline-1-carboxylic acid (2) (105 g, 0.45 mol) in CH$_2$Cl$_2$ (200 mL) was added t-butanol (52 mL, 0.54 mol) and DCC (92 g, 0.45 mol). After 2 h at 0° C. and 24 h at room temperature the solvent was removed in vacuo, and ethyl acetate (800 mL)/1N NaHCO$_3$ (300 mL) was added to the residue. The organic layer was separated, washed with water, 1.5N citric acid, and water. The organic layer was dried (MgSO$_4$), filtered, and the filtrate was concentrated in vacuo to afford an oil of pure title compound (106 g, 81%); FAB-MS 292 (MH$^+$); TLC R$_f$ (A) 0.61; elemental analysis (calcd) C$_{16}$H$_{21}$NO$_4$: C, 65.96; H, 7.27; N, 4.81; Found: C, 66.24, H, 7.28, N, 4.73.

D) 2-Methoxycarbonyl-(1RS,4aSR,8aSR)-perhydoisoquinoline-1-carboxylic acid t-butyl ester A solution of 2-methylcarbonyl-DL-1,2,3,4-tetrahydoisoquinoline-1-carboxylic acid t-butyl ester (105 g, 0.36 mol) in t-butanol (800 mL) was reduced over 5% Rh/Al$_2$O$_3$ (52.5 g) at 55 bar (800 psi) of hydrogen in a high pressure apparatus at 50° C. for 24 hours. The reaction mixture was filtered through a pad of diatomaceous earth, and the filtrate was concentrated in vacuo. The resulting oil was dried to give pure title compound (96.5 g, 90%) FD-MS 298 (MH$^+$); TLC R$_f$ (C) 0.63.

E) 2-Methoxycarbonyl-(1RS,4aRS,8aRS)-perhydoisoquinoline-1-carboxylic acid ethyl ester To a solution of 2-methoxycarbonyl-(1RS,4aSR,8aSR)-perhydoisoquinoline-1-carboxylic acid t-butyl ester (81.2 g, 273 mmol) in EtOH (500 mL) was added sodium ethoxide (21% in ethanol) (88.4 mL, 273 mmol) and the reaction mixture was refluxed (24 h). The organic solvent was evaporated in vacuo, ethyl acetate (400 mL) and water (100 mL) was added to the residue. The organic layer was separated, washed twice with water, dried (MgSO$_4$), filtered, and the filtrate was concentrated in vacuo to afford an oil of pure title compound (70 g,0.95%); FAB-MS 270 (MH$^+$); TLC R$_f$ (A) 0.61.

F) 2-Methoxycarbonyl-(1RS,4aRS,8aRS)-perhydoisoquinoline-1-carboxylic acid

To a solution of the product of step E (70 g, 260 mmol) in THF (250 mL) was added 2N NaOH (156 mL, 312 mmol) and the reaction mixture stirred at room temperature (30 h). The organic solvent was evaporated in vacuo, diethyl ether (400 mL) and water (100 mL) was added to the residue. The aqueous layer separated and ethyl acetate (400 mL) was added. The pH of the solution was adjusted to 2.0 with 5N HCl. The organic layer was dried (MgSO$_4$), filtered, and the filtrate was concentrated in vacuo to give a clear oil. The oil was crystallized from hexane (200 mL) to afford pure title compound (46.4 g,0.74%); FAB-MS 242 (MH$^+$); TLC R$_f$ (A) 0.36; elemental analysis (calcd) C$_{12}$H$_{19}$NO$_4$: C, 59.74; H, 7.94; N, 5.81; Found: C, 59.95, H, 7.88, N, 5.54. NMR assignments were made by homonuclear decoupling, COSY, HMQC, and DEPT experiments.

G) 2-Cbz-(1RS,4aRS,8aRS)-perhydoisoquinoline-1-carboxylic acid

To a stirred solution of the product of step F (46 g, 191 mmol), at room temperature, in anhydrous CH$_3$CN (200 mL) under an inert atmosphere was added a solution of iodotrimethylsilane (62.4 mL, 440 mmol) in CH$_3$CN (60 mL). The reaction mixture was stirred at 55° C. for 30 min and cooled to room temperature. The reaction was quenched with water (100 mL) followed by sodium metabisulfite (1 g). The pH of the reaction was raised to 10.0 with 5N NaOH, and benzyl chloroformate (27.3 mL, 191 mmol) was added dropwise while the pH maintained at 10 with 2N NaOH. After the reaction was stirred for an additional 30 min at room temperature, the organic solvent was evaporated in vacuo, and diethyl ether (200 mL) was added. The reaction was allowed to stand at room temperature (2 h) and ethyl acetate (200 mL) was added. The aqueous solution was acidified to pH 2.5 with 5N HCl; the organic layer was separated, dried (MgSO$_4$), filtered, and the filtrate was concentrated in vacuo to give pure title compound as an oil (39.5 g, 65%); FAB-MS 318 (MH$^+$); elemental analysis (calcd) C$_{18}$H$_{23}$NO$_4$: C, 68.12; H, 7.30; N, 4.41; Found: C, 66.37, H, 7.52, N, 4.37.

H) 2-Cbz-(1RS,4aRS,8aRS)-perhydoisoquinoline-1-carbonyl-Pro-O-t-Bu

To a stirred, cooled (0° C.) solution of the product of step G (39 g, 123 mmol) in DMF (200 mL) was added proline t-butyl ester (21.1 g, 123 mmol), 1-hydroxybenzotriazole (16.6 g, 123 mmol), and DCC (25.3 g, 123 mmol). The reaction mixture was stirred for 2 h at 0° C. and 24 h at room temperature. The reaction precipitate was filtered and the filtrate concentrated in vacuo to an oil. The oil was dissolved in EtOAc (200 mL) and water (100 mL). The organic layer was washed sequentially with 1N NaHCO$_3$, water, 1.5N citric acid, and water. The organic layer was dried (MgSO$_4$), filtered, and the filtrate evaporated to an amorphous solid of the title compound as a mixture of diastereomers (52.7 g, 91%) FAB-MS 471 (MH$^+$).

I) 2-Cbz-(4aR,8aR)-perhydoisoquinoline-1(R)-carbonyl-Pro-OH

To a stirred solution of the product of step H (52.4 g, 111 mmol) in CH$_2$Cl$_2$ (20 mL) was added trifluoroacetic acid (70 ml) and anisole (5 ml). The reaction mixture was stirred at room temperature for 1 h and concentrated in vacuo without heating. The residue was diluted with diethyl ether (400 ml), water (100 mL), and the pH of the solution was adjusted to 10.0 with 5N NaOH. The aqueous layer separated and ethyl acetate (300 mL) was added. The pH of the solution was adjusted to 2.5 with 5N HCl; the organic layer was separated, dried (MgSO$_4$), filtered, and the filtrate was concentrated in vacuo to give a clear oil. The oil was dissolved in diethyl ether (500 mL) and (L)-(-)-alphamethylbenzylamine was added to the solution. The solution was allowed to stand at room temperature (24 h). The resulting solid was filtered, washed with diethyl ether and dried. The solid was suspended in ethyl acetate, washed with 1.5N citric acid, and water. The organic layer was dried (MgSO$_4$), filtered, and the filtrate evaporated to give the title compound as an oil (20.2 g, 44%) FAB-MS 415 (MH$^+$); [a]$_D$=3.2° (C=0.5, MeOH); elemental analysis (calcd) C$_{23}$H$_{30}$N$_2$O$_5$: C, 66.65; H, 7.30; N, 6.76. Found: C, 66.38, H, 7.36, N, 6.63.

J) 2-Cbz-(4aR,8aR)-perhydoisoquinoline-1(R)-carbonyl-Pro-NH-(CH$_2$)$_4$-NH-Boc

In flask 1 the product of step I (1.06 g, 2.55 mmole) was dissolved in DMF (10 ml), cooled to -15° C., and N-methylmorpholine (0.28 ml, 2.55 mmole was added, followed by isobutyl chloroformate (0.33 ml, 2.55 mmole). The reaction mixture was stirred at -15° C. for 2 min.

In flask 2 N-Boc-1,4-diamino-butane (0.48 g, 2.55 mmole) was dissolved in DMF (10 ml), cooled to 0° C., and N-methylmorpholine (0.28 ml, 2.55 mmole) was added to the solution. The reaction mixture was stirred at 0° C. for 2 min.

The contents of flask 2 was added to flask 1, and the reaction mixture was stirred for 4 h (-15° C.) and 24 h at room temperature. To the reaction was added 1N NaHCO$_3$ (1 ml) and the reaction solvent was removed in vacuo to an oil. The residue was dissolved in EtOAc (200 ml) and washed sequentially with 1.5N citric acid, water, 1N NaHCO$_3$ (100 ml), and water. The organic solution was dried (MgSO$_4$), filtered, and concentrated to dryness in vacuo to give crude title compound as a solid (1.47 g, 99%): FAB-MS 585 (MH$^+$); TLC R$_f$ (A) 0.70.

K) (4aR,8aR)-Perhydoisoquinoline-1(R)-carbonyl-Pro-Agm.3HCl

To a stirred solution of the product of step J (1.4 g, 2.4 mmol) in CH$_2$Cl$_2$ (2 mL) was added trifluoroacetic acid (25 ml) and anisole (2.5 ml). The reaction mixture was stirred at room temperature for 30 min and concentrated in vacuo without heating. The reaction was diluted with diethyl ether (100 ml) and the supernatant decanted. The resulting oil was triturated twice with diethyl ether and dried. The dried oil was dissolved in THF (20 mL), triethylamine (0.66 mL, 4.8 mmol), and bis-Cbz-S-methylisothiourea (0.859 g, 2.4 mmol) was added to the mixture. The reaction mixture was stirred at room temperature for 48 h. The organic solvent was evaporated in vacuo and the residue was dissolved in EtOAc (200 ml) and washed sequentially with 1N NaHCO$_3$ (100 ml), and water. The organic solution was dried (MgSO$_4$), filtered, and concentrated to dryness in vacuo to give a crude solid (1.5 g, 79%): TLC R$_f$(D) 0.33. The crude solid (1.5 g,1.93 mmol) dissolved in ethanol (50 mL), water (10 mL), and 1N HCl (5.8 mL, 5.8 mmol) was hydrogenated in the presence of 5% Pd/C catalyst (2.5 g) at ambient temperature and pressure. The catalyst was removed by filtration and the filtrate concentrated to an oil in vacuo. The oil was dissolved in trifluoroacetic acid (10 mL), thioanisole (1.0 mL) and trifluoromethanesulfonic acid (1.0 mL) were added to the mixture. The reaction mixture was stirred at room temperature for 0.5 h and diethyl ether (100 ml) was added. The supernatant was decanted, and the resulting oil was triturated twice with diethyl ether and dried in vacuo to give a crude solid (1.3 g). The solid (1.3 g) was dissolved in 0.05% HCl and applied to a 5×25 cm column of Vydac C$_{18}$ resin. A gradient of increasing concentrations of CH$_3$CN (2% to 25%) was used to elute the peptide from the column. Fractions were collected and pooled on the basis of analytical RPHPLC profile and lyophilized to afford the pure title compound (0.139 g, 15%): FAB-MS 393 (MH$^+$); elemental analysis (calcd) C$_{20}$H$_{36}$N$_6$O$_2$.5HCl.3H$_2$O: C, 38.28. Found: C, 38.34.

EXAMPLE 62

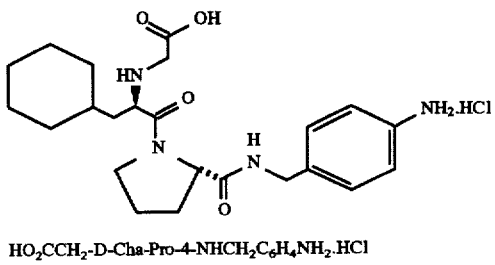

HO$_2$CCH$_2$-D-Cha-Pro-4-NHCH$_2$C$_6$H$_4$NH$_2$.HCl

Preparation of HO$_2$CCH$_2$-D-Cha-Pro-4-NHCH$_2$C$_6$H$_4$NH$_2$.HCl

By methods substantially equivalent to those described in examples 1-G (using N-(t-BuO$_2$CCH$_2$)-N-Boc-D-Cha-ProOH), 23-D, and 58-E, 0.17 g of HO$_2$CCH$_2$-D-Cha-Pro-4-NHCH$_2$C$_6$H$_4$NH$_2$.HCl was prepared from 4-nitrobenzylamine hydrochloride. The final product was purified by RPHPLC method 2 (98/2 (A/B) through 70/30 (A/B), 2 h).

IR
¹H NMR
FAB-MS, m/e 431.3 (MH⁺)

Analysis for $C_{23}H_{34}N_4O_4 \cdot 2.2$ HCl$\cdot 1.5$ H₂O: Calc: C, 51.37; H, 7.35; N, 10.42; Cl, 14.50; Found: C, 50.87; H, 6.72; N, 10.41; Cl, 14.18.

EXAMPLE 63

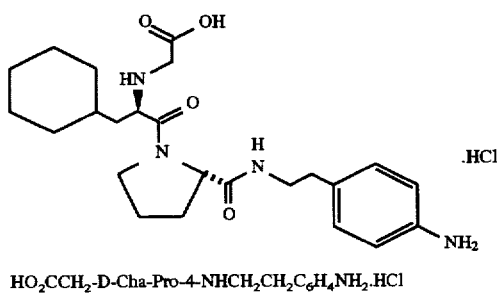

HO₂CCH₂-D-Cha-Pro-4-NHCH₂CH₂C₆H₄NH₂.HCl

Preparation of HO₂CCH₂-D-Cha-Pro-4-NHCH₂CH₂C₆H₄NH₂.HCl

By methods substantially equivalent to those described in example 62, 0.19 g of HO₂CCH₂-D-Cha-Pro-4-NHCH₂CH₂C₆H₄NH₂.HCl was prepared from 4-nitrophenethylamine hydrochloride. The final product was purified by RPHPLC method 2 (98/2 (A/B) through 70/30 (A/B), 2 h).

IR
¹H NMR
FAB-MS, m/e 445.3 (MH⁺)

Analysis for $C_{24}H_{36}N_4O_4 \cdot 2.2HCl \cdot 0.5H_2O$: Calc: C, 54.00; H, 7.40; N, 10.50; Cl, 14.61; Found: C, 53.65; H, 7.59; N, 10.24; Cl, 14.33.

EXAMPLE 64

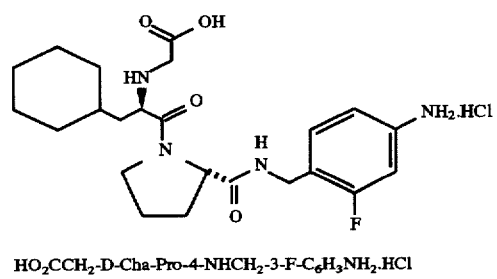

HO₂CCH₂-D-Cha-Pro-4-NHCH₂-3-F-C₆H₃NH₂.HCl

A) Preparation of 4-Boc₂NCH₂-3-F-C₆H₃NO₂

To a stirring solution of 2-fluoro-4-nitrotoluene (5 g, 32 mmol) in carbon tetrachloride (160 mL) was added N-bromosuccinimide/5.7 g, 32 mmol) followed by benzoyl peroxide (0.78 g, 3.2 mmol) and the solution was heated to reflux. After 12 h, the heat was removed and the mixture was diluted with carbon tetrachloride (100 mL) and washed with water. The organic phase was then diluted with ethyl acetate (300 mL), dried (MgSO₄), filtered and concentrated in vacuo. The residue was dissolved in tetrahydrofuran (50 mL) and added to a stirring solution of NaH (60% dispersion in oil; 1.3 g, 32 mmol) and di-t-butyl iminodicarboxylate (6.9 g, 32 mmol) in tetrahydrofuran (100 mL). After stirring overnight the solvent was removed in vacuo and the residue was chromatographed over silica gel, eluting with a step gradient of hexanes through 20% ethyl acetate/hexanes. The product containing fractions (judged by TLC) were combined and concentrated in vacuo to give 3.9 g (33%) of a white solid.

IR
¹H NMR
FD-MS, m/e 370 (M⁺)

Analysis for $C_{17}H_{23}N_2O_6$: Calc: C, 55.13; H, 6.26; N, 7.56; Found: C, 55.27; H, 6.23; N, 7.44.

B) Preparation of HO₂CCH₂-D-Cha-Pro-4-NHCH₂-3-F-C₆H₃NH₂.HCl

By methods substantially equivalent to those described in example 23-A, 1-G (using N-(t-BuO₂CCH₂)-N-Boc-D-Cha-ProOH), 23-D and 58-E, 0.44 g of HO₂CCH₂-D-Cha-Pro-4-NHCH₂-3-F-C₆H₃NH₂.HCl was prepared. The final product was purified using RPHPLC method 2, 98/2 (A/B) through 70/30 (A/B), 2 h).

IR
¹H NMR
FAB-MS, m/e 449.3 (MH⁺)

Analysis for $C_{23}H_{33}N_4O_4F \cdot 1.3HCl$: Calc: C, 55.70; H, 6.97; N, 11.30; Cl, 9.29; Found: C, 55.38; H, 6.97; N, 11.05; Cl, 9.31.

EXAMPLE 65

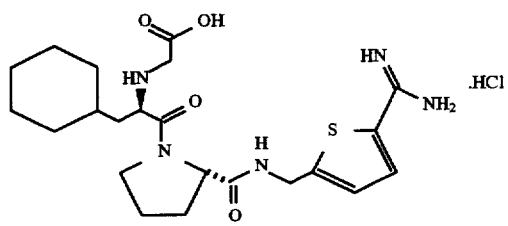

HO₂CCH₂-D-Cha-Pro-4-NHCH₂-2-amidinothiophene.HCl
(N-(carboxymethyl)-D-cyclohexylalanyl-N-[[5-(aminoiminomethyl) thiophen-2-yl] methyl]-L-prolinamide hydrochloride)

A) Preparation of 2-cyano-5-formylthiophene

To a flame-dried 3 neck 1 L round bottom flask was added diisopropylamine (9 mL, 66 mmol) and THF (150 mL) under a nitrogen atmosphere. The flask was cooled to an internal temperature of −78° C. (dry ice/acetone). To this stirring solution was added n-butyllithium (1.6M in hexanes, 41.3 mL, 66.1 mmol) via syringe and the mixture was allowed to stir for 5 min. To this solution was added a solution of 2-thiophenecarbonitrile (6.55 g, 60 mmol) in THF (30 mL) over 10 min. The resulting bright red solution was allowed to stir at −78° C. for 45 min, at which time dimethylformamide (23.3 mL, 300 mmol) was added via syringe. This mixture was allowed to stir for 2 h at −78° C. and then solid citric acid (about 10 g) was added followed by water (60 mL). Volatile solvents were removed in vacuo and the residue was partitioned between diethyl ether and brine (200 mL each). Layers were separated and the aqueous phase was washed once with diethyl ether. The combined organic phase was washed once with brine, dried (MgSO₄), filtered and concentrated in vacuo to give a yellow solid which was purified by silica gel chromatography using an ethyl acetate/hexanes gradient (hexanes to 50% ethyl acetate/hexanes). Fractions containing pure product were pooled and concentrated in vacuo to give 6.9 g (84%) of 2-cyano-5-formyl-thiophene.

¹H NMR

B) Preparation of 2-cyano-5-(hydroxymethyl)thiophene

To a solution of 2-cyano-5-formyl-thiophene (6.9 g, 50 mmol) in EtOH (100 mL) was added sodium borohydride (1.9 g, 50 mmol) in portions. After 5 min of stirring, the solvent was removed in vacuo and the residue was partitioned between ethyl acetate and brine. The layers were separated and the organic phase was washed once with 1M citric acid and once with brine, then dried (MgSO₄), filtered and concentrated in vacuo to give 6.1 g (88%) of 2-cyano-5-(hydroxymethyl)thiophene.

¹H NMR
FD-MS, m/e 140 (M⁺)
Analysis for C₆H₅NOS: Calc: C, 51.78; H, 3.62; N, 10.06; Found: C, 51.54; H, 3.62; N, 9.86.

C) Preparation of 2-cyano-5-(bromomethyl)thiophene

To a solution of 2-cyano-5-(hydroxymethyl)thiophene (6.0 g, 43 mmol) in THF (50 mL) was added triphenylphosphine (15.7 g, 47 mmol) and carbon tetrabromide (12.3 g, 47 mmol). After stirring overnight under nitrogen atmosphere at room temperature, the solvent was removed in vacuo and the residue was dissolved in chloroform, then adsorbed onto silica gel and loaded onto a silica gel column. The product was eluted using an ethyl acetate/hexanes gradient. Fractions containing pure product (as judged by TLC) were pooled and concentrated in vacuo to give 6.5 g (75%) of 2-cyano-5-(bromomethyl)thiophene.

¹H NMR
FD-MS, m/e 203 (M⁺)
Analysis for C₆H₄NSBr: Calc: C, 35.66; H, 1.99; N, 6.93; Found: C, 35.71; H, 2.03; N, 6.95.

D) Preparation of 2-cyano-5-(aminomethyl)thiophene.HCl

To a cold (0° C.) solution of 2-cyano-5-(bromomethyl)thiophene (6.0 g, 30 mmol) in THF 50 mL) under nitrogen was added NaH (60% dispersion in oil, 1.3 g, 33 mmol) in portions. To this stirring suspension was added a solution of di-t-butyl iminodicarboxylate (7.1 g, 33 mmol) in THF (50 mL) over 30 min. After stirring for 3 h, saturated aqueous ammonium chloride (100 mL) was added. Volatile solvents were then removed in vacuo and the residue was partitioned between ethyl acetate and water. The layers were separated and the organic phase was washed twice with brine, dried (MgSO₄), filtered and concentrated in vacuo to give 10.5 g (100%) of 2-cyano-5-Boc₂NCH₂-thiophene which crystallized upon standing. This solid was dissolved in EtOAc (200 mL) and cooled to 0° C. using an ice/water bath. Anhydrous HCl gas was bubbled through the solution for 10 min and the mixture was stirred for 2 h while warming to room temperature. Solvents were removed in vacuo and the resulting solid was suspended in diethyl ether and isolated by filtration. The white solid was dried overnight under vacuum to give 5.2 g (100%) of 2-cyano-5-(aminomethyl)thiophene.HCl.

¹H NMR
FD-MS, m/e 139 (M⁺)
Analysis for C₆H₇N₂SCl: Calc: C, 41.26; H, 4.04; N, 16.04; Found: C, 41.19; H, 4.12; N, 15.82.

E) Preparation of N-(t-BuO₂CCH₂)-N-Boc-D-Cha-Pro-4-NHCH₂-2-cyanothiophene

By a method substantially equivalent to that described in example 1-G (using N-(t-BuO₂CCH₂)-N-Boc-D-Cha-ProOH), 4.6 g (93%) of N-(t-BuO₂CCH₂)-N-Boc-D-Cha-Pro-4-NHCH₂-2-cyanothiophene was prepared from 2-cyano-5-(aminomethyl)thiophene.HCl.

IR
¹H NMR
FD-MS, m/e 602 (M⁺)

F) Preparation of N-(t-BuO₂CCH₂)-N-Boc-D-Cha-Pro-4-NHCH₂-2-C(NH)NHBoc-thiophene

Hydrogen sulfide gas was bubbled through a solution of N-(t-BuO₂CCH₂)-N-Boc-D-Cha-Pro-4-NHCH₂-2-cyanothiophene (1.5 g, 2.5 mmol) and triethylamine (4.5 mL) in pyridine (45 mL) for 5 min and then the vessel was sealed and allowed to stand overnight. The next morning, nitrogen was bubbled through the solution for 5 min and the solvent was removed in vacuo. The residue was dissolved in ethyl acetate and washed once with water and once with brine, then dried (MgSO₄), filtered and concentrated in vacuo. The residue was then dissolved in toluene and concentrated in vacuo two times.

The residue was then dissolved in acetone (100 mL) and iodomethane (5 mL) was added. After stirring overnight at room temperature, the solvents were removed in vacuo. The resulting gold foam was then dissolved in methanol (20 mL), NH₄OAc (0.39 g, 5 mmol) was added, and the solution was heated to reflux. After 1 h, the solvent was removed in vacuo and the residue was dissolved in tetrahydrofuran (10 mL). To this stirring solution was added a solution of K₂CO₃ (1.73 g, 12.5 mmol) in water (10 mL) followed by di-t-butyl dicarbonate (2.2 g, 10 mmol). After stirring for 1 h, the suspension was diluted with ethyl acetate (400 mL) and washed with water followed by brine. The organic phase was then concentrated in vacuo and chromatographed over silica gel, eluting with a step gradient of 10% ethyl acetate/hexanes through 75% ethyl acetate/hexanes. The product containing fractions, as judged by TLC, were combined and concentrated in vacuo to give 1.1 g (61%) of a white foam.

¹H NMR
FD-MS, m/e 720 (M⁺)
Analysis for C₃₆H₅₇N₅O₈S: Calc: C, 60.06; H, 7.98; N, 9.73; Found: C, 59.76; H, 8.07; N, 9.52.

G) Preparation of HO₂CCH₂-D-Cha-Pro-4-NHCH₂-2-amidinothiophene.HCl

By a method substantially equivalent to that described in example 58-E, 500 mg of HO₂CCH₂-D-Cha-Pro-4-NHCH₂-2-amidinothiophene.HCl were prepared. The product was purified by RPHPLC method 2 (98/2 (A/B) through 70/30 (A/B), 2 h).

IR
¹H NMR
FAB-MS, m/e 464.2 (MH⁺)
Analysis for C₂₂H₃₃N₅O₄S.2HCl.H₂O: Calc: C, 47.65; H, 6.73; N, 12.63; Cl, 12.79; Found: C, 47.53; H, 6.57; N, 12.59; Cl, 12.67.

EXAMPLE 66

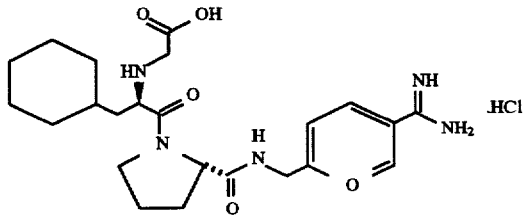

HO₂CCH₂-D-Cha-Pro-2-NHCH₂-5-amidinopyridine.HCl
(N-(carboxymethyl)-D-cyclohexylanyl-N-
[[5-(aminoiminomethyl) pyridin-2-yl] methyl)]-L-prolinamide hydrochloride)

A) Preparation of N-(t-BuO₂CCH₂)-N-Boc-D-Cha-Pro-2-NHCH₂-5-cyanopyridine

By methods substantially equivalent to those described in example 64-A, 23-A and 1-G (using N-(t-BuO₂CCH₂)-N-Boc-D-Cha-ProOH), 4.4 g of N-(t-BuO₂CCH₂)-N-Boc-D-Cha-Pro-2-NHCH₂-5-cyanopyridine was prepared from 2-methyl-5-cyanopyridine.

IR
¹H NMR
FD-MS, m/e 597 (M⁺)

B) Preparation of HO₂CCH₂-D-Cha-Pro-2-NHCH₂-5-amidinopyridine.HCl

By methods substantially equivalent to those described in example 65-F and 65-G, 130 mg of HO₂CCH₂-D-Cha-Pro- 2-NHCH$_2$-5-amidinopyridine.HCl was prepared from N-(t-BuO$_2$CCH$_2$)-N-Boc-D-Cha-Pro-2-NHCH$_2$-5-cyanopyridine. The product was purified by RPHPLC method 2 (98/2 (A/B) through 70/30 (A/B), 2 h).

IR
$^1$H NMR
FAB-MS, m/e 459.3 (MH$^+$)
HRMS (FAB), m/e calcd. for C$_{23}$H$_{35}$N$_6$O$_4$: 459.2720 Found: 459.2707

EXAMPLE 67

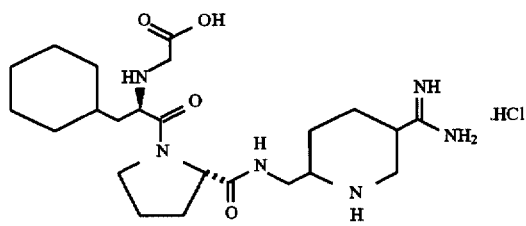

HO$_2$CCH$_2$-D-Cha-Pro-2-NHCH$_2$-5-amidinopiperidine.HCl

Preparation of HO$_2$CCH$_2$-D-Cha-Pro-2-NHCH$_2$-5-amidinopiperidine.HCl

N-(t-BuO$_2$CCH$_2$)-N-Boc-D-Cha-Pro-2-NHCH$_2$-5-cyanopyridine (1.2 g, 2 mmol) was elaborated by methods substantially equivalent to those described in example 23-A, 23-B, and 1-B. The product was purified by RPHPLC method 2 (98/2 (A/B) through 70/30 (A/B), 2 h). The fractions containing the minor product as judged by analytical RPHPLC were combined, partially concentrated in vacuo and lyophilized to give 93 mg (9%) of a pale green solid.

IR
$^1$H NMR
IS-MS, m/e 465.5 (MH$^+$)
HRMS (FAB), m/e calcd. for C$_{23}$H$_{41}$N$_6$O$_4$: 465.3189 Found: 465.3191

EXAMPLE 68

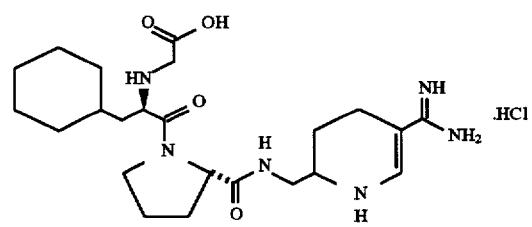

HO$_2$CCH$_2$-D-Cha-Pro-2-NHCH$_2$-5-amidino-5, 6-dehydro-piperidine.HCl
(N-(carboxymethyl)-D-cyclohexylalanyl-N-[[5-(aminoiminomethyl)-1, 2, 3, 4-tetrahydropyridin-2-yl] methyl] L-prolinamide hydrochloride)

Preparation of HO$_2$CCH$_2$-D-Cha-Pro-2-NHCH$_2$-5-amidino-5,6-dehydro-piperidine.HCl N-(t-BuO$_2$CCH$_2$)-N-Boc-D-Cha-Pro-2-NHCH$_2$-5-cyanopyridine (1.2 g, 2 mmol) was elaborated by methods substantially equivalent to those described in example 23-A, 23-B, and 1-B. The product was purified by RPHPLC method 2 (98/2 (A/B) through 70/30 (A/B), 2 h). The fractions containing the major product as judged by analytical RPHPLC were combined, partially concentrated and lyophilized to give 422 mg (39%) of a white solid.

IR
$^1$H NMR
IS-MS, m/e 463.3 (MH$^+$)

Analysis for C$_{23}$H$_{38}$N$_6$O$_4$·2.9HCl·2H$_2$O: Calc: C, 45.71; H, 7.49; N, 13.91; Cl, 17.01; Found: C, 45.51; H, 6.83; N, 13.66; Cl, 16.83.

EXAMPLE 69

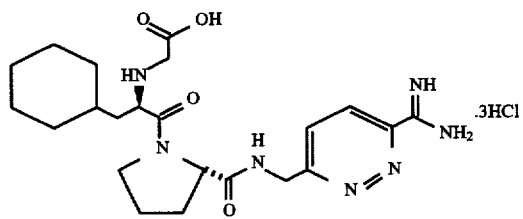

HO$_2$CCH$_2$-D-Cha-Pro-3-NHCH$_2$-6-amidino-pyridazine.3HCl
(N-(carboxymethyl)-D-cyclohexylalanyl-N-[[6-(aminoiminomethyl) pyridazin-3-yl] methyl]-L-prolinamide tri-hydrochloride A) Preparation of 3-methyl-6-cyanopyridazine To a stirring solution of 3-methylpyridazine (11 g, 118 mmol) in dichloromethane (200 mL) was added AlCl$_3$ (0.05 g) followed by trimethylsilylcyanide (21 g, 211 mmol). After 20 min, a solution of p-toluenesulfonyl chloride (38 g, 201 mmol) in dichloromethane (50 mL) was added via addition funnel and the solution continued to stir overnight. The next morning, the solvent was removed in vacuo and the residue was suspended in ethanol with stirring for 15 min and then filtered to give a white solid. The solid was dissolved in tetrahydrofuran (200 mL) and to this stirring solution was added 1,8-diazabicyclo[5.4.0]undec-7-ene (16 mL, 105 mmol). After 1 h, the solvent was removed in vacuo and the residue was partitioned between hexanes and saturated aqueous NH$_4$Cl. The phases were separated and the aqueous phase was basified with solid Na$_2$CO$_3$, then extracted three times with ethyl acetate. The combined ethyl acetate phases were dried (MgSO$_4$), filtered and concentrated in vacuo to give 9 g (64%) of white solid.

IR
$^1$H NMR
FD-MS, m/e 119.1(M$^+$)

B) Preparation of HO$_2$CCH$_2$-D-Cha-Pro-3-NHCH$_2$-6-amidino-pyridazine.HCl

By methods substantially equivalent to those described in example 66, 90 mg of HO$_2$CCH$_2$-D-Cha-Pro-3-NHCH$_2$-6-amidinopyridazine.HCl was prepared from 3-methyl-6-cyanopyridazine. The product was purified by RPHPLC method 2 (98/2 (A/B) through 70/30 (A/B), 2 h).

IR
$^1$H NMR
FAB-MS, m/e 460.3 (MH$^+$)

Analysis for C$_{22}$H$_{33}$N$_7$O$_4$·3HCl·2H$_2$O: Calc: C, 43.68; H, 6.66; N, 16.21; Found: C, 44.04; H, 6.45; N, 15.57.

EXAMPLE 70

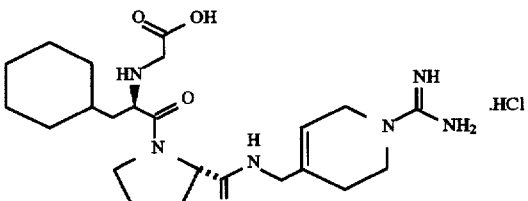

HO$_2$CCH$_2$-D-Cha-Pro-4-NHCH$_2$-1-amidino-3, 4-dehydro-piperidine.HCl
(N-(carboxymethyl)-D-cyclohexylalanyl-N-[[1-

81

-continued (aminoiminomethyl)-1, 2, 3, 6-tetrahydropyridin-4-yl] methyl]-L-prolinamide hydrochloride)

A) Preparation of N,N'-Boc$_2$-thiourea

To a stirring suspension of NaH (60% oil dispersion, 9.4 g, 234 mmol) in tetrahydrofuran (500 mL) at 0° C. was added thiourea (4.0 g, 52 mmol). After 30 min, the cold bath was removed and the reaction was allowed to stir for 30 min at room temperature. Once again, the vessel was cooled to 0° C. and a solution of di-t-butyl dicarbonate (25 g, 115 mmol) in tetrahydrofuran (100 mL) was added via addition funnel. After stirring for 30 min at 0° C. and an additional 2 h at room temperature, saturated aqueous NaHCO$_3$ was added. The solution was then concentrated to about half the original volume in vacuo and ethyl acetate was added. The organic phase was then washed with saturated aqueous NaHCO$_3$, followed by brine and was then dried with MgSO$_4$, filtered and concentrated to give 11.9 g (83%) of a white solid.

IR $^1$H NMR

FD-MS, m/e 276 (M$^+$)

Analysis for C$_{11}$H$_{20}$N$_2$O$_4$S: Calc: C, 47.81; H, 7.30; N, 10.14; Found: C, 47.69; H, 7.28; N, 10.34.

B) Preparation of N-(t-BuO$_2$CCH$_2$)-N-Boc-D-Cha-Pro-4-NHCH$_2$-1-(N,N'-Boc$_2$-amidino)-3,4-dehydro-piperidine To a stirring solution of N-(t-BuO$_2$CCH$_2$)-N-Boc-D-Cha-Pro-4-NHCH$_2$-3,4-dehydro-piperidine (0.6 g, 1 mmol) and triethylamine (0.35 g, 3.4 mmol) in dimethylformamide (10 mL) was added N,N'-Boc$_2$-thiourea (0.28 g, 1 mmol) followed by HgCl$_2$ (0.28 g, 1 mmol). After 4 h, the solvent was removed in vacuo, and the residue was dissolved in ethyl acetate and washed twice with brine. The organic phase was then dried with MgSO$_4$, filtered and concentrated in vacuo. The product was purified by chromatography over silica gel, eluting with 20% ethyl acetate/hexanes through 75% ethyl acetate hexanes. The product containing fractions as judged by TLC were combined and concentrated in vacuo to give 800 mg (94%) of a white foam.

IR $^1$H NMR

FD-MS, m/e 820 (MH$^+$)

Analysis for C$_{42}$H$_{70}$N$_6$O$_{10}$: Calc: C, 51.59; H, 8.61; N, 10.26; Found: C, 61.81; H, 8.79; N, 10.45.

C) Preparation of HO$_2$CCH$_2$-D-Cha-Pro-4-NHCH$_2$-1-amidino-3,4-dehydro-piperidine.HCl By methods substantially equivalent to those described in example 58-E, 0.22 g (55%) of HO$_2$CCH$_2$-D-Cha-Pro-4-NHCH$_2$-1-amidino-3,4-dehydro-piperidine.HCl was prepared from N-(t-BuO$_2$CCH$_2$)-N-Boc-D-Cha-Pro-4-NHCH$_2$-1-(N,N'-Boc$_2$-amidino)-3,4-dehydro-piperidine. The product was purified by RPHPLC method 2 (98/2 (A/B) through 70/30 (A/B), 2 h).

IR $^1$H NMR

FAB-MS, m/e 463.3 (MH$^+$)

Analysis for C$_{23}$H$_{38}$N$_6$O$_4$.2.2HCl.2H$_2$O: Calc: C, 47.73; H, 7.70; N, 14.52; Cl, 13.47; Found: C, 47.49; H, 7.64; N, 14.55; Cl, 13.48.

82

EXAMPLE 71

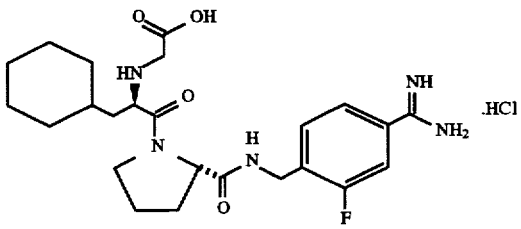

HO$_2$CCH$_2$-D-Cha-Pro-4-NHCH$_2$-3-F-benzamidine.HCl
(N-(carboxymethyl)-D-cyclohexylalanyl-N-
[[4-(aminoiminomethyl)-2-fluorophenyl] methyl]-L-prolinamide hydrochloride)

Preparation of HO$_2$CCH$_2$-D-Cha-Pro-4-NHCH$_2$-3-F-benzamidine.HCl

By methods substantially equivalent to those described in example 66, 0.27 g of HO$_2$CCH$_2$-D-Cha-Pro-4-NHCH$_2$-3-F-benzamidine.HCl was prepared from 3-F-4-Me-benzonitrile. The product was purified by RPHPLC method 2 (98/2 (A/B) through 70/30 (A/B), 2 h).

IR $^1$H NMR

FAB-MS, m/e 476.3 (MH$^+$)

Analysis for C$_{24}$H$_{34}$N$_5$O$_4$F.2HCl.1.5H$_2$O: Calc: C, 50.09; H, 6.83; N, 12.17; Cl, 12.32; Found: C, 49.89; H, 6.65; N, 12.17; Cl, 12.42.

EXAMPLE 72

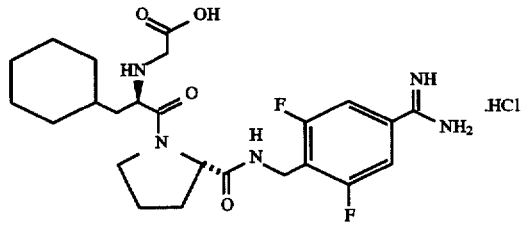

HO$_2$CCH$_2$-D-Cha-Pro-4-NHCH$_2$-3, 5-F$_2$-benzamidine.HCl
(N-(carboxymethyl)-D-cyclohexylalanyl-N-
[[4-(aminoiminomethyl)-2, 6-difluorophenyl] methyl]-L-prolinamide hydrochloride)

Preparation of HO$_2$CCH$_2$-D-Cha-Pro-4-NHCH$_2$-3,5-F$_2$-benzamidine.HCl

By methods substantially equivalent to those described in example 65, 0.28 g of HO$_2$CCH$_2$-D-Cha-Pro-4-NHCH$_2$-3, 5-F$_2$-benzamidine.HCl was prepared from 3,5-F$_2$-benzonitrile. The product was purified by RPHPLC method 2 (98/2 (A/B) through 70/30 (A/B), 150 min).

IR $^1$H NMR

FAB-MS, m/e 494.2 (MH$^+$)

Analysis for C$_{24}$H$_{33}$N$_5$O$_4$F$_2$.2HCl.1.5H$_2$O: Calc: C, 48.57; H, 6.45; N, 11.80; Cl, 11.95; Found: C, 48.26; H, 6.17; N, 11.89; Cl, 11.90.

EXAMPLE 73

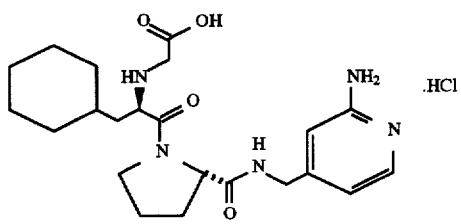

HO$_2$CCH$_2$—D—Cha—Pro-4-NHCH$_2$-2-aminopyridine.HCl

A) Preparation of 4-methyl-2-phthalimidopyridine

To a stirring solution of 4-methyl-2-aminopyridine (50 g, 460 mmol) in acetic acid (1 L) was added phthalic anhydride (68 g, 460 mmol) and the reaction was heated to reflux. After 12 h, acetic anhydride (43 mL, 460 mmol) was added and the solution continued to stir at reflux for an additional 48 h. The solvent was then removed in vacuo and the solid residue was suspended in toluene and concentrated in vacuo twice. The solid was then suspended in ethyl acetate with vigorous stirring and filtered. After repeating this ethyl acetate washing procedure the solid was dried overnight in vacuo to give 46.6 g (42%) of a white solid.

IR $^1$H NMR

FD-MS, m/e 238 (M$^+$)

Analysis for C$_{14}$H$_{10}$N$_2$O$_2$: Calc: C, 70.58; H, 4.23; N, 11.76; Found: C, 70.42; H, 4.29; N, 11.70.

B) Preparation of N-(t-BuO$_2$CCH$_2$)-N-Boc-D-Cha-Pro-4-NHCH$_2$-2-phthalimidopyridine By methods substantially equivalent to those described in example 64-A, 23-A and 1-G (using N-(t-BuO$_2$CCH$_2$)-N-Boc-D-Cha-ProOH), 2.4 g of N-(t-BuO$_2$CCH$_2$)-N-Boc-D-Cha-Pro-4-NHCH$_2$-2-phthalimidoopyridine was prepared from 4-methyl-2-phthalimidopyridine.

IR $^1$H NMR

FD-MS, m/e 717.7 (M$^+$)

C) Preparation of HO$_2$CCH$_2$-D-Cha-Pro-4-NHCH$_2$-2-aminopyridine.HCl

To a stirring solution of N-(t-BuO$_2$CCH$_2$)-N-Boc-D-Cha-Pro-4-NHCH$_2$-2-phthalimidoopyridine (1.6 g, 2.2 mmol) in ethanol (25 mL) was added hydrazine hydrate (0.52 mL, 10.4 mmol). After 1 h, the solvents were removed in vacuo and the residue was dissolved in ethyl acetate and concentrated in vacuo twice. The residue was elaborated by a procedure substantially equivalent to that described in example 58-E to give 380 mg (37%) of a white solid. The product was purified by RPHPLC method 2 (98/2 (A/B) through 70/30 (A/B), 150 min).

IR $^1$H NMR

FAB-MS, m/e 432.3 (MH$^+$)

Analysis for C$_{22}$H$_{33}$N$_5$O$_4$.2.1 HCl.H$_2$O: Calc: C, 50.23; H, 7.11; N, 13.31; Found: C, 50.05; H, 7.08; N, 13.54.

EXAMPLE 74

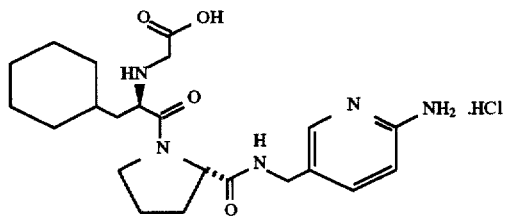

HO$_2$CCH$_2$—D—Cha—Pro-5-NHCH$_2$-2-aminopyridine.HCl

Preparation of HO$_2$CCH$_2$-D-Cha-Pro-5-NHCH$_2$-2-aminopyridine.HCl

By methods substantially equivalent to those described in example 73, 0.88 g of HO$_2$CCH$_2$-D-Cha-Pro-5-NHCH$_2$-2-aminopyridine.HCl was prepared from 5-methyl-2-aminopyridine. The product was purified by RPHPLC method 2 (98/2 (A/B) through 70/30 (A/B), 150 min).

IR $^1$H NMR

FAB-MS, m/e 432.3(MH$^+$)

Analysis for C$_{22}$H$_{33}$N$_5$O$_4$.2HCl.H$_2$O: Calc: C, 50.58; H, 7.14; N, 13.40; Found: C, 50.79; H, 7.20; N, 13.58.

EXAMPLE 75

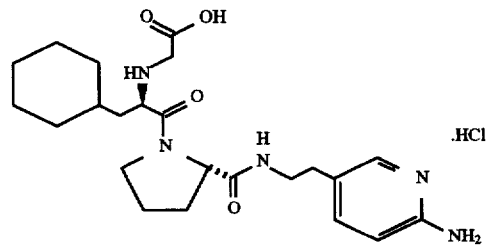

HO$_2$CCH$_2$—D—Cha—Pro-5-NHCH$_2$CH$_2$-2-aminopyridine.HCl

A) Preparation of 5-Me-2-Boc$_2$N-pyridine

To a stirring solution of 5-methyl-2-aminopyridine (10.5 g, 100 mmol) in dichloromethane (200 mL) at 0° C. was added N,N-diisopropylethylamine (25.8 g, 200 mmol), followed by di-t-butyl dicarbonate (55 g, 250 mmol) and finally 4-(N,N-dimethylamino)pyridine (12.2 g, 100 mmol). The cold bath was removed and the solution was allowed to continue stirring overnight. The mixture was then diluted with ethyl acetate (600 mL) and washed three times with saturated aqueous NH$_4$Cl, once with brine, twice with saturated aqueous NaHCO$_3$, and once again with brine. The organic phase was then dried (MgSO$_4$), filtered, concentrated in vacuo and chromatographed over silica gel eluting with 10% ethyl acetate/hexanes through 75% ethyl acetate/hexanes. The fractions containing product, as judged by TLC, were combined and concentrated in vacuo to give 12.8 g (42%) of a white solid.

IR $^1$H NMR

FD-MS, m/e 308 (M$^+$)

Analysis for C$_{16}$H$_{24}$N$_2$O$_4$: Calc: C, 62.32; H, 7.84; N, 9.08; Found: C, 62.51; H, 8.11; N, 9.37.

B) Preparation of 5-BrCH$_2$-2-Boc$_2$N-pyridine

By methods substantially equivalent to those described in example 64-A, approximately 11.6 g of 5-BrCH$_2$-2-Boc$_2$N-pyridine (which was contaminated with starting material) was prepared from 5-Me-2-Boc$_2$N-pyridine.

¹H NMR
FD-MS, m/e 386.3 (M⁺)

Analysis for $C_{16}H_{23}N_2O_4Br$: Calc: C, 49.62; H, 5.99; N, 7.23; Found: C, 49.86; H, 6.00; N, 7.07.

C) Preparation of 5-NCCH₂-2-Boc₂N-pyridine

To a stirring solution of slightly impure 5-BrCH₂-2-Boc₂N-pyridine (9.7 g, 25 mmol) in dimethylformamide (150 mL) was added 18-crown-6 (1.32 g, 5 mmol) followed by KCN (1.95 g, 30 mmol). After stirring for 6 h, the solvent was removed in vacuo and the residue was chromatographed over silica gel, eluting with a step gradient of hexanes through 40% ethyl acetate/hexanes. The product containing fractions as judged by TLC, were combined and concentrated in vacuo to give a 2.6 g (31% over 2 steps) of a white solid.

IR
¹H NMR
FD-MS, m/e 333.4 (M⁺)

Analysis for $C_{17}H_{23}N_3O_4$: Calc: C, 61.25; H, 6.95; N, 12.60; Found: C, 61.09; H, 6.92; N, 12.53.

D) Preparation of HO₂CCH₂-D-Cha-Pro-5-NHCH₂CH₂-2-aminopyridine.HCl

To a stirring solution of 5-NCCH₂-2-Boc₂N-pyridine (2.5 g, 7.5 mmol) in methanol (150 mL) was added CoCl₂ (0.97 g, 7.5 mmol) and water (0.81 g, 45 mmol). After 5 min, NaBH₄ (2.84 g, 75 mmol) was added in small portions over 15 min. After an additional 15 min, the solvent was removed in vacuo and the residue was dissolved in concentrated aqueous NH₄OH and extracted several times with ethyl acetate. The combined ethyl acetate extracts were dried with MgSO₄, filtered and concentrated in vacuo.

Then, by methods substantially equivalent to those described in example 1-A and 73-C, the residue was elaborated to give 1.2 g (33%) of HO₂CCH₂-D-Cha-Pro-5-NHCH₂CH₂-2-aminopyridine.HCl. The product was purified by RPHPLC method 2 (98/2 (A/B) through 60/40 (A/B), 150 min).

IR
¹H NMR
FAB-MS, m/e 446.3 (MH⁺)

HRMS (FAB) calc. for $C_{23}H_{36}N_5O_4$: 446.2767 Found: 446.2769

EXAMPLE 76

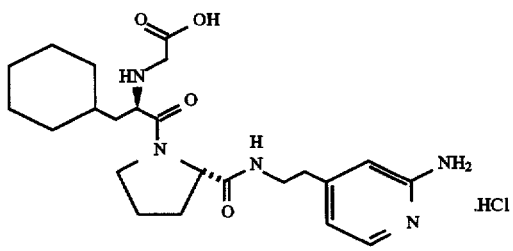

HO₂CCH₂—D—Cha—Pro-4-NHCH₂CH₂-2-aminopyridine.HCl

A) Preparation of 4-BocNHCH₂CH₂-2-CN-pyridine

To a solution of 4-BocNHCH₂CH₂-pyridine (2.22 g, 10 mmol) in acetone (50 mL) was added a solution of m-chloroperbenzoic acid (5.2 g, 30 mmol) in acetone (50 mL) via an addition funnel over 10 min. After stirring overnight, the solvent was removed in vacuo and the residue was partitioned between water (100 mL) and diethyl ether (100 mL). The organic phase was separated and extracted three times with water. The combined aqueous phase was then saturated with solid NaCl and extracted three times with dichloromethane (100 mL). The combined dichloromethane extracts were washed once with brine, dried with Na₂SO₄, filtered and concentrated to a small volume in vacuo and then diethyl ether was added. The white precipitate (2.0 g) was filtered and dried in vacuo.

One half of the isolated solid (4.2 mmol) was dissolved in dichloromethane (10 mL) and to this stirring solution was added trimethylsilyl cyanide (0.84 mL, 6.3 mmol) followed by N,N-dimethylcarbamoyl chloride (0.58 mL, 6.3 mmol). After stirring overnight, 1M aq. KHCO₃ (1 mL) was added slowly and the mixture was partitioned between ethyl acetate and water. The organic phase was then washed twice with brine, dried with MgSO₄, filtered and concentrated in vacuo to give 0.6 g (58%) of an amber oil which crystallized upon standing.

IR
¹H NMR
FD-MS, m/e 247 (M⁺)

Analysis for $C_{13}H_{17}N_3O_2$: Calc: C, 63.31; H, 7.02; N, 16.99; Found: C, 63.31; H, 7.02; N, 16.71.

B) Preparation of 4-BocNHCH₂CH₂-2-CbzNH-pyridine

To a stirring solution of 4-BocNHCH₂CH₂-2-CN-pyridine (0.5 g, 2 mmol) in methanol (2.4 mL), was added 5N NaOH (1.6 mL, 8 mmol) and the solution was heated to reflux. After 24 h, the solution was cooled to room temperature and allowed to stir for an additional 48 h. The pH was then adjusted to 7 with 1N HCl and the solvents were removed in vacuo.

The residue was suspended in toluene (50 mL) and heated to reflux. To this stirring solution was sequentially added, triethylamine (0.36 mL, 2.6 mmol), benzyl alcohol (0.27 mL, 2.6 mmol) and diphenylphosphoryl azide (0.72 g, 2.6 mmol). After stirring at reflux overnight, the solution was allowed to cool and then diluted with ethyl acetate (200 mL) and washed twice with saturated aqueous NH₄Cl and twice with brine. The organic phase was then dried with MgSO₄, filtered and concentrated in vacuo. The residue was then chromatographed over silica gel eluting with a step gradient of hexanes through 50% ethyl acetate/hexanes. The product containing fractions as determined by TLC were combined and concentrated in vacuo to give 0.37 g (50%) of a white solid.

¹H NMR
FD-MS, m/e 371.2 (M⁺)

Analysis for $C_{20}H_{25}N_3O_4$: Calc: C, 64.67; H, 6.78; N, 11.31; Found: C, 64.90; H, 7.07; N, 11.06.

C) Preparation of HO₂CCH₂-D-Cha-Pro-4-NHCH₂CH₂-2-aminopyridine.HCl

By methods substantially equivalent to those described in example 23-A, 1-G (using N-(t-BuO₂CCH₂)-N-Boc-D-Cha-ProOH), 23-D and 58-E, 48 mg of HO₂CCH₂-D-Cha-Pro-4-NHCH₂CH₂-2-aminopyridine.HCl was prepared from 4-BocNHCH₂CH₂-2-CbzNH-pyridine. The product was purified by RPHPLC method 2 (98/2 (A/B) through 70/30 (A/B), 150 min).

¹H NMR
FAB-MS, m/e 446.4 (MH⁺)

Analysis for $C_{23}H_{35}N_5O_4 \cdot 1.5HCl \cdot H_2O$: Calc: C, 53.30; H, 7.49; N, 13.51; Found: C, 53.64; H, 7.27; N, 13.80.

EXAMPLE 77

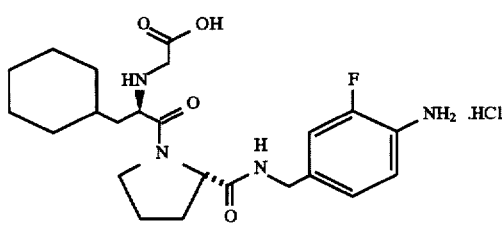

HO₂CCH₂—D—Cha—Pro-4-NHCH₂-2-F-aniline.HCl

Preparation of HO₂CCH₂-D-Cha-Pro-4-NHCH₂-2-F-aniline.HCl

By methods substantially equivalent to those described in example 64, 0.55 g of HO₂CCH₂-D-Cha-Pro-4-NHCH₂-2-F-aniline.HCl was prepared from 3-F-4-NO₂-toluene. The product was purified by RPHPLC method 2 (98/2 (A/B) through 60/40 (A/B), 180 min).

IR

¹H NMR

FAB-MS, m/e 449.3 (MH⁺)

Analysis for C₂₃H₃₃N₄O₄F.0.9HCl.H₂O: Calc: C, 55.32; H, 7.25; N, 11.22; Cl, 6.39; Found: C, 55.49; H, 6.93; N, 11.15; Cl, 6.23.

EXAMPLE 78

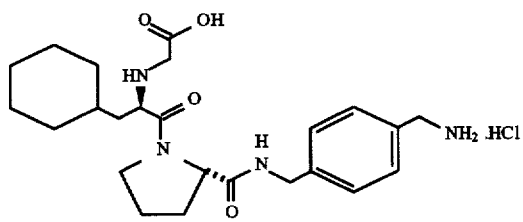

HO₂CCH₂—D—Cha—Pro-4-NHCH₂C₆H₄CH₂NH₂.HCl

Preparation of HO₂CCH₂-D-Cha-Pro-4-NHCH₂C₆H₄CH₂NH₂.HCl

By methods substantially equivalent to those described in example 10, using N-(t-BuO₂CCH₂)-N-Boc-D-Cha-ProOH in place of Boc-D-Phe-ProOH, 0.53 g of HO₂CCH₂-D-Cha-Pro-4-NHCH₂C₆H₄CH₂NH₂.HCl was prepared. The product was purified by RPHPLC method 2 (98/2 (A/B) through 70/30 (A/B), 150 min).

IR

¹H NMR

FD-MS, m/e 445.4 (MH⁺)

Analysis for C₂₄H₃₆N₄O₄.2.2HCl.0.5H₂O: Calc: C, 54.00; H, 7.40; N, 10.50; Cl, 14.61; Found: C, 54.18; H, 7.54; N, 10.31; Cl, 14.86.

EXAMPLE 79

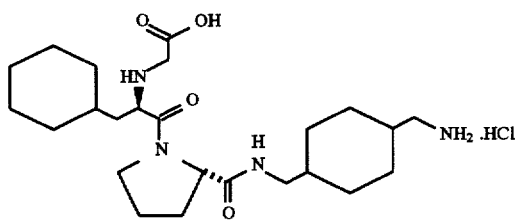

HO₂CCH₂—D—Cha—Pro-4-NHCH₂C₆H₁₀CH₂NH₂.HCl

Preparation of HO₂CCH₂-D-Cha-Pro-4-NHCH₂C₆H₁₀CH₂NH₂.HCl

By methods substantially equivalent to those described in example 12, using N-(t-BuO₂CCH₂)-N-Boc-D-Cha-ProOH in place of Boc-D-Phe-ProOH, 0.04 g of HO₂CCH₂-D-Cha-Pro-4-NHCH₂C₆H₁₀CH₂NH₂.HCl was prepared. The product was purified by RPHPLC method 2 (98/2(A/B) through 70/30 (A/B), 150 min.).

¹H NMR

FD-MS, m/e 451 (MH⁺)

Analysis for C₂₄H₄₂N₄O₄.2.7HCl.0.5H₂O: Calc: C, 51.65; H, 8.25; N, 10.04; Found: C, 51.47; H, 7.87; N, 9.97.

EXAMPLE 80

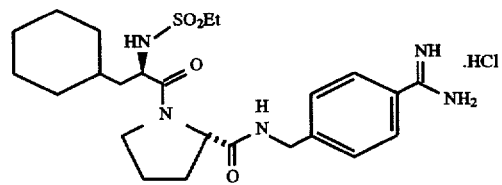

EtSO₂—D—Cha—Pro-4-NHCH₂C₆H₄C(NH)NH₂.HCl
(N-(ethylsulfonyl)-D-cyclohexylalanyl-N-
[[4-(aminoiminomethyl)phenyl]methyl]-L-prolinamide hydrochloride)

Preparation of EtSO₂-D-Cha-Pro-4-NHCH₂C₆H₄C(NH)NH₂.HCl

By methods substantially equivalent to those described in example 18, using EtSO₂-D-Cha-ProOH in place of Cbz-D-1-Piq-ProOH, 3.6 g of EtSO₂-D-Cha-Pro-4-NHCH₂C₆H₄C(NH)NH₂.HCl was prepared. The product was purified by RPHPLC method 2, (90/10 (A/B) through 50/50 (A/B), 180 min).

IR

¹H NMR

FAB-MS, m/e 492.3 (MH⁺)

Analysis for C₂₄H₃₇N₅O₄S.HCl: Calc: C, 54.58; H, 7.25; N, 13.26; Cl, 6.71; Found: C, 54.31; H, 7.31; N, 13.37; Cl, 6.71.

EXAMPLE 81

EtSO₂—D—Cha—Pro-4-NHCH₂C₆H₄CH₂NH₂·HCl

Preparation of EtSO₂-D-Cha-Pro-4-NHCH₂C₆H₄CH₂NH₂·HCl

By methods substantially equivalent to those described in example 10, using EtSO₂-D-Cha-ProOH in place of Boc-D-Phe-ProOH, EtSO₂-D-Cha-Pro-4-NHCH₂C₆H₄CH₂NH₂·HCl was prepared. The product was purified by RPHPLC method 2, (90/10 (A/B) through 50/50 (A/B), 180 min).

IR
¹H NMR
FAB-MS, m/e 479.4 (MH⁺)

Analysis for $C_{24}H_{38}N_4O_4S \cdot HCl \cdot H_2O$: Calc: C, 54.07; H, 7.75; N, 10.51; Cl, 6.65; Found: C, 54.13; H, 7.44; N, 10.51; Cl, 6.78.

EXAMPLE 82

EtSO₂—D—Cha—Pro-4-NHCH₂-3-F—C₆H₃NH₂·HCl.

Preparation of EtSO₂-D-Cha-Pro-4-NHCH₂-3-F-C₆H₃NH₂·HCl

By methods substantially equivalent to those described in example 64, using EtSO₂-D-Cha-ProOH in place of N-(t-BuO₂CCH₂)-N-Boc-D-Cha-ProOH, 0.53 g of EtSO₂-D-Cha-Pro-4-NHCH₂-3-F-C₆H₃NH₂·HCl was prepared. The product was purified by RPHPLC method 2, (90/10 (A/B) through 50/50 (A/B), 180 min).

IR
¹H NMR
FAB-MS, m/e 483.3 (MH⁺)

Analysis for $C_{23}H_{35}N_4O_4SF \cdot 1.1HCl \cdot 0.5H_2O$: Calc: C, 51.95; H, 7.03; N, 10.54; Cl, 7.33; Found: C, 52.09; H, 6.94; N, 10.39; Cl, 7.24.

EXAMPLE 83

EtSO₂—D—Cha—Pro-4-NHCH₂-2-aminopyridine·HCl

Preparation of EtSO₂-D-Cha-Pro-4-NHCH₂-2-aminopyridine·HCl

By methods substantially equivalent to those described in example 73, using EtSO₂-D-Cha-ProOH in place of N-(t-BuO₂CCH₂)-N-Boc-D-Cha-ProOH, 0.22 g of EtSO₂-D-Cha-Pro-4-NHCH₂-2-aminopyridine·HCl was prepared from 4-methyl-2-aminopyridine. The product was purified by RPHPLC method 2, (90/10 (A/B) through 50/50 (A/B), 180 min.).

¹H NMR
FAB-MS, m/e 466.4 (MH⁺)

Analysis for $C_{22}H_{35}N_5O_4S \cdot 1.1HCl$: Calc: C, 52.25; H, 7.19; N, 13.85; Cl, 7.71; Found: C, 52.49; H, 6.96; N, 13.96; Cl, 7.76.

EXAMPLE 84

EtSO₂—D—Cha—Pro-5-NHCH₂-2-aminopyridine·HCl

Preparation of EtSO₂-D-Cha-Pro-5-NHCH₂-2-aminopyridine·HCl

By methods substantially equivalent to those described in example 73, using EtSO₂-D-Cha-ProOH in place of N-(t-BuO₂CCH₂)-N-Boc-D-Cha-ProOH, 0.24 g of EtSO₂-D-Cha-Pro-5-NHCH₂-2-aminopyridine·HCl was prepared from 5-methyl-2-aminopyridine. The product was purified by RPHPLC method 2, (90/10 (A/B) through 50/50 (A/B), 180 min).

¹H NMR
FAB-MS, m/e 466.4 (MH⁺)

Analysis for $C_{22}H_{35}N_5O_4S \cdot 1.15HCl$: Calc: C, 52.06; H, 7.18; N, 13.80; Cl, 8.03; Found: C, 52.38; H, 6.97; N, 14.20; Cl, 8.46.

EXAMPLE 85

HOOCCH₂CH₂CH₂—D—Cha—Pro-p-NHCH₂C₆H₄C(NH)NH₂·HCl
(N—(3-carboxypropyl)—D—cyclohexylalanyl—N—
[[4-(aminoiminomethyl)phenyl]methyl]—L—prolinamide hydrochloride)

A) Preparation of Cbz-MeOOCCH=CHCH₂-D-Cha-Pro-p-NHCH₂C₆H₄C(NH)NHCbz

To a solution of D-Cha-Pro-p-NHCH₂C₆H₄C(NH)NHCbz·2HCl (2.5 g, 4.1 mmol) in DMF (50 mL) was added N,N-diisopropylethylamine (2.2 mL, 12.2 mmol) and methyl 3-bromocrotonate (0.95 g, 4.5 mmol). After stirring for 48 h, Cbz-Cl (0.7 mL, 5 mmol) and additional N,N-diisopropylethylamine (0.85 mL, 5 mmol) were added. After an additional 16 h of stirring, the volatiles were removed in vacuo. The residue was partitioned between ethyl acetate (100 mL) and saturated aqueous ammonium chloride (100 mL). The layers were separated and the organic phase was washed once with saturated aqueous ammonium chloride (50 mL), twice with saturated aqueous sodium bicarbonate (50 mL) and twice with brine (50 mL). The organic phase was dried (MgSO$_4$), filtered, and concentrated in vacuo. The crude residue was purified by flash chromatography (ethyl acetate/hexanes gradient) to yield 660 mg (22%) of a white foam.

$^1$H NMR
FD-MS, m/e 766 (M$^+$)
Analysis for C$_{43}$H$_{51}$N$_5$O$_8$: Calc: C, 67.43; H, 6.71; N, 9.14; Found: C, 67.22; H, 6.57; N, 8.98.

B) Preparation of HOOCCH$_2$CH$_2$CH$_2$-D-Cha-Pro-p-NHCH$_2$C$_6$H$_4$C(NH)NH$_2$.HCl To a solution of Cbz-MeOOCCH=CHCH$_2$-D-Cha-Pro-p-NHCH$_2$C$_6$H$_4$C(NH)NHCbz (0.5 g, 0.65 mmol) in ethanol (5 mL) was added 1N sodium hydroxide (0.65 mL). After stirring for 5 h at room temperature, 1N HCl (3 mL), 10% Pd/C (0.5 g), H$_2$O (15 mL) and ethanol (25 mL) were added. The stirring suspension was degassed under vacuum, then placed under an atmosphere of hydrogen for 18 h. Diatomaceous earth was added and the slurry was filtered. The filtrate was concentrated in vacuo and purified by RPHPLC (method 2, 98/2 (A/B), ramp to 75/25 (A/B) over 150 minutes). Fractions containing pure product were pooled and lyophilized to give 46 mg (13%).

$^1$H NMR
FAB-MS, m/e 486.3 (MH$^+$)
Analysis for C$_{26}$H$_{39}$N$_5$O$_4$.2.1HCl: Calc: C, 55.15; H, 7.35; N, 12.19; Cl, 13.24; Found: C, 55.55; H, 7.37; N, 12.19; Cl, 13.58.

EXAMPLE 86

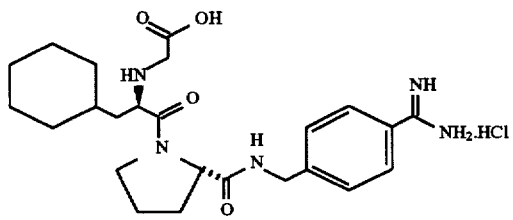

HOOCCH$_2$ — D — CHg — Pro-p-NHCH$_2$C$_6$H$_4$C(NH)NH$_2$.HCl
(N — (carboxymethyl) — D — cyclohexylglycyl — N —
[[4-(aminoiminomethyl)phenyl]methyl] — L — prolinamide hydrochloride)

A) Preparation of D-cyclohexylglycine

By a method substantially equivalent to that described in Example 53-B, 16.1 g (16%) of D-cyclohexylglycine was prepared starting from D-phenylglycine.

$^1$H NMR
FD-MS, m/e 117 (M$^+$)
Analysis for C$_8$H$_{15}$NO$_2$: Calc: C, 61.12; H, 9.62; N, 8.91; Found: C, 61.23; H, 9.56; N, 8.73.

B) Preparation of Boc-D-cyclohexylglycine

By a method substantially equivalent to that described in Example 17-A (using di-tert-butyl dicarbonate), 22 g (90%) of Boc-D-cyclohexylglycine was prepared.

$^1$H NMR
FD-MS, m/e 258 (M$^+$)
Analysis for C$_{13}$H$_{23}$NO$_4$: Calc: C, 60.68; H, 9.01; N, 5.44; Found: C, 60.91; H, 9.18; N, 5.38.

C) Preparation of Boc-Pro-p-NHCH$_2$C$_6$H$_4$C(NH)NHCbz

By a method substantially equivalent to that described in Example 1-G, 20.5 g (76%) of Boc-Pro-p-NHCH$_2$C$_6$H$_4$C(NH)NHCbz was prepared from Boc-Pro-OH and NH$_2$CH$_2$C$_6$H$_4$C(NH)NHCbz.2HCl.

$^1$H NMR
FD-MS, m/e 481 (M$^+$)

Analysis for C$_{26}$H$_{32}$N$_4$O$_5$: Calc: C, 64.98; H, 6.71; N, 11.66; Found: C, 64.76; H, 6.78; N, 11.62.

D) Preparation of Pro-p-NHCH$_2$C$_6$H$_4$C(NH)NHCbz.2HCl

By a method substantially equivalent to that described in Example 23-A, 18.4 g (100%) of Pro-p-NHCH$_2$C$_6$H$_4$C(NH)NHCbz.2HCl was prepared.

$^1$H NMR
FD-MS, m/e 381 (M$^+$)
Analysis for C$_{21}$H$_{26}$N$_4$O$_3$Cl$_2$: Calc: C, 55.63; H, 5.78; N, 12.36; Found: C, 54.19; H, 6.27; N, 12.15.

E) Preparation of Boc-D-Chg-Pro-p-NHCH$_2$C$_6$H$_4$C(NH)NHCbz

By a method substantially equivalent to that described in Example 1-G, 3.6 g (97%) of Boc-D-Chg-Pro-p-NHCH$_2$C$_6$H$_4$C(NH)NHCbz were prepared.

$^1$H NMR
FD-MS, m/e 619 (M$^+$)
Analysis for C$_{34}$H$_{45}$N$_5$O$_6$: Calc: C, 65.89; H, 7.32; N, 11.30; Found: C, 67.59; H, 8.07; N, 10.99.

F) Preparation of Cbz-t-BuOOCCH$_2$-D-Chg-Pro-p-NHCH$_2$C$_6$H$_4$C(NH)NHCbz

By methods substantially equivalent to those described in Examples 23-A and 85-A (using t-butyl bromoacetate and benzyl chloroformate), 1.6 g (45%) of N-Cbz-N-(t-BuOOCCH$_2$)-D-Chg-Pro-p-NHCH$_2$C$_6$H$_4$C(NH)NHCbz were prepared.

$^1$H NMR
FD-MS, m/e 769 (M$^+$)
Analysis for C$_{43}$H$_{53}$N$_5$O$_8$: Calc: C, 67.26; H, 6.96; N, 9.12; Found: C, 67.50; H, 6.97; N, 9.11.

G) Preparation of HOOCCH$_2$-D-Chg-Pro-p-NHCH$_2$C$_6$H$_4$C(NH)NH$_2$.HCl

By methods substantially equivalent to those described in Examples 23-A (using dioxane as solvent) and 18-F, 411 mg (61%) of HOOCCH$_2$-D-Chg-Pro-p-NHCH$_2$C$_6$H$_4$C(NH)NH$_2$.HCl were prepared.

$^1$H NMR
FAB-MS, m/e 444.3 (MH$^+$)
Analysis for C$_{23}$H$_{33}$N$_5$O$_4$.2.5HCl: Calc: C, 51.67; H, 6.69; N, 13.10; Found: C, 51.84; H, 6.50; N, 13.15.

EXAMPLE 87

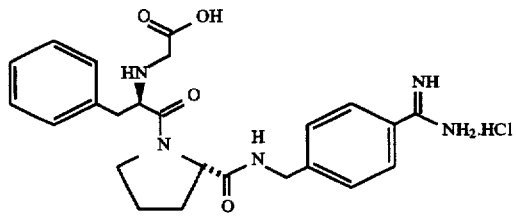

HOOCCH$_2$ — D — hPhe — Pro-p-NHCH$_2$C$_6$H$_4$C(NH)NH$_2$.HCl
(N — (carboxymethyl) — D — homophenylalanyl — N —
[[4-(aminoiminomethyl)phenyl]methyl] — L — prolinamide hydrochloride)

A) Preparation of HOOCCH$_2$-D-hPhe-Pro-p-NHCH$_2$C$_6$H$_4$C(NH)NH$_2$.HCl

By methods substantially equivalent to those described in Example 86, 335 mg of HOOCCH$_2$-D-hPhe-Pro-p-NHCH$_2$C$_6$H$_4$C(NH)NH$_2$.HCl were prepared starting from Boc-D-hPhe-OH.

$^1$H NMR
FAB-MS, m/e 466.3 (MH$^+$)
Analysis for C$_{25}$H$_{31}$N$_5$O$_4$.2.1HCl.H$_2$O: Calc: C, 53.61; H, 6.32; N, 12.50; Cl, 13.29; Found: C, 53.58; H, 6.08; N, 12.59; Cl, 13.67.

EXAMPLE 88

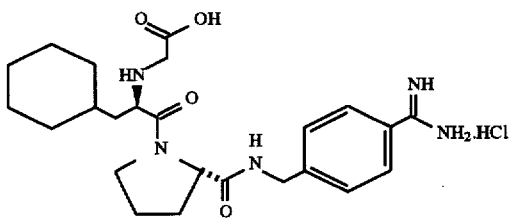

HOOCCH$_2$—D—hCha—Pro-p-NHCH$_2$C$_6$H$_4$C(NH)NH$_2$.HCl
(N—(carboxymethyl)—D—homocyclohexylglycyl—N—
[[4-(aminoiminomethyl)phenyl]methyl]—L—prolinamide
hydrochloride)

A) Preparation of Boc-D-hCha-OH

By a method substantially equivalent to that described in Example 53-D, 5.1 g (100%) of Boc-D-hCha-OH was prepared from Boc-D-hPhe-OH.

$^1$H NMR

FD-MS, m/e 240 (M$^+$)

Analysis for C$_{15}$H$_{27}$NO$_4$: Calc: C, 63.13; H, 9.54; N, 4.91; Found: C, 63.38; H, 9.39; N, 5.12.

B) Preparation of HOOCCH$_2$-D-hCha-Pro-p-NHCH$_2$C$_6$H$_4$C(NH)NH$_2$.HCl

By methods substantially equivalent to those described in Example 86, 135 mg of HOOCCH$_2$-D-hCha-Pro-p-NHCH$_2$C$_6$H$_4$C(NH)NH$_2$.HCl were prepared.

$^1$H NMR

FAB-MS, m/e 472.3 (MH$^+$)

Analysis for C$_{25}$H$_{37}$N$_5$O$_4$.2.2HCl.0.5H$_2$O: Calc: C, 53.54; H, 7.22; N, 12.49; Cl, 13.91; Found: C, 53.29; H, 7.01; N, 12.46; Cl, 14.30.

EXAMPLE 89

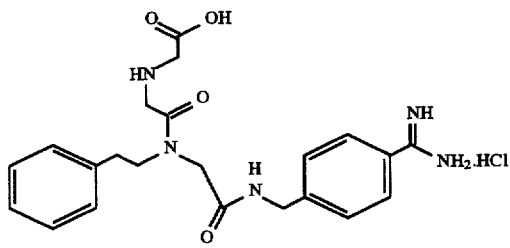

HOOCCH$_2$—Gly—N—C$_6$H$_5$CH$_2$CH$_2$Gly-p-NHCH$_2$C$_6$H$_4$C(NH)NH$_2$.HCl

A) Preparation of HOOCCH$_2$-Gly-N-C$_6$H$_5$CH$_2$CH$_2$Gly-p-NHCH$_2$C$_6$H$_4$C(NH)NH$_2$.HCl By methods substantially equivalent to those described in Examples 1-G, 1-D, 1-G, 23-A, 85-A, and 18-F, 365 mg of N-HOOCCH$_2$-Gly-N-C$_6$H$_5$CH$_2$CH$_2$-Gly-p-NHCH$_2$C$_6$H$_4$C(NH)NH$_2$.HCl were prepared.

$^1$H NMR

FAB-MS, m/e 426.2 (MH$^+$)

Analysis for C$_{22}$H$_{27}$N$_5$O$_4$.2.2HCl.1.5H$_2$O: Calc: C, 49.60; H, 6.09; N, 13.15; Cl, 14.64; Found: C, 49.79; H, 5.71; N, 13.31; Cl, 14.49.

EXAMPLE 90

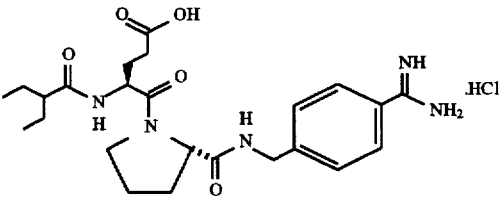

(C$_2$H$_5$)$_2$CHCO—Glu—Pro-p-NHCH$_2$C$_6$H$_4$C(NH)NH$_2$.HCl

A) Preparation of Boc-(γ-OBn)-Glu-Pro-p-NHCH$_2$C$_6$H$_4$C(NH)NHCbz

By a method substantially equivalent to that described in Example 1-G, 2.7 g (64%) of Boc-(γ-OBn)-Glu-Pro-p-NHCH$_2$C$_6$H$_4$C(NH)NHCbz were prepared starting from Boc-(γ-OBn)-Glu-OH and Pro-p-NHCH$_2$C$_6$H$_4$C(NH)NHCbz.2HCl.

$^1$H NMR

FD-MS, m/e 700 (M$^+$)

Analysis for C$_{38}$H$_{45}$N$_5$O$_8$: Calc: C, 65.22; H, 6.48; N, 10.01; Found: C, 65.00; H, 6.56; N, 10.06.

B) Preparation of (γ-OBn)-Glu-Pro-p-NHCH$_2$C$_6$H$_4$C(NH)NHCbz.2HCl

By a method substantially equivalent to that described in Example 23-A, 2.38 g (98%) of (γ-OBn)-Glu-Pro-p-NHCH$_2$C$_6$H$_4$C(NH)NHCbz.2HCl were prepared.

$^1$H NMR

FD-MS, m/e 600 (M$^+$)

Analysis for C$_{33}$H$_{39}$N$_5$O$_6$Cl$_2$: Calc: C, 58.93; H, 5.84; N, 10.41; Found: C, 58.64; H, 6.00; N, 10.63.

C) Preparation of (C$_2$H$_5$)$_2$CHCO-(γ-OBn)-Glu-Pro-p-NHCH$_2$C$_6$H$_4$C(NH)NHCbz To a stirring mixture of (γ-OBn)-Glu-Pro-p-NHCH$_2$C$_6$H$_4$C(NH)NHCbz.2HCl (1.3 g, 2 mmol) in THF/H$_2$O (50 mL each) was added K$_2$CO$_3$ (1.38 g, 10 mmol) and 2-ethylbutyryl chloride (0.3 g, 2.2 mmol). After stirring 10 min, volatiles were removed in vacuo. The resulting residue was partitioned between water and ethyl acetate (100 mL each). Layers were separated and the organic phase was washed twice with each saturated aqueous ammonium chloride and brine, dried (MgSO$_4$), filtered and concentrated in vacuo to give 1.45 g (100%).

$^1$H NMR

FD-MS, m/e 698 (M$^+$)

Analysis for C$_{39}$H$_{47}$N$_5$O$_7$: Calc: C, 67.13; H, 6.79; N, 10.04; Found: C, 67.11; H, 6.70; N, 9.74.

D) Preparation of (C$_2$H$_5$)$_2$CHCO-Glu-Pro-p-NHCH$_2$C$_6$H$_4$C(NH)NH$_2$.HCl By a method substantially equivalent to that described in example 18-F, 425 mg (47%) of (C$_2$H$_5$)$_2$CHCO-Glu-Pro-p-NHCH$_2$C$_6$H$_4$C(NH)NH$_2$.HCl were prepared. HPLC Method 2 (Ramp 98/2 A/B to 75/25 A/B over 150 min) was used to purify the product.

$^1$H NMR

FAB-MS, m/e 474.3 (MH$^+$)

Analysis for C$_{24}$H$_{35}$N$_5$O$_5$.1.5HCl.1.1H$_2$O: Calc: C, 51.10; H, 6.91; N, 12.41; Cl, 9.43; Found: C, 51.10; H, 6.81; N, 12.41; Cl, 9.62.

EXAMPLE 91

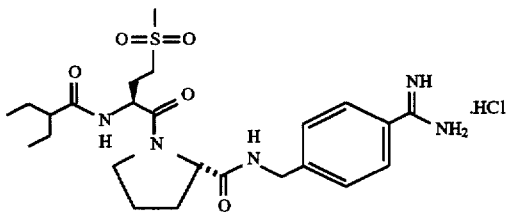

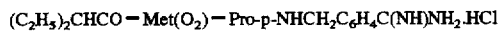

A) Preparation of $(C_2H_5)_2CHCO-Met(O_2)-Pro-p-NHCH_2C_6H_4C(NH)NH_2 \cdot HCl$ By methods substantially equivalent to those described in Example 90, 530 mg of $(C_2H_5)_2CHCO-Met(O_2)-Pro-p-NHCH_2C_6H_4C(NH)NH_2 \cdot HCl$ were prepared.

$^1$H NMR

FAB-MS, m/e 508.2 (MH$^+$)

Analysis for $C_{24}H_{37}N_5O_5S \cdot 1.1HCl$: Calc: C, 52.63; H, 7.01; N, 12.79; Cl, 7.12; Found: C, 52.42; H, 7.03; N, 12.80; Cl, 6.99.

EXAMPLE 92

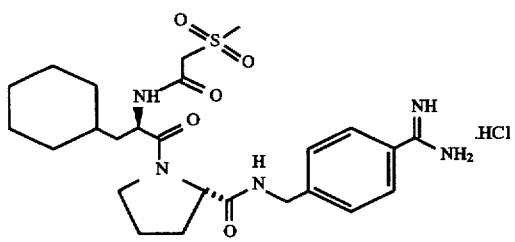

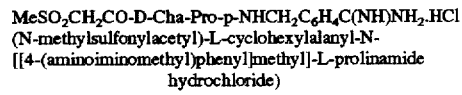

(N-methylsulfonylacetyl)-L-cyclohexylalanyl-N-[[4-(aminoiminomethyl)phenyl]methyl]-L-prolinamide hydrochloride)

Preparation of $MeSO_2CH_2CO-D-Cha-Pro-p-NHCH_2C_6H_4C(NH)NH_2 \cdot HCl$

By methods substantially equivalent those described in Examples 1-G and 18-F, 550 mg of $MeSO_2CH_2CO-D-Cha-Pro-p-NHCH_2C_6H_4C(NH)NH_2 \cdot HCl$ were prepared.

$^1$H NMR

FAB-MS, m/e 520.5 (MH$^+$)

Analysis for $C_{25}H_{37}N_5O_5S \cdot 1.2HCl \cdot H_2O$: Calc: C, 51.64; H, 6.97; N, 12.04; Cl, 7.32; Found: C, 51.58; H, 6.84; N, 12.18; Cl, 7.61.

The compounds of the invention are believed to selectively inhibit thrombin over other proteinases and nonenzyme proteins involved in blood coagulation without appreciable interference with the body's natural clot lysing ability (the compounds have a low inhibitory effect on fibrinolysis). Further, such selectivity is believed to permit use with thrombolytic agents without substantial interference with thrombolysis and fibrinolysis. Further, the compounds of the present invention are believed to be orally active.

The invention in one of its aspects provides a method of inhibiting thrombin in mammals comprising administering to a mammal in need of treatment an effective (thrombin inhibiting) dose of a compound of Formula I.

The thrombin inhibition contemplated by the present method includes both medical therapeutic and/or prophylactic treatment as appropriate.

In a further embodiment the invention relates to treatment, in a human or animal, of conditions where inhibition of thrombin is required. The compounds of the invention are expected to be useful in animals, including man, in treatment or prophylaxis of thrombosis and hypercoagulability in blood and tissues. Disease states in which the compounds have a potential utility are in treatment or prophylaxis of thrombosis and hypercoagulability in blood and tissues. Disease states in which the compounds have a potential utility, in treatment and/or prophylaxis, include venous thrombosis and pulmonary embolism, arterial thrombosis, such as in myocardial ischemia, myocardial infarction, unstable angina, thrombosis-based stroke and peripheral arterial thrombosis. Further, the compounds have expected utility in prophylaxis of atherosclerotic diseases such as coronary arterial disease, cerebral arterial disease and peripheral arterial disease. Further, the compounds are expected to be useful together with thrombolytics in myocardial infarction. Further, the compounds have expected utility in the treatment or prophylaxis for reocclusion after thrombolysis, percutaneous transluminal angioplasty (PTCA) and coronary bypass operations. Further, the compounds have expected utility in prevention of rethrombosis after microsurgery. Further, the compounds are expected to be useful in anticoagulant treatment in connection with artificial organs and cardiac valves. Further, the compounds have expected utility in anticoagulant treatment in hemodialysis and disseminated intravascular coagulation. A further expected utility is in rinsing of catheters and mechanical devices used in patients in vivo, and as an anticoagulant for preservation of blood, plasma and other blood products in vitro. Still further, the compounds have expected utility in other diseases where blood coagulation could be a fundamental contributing process or a source of secondary pathology, such as cancer, including metastasis, and inflammatory diseases, including arthritis and diabetes. The anticoagulant compound is administered orally, or parenterally, e.g., by intravenous infusion (iv), intramuscular injection (im) or subcutaneous injection (sc).

The specific dose of a compound administered according to this invention to obtain therapeutic and/or prophylactic effects will, of course, be determined by the particular circumstances surrounding the case, including, for example, the compound administered, the rate of administration, and the condition being treated.

A typical daily dose for each of the above utilities is between about 0.01 mg/kg and about 1000 mg/kg. The dose regime may vary, e.g., for prophylactic use a single daily dose may be administered or multiple doses such as 3 or 5 times daily may be appropriate. In critical care situations a compound of the invention is administered by iv infusion at a rate between about 0.01 mg/kg/h and about 20 mg/kg/h and preferably between about 0.1 mg/kg/h and about 5 mg/kg/h.

The method of this invention also is practiced in conjunction with a clot lysing agent, e.g., tissue plasminogen activator (t-PA), modified t-PA, streptokinase or urokinase. In cases when clot formation has occurred and an artery or vein is blocked, either partially or totally, a clot lysing agent is usually employed. A compound of the invention can be administered prior to or along with the lysing agent or subsequent to its use alone and preferably further is administered along with aspirin to prevent the reoccurrence of clot formation.

The method of this invention is also practiced in conjunction with a platelet glycoprotein receptor (IIb/IIIa) antagonist, that inhibits platelet aggregation. A compound of the invention can be administered prior to or along with the IIb/IIIa antagonist or subsequent to its use to prevent the reoccurrence of clot formation.

The method of this invention is also practiced in conjunction with aspirin. A compound of the invention can be administered prior to or along with aspirin or subsequent to its use to prevent the reoccurrence of clot formation. As stated above, preferably a compound of the present invention is administered in conjunction with a clot lysing agent and aspirin.

This invention also provides pharmaceutical formulations for use in the above described therapeutic method. Pharmaceutical formulations of the invention comprise an effective thrombin inhibiting amount of a compound of Formula I in association with a pharmaceutically acceptable carrier, excipient or diluent. For oral administration the antithrombotic compound is formulated in gelatin capsules or tablets which may contain excipients such as binders, lubricants, disintegration agents and the like. For parenteral administration the antithrombotic is formulated in a pharmaceutically acceptable diluent, e.g., physiological saline (0.9%), 5% dextrose, Ringer's solution, and the like.

The compound of the present invention can be formulated in unit dosage formulations comprising a dose between about 0.1 mg and about 1000 mg. Preferably the compound is in the form of a pharmaceutically acceptable salt such as for example the sulfate salt, acetate salt or a phosphate salt. An example of a unit dosage formulation comprises 5 mg of a compound of the present invention as a pharmaceutically acceptable salt in a 10 mL sterile glass ampoule. Another example of a unit dosage formulation comprises about 10 mg of a compound of the present invention as a pharmaceutically acceptable salt in 20 mL of isotonic saline contained in a sterile ampoule.

The compounds can be administered by a variety of routes including oral, rectal, transdermal, subcutaneous, intravenous, intramuscular, and intranasal. The compounds of the present invention are preferably formulated prior to administration. Therefore, another embodiment of the present invention is a pharmaceutical formulation comprising an effective amount of a compound of Formula I or a pharmaceutically acceptable salt or solvate thereof in association with a pharmaceutically acceptable carrier, diluent or excipient therefor.

The active ingredient in such formulations comprises from 0.1% to 99.9% by weight of the formulation. By "pharmaceutically acceptable" it is meant the carrier, diluent or excipient must be compatible with the other ingredients of the formulation and not deleterious to the recipient thereof.

The present pharmaceutical formulations are prepared by known procedures using well known and readily available ingredients. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), soft and hard gelatin capsules, suppositories, sterile injectable solutions, sterile packaged powders, and the like. The compositions of this invention may be formulated so as to provide quick, sustained, or delayed release of the active ingredient after administration to the patient by employing procedures well known in the art.

The following formulation examples are illustrative only and are not intended to limit the scope of the invention in any way. "Active ingredient," of course, means a compound according to Formula I or a pharmaceutically acceptable salt or solvate thereof.

Formulation 1

Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2

A tablet is prepared using the ingredients below:

|  | Quantity (mg/capsule) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Weight |
| --- | --- |
| Active ingredient | 0.25 |
| Ethanol | 25.75 |
| Propellant 22 (Chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

| Active ingredient | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

| Active ingredient | 80 mg |
|---|---|
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| Active ingredient | 225 mg |
|---|---|
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 mL dose, are made as follows:

| Active ingredient | 50 mg |
|---|---|
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| Active ingredient | 100 mg |
|---|---|
| Isotonic saline | 1,000 mL |

The solution of the above ingredients generally is administered intravenously to a subject at a rate of 1 mL per minute.

The compounds provided by the invention (Formula I) are orally active and selectively inhibit the action of thrombin in mammals.

The ability of the compounds of the present invention to be an effective and orally active thrombin inhibitor is evaluated in one or more of the following assays.

The inhibition of thrombin is demonstrated by in vitro inhibition of the amidase activity of thrombin as measured in an assay in which thrombin hydrolyzes the chromogenic substrate, N-benzoyl-L-phenylalanyl-L-valyl-L-arginyl-p-nitroanilide.

The assay is carried out by mixing 50 μL buffer (0.03M Tris, 0.15M NaCl, pH 7.4) with 25 μL of bovine thrombin or human thrombin solution (0.21 mg/mL of thrombostat bovine thrombin, Parke-Davis, or purified human thrombin, Enzyme Research Laboratories, South Bend, Ind., at about 8 NIH units/mL, in the same buffer) and 25 μL of test compound in a solvent (in 50% aqueous methanol, v:v). The 150 μL of an aqueous solution of the chromogenic substrate (at 0.25 mg/mL) are added and the rates of hydrolysis of the substrate are measured by monitoring the reactions at 405 nm for the release of p-nitroaniline. Standard curves are constructed by plotting free thrombin concentration against hydrolysis rate. The hydrolysis rates observed with test compounds are then converted to "free thrombin" values in the respective assays by use of the standard curves. The bound thrombin (bound to test compound) is calculated by subtracting the amount of free thrombin observed in each assay from the known initial amount of thrombin used in the assay. The amount of free inhibitor in each assay is calculated by subtracting the number of moles of bound thrombin from the number of moles of added inhibitor (test compound).

The Kass value is the hypothetical equilibrium constant for the reaction between thrombin and the test compound (I).

$$Kass = \frac{[Thrombin - I]}{[(Thrombin) \times (I)]}$$

Kass is calculated for a range of concentrations of test compounds and the mean value is reported in units of liter per mole.

By substantially following the procedures described above for human thrombin, and using other human blood coagulation system serine proteases and proteases of the fibrinolytic system with the appropriate chromogenic substrates, identified below, selectivity of the compounds of the present invention with respect to the coagulation factor serine proteases and with respect to the fibrinolytic system serine proteases are evaluated as well as their substantial lack of interference with serine proteases of the fibrinolytic system. Thrombin inhibitors preferably should spare fibrinolysis induced by urokinase, tissue plasminogen activator (t-PA) and streptokinase. This would be important to the therapeutic use of such agents as an adjunct to streptokinase, t-PA or urokinase thrombolytic therapy and to the use of such agents as an endogenous fibrinolysis-sparing (with respect to t-PA and urokinase) antithrombotic agent. In addition to the lack of interference with the amidase activity of the fibrinolytic proteases, such fibrinolytic system sparing can be studied by the use of human plasma clots and their lysis by the respective fibrinolytic plasminogen activators.

Human factors X, Xa, IXa, XIa, and XIIa are purchased from Enzyme Research Laboratories, South Bend, Ind.; human urokinase from Leo Pharmaceuticals, Denmark; and recombinant activated Protein C (aPC) is prepared at Eli Lilly and Co. Substantially according to U.S. Pat. No. 4,981,952. Chromogenic substrates: N-Benzoyl-Ile-Glu-Gly-Arg-p-nitroanilide (for factor Xa); N-Cbz-D-Arg-Gly-Arg-p-nitroanilide (for factor IXa assay as the factor Xa substrate); Pyroglutamyl-Pro-Arg-p-nitroanilide (for Factor XIa and for aPC); H-D-Pro-Phe-Arg-p-nitroanilide (for factor XIIa); and Pyroglutamyl-Gly-Arg-p-nitroanilide (for urokinase); are purchased from KabiVitrum, Stockholm, Sweden, or from Midwest Biotech, Fishers, Ind. Bovine trypsin is purchased from Worthington Biochemicals, Freehold, N.J., and human plasma kallikrein from Kabi Vitrum, Stockholm, Sweden. Chromogenic substrate H-D-Pro-Phe-Arg-p-nitroanilide for plasma kallikrein is purchased from Kabi Vitrum, Stockholm, Sweden. N-Benzoyl-Phe-Val-Arg-p-nitroanilide, the substrate for human thrombin and for trypsin, is synthesized according to procedures described above for the compounds of the present invention, using known methods of peptide coupling from commercially available reactants or purchased from Midwest Biotech, Fishers, Ind.

Human plasmin is purchased from Boehringer Mannheim, Indianapolis, Ind.; nt-PA is purchased as single chain activity reference from American Diagnostica, Greenwich, Conn.; modified-t-PA6 (mt-PA6) is prepared at Eli Lilly and Company by procedure known in the art (See, Burck, et al., *J. Biol. Chem.*, 265, 5120–5177 (1990). Plasmin chromogenic substrate H-D-Val-Leu-Lys-p-nitroanilide and tissue plasminogen activator (t-PA) substrate H-D-Ile-Pro-Arg-p-nitroanilide are purchased from Kabi Vitrum, Stockholm, Sweden.

In the chromogenic substrates described above the three-letter symbols Ile, Glu, Gly, Pro, Arg, Phe, Val, Leu and Lys are used to indicate the corresponding amino acid group isoleucine, glutamic acid, glycine, proline, arginine, phenylalanine, valine, leucine and lysine, respectively.

Table 1 which follows lists the Kass values obtained with the indicated compound represented by the Formula I.

TABLE 1

Inhibition Properties $K_{ass} \times 10^6$ (L/mole)

| Example | Human Thrombin | Xa | Trypsin | Plasmin | t-PA |
|---|---|---|---|---|---|
| 1 | 3.3 | 0.0017 | 0.38 | 0.010 | 0.082 |
| 2 | 4.4 | 0.0092 | 1.0 | 0.045 | 0.023 |
| 3 | 2.1 | 0.0021 | 0.24 | 0.0046 | 0.033 |
| 4 | 13. | 0.0057 | 0.076 | 0.0033 | 0.074 |
| 5 | 0.035 | 0.00039 | 0.00015 | 0.00022 | <0.001 |
| 6 | 2.3 | 0.00024 | 0.0016 | 0.00023 | <0.001 |
| 7 | 1.9 | 0.0041 | 0.0081 | 0.00022 | 0.0037 |
| 8 | 5.3 | 0.00038 | 0.022 | 0.00080 | 0.0012 |
| 9 | 0.033 | 0.00058 | 0.00017 | <0.001 | <0.001 |
| 10 | 1.4 | 0.000024 | 0.077 | 0.0045 | 0.00055 |
| 11 | 0.064 | 0.000068 | 0.0036 | 0.0060 | <0.001 |
| 12 | 0.44 | 0.000042 | 0.0022 | 0.00087 | 0.000042 |
| 13 | 0.49 | 0.00098 | 0.00066 | 0.00011 | <0.001 |
| 14 | 0.021 | 0.00014 | 0.000056 | 0.000046 | <0.001 |
| 15 | 220 | 0.0070 | 2.6 | 0.017 | 0.004 |
| 16 | 0.97 | 0.0051 | 0.02 | 0.0017 | 0.0012 |
| 17 | 33 | 0.049 | 3.8 | 0.024 | 0.0034 |
| 18 | 180 | 0.21 | 14 | 0.085 | 0.0094 |
| 19 | 11 | 0.14 | 41 | 0.16 | 0.0056 |
| 20 | 10 | 0.10 | 19 | 0.10 | 0.0077 |
| 21 | 3.6 | 0.62 | 0.96 | 0.031 | 0.002 |
| 22 | 3.0 | 0.043 | 8.5 | 0.042 | 0.004 |
| 23 | 770 | 0.14 | 21 | 0.44 | 0.31 |
| 24 | 0.78 | <0.001 | 0.03 | <0.001 | <0.001 |
| 25 | 0.43 | <0.001 | 0.01 | <0.001 | 0.01 |
| 26 | 13. | 0.01 | 0.21 | 0.01 | 0.01 |
| 27 | 0.29 | 0.02 | 0.02 | <0.001 | 0.02 |
| 28 | 0.95 | 0.01 | 0.11 | <0.001 | <0.001 |
| 29 | 0.76 | 0.02 | 0.02 | <0.001 | <0.001 |
| 30 | 0.55 | 0.02 | 0.03 | <0.001 | <0.001 |
| 31 | 0.07 | 0.14 | 0.05 | <0.001 | <0.001 |
| 32 | 0.13 | 0.03 | 0.04 | <0.001 | 0.01 |
| 33 | 0.04 | 0.04 | 0.02 | <0.001 | <0.001 |
| 34 | 0.65 | <0.001 | 0.49 | 0.01 | 0.01 |
| 35 | 0.09 | <0.001 | 0.04 | <0.001 | <0.001 |
| 36 | 0.06 | <0.001 | 0.01 | <0.001 | <0.001 |
| 37 | 0.02 | <0.009 | | | |
| 38 | 1.1 | <0.001 | 0.07 | <0.001 | |
| 39 | 0.12 | <0.001 | <0.02 | <0.001 | |

TABLE 1-continued

Inhibition Properties $K_{ass} \times 10^6$ (L/mole)

| Example | Human Thrombin | Xa | Trypsin | Plasmin | t-PA |
|---|---|---|---|---|---|
| 40 | 0.03 | <0.001 | 0.01 | <0.001 | |
| 41 | 0.01 | <0.001 | <0.001 | <0.001 | |
| 42 | 38. | 0.07 | 43. | 0.12 | 0.01 |
| 43 | 1.4 | 0.05 | 100. | 0.30 | 0.01 |
| 44 | 630 | 0.66 | 2,600. | 1.8 | 0.04 |
| 45 | 610 | 1.5 | 110. | 1.1 | 0.77 |
| 46 | 240 | 0.07 | 48. | 0.13 | 0.01 |
| 47 | 45 | 0.04 | 82. | 0.18 | 0.01 |
| 48 | 4,100 | 5.5 | 250. | 0.43 | 0.05 |
| 49 | 400 | 3.4 | 940. | 0.84 | 0.04 |
| 50 | 40 | 4.3 | 2,200. | 1.8 | 0.04 |
| 51 | 1,300 | 0.84 | 27. | 0.13 | 0.01 |
| 52 | 700 | 0.46 | 47. | 0.11 | 0.01 |
| 53 | 0.36 | <0.001 | 0.1 | <0.001 | <0.001 |
| 54 | 2.8 | <0.001 | 0.52 | 0.01 | <0.001 |
| 55 | 0.01 | <0.001 | 0.01 | <0.001 | <0.001 |
| 56 | 490 | 0.20 | 3.6 | 0.01 | <0.001 |
| 57 | 39 | 0.01 | 0.24 | 0.01 | <0.001 |
| 58 | 0.60 | <0.001 | 0.40 | <0.001 | <0.001 |
| 59 | 1.10 | <0.001 | 0.21 | <0.001 | <0.001 |
| 60 | 0.24 | <0.001 | 0.03 | <0.001 | <0.001 |
| 61 | 63 | 0.03 | 1.0 | 0.004 | 0.008 |
| 62 | 7.6 | | | | |
| 63 | 0.31 | | | | |
| 64 | 15 | 0.01 | | | |
| 65 | 4,500 | | 570. | | |
| 66 | 120 | | 4.6 | | |
| 67 | 11 | | | | |
| 68 | 600 | | | | |
| 69 | 340 | | 3.7 | | |
| 70 | 430 | | 9.8 | | |
| 71 | 1,400 | | 240. | | |
| 72 | 2,300 | | 280 | | |
| 73 | 28 | | | | |
| 74 | 29 | | | | |
| 75 | 0.45 | | | | |
| 76 | 12 | | 0.36 | | |
| 77 | 11 | | | | |
| 78 | 11 | | 8.6 | | |
| 79 | 2.0 | | 0.24 | | |
| 80 | 1,700. | | 90. | | |
| 81 | 5.3 | | 2.1 | | |
| 82 | 5.0 | | | | |
| 83 | 2.4 | | 0.03 | | |
| 84 | 2.9 | | 0.07 | | |
| 85 | 265 | | 30.8 | | |
| 86 | 200 | 0.63 | | | |
| 87 | 30 | 2.5 | | | |
| 88 | 410 | 3.9 | | | |
| 89 | 0.14 | 0.071 | | | |
| 90 | 0.61 | 0.002 | | | |
| 91 | 3.6 | 0.007 | | | |
| 92 | 130 | | 7.7 | | |

It is noted that compounds in which X contains a D-cyclohexylalanyl moiety have unexpected improved potency with respect to inhibition of thrombin and display especially surprisingly enhanced potency with respect to the inhibition of factor Xa when compared with, for example, the corresponding compounds in which X contains a D-phenylalanyl moiety.

Materials

Dog plasma is obtained from conscious mixed-breed hounds (either sex Hazelton-LRE, Kalamazoo, Mich., U.S.A.) by venipuncture into 3.8 percent citrate. Fibrinogen is prepared from fresh dog plasma and human fibrinogen is prepared from in-date ACD human blood at the fraction I-2 according to previous procedures and specifications. Smith, Biochem. J., 185, 1–11 (1980); and Smith, et al., Biochemistry, 11, 2958–2967, (1972). Human fibrinogen (98 percent pure/plasmin free) is from American Diagnostica, Greenwich, Conn. Radiolabeling of fibrinogen I-2 preparations is performed as previously reported. Smith, et al., Biochemistry, 11, 2958–2967, (1972). Urokinase is purchased form Leo Pharmaceuticals, Denmark, as 2200 Ploug units/vial. Streptokinase is purchased from Hoechst-Roussel Pharmaceuticals, Somerville, N.J.

Methods—Effects on Lysis of Human Plasma Clots by t-PA

Human plasma clots are formed in micro test tubes by adding 50 μL thrombin (73 NIH unit/mL) to 100 μL human plasma which contains 0.0229 μCi 125-iodine labeled fibrinogen. Clot lysis is studied by overlaying the clots with 50 μL of urokinase or streptokinase (50, 100, or 1000 unit/mL) and incubating for 20 hours at room temperature. After incubation the tubes are centrifuged in a Beckman Microfuge. 25 μL of supernate is added into 1.0 mL volume of 0.03M tris/0.15M NaCl buffer for gamma counting. Counting controls 100 percent lysis are obtained by omitting thrombin (and substituting buffer). The thrombin inhibitors are evaluated for possible interference with fibrinolysis by including the compounds in the overlay solutions at 1, 5, and 10 ug/mL concentrations. Rough approximations of $IC_{50}$ values are estimated by linear extrapolations from data points to a value which would represent 50 percent of lysis for that particular concentration of fibrinolytic agent.

Anticoagulant Activity
Materials

Dog plasma and rat plasma is obtained from conscious mixed-breed hounds (either sex, Hazelton-LRE, Kalamazoo, Mich., U.S.A.) or from anesthetized male Sprague-Dawley rats (Harlan Sprague-Dawley, Inc., Indianapolis, Ind., U.S.A.) by venipuncture into 3.8 percent citrate. Fibrinogen is prepared from in-date ACD human blood as the fraction I-2 according to previous procedures and specifications. Smith, Biochem. J., 185, 1-11 (1980); and Smith, et al., Biochemistry, 11, 2958-2967 (1972). Human fibrinogen is also purchased as 98 percent pure/plasmin free from American Diagnostica, Greenwich, Conn. Coagulation reagents ACTIN, Thromboplastin, and Human plasma are from Baxter Healthcare Corp., Dade Division, Miami, Fla. Bovine thrombin from Parke-Davis (Ann Detroit, Mich.) is used for coagulation assays in plasma.

Methods
Anticoagulation Determinations

Coagulation assay procedures are as previously described. Smith, et al., Thrombosis Research, 50, 163-174 (1988). A CoAScreener coagulation instrument (American LABor, Inc.) is used for all coagulation assay measurements. The prothrombin time (PT) is measured by adding 0.05 mL saline and 0.05 mL Thromboplastin-C reagent to 0.05 mL test plasma. The activated partial thromboplastin time (APTT) is measured by incubation of 0.05 mL test plasma with 0.05 mL Actin reagent for 120 seconds followed by 0.05 mL $CaCl_2$ (0.02M). The thrombin time (TT) is measured by adding 0.05 mL saline and 0.05 mL thrombin (10 NIH units/mL) to 0.05 mL test plasma. The compounds of Formula I are added to human or animal plasma over a wide range of concentrations to determine prolongation effects on the APTT, PT, and TT assays. Linear extrapolations are performed to estimate the concentrations required to double the clotting time for each assay.

Animals

Male Sprague Dawley rats (350-425 gm, Harlan Sprague Dawley Inc., Indianapolis, Ind.) are anesthetized with xylazine (20 mg/kg, s.c.) and ketamine (120 mg/kg, s.c.) and maintained on a heated water blanket (37° C.). The jugular vein(s) is cannulated to allow for infusions.

Arterio-Venous shunt model

The left jugular vein and right carotid artery are cannulated with 20 cm lengths of polyethylene PE 60 tubing. A 6 cm center section of larger tubing (PE 190) with a cotton thread (5 cm) in the lumen, is friction fitted between the longer sections to complete the arterio-venous shunt circuit. Blood circulated through the shunt for 15 minutes before the thread is carefully removed and weighed. The weight of a wet thread is subtracted from the total weight of the thread and thrombus (see J. R. Smith, Br. J. Pharmacol., 77,29 (1982)).

$FeCl_3$ model of arterial injury

The carotid arteries are isolated via a midline ventral cervical incision. A thermocouple is placed under each artery and vessel temperature is recorded continuously on a strip chart recorder. A cuff of tubing (0.058 ID×0.077 OD×4 mm, Baxter Med. Grade Silicone), cut longitudinally, is placed around each carotid directly above the thermocouple. $FeCl_3$ hexahydrate is dissolved in water and the concentration (20%) is expressed in terms of the actual weight of $FeCl_3$ only. To injure the artery and induce thrombosis, 2.85 μl is pipetted into the cuff to bathe the artery above the thermocouple probe. Arterial occlusion is indicated by a rapid drop in temperature. The time to occlusion is reported in minutes and represented the elapsed time between application of $FeCl_3$ and the rapid drop in vessel temperature (see K. D. Kurz, Thromb. Res., 60, 269 (1990)).

Spontaneous thrombolysis model

In vitro data suggested that the peptide thrombin inhibitors inhibit thrombin and other serine proteases, such as plasmin and tissue plasminogen activator. To assess if the compounds inhibited fibrinolysis in vivo, the rate of spontaneous thrombolysis is determined by implanting a labeled whole blood clot into the pulmonary circulation. Rat blood (1 mL) is mixed rapidly with bovine thrombin (4 IU, Parke Davis) and $^{125}I$ human fibrogen (5 μCi, ICN), immediately drawn into silastic tubing and incubated at 37° C. for 1 hour. The aged thrombus is expelled from the tubing, cut into 1 cm segments, washed 3× in normal saline and each segment is counted in a gamma counter. A segment with known counts is aspirated into a catheter that is subsequently implanted into the jugular vein. The catheter tip is advanced to the vicinity of the right atrium and the clot is expelled to float into the pulmonary circulation. One hour after implant, the heart and lungs are harvested and counted separately. Thrombolysis is expressed as a percentage where:

$$\% \text{ Thrombolysis} = \frac{(\text{injected cpm} - \text{lung cpm})}{\text{injected cpm}} \times 100$$

The fibrinolytic dissolution of the implanted clot occurs time-dependently (see J. P. Clozel, Cardiovas. Pharmacol., 12, 520 (1988)).

Coagulation parameters

Plasma thrombin time (TT) and activated partial thromboplastin time (APTT) are measured with a fibrometer. Blood is sampled from a jugular catheter and collected in syringe containing sodium citrate (3.8%, 1 part to 9 parts blood). To measure TT, rat plasma (0.1 mL) is mixed with saline (0.1 mL) and bovine thrombin (0.1 mL, 30 U/mL in TRIS buffer; Parke Davis) at 37° C. For APTT, plasma (0.1 mL) and APTT solution (0.1 mL, Organon Teknika) are incubated for 5 minutes (37° C.) and $CaCl_2$ (0.01 mL, 0.025M) is added to start coagulation. Assays are done in duplicate and averaged.

Index of Bioavailability

A measure of bioactivity, plasma thrombin time (TT), served as a substitute for the assay of parent compound on the assumption that increments in TT resulted from thrombin inhibition by parent only. The time course of the effect of the thrombin inhibitor upon TT is determined after i.v. bolus administration to anesthetized rats and after oral treatment of fasted conscious rats. Due to limitations of blood volume and the number of points required to determine the time course from time of treatment to the time when the response returned to pretreatment values, two populations of rats are used. Each sample population represented alternating sequential time points. The average TT over the time course is used to calculate area under the curve (AUC). The index of bioavailability is calculated by the formula shown below and is expressed as percent relative activity.

The area under the curve (AUC) of the plasma TT time course is determined and adjusted for the dose. This index of bioavailability is termed "% Relative Activity" and is calculated as $$\text{\% Relative Activity} = \frac{AUC\ po}{AUC\ iv} \times \frac{\text{Dose iv}}{\text{Dose po}} \times 100$$

Compounds

Compound solutions are prepared fresh daily in normal saline and are injected as a bolus or are infused starting 15 minutes before and continuing throughout the experimental perturbation which is 15 minutes in the arteriovenous shunt model and 60 minutes in the $FeCl_3$ model of arterial injury and in the spontaneous thrombosis model. Bolus injection volume is 1 mL/kg for i.v., and 5 mL/kg for p.o. and infusion volume is 3 mL/hr.

Statistics

Results are expressed as means ±SEM. One-way analysis of variance is used to detect statistically significant differences and then Dunnett's test is applied to determine which means are different. Significance level for rejection of the null hypothesis of equal means is $P<0.05$.

Animals

Male dogs (Beagles; 18 months–2 years; 12–13 kg, Marshall Farms, North Rose, N.Y. 14516) are fasted overnight and fed Purina certified Prescription Diet (Purina Mills, St. Louis, Mo.) 240 minutes after dosing. Water is available ad libitum. The room temperature is maintained between 66°–74° F.; 45–50% relative humidity; and lighted from 0600–1800 hours.

Pharmacokinetic model

Test compound is formulated immediately prior to dosing by dissolving in sterile 0.9% saline to a 5 mg/mL preparation. Dogs are given a single 2 mg/kg dose of test compound by oral gavage. Blood samples (4.5 mL) are taken from the cephalic vein at 0.25, 0.5, 0.75, 1, 2, 3, 4 and 6 hours after dosing. Samples are collected in citrated Vacutainer tubes and kept on ice prior to reduction to plasma by centrifugation. Plasma samples are derivatized with dinitrophenylhydrazine and analyzed by HPLC (Zorbax SB-C8 column) eluting with methanol/500 mM sodium acetate adjusted to pH 7 with phosphoric acid (60:40, v/v). Plasma concentration of test compound is recorded and used to calculate the pharmacokinetic parameters: elimination rate constant, Ke; total clearance, Clt; volume of distribution, $V_D$; time of maximum plasma test compound concentration, Tmax; maximum concentration of test compound at Tmax, Cmax; plasma half-life, t0.5; area under the curve, A.U.C.; and fraction of test compound absorbed, F.

Canine Model of Coronary Artery Thrombosis

Surgical preparation and instrumentation of the dogs are as described in Jackson, et al., *Circulation*, 82, 930–940 (1990). Mixed-breed hounds (aged 6–7 months, either sex, Hazelton-LRE, Kalamazoo, Mich., U.S.A.) are anesthetized with sodium pentobarbital (30 mg/kg intravenously, i.v.), intubated, and ventilated with room air. Tidal volume and respiratory rates are adjusted to maintain blood $PO_2$, $PCO_2$, and pH within normal limits. Subdermal needle electrodes are inserted for the recording of a lead II ECG.

The left jugular vein and common carotid artery are isolated through a left mediolateral neck incision. Arterial blood pressure (ABP) is measured continuously with a precalibrated Millar transducer (model MPC-500, Millar Instruments, Houston, Tex., U.S.A.) inserted into the carotid artery. The jugular vein is cannulated for blood sampling during the experiment. In addition, the femoral veins of both hindlegs are cannulated for administration of test compound.

A left thoracotomy is performed at the fifth intercostal space, and the heart is suspended in a pericardial cradle. A 1- to 2-cm segment of the left circumflex coronary artery (LCX) is isolated proximal to the first major diagonal ventricular branch. A 26-gauge needle-tipped wire anodal electrode (Teflon®-coated, 30-gauge silverplated copper wire) 3–4 mm long is inserted into the LCX and placed in contact with the intimal surface of the artery (confirmed at the end of the experiment). The stimulating circuit is completed by placing the cathode in a subcutaneous (s.c.) site. An adjustable plastic occluder is placed around the LCX, over the region of the electrode. A precalibrated electromagnetic flow probe (Carolina Medical Electronics, King, N.C., U.S.A.) is placed around the LCX proximal to the anode for measurement of coronary blood flow (CBF). The occluder is adjusted to produce a 40–50% inhibition of the hyperemic blood flow response observed after 10-s mechanical occlusion of the LCX. All hemodynamic and ECG measurements are recorded and analyzed with a data acquisition system (model M3000, Modular instruments, Malvern, Pa. U.S.A.).

Thrombus Formation and Compound Administration Regimens

Electrolytic injury of the intima of the LCX is produced by applying 100-µA direct current (DC) to the anode. The current is maintained for 60 minutes and then discontinued whether the vessel has occluded or not. Thrombus formation proceeds spontaneously until the LCX is totally occluded (determined as zero CBF and an increase in the S-T segment). Compound administration is started after the occluding thrombus is allowed to age for 1 hour. A 2-hour infusion of the compounds of the present invention at doses of 0.5 and 1 mg/kg/h is begun simultaneously with an infusion of thrombolytic agent (e.g. tissue plasminogen activator, streptokinase, APSAC). Reperfusion is followed for 3 hours after administration of test compound. Reocclusion of coronary arteries after successful thrombolysis is defined as zero CBF which persisted for $\geq 30$ minutes.

Hematology and template bleeding time determinations

Whole blood cell counts, hemoglobin, and hematocrit values are determined on a 40-µl sample of citrated (3.8%) blood (1 part citrate:9 parts blood) with a hematology analyzer (Cell-Dyn 900, Sequoia-Turner, Mount View, Calif., U.S.A.). Gingival template bleeding times are determined with a Simplate II bleeding time device (Organon Teknika Durham, N.C., U.S.A.). The device is used to make 2 horizontal incisions in the gingiva of either the upper or lower left jaw of the dog. Each incision is 3 mm wide×2 mm deep. The incisions are made, and a stopwatch is used to determine how long bleeding occurs. A cotton swab is used to soak up the blood as it oozes from the incision. Template bleeding time is the time from incision to stoppage of bleeding. Bleeding times are taken just before administration of test compound (0 minutes), 60 minutes into infusion, at conclusion of administration of the test compound (120 minutes), and at the end of the experiment.

All data are analyzed by one-way analysis of variance (ANOVA) followed by Student-Neuman-Kuels post hoc t test to determine the level of significance. Repeated-measures ANOVA are used to determine significant differences between time points during the experiments. Values are determined to be statistically different at least at the level of $p<0.05$. All values are mean±SEM. All studies are conducted in accordance with the guiding principles of the American Physiological Society. Further details regarding the procedures are described in Jackson, et al., *J. Cardiovasc. Pharmacol.*, 21, 587–599 (1993).

TABLE 2

| Example | Human Plasma Anticoagulation 2x Clotting time (ng/mL) | | | % oral/i.v. activity (Rat) |
|---|---|---|---|---|
| | TT | APTT | PT | |
| 1 | 250 | NT | NT | 8 |
| 2 | 170 | NT | NT | NT |
| 3 | 590 | NT | NT | NT |
| 4 | 230 | NT | NT | NT |
| 5 | 30,000 | NT | NT | NT |
| 6 | 390 | NT | NT | NT |
| 7 | 490 | NT | NT | NT |
| 8 | 130 | NT | NT | NT |
| 9 | >91,000 | NT | NT | NT |
| 10 | 420 | NT | NT | NT |
| 11 | 8,800 | NT | NT | NT |
| 12 | 1,700 | NT | NT | NT |
| 13 | 660 | NT | NT | NT |
| 14 | 21,000 | NT | NT | NT |
| 15 | 9 | 89 | 200 | 4 |
| 16 | 650 | 8,600 | 8,500 | NT |
| 17 | 26 | 370 | 400 | 15 |
| 18 | 7 | 79 | 170 | 12 |
| 19 | 58 | 300 | 540 | NT |
| 20 | 62 | 550 | 600 | 23 |
| 21 | 160 | 2,000 | 1,000 | NT |
| 22 | 170 | 2,300 | 1,000 | NT |
| 23 | 7 | 86 | 120 | 12 |
| 24 | 1,000 | 25,900 | 25,000 | NT |
| 25 | 1,430 | 34,600 | 40,400 | NT |
| 26 | 37 | 870 | 750 | NC[1] |
| 27 | 1,940 | 27,800 | 27,000 | NT |
| 28 | 520 | 8,100 | 8,300 | NT |
| 29 | 750 | 9,800 | 15,800 | NT |
| 30 | 1,000 | 14,000 | 14,400 | NT |
| 31 | 10,800 | 34,500 | 30,000 | NT |
| 32 | 3,100 | 28,500 | 47,800 | NT |
| 33 | 18,900 | 59,300 | 70,900 | NT |
| 34 | 530 | 4,900 | 5,500 | NT |
| 35 | 4,500 | 50,400 | 78,400 | NT |
| 36 | 7,700 | >91,000 | >91,000 | NT |
| 37 | >9,000 | >9,000 | >9,000 | NT |
| 38 | 540 | 6,100 | 11,100 | NT |
| 39 | 5,300 | 69,200 | 78,600 | NT |
| 40 | 35,100 | >91,000 | >91,000 | NT |
| 41 | 82,200 | >91,000 | >91,000 | NT |
| 42 | 20 | 270 | 320 | NC[2] |
| 43 | 280 | 1,100 | 930 | NT |
| 44 | 4. | 100 | 170 | NT |
| 45 | 8 | 200 | 330 | NC[2] |
| 46 | 2. | 67 | 77 | NC[3] |
| 47 | 12. | 140 | 270 | NC[2] |
| 48 | 2. | 33 | 59 | 22 |
| 49 | 5 | 130 | 130 | NC[2] |
| 50 | 35 | 460 | 420 | NT |
| 51 | 2 | 48 | 110 | NT |
| 52 | 6 | 80 | 170 | NT |
| 53 | 1,400 | 33,800 | 34,500 | NT |
| 54 | 140 | 3,300 | 2,200 | NT |
| 55 | 55,800 | >91,000 | >91,000 | NT |
| 56 | 5 | 160 | 200 | NT |
| 57 | 14 | 360 | 340 | NT |
| 58 | 710 | 14,300 | 11,400 | NT |
| 59 | 420 | 5,500 | 7,000 | NT |
| 60 | 3,200 | 22,200 | 77,700 | NT |
| 61 | 45 | 679 | 756 | NT |
| 62 | 54 | | | NT |
| 63 | 680 | | | NT |
| 64 | 23 | 900 | 650 | NC[3] |
| 65 | 1 | 48 | 85 | NT |
| 66 | 7.9 | 180 | 270 | NT |
| 67 | 34. | 1,800 | 1,300 | NT |
| 68 | 4. | 49 | 190 | NT |
| 69 | 5. | 110 | 220 | NT |
| 70 | 2 | 160 | 180 | NT |
| 71 | 1 | 89 | 150 | NC[1] |
| 72 | 1 | 160 | 160 | NC[1] |
| 73 | 21 | 340 | 330 | NT |
| 74 | 20 | 420 | 350 | NT |

TABLE 2-continued

| Example | Human Plasma Anticoagulation 2x Clotting time (ng/mL) | | | % oral/i.v. activity (Rat) |
|---|---|---|---|---|
| | TT | APTT | PT | |
| 75 | | | | NT |
| 76 | 29 | 490 | 560 | NT |
| 77 | 53 | 1,600 | 890 | NT |
| 78 | 46 | 430 | 760 | NT |
| 79 | 140 | 1,700 | 2,400 | NT |
| 80 | 4 | 40 | 130 | NT |
| 81 | 110 | 1,500 | 2,700 | NT |
| 82 | 130 | 3,800 | 3,000 | NT |
| 83 | 91 | 1,000 | 1,300 | NT |
| 84 | 110 | 1,500 | 1,900 | NT |
| 85 | 4.9 | 100 | 197 | NT |
| 86 | 4 | 81 | 180 | NT |
| 87 | 9 | 260 | 310 | NT |
| 88 | 4 | 100 | 200 | NT |
| 89 | 570 | 51,000 | 37,000 | NT |
| 90 | 330 | 14,500 | 14,600 | NT |
| 91 | 63 | 3,000 | 3,500 | NT |
| 92 | 8.9 | 210 | 340 | NT |

Notes to Table 2
NC[1] indicates screening not completed; low or very low activity observed on 20 mg/kg p.o.
NC[2] indicates screening not completed; low or very low activity observed at 60 mg/kg p.o.
NC[3] indicates screening not completed; low or very low activity observed at 50 mg/kg p.o.
NT indicates not tested, as does a blank entry.

We claim:

1. A compound having the Formula I

X—Y—NH—(CH$_2$)$_r$—G      I wherein

X is prolinyl, homoprolinyl, R$^m$—(CH$_2$)$_g$—NH—CH$_2$—C(O)—,

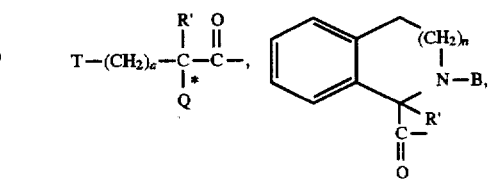

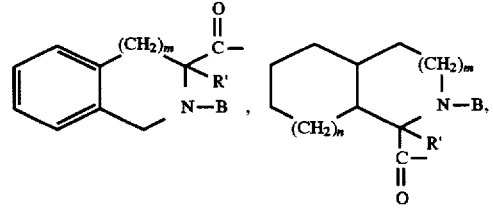

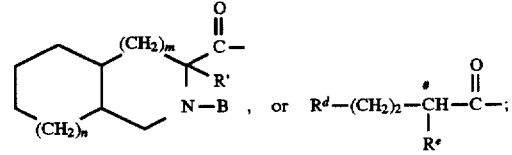

in which

R$^d$ is carboxy or methylsulfonyl;

R$^e$ is NHR$^c$, NHCOR$^c$ or NHCOOR$^c$; in which

R$^c$ is C$_1$–C$_{10}$ alkyl, C$_3$–C$_8$ cycloalkyl or a (C$_3$–C$_8$) cycloalkyl (C$_1$–C$_6$) alkyl radical of 4–10 carbons;

111

T is $C_3$–$C_8$ cycloalkyl, $C_1$–$C_8$ alkyl,

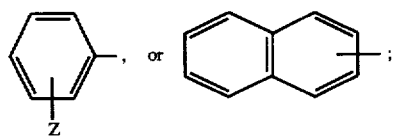

a is 0, 1 or 2; and

Q is —OH, $C_1$–$C_4$ alkoxy, or —NH—A;

A is hydrogen, $C_1$–$C_4$ alkyl, R"$SO_2$—, R"OC(O)—, R"C(O)—, R"C(O)— or —$(CH_2)_g$—R'";

g is 1, 2, or 3;

B is hydrogen or $C_1$–$C_4$ alkyl;

R' is hydrogen or $C_1$–$C_4$ alkyl;

R" is $C_1$–$C_4$ alkyl, $C_1$–$C_4$ perfluoroalkyl, —$(CH_2)_d$—R'", or unsubstituted or substituted aryl, where aryl is phenyl, naphthyl, a 5- or 6-membered unsubstituted or substituted aromatic heterocyclic ring, having one or two heteroatoms which are the same or different and which are selected from sulfur, oxygen and nitrogen, or a 9- or 10-membered unsubstituted or substituted fused bicyclic aromatic heterocyclic group having one or two heteroatoms which are the same or different and which are selected from sulfur, oxygen and nitrogen;

R'" is —COOR$^b$, —$SO_2$($C_1$–$C_4$ alkyl), —$SO_3H$, —$P(O)(OR^b)_2$ or tetrazol-5-yl;

R" is —COOR$^b$ or tetrazol-5-yl;

each R$^b$ is independently hydrogen or $C_1$–$C_4$ alkyl;

d is 1, 2, or 3;

m is 0, 1, or 2;

n is 0, 1, or 2; and

Z is hydrogen, $C_1$–$C_4$ alkyl, $C_1$–$C_4$ alkoxy, hydroxy, halo or $R_aSO_2NH$—, where $R_a$ is $C_1$–$C_4$ alkyl;

Y is

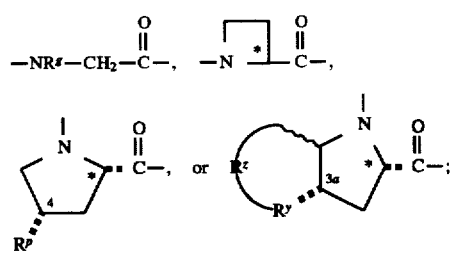

in which

R$^g$ is $C_1$–$C_6$ alkyl, $C_3$–$C_8$ cycloalkyl, or —$(CH_2)_p$—L—$(CH_2)_q$—T';

R$^p$ is hydrogen, $C_1$–$C_6$ alkyl, $C_3$–$C_8$ cycloalkyl, or —$(CH_2)_p$—L—$(CH_2)_q$—T';

where p is 0, 1, 2, 3, or 4; L is a bond, —O—, —S—, or —NH—; q is 0, 1, 2 or 3; and T' is hydrogen, $C_1$–$C_4$ alkyl, $C_3$–$C_8$ cycloalkyl, —COOH, —CONH$_2$, or Ar, where Ar is unsubstituted or substituted aryl, where aryl is phenyl, naphthyl, a 5- or 6-membered unsubstituted or substituted aromatic heterocyclic ring, having one or two heteroatoms which are the same or different and which are selected from sulfur, oxygen and nitrogen, or a 9- or 10-membered unsubstituted or substituted fused bicyclic aromatic heterocyclic group having one or two heteroatoms which are the same or different and which are selected from sulfur, oxygen and nitrogen;

112

R$^y$ is —$CH_2$—, —O—, —S—, or —NH—; and

R$^z$ is a bond or, when taken with R$^y$ and the three adjoining carbon atoms, forms a saturated carbocyclic ring of 5–8 atoms, one atom of which may be —O—, —S—, or —NH—;

r is 1, 2 or 3; and

G is —$(CH_2)_s$—R, where s is 0–5, —CH=CH—$(CH_2)_t$—R, where t is 0–3; and

R is

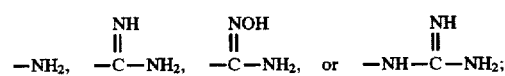

or a pharmaceutically acceptable salt thereof; or a pharmaceutically acceptable solvate of said compound or salt thereof;

provided that A is not hydrogen, $C_1$–$C_4$ alkyl, R"C(O)— when R" is —COOR$^b$, —$(CH_2)_g$—R'" where R'" is COOR$^b$ or t-butyloxycarbonyl when R is —C(NH)NH$_2$ or —NH—C(NH)NH$_2$, Y is

or unsubstituted prolinyl (R$^p$ is hydrogen), and T is

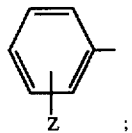

and provided further that R is not amino or guanidino when r=1 and s=0;

and provided further that A is not hydrogen, $C_1$–$C_4$ alkyl, methylsulfonyl, R"C(O)— where R" is —COOR$^b$ or —$(CH_2)_g$—R'" when G is —$(CH_2)_s$—R in which R is

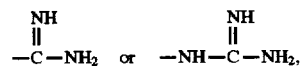

Y is

unsubstituted prolinyl (R$^p$ is hydrogen) or 4-hydroxyprolinyl (R$^p$ is OH), R' is hydrogen, T is cyclohexyl and Q is —NH—A;

and further provided that A is not hydrogen, $C_1$–$C_4$ alkyl, R"$SO_2$— (where R" is $C_1$–$C_4$ alkyl), R"C(O)— (where R" is —COOR$^b$) or —$(CH_2)_g$—R'" (where R'" is —COOR$^b$) when T is cyclohexyl or

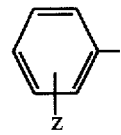

Y is

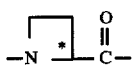

or unsubstituted prolinyl ($R^p$ is hydrogen), and R is
—C(NH)NH$_2$ or —NH—C(NH)NH$_2$;

and provided further that R"SO$_2$ is not arylsulfonyl when
G is —(CH$_2$)$_s$—R in which R is

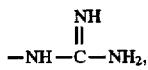

Y is unsubstituted prolinyl ($R^p$ is hydrogen) or
4-methylthioprolinyl ($R^p$ is —SCH$_3$), and Q is —NH—A.

2. The compound of Formula I or salt or solvate thereof as claimed in claim 1 wherein X is prolinyl, homoprolinyl,

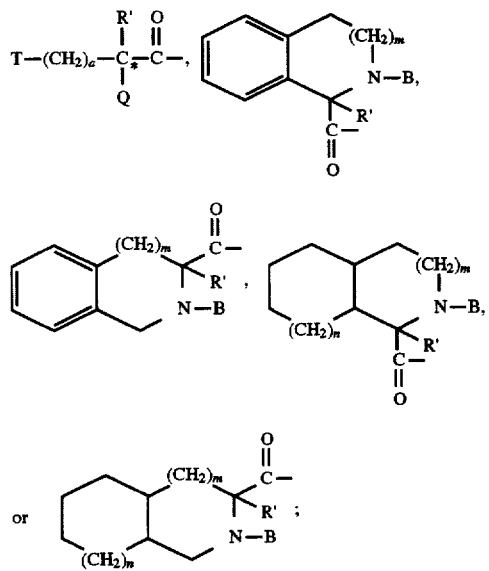

T is $C_3$–$C_8$ cycloalkyl, $C_1$–$C_8$ alkyl,

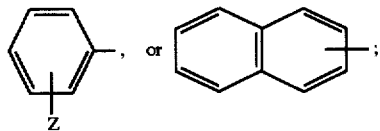

a is 0 or 1;

Q is —OH, $C_1$–$C_4$ alkoxy, or —NH—A;

A is hydrogen, $C_1$–$C_4$ alkyl, R"SO$_2$—, R"OC(O)—, R"C(O)—, or —(CH$_2$)$_g$—COOH;

g is 1, 2, or 3;

B is hydrogen or $C_1$–$C_4$ alkyl;

R' is hydrogen or $C_1$–$C_4$ alkyl;

R" is $C_1$–$C_4$ alkyl, $C_1$–$C_4$ perfluoroalkyl, —(CH$_2$)$_d$—COOH, or unsubstituted or substituted aryl, where aryl is phenyl, naphthyl, a 5- or 6-membered unsubstituted or substituted aromatic heterocyclic ring, having one or two heteroatoms which are the same or different and which are selected from sulfur, oxygen and nitrogen, or a 9- or 10-membered unsubstituted or substituted fused bicyclic aromatic heterocyclic group having one or two heteroatoms which are the same or different and which are selected from sulfur, oxygen and nitrogen;

d is 1, 2, or 3;

m is 0, 1, or 2;

n is 0, 1, or 2; and

Z is hydrogen, $C_1$–$C_4$ alkyl, $C_1$–$C_4$ alkoxy, hydroxy, halo, or $R_a$SO$_2$NH—, where $R_a$ is $C_1$–$C_4$ alkyl;

Y is

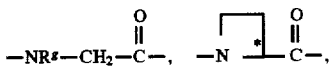

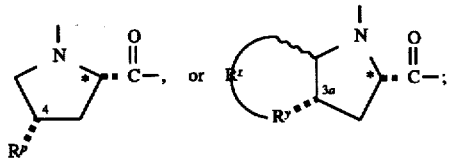

in which $R^g$ is $C_1$–$C_6$ alkyl, $C_3$–$C_8$ cycloalkyl, or —(CH$_2$)$_p$—L—(CH$_2$)$_q$—T';

$R^p$ is hydrogen, $C_1$–$C_6$ alkyl, $C_3$–$C_8$ cycloalkyl, or —(CH$_2$)$_p$—L—(CH$_2$)$_q$—T';

where p is 0, 1, 2, 3, or 4; L is a bond, —O—, —S—, or —NH—; q is 0, 1, 2 or 3, and T' is hydrogen, $C_1$–$C_4$ alkyl, $C_3$–$C_8$ cycloalkyl, —COOH, —CONH$_2$, or Ar, where Ar is unsubstituted or substituted aryl, where aryl is phenyl, naphthyl, a 5- or 6-membered unsubstituted or substituted aromatic heterocyclic ring, having one or two heteroatoms which are the same or different and which are selected from sulfur, oxygen and nitrogen, or a 9- or 10-membered unsubstituted or substituted fused bicyclic aromatic heterocyclic group having one or two heteroatoms which are the same or different and which are selected from sulfur, oxygen and nitrogen;

$R^y$ is —CH$_2$—, —O—, —S—, or —NH—; and $R^z$ is a bond or, when taken with $R^y$ and the three adjoining carbon atoms, forms a saturated carbocyclic ring of 5–8 atoms, one atom of which may be —O—, —S—, or —NH—;

r is 1 or 2; and

G is —(CH$_2$)$_s$—R, where s is 0–5, —CH=CH—(CH$_2$)$_t$—R, where t is 0–3; and R is

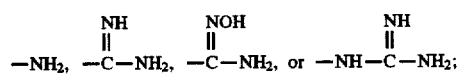

or a pharmaceutically acceptable salt thereof; or a pharmaceutically acceptable solvate of said compound or salt thereof;

provided that A is not hydrogen, $C_1$–$C_4$ alkyl or t-butyloxycarbonyl when R is —C(NH)NH$_2$ or —NH—C(NH)NH$_2$, Y is

or unsubstituted prolinyl ($R^p$ is hydrogen), and T is

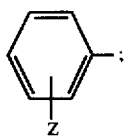

and provided further that R is not amino or guanidino when r=1 and s=0;

and provided further that A is not hydrogen, $C_1$-$C_4$ alkyl, methylsulfonyl or —($CH_2$)$_g$—COOH when G is —($CH_2$)$_s$—R in which R is

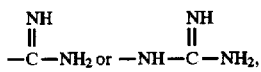

Y is

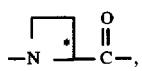

unsubstituted prolinyl ($R^p$ is hydrogen) or 4-hydroxyprolinyl ($R^p$ is OH), R' is hydrogen, T is cyclohexyl and Q is —NH—A;

and further provided that A is not hydrogen, $C_1$-$C_4$ alkyl, R"$SO_2$— (where R" is $C_1$-$C_4$ alkyl) or —($CH_2$)g—COOH when T is cyclohexyl or

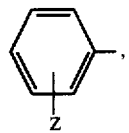

Y is

or unsubstituted prolinyl ($R^p$ is hydrogen), and R is —C(NH)$NH_2$ or —NH—C(NH)$NH_2$;

and provided further that R"$SO_2$ is not arylsulfonyl when G is —($CH_2$)$_s$—R in which R is

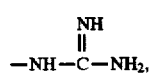

Y is unsubstituted prolinyl ($R^p$ is hydrogen) or 4-methylthioprolinyl ($R^p$ is —$SCH_3$), and Q is —NH—A.

3. The compound of claim 2 where X is

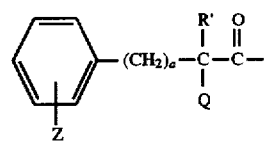

homoprolinyl, 1- or 3-Tiq, or 1- or 3-Piq, or a pharmaceutically acceptable salt or solvate thereof.

4. The compound of claim 3 where A is hydrogen or R"$SO_2$—, or a pharmaceutically acceptable salt or solvate thereof.

5. The compound of claim 1 where G is guanidino.
6. The compound of claim 2 where G is guanidino.
7. The compound or salt or solvate thereof as claimed in claim 1 where alkyl by itself or as part of another substituent is methyl, ethyl, n-propyl, isopropyl, n-butyl, t-butyl, isobutyl or sec-butyl;

perfluoroalkyl by itself or as part of another substituent is trifluoromethyl, perfluoroethyl, perfluoro-n-propyl, perfluoroisopropyl, perfluoro-n-butyl, perfluoro-t-butyl, perfluoroisobutyl or perfluoro-sec-butyl;

$C_3$-$C_8$ cycloalkyl is cyclopropyl, methylcyclopropyl, cyclobutyl, cyclopentyl, cyclohexyl, 4-methylcyclohexyl or cyclooctyl;

halo is chloro, fluoro, bromo or iodo;

a 5- or 6-membered heterocyclic ring is furyl, thienyl, pyrrolyl, pyrazolyl, oxazolyl, isoxazolyl, thiazolyl, isothiazolyl, pyranyl, pyridinyl, pyrimidinyl, pyrazinyl, oxazinyl or thiazinyl;

a 9- or 10-membered heterocyclic ring is indolyl, benzothienyl, benzofuryl, benzoxazolyl, benzoisoxazolyl, benzopyrazolyl, quinolinyl, isoquinolinyl, benzimidazolyl or benzothiazolyl;

and further where any of the aromatic or heteroaromatic groups listed for the definition of Ar or R" is independently unsubstituted or substituted with one or two substituents that will afford a stable structure independently selected from halo, hydroxyl, $C_1$-$C_4$ alkyl, $C_1$-$C_4$ alkoxy, amino (—$NH_2$), mono($C_1$-$C_4$ alkyl) amino, —($CH_2$)$_j$COOH, mercapto, —S(O)$_h$($C_1$-$C_4$ alkyl), —NHS(O)$_h$($C_1$-$C_4$ alkyl), —NHC(O)($C_1$-$C_4$ alkyl), —S(O)$_h$$NH_2$, —S(O)$_h$NH($C_1$-$C_4$ alkyl), or —S(O)$_h$N($C_1$-$C_4$ alkyl)$_2$, h is 0, 1 or 2, and j is 0, 1, 2, 3, or 4.

8. The compound or salt or solvate thereof as claimed in claim 7 wherein

X is

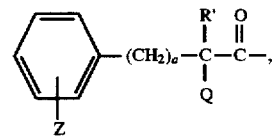

homoprolinyl, 1- or 3-Tiq, or 1- or 3-Piq; Y is prolinyl; and Q is NHA in which A is hydrogen or R"$SO_2$—, R' is hydrogen, Z is hydrogen, and B is hydrogen; and R is a guanidino group.

9. The compound or salt or solvate thereof as claimed in claim 7 wherein

X is

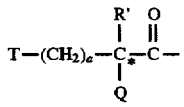

in which T is cyclohexyl, a is 1, R' is hydrogen and Q is —NH—A in which A is hydrogen, R"$SO_2$— or —($CH_2$)$_g$—COOH.

10. The compound or salt or solvate thereof as claimed in claim 9 in which A is R"$SO_2$— and R" is ethyl.

11. The compound or salt or solvate thereof as claimed in claim 9 in which A is —($CH_2$)$_g$—COOH and g is 1.

12. The compound or salt or solvate thereof as claimed in claim 7 in which Y is (L)-prolinyl, (S)-cis-octahydro-1H-indole-2-carbonyl, or N-(2-phenylethyl)glycyl.

13. The compound, or salt or solvate thereof, as claimed in claim 2 which compound is N-[4-[(aminoiminomethyl)amino]butyl]-1-[[(4aR,8aR)-decahydro-1(R)-isoquinolinyl]carbonyl]-1-prolinamide.

14. A pharmaceutical formulation comprising the compound or a salt or solvate thereof of claim 1 in association with a pharmaceutically acceptable carrier, diluent, or excipient, thereof.

15. The formulation of claim 14 wherein X is prolinyl, homoprolinyl,

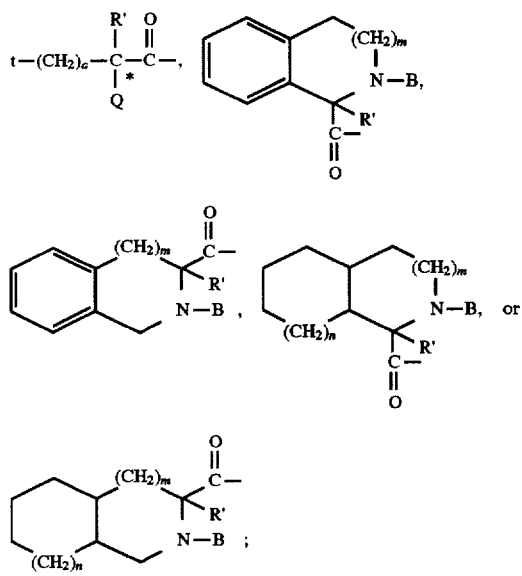

T is $C_3$–$C_8$ cycloalkyl, $C_1$–$C_8$ alkyl,

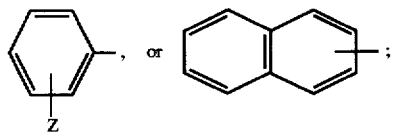

a is 0 or 1;
Q is —OH, $C_1$–$C_4$ alkoxy, or —NH—A;
A is hydrogen, $C_1$–$C_4$ alkyl, R"$SO_2$—, R"OC(O)—, R"C(O)—, or —$(CH_2)_g$—COOH;
g is 1, 2, or 3;
B is hydrogen or $C_1$–$C_4$ alkyl;
R' is hydrogen or $C_1$–$C_4$ alkyl;
R" is $C_1$–$C_4$ alkyl, $C_1$–$C_4$ perfluoroalkyl, —$(CH_2)_d$—COOH, or unsubstituted or substituted aryl, where aryl is phenyl, naphthyl, a 5- or 6-membered unsubstituted or substituted aromatic heterocyclic ring, having one or two heteroatoms which are the same or different and which are selected from sulfur, oxygen and nitrogen, or a 9- or 10-membered unsubstituted or substituted fused bicyclic aromatic heterocyclic group having one or two heteroatoms which are the same or different and which are selected from sulfur, oxygen and nitrogen;
d is 1, 2, or 3;
m is 0, 1, or 2;
n is 0, 1, or 2; and
Z is hydrogen, $C_1$–$C_4$ alkyl, $C_1$–$C_4$ alkoxy, hydroxy, halo, or $R_a SO_2 NH$—, where $R_a$ is $C_1$–$C_4$ alkyl;

Y is

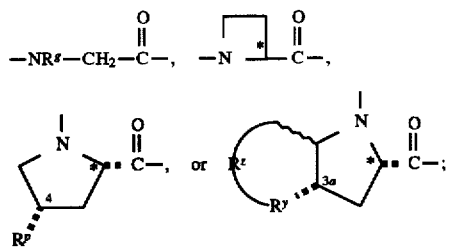

in which $R^g$ is $C_1$–$C_6$ alkyl, $C_3$–$C_8$ cycloalkyl, or —$(CH_2)_p$—L—$(CH_2)_q$—T';

$R^p$ is hydrogen, $C_1$–$C_6$ alkyl, $C_3$–$C_8$ cycloalkyl, or —$(CH_2)_p$—L—$(CH_2)_q$—T';

where p is 0, 1, 2, 3, or 4; L is a bond, —O—, —S—, or —NH—; q is 0, 1, 2 or 3; and T' is hydrogen, $C_1$–$C_4$ alkyl, $C_3$–$C_8$ cycloalkyl, —COOH, —$CONH_2$, or Ar, where Ar is unsubstituted or substituted aryl, where aryl is phenyl, naphthyl, a 5- or 6-membered unsubstituted or substituted aromatic heterocyclic ring, having one or two heteroatoms which are the same or different and which are selected from sulfur, oxygen and nitrogen, or a 9- or 10-membered unsubstituted or substituted fused bicyclic aromatic heterocyclic group having one or two heteroatoms which are the same or different and which are selected from sulfur, oxygen and nitrogen;

$R^y$ is —$CH_2$—, —O—, —S—, or —NH—; and $R^z$ is a bond or, when taken with $R^y$ and the three adjoining carbon atoms, forms a saturated carbocyclic ring of 5–8 atoms, one atom of which may be —O—, —S—, or —NH—;

r is 1, or 2; and

G is —$(CH_2)_s$—R, where s is 0–5, —CH=CH—$(CH_2)_t$—R, where t is 0–3; and

R is

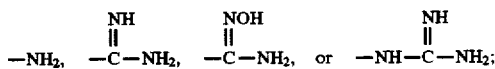

or a pharmaceutically acceptable salt thereof; or a pharmaceutically acceptable solvate of said compound or salt thereof;

provided that A is not hydrogen, $C_1$–$C_4$ alkyl or t-butyloxycarbonyl when R is —C(NH)$NH_2$ or —NH—C(NH)$NH_2$, Y is

or unsubstituted prolinyl ($R^p$ is hydrogen), and T is

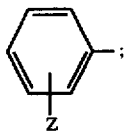

and provided further that R is not amino or guanidino when r=1 and s=0;

and provided further that A is not hydrogen, $C_1$–$C_4$ alkyl, methylsulfonyl or —$(CH_2)_g$—$R^m$ when G is —$(CH_2)_s$—R in which R is $$-\overset{NH}{\underset{\|}{C}}-NH_2 \quad \text{or} \quad -NH-\overset{NH}{\underset{\|}{C}}-NH_2,$$

Y is $$-N\underset{*}{\overset{\Large\sqcap}{\rule{0pt}{1em}}}\overset{O}{\underset{\|}{C}}-,$$

unsubstituted prolinyl ($R^p$ is hydrogen) or 4-hydroxyprolinyl ($R^p$ is OH), R' is hydrogen, T is cyclohexyl and Q is —NH—A;

and further provided that A is not hydrogen, $C_1$–$C_4$ alkyl, R"$SO_2$— (where R" is $C_1$–$C_4$ alkyl) or —$(CH_2)g$—COOH when T is cyclohexyl or (benzene ring with Z substituent), Y is $$-N\underset{*}{\overset{\Large\sqcap}{\rule{0pt}{1em}}}\overset{O}{\underset{\|}{C}}-$$

or unsubstituted prolinyl ($R^p$ is hydrogen), and R is —C(NH)$NH_2$ or —NH—C(NH)$NH_2$;

and provided further that R"$SO_2$ is not arylsulfonyl when G is —$(CH_2)_s$—R in which R is $$-NH-\overset{NH}{\underset{\|}{C}}-NH_2,$$

Y is unsubstituted prolinyl ($R^p$ is hydrogen) or 4-methylthioprolinyl ($R^p$ is —$SCH_3$), and Q is —NH—A.

16. The formulation of claim 15 where X is (benzene ring with Z)—$(CH_2)_a$—$\underset{Q}{\overset{R'}{\underset{|}{C}}}$—$\overset{O}{\underset{\|}{C}}$—, homoprolinyl, 1- or 3-Tiq, or 1- or 3-Piq; or a pharmaceutically acceptable salt or solvate thereof.

17. The formulation of claim 16 where A is hydrogen or R"$SO_2$—, or a pharmaceutically acceptable salt or solvate thereof.

18. The formulation of claim 14 where G is guanidino.
19. The formulation of claim 15 where G is guanidino.
20. The formulation as claimed in claim 14 wherein alkyl by itself or as part of another substituent is methyl, ethyl, n-propyl, isopropyl, n-butyl, t-butyl, isobutyl or sec-butyl;

perfluoroalkyl by itself or as part of another substituent is trifluoromethyl, perfluoroethyl, perfluoro-n-propyl, perfluoroisopropyl, perfluoro-n-butyl, perfluoro-t-butyl, perfluoroisobutyl or perfluoro-sec-butyl;

$C_3$–$C_8$ cycloalkyl is cyclopropyl, methylcyclopropyl, cyclobutyl, cyclopentyl, cyclohexyl, 4-methylcyclohexyl or cyclooctyl;

halo is chloro, fluoro, bromo or iodo;

a 5- or 6-membered heterocyclic ring is furyl, thienyl, pyrrolyl, pyrazolyl, oxazolyl, isoxazolyl, thiazolyl, isothiazolyl, pyranyl, pyridinyl, pyrimidinyl, pyrazinyl, oxazinyl or thiazinyl;

a 9- or 10-membered heterocyclic ring is indolyl, benzothienyl, benzofuryl, benzoxazolyl, benzoisoxazolyl, benzopyrazolyl, quinolinyl, isoquinolinyl, benzimidazolyl or benzothiazolyl;

and further where any of the aromatic or heteroaromatic groups listed for the definition of Ar or R" is independently unsubstituted or substituted with one or two substituents that will afford a stable structure independently selected from halo, hydroxyl, $C_1$–$C_4$ alkyl, $C_1$–$C_4$ alkoxy, amino (—$NH_2$), mono($C_1$–$C_4$ alkyl) amino, —$(CH_2)_j$COOH, mercapto, —$S(O)_h(C_1$–$C_4$ alkyl), —NHS(O)$_h(C_1$–$C_4$ alkyl), —NHC(O)($C_1$–$C_4$ alkyl), —$S(O)_h NH_2$, —$S(O)_h NH(C_1$–$C_4$ alkyl), or —$S(O)_h N(C_1$–$C_4$ alkyl)$_2$, h is 0, 1 or 2, and j is 0, 1, 2, 3, or 4.

21. The formulation as claimed in claim 20 wherein X is (benzene ring with Z)—$(CH_2)_a$—$\underset{Q}{\overset{R'}{\underset{|}{C}}}$—$\overset{O}{\underset{\|}{C}}$—, homoprolinyl, 1- or 3-Tiq, or 1- or 3-Piq; Y is prolinyl; and Q is NHA in which A is hydrogen or R"$SO_2$—, R' is hydrogen, Z is hydrogen, and B is hydrogen; and R is a guanidino group.

22. The formulation is claimed in claim 20 wherein X is

T—$(CH_2)_a$—$\underset{Q}{\overset{R'}{\underset{|}{\underset{*}{C}}}}$—$\overset{O}{\underset{\|}{C}}$— in which t is cyclohexyl, a is 1, R' is hydrogen and Q is —NH—A in which A is hydrogen, R"$SO_2$— or —$(CH_2)_g$—COOH.

23. The formulation is claimed in claim 22 in which A is R"$SO_2$— and R" is ethyl.

24. The formulation as claimed in claim 22 in which A is —$(CH_2)_g$—COOH and g is 1.

25. The formulation as claimed in claim 20 in which Y is (L)-prolinyl, (S)-cis-octahydro-1H-indole-2-carbonyl, or N-(2-phenylethyl)glycyl.

26. The formulation as claimed in claim 15 in which said compound is

N-[4[(aminoiminomethyl)amino]butyl]-1-[[(4aR,8aR)-decahydro-1(R)-isoquinolinyl]carbonyl]-1-prolinamide.

27. A method of inhibiting thrombin in mammals, comprising administering to a mammal requiring thrombin inhibition, an effective dose of the compound of claim 1 or a pharmaceutically acceptable salt or solvate thereof.

28. The method of claim 27 wherein X is prolinyl, homoprolinyl,

121

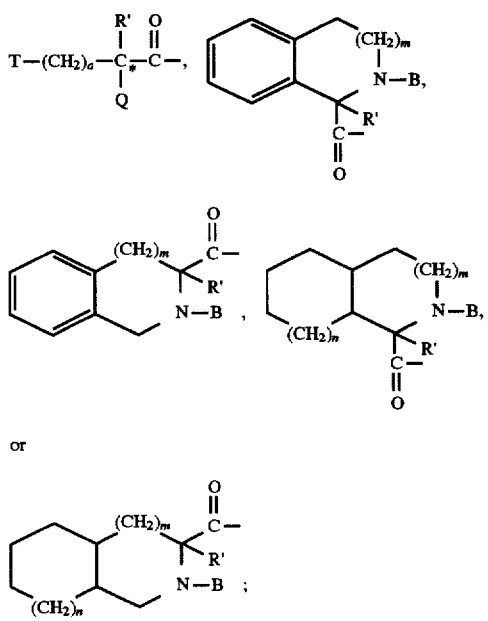

T is $C_3$–$C_8$ cycloalkyl, $C_1$–$C_8$ alkyl,

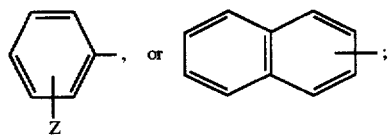

a is 0 or 1;

Q is —OH, $C_1$–$C_4$ alkoxy, or —NH—A;

A is hydrogen, $C_1$–$C_4$ alkyl, R"SO$_2$—, R"OC(O)—, R"C(O)—, or —(CH$_2$)$_g$—COOH;

g is 1, 2, or 3;

B is hydrogen or $C_1$–$C_4$ alkyl;

R' is hydrogen or $C_1$–$C_4$ alkyl;

R" is $C_1$–$C_4$ alkyl, $C_1$–$C_4$ perfluoroalkyl, —(CH$_2$)$_d$—COOH, or unsubstituted or substituted aryl, where aryl is phenyl, naphthyl, a 5- or 6-membered unsubstituted or substituted aromatic heterocyclic ring, having one or two heteroatoms which are the same or different and which are selected from sulfur, oxygen and nitrogen, or a 9- or 10-membered unsubstituted or substituted fused bicyclic aromatic heterocyclic group having one or two heteroatoms which are the same or different and which are selected from sulfur, oxygen and nitrogen;

d is 1, 2, or 3;

m is 0, 1, or 2;

n is 0, 1, or 2; and

Z is hydrogen, $C_1$–$C_4$ alkyl, $C_1$–$C_4$ alkoxy, hydroxy, halo, or R$_a$SO$_2$NH—, where R$_a$ is $C_1$–$C_4$ alkyl;

Y is

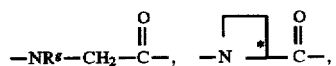

122

-continued

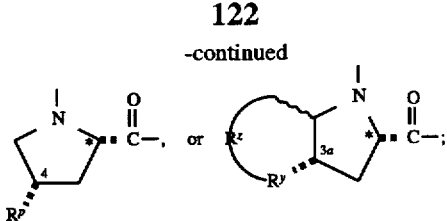

in which

R$^g$ is $C_1$–$C_6$ alkyl, $C_3$–$C_8$ cycloalkyl, or —(CH$_2$)$_p$—L—(CH$_2$)$_q$—T';

R$^p$ is hydrogen, $C_1$–$C_6$ alkyl, $C_3$–$C_8$ cycloalkyl, or —(CH$_2$)$_p$—L—(CH$_2$)$_q$—T';

where p is 0, 1, 2, 3, or 4; L is a bond, —O—, —S—, or —NH—; q is 0, 1, 2 or 3, and T' is hydrogen, $C_1$–$C_4$ alkyl, $C_3$–$C_8$ cycloalkyl, —COOH, —CONH$_2$, or Ar, where Ar is unsubstituted or substituted aryl, where aryl is phenyl, naphthyl, a 5- or 6-membered unsubstituted or substituted aromatic heterocyclic ring, having one or two heteroatoms which are the same or different and which are selected from sulfur, oxygen and nitrogen, or a 9- or 10-membered unsubstituted or substituted fused bicyclic aromatic heterocyclic group having one or two heteroatoms which are the same or different and which are selected from sulfur, oxygen and nitrogen;

R$^y$ is —CH$_2$—, —O—, —S—, or —NH—; and

R$^z$ is a bond or, when taken with R$^y$ and the three adjoining carbon atoms, forms a saturated carbocyclic ring of 5–8 atoms, one atom of which may be —O—, —S—, or —NH—;

r is 1 or 2; and

G is —(CH$_2$)$_s$—R, where s is 0–5, —CH=CH—(CH$_2$)$_t$—R, where t is 0–3; and R is —NH$_2$,  $-\overset{\underset{\|}{NH}}{C}$—NH$_2$,  $-\overset{\underset{\|}{NOH}}{C}$—NH$_2$,  or  —NH—$\overset{\underset{\|}{NH}}{C}$—NH$_2$;

or a pharmaceutically acceptable salt thereof; or a pharmaceutically acceptable solvate of said compound or salt thereof;

provided that A is not hydrogen, $C_1$–$C_4$ alkyl or t-butyloxycarbonyl when R is —C(NH)NH$_2$ or —NH—C(NH)NH$_2$, Y is

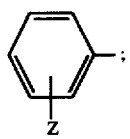

or unsubstituted prolinyl (R$^p$ is hydrogen), and T is

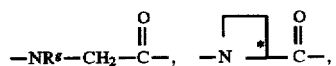

and provided further that R is not amino or guanidino when r=1 and s=0;

and provided further that A is not hydrogen, $C_1$–$C_4$ alkyl, methylsulfonyl or —(CH$_2$)$_g$—COOH when G is —(CH$_2$)$_s$—R in which R is $$\begin{matrix} \text{NH} \\ \| \\ -\text{C}-\text{NH}_2 \end{matrix} \quad \text{or} \quad \begin{matrix} \text{NH} \\ \| \\ -\text{NH}-\text{C}-\text{NH}_2, \end{matrix}$$

Y is

[structure: -N-*-C(=O)-, pyrrolidine ring]

unsubstituted prolinyl ($R^p$ is hydrogen) or 4-hydroxyprolinyl ($R^p$ is OH), R' is hydrogen, T is cyclohexyl and Q is —NH—A;

and further provided that A is not hydrogen, $C_1$-$C_4$ alkyl, R"SO$_2$— (where R" is $C_1$-$C_4$ alkyl) or —(CH$_2$)$_g$—COOH when T is cyclohexyl or

[phenyl ring with Z substituent]

Y is

[structure: -N-*-C(=O)-, pyrrolidine ring]

or unsubstituted prolinyl ($R^p$ is hydrogen), and R is —C(NH)NH$_2$ or —NH—C(NH)NH$_2$;

and provided further that R"SO$_2$ is not arylsulfonyl when G is —(CH$_2$)$_s$—R in which R is $$\begin{matrix} \text{NH} \\ \| \\ -\text{NH}-\text{C}-\text{NH}_2, \end{matrix}$$

Y is unsubstituted prolinyl ($R^p$ is hydrogen) or 4-methylthioprolinyl ($R^p$ is —SCH$_3$), and Q is —NH—A.

29. The method of claim 28 where X is

[phenyl-Z with —(CH$_2$)$_a$—C(R')(Q)—C(=O)—]

homoprolinyl, 1- or 3-Tiq, or 1- or 3-Piq, or pharmaceutically acceptable salt or solvate thereof.

30. The method of claim 29 where A is hydrogen or R"SO$_2$—, or a pharmaceutically acceptable salt or solvate thereof.

31. The method of claim 27 where G is guanidino.

32. The method of claim 28 where G is guanidino.

33. The method as claimed in claim 27 wherein alkyl by itself or as part of another substituent is methyl, ethyl, n-propyl, isopropyl, n-butyl, t-butyl, isobutyl or sec-butyl;

perfluoroalkyl by itself or as part of another substituent is trifluoromethyl, perfluoroethyl, perfluoro-n-propyl, perfluoroisopropyl, perfluoro-n-butyl, perfluoro-t-butyl, perfluoroisobutyl or perfluoro-sec-butyl;

$C_3$-$C_8$ cycloalkyl is cyclopropyl, methylcyclopropyl, cyclobutyl, cyclopentyl, cyclohexyl, 4-methylcyclohexyl or cyclooctyl;

halo is chloro, fluoro, bromo or iodo;

a 5- or 6-membered heterocyclic ring is furyl, thienyl, pyrrolyl, pyrazolyl, oxazolyl, isoxazolyl, thiazolyl, isothiazolyl, pyranyl, pyridinyl, pyrimidinyl, pyrazinyl, oxazinyl or thiazinyl;

a 9- or 10-membered heterocyclic ring is indolyl, benzothienyl, benzofuryl, benzoxazolyl, benzoisoxazolyl, benzopyrazolyl, quinolinyl, isoquinolinyl, benzimidazolyl or benzothiazolyl;

and further where any of the aromatic or heteroaromatic groups listed for the definition of Ar or R" is independently unsubstituted or substituted with one or two substituents that will afford a stable structure independently selected from halo, hydroxyl, $C_1$-$C_4$ alkyl, $C_1$-$C_4$ alkoxy, amino (—NH$_2$), mono($C_1$-$C_4$ alkyl) amino, —(CH$_2$)$_j$COOH, mercapto, —S(O)$_h$($C_1$-$C_4$ alkyl), NHS(O)$_h$($C_1$-$C_4$ alkyl), —NHC(O)($C_1$-$C_4$ alkyl), —S(O)$_h$NH$_2$, —S(O)$_h$NH($C_1$-$C_4$ alkyl), or —S(O)$_h$N($C_1$-$C_4$ alkyl)$_2$, h is 0, 1 or 2, and j is 0, 1, 2, 3, or 4.

34. The method as claimed in claim 33 wherein X is

[phenyl-Z with —(CH$_2$)$_a$—C(R')(Q)—C(=O)—]

homoprolinyl, 1- or 3-Tiq, or 1- or 3-Piq; Y is prolinyl; and Q is NHA in which A is hydrogen or R"SO$_2$—, R' is hydrogen, Z is hydrogen, and B is hydrogen; and R is a guanidino group.

35. The method as claimed in claim 33 wherein X is $$T-(CH_2)_a-\underset{Q}{\overset{R'}{\underset{|}{C_*}}}-\overset{O}{\overset{\|}{C}}-$$

in which T is cyclohexyl, A is 1, R' is hydrogen and Q is —NH—A in which A is hydrogen, R"SO$_2$— or —(CH$_2$)$_g$—COOH.

36. The method as claimed in claim 35 in which A is R"SO$_2$— and R" is ethyl.

37. The method as claimed in claim 35 in which A is —(CH$_2$)$_g$—COOH and g is 1.

38. The method as claimed in claim 33 in which Y is (L)-prolinyl, (S)-cis-octahydro-1H-indole-2-carbonyl, or N-(2-phenylethyl)glycyl.

39. The method as claimed in claim 28 in which said compound is N-[4[(aminoiminomethyl)amino]butyl]-1-[[(4aR,8aR)-decahydro-1(R)-isoquinolinyl]carbonyl]-1-prolinamide.

40. The compound, or salt or solvate thereof, as claimed in claim 2 which compound is N-[(1-methyl-1H-indol-2-yl)carbonyl]-D-phenylalanyl-N-[4-[(aminoiminomethyl)amino]butyl]-L-prolinamide.

41. The formulation as claimed in claim 15 in which said compound is N-[(1-methyl-1H-indol-2-yl)carbonyl]-D-phenylalanyl-N-[4-[(aminoiminomethyl)amino]butyl]-L-prolinamide.

42. The method as claimed in claim 28 in which said compound is N-[(1-methyl-1H-indol-2-yl)carbonyl]-D-phenylalanyl-N-[4-[(aminoiminomethyl)amino]butyl]-L-prolinamide.

* * * * *